US012447048B2

(12) United States Patent
Hipsley

(10) Patent No.: US 12,447,048 B2
(45) Date of Patent: Oct. 21, 2025

(54) SYSTEMS AND METHODS FOR OCULAR LASER SURGERY AND THERAPEUTIC TREATMENTS

(71) Applicant: ACE VISION GROUP, INC., Silver Lake, OH (US)

(72) Inventor: AnnMarie Hipsley, Silver Lake, OH (US)

(73) Assignee: ACE VISION GROUP, INC., Silver Lake, OH (US)

( * ) Notice: Subject to any disclaimer, the term of this patent is extended or adjusted under 35 U.S.C. 154(b) by 932 days.

(21) Appl. No.: 17/518,211

(22) Filed: Nov. 3, 2021

(65) Prior Publication Data

US 2022/0125639 A1 Apr. 28, 2022

Related U.S. Application Data

(63) Continuation of application No. PCT/US2020/031392, filed on May 5, 2020.

(60) Provisional application No. 62/843,403, filed on May 4, 2019.

(51) Int. Cl.
*A61F 9/008* (2006.01)

(52) U.S. Cl.
CPC *A61F 9/00802* (2013.01); *A61F 2009/00846* (2013.01); *A61F 2009/00851* (2013.01); *A61F 2009/00865* (2013.01); *A61F 2009/00882* (2013.01); *A61F 2009/00895* (2013.01); *A61F 2009/00897* (2013.01)

(58) Field of Classification Search
None
See application file for complete search history.

(56) References Cited

U.S. PATENT DOCUMENTS 4,473,074 A * 9/1984 Vassiliadis ........... A61B 18/201
D24/170
4,812,613 A * 3/1989 Gorisch ............. B23K 26/0643
219/121.74
4,911,160 A * 3/1990 Thyzel .................... A61F 9/008
606/4
6,322,216 B1 * 11/2001 Yee ..................... A61F 9/00804
606/5

(Continued)

FOREIGN PATENT DOCUMENTS

WO WO-2018183987 A1 * 10/2018 ............. A61F 9/008

OTHER PUBLICATIONS

PCT/US2020/031392, ISR and Written Opinion, Aug. 4, 2020.

*Primary Examiner* — Carl H Layno
*Assistant Examiner* — Manolis Pahakis
(74) *Attorney, Agent, or Firm* — ONE LLP

(57) ABSTRACT

Disclosed are systems, devices and methods for laser microporation for rejuvenation of tissue of the eye, for example, regarding aging of connective tissue and rejuvenation of connective tissue by scleral rejuvenation. The systems, devices and methods disclosed herein restore physiological functions of the eye including restoring physiological accommodation or physiological pseudo-accommodation through natural physiological and biomechanical phenomena associated with natural accommodation of the eye. In some embodiments, the laser system may be configured to treat ocular tissue off axis or in a region of the eye which is distinct from the visual axis or directed away from the pupil of the eye where the gaze of the eye is.

18 Claims, 148 Drawing Sheets

System with Integrated OCT Depth Control & Scanning

(56) References Cited

U.S. PATENT DOCUMENTS 6,488,676 B1 * 12/2002 Glockler ............. A61F 9/00804 356/138
7,871,404 B2 1/2011 Hipsley
8,348,932 B2 1/2013 Hipsley
9,510,802 B2 * 12/2016 Barthe ................... A61B 8/467
10,914,942 B2 * 2/2021 Dresser .................. G02B 26/12
2002/0082466 A1 * 6/2002 Han ...................... A61F 11/202 600/19
2005/0107773 A1 * 5/2005 Bergt .................. A61F 9/00827 606/4
2008/0033410 A1 * 2/2008 Rastegar ................ A61B 34/30 606/9
2008/0058779 A1 3/2008 Hipsley et al.
2008/0208104 A1 * 8/2008 Bragagna ............. A61B 18/203 604/20
2009/0161827 A1 * 6/2009 Gertner ................ A61N 5/1017 378/65
2009/0299262 A1 12/2009 Bragagna et al.
2010/0016843 A1 * 1/2010 Bragagna ............. A61B 18/203 606/13
2010/0312231 A1 * 12/2010 Singh ...................... A61F 9/008 606/5
2011/0190798 A1 8/2011 Hipsley
2013/0093870 A1 4/2013 Shibutani
2014/0046308 A1 * 2/2014 Bischoff ................. A61F 9/008 606/4
2014/0107634 A1 * 4/2014 Vogler ................ A61F 9/00825 606/6
2014/0163597 A1 * 6/2014 Hipsley .................. A61B 17/32 606/185
2014/0316388 A1 * 10/2014 Hipsley ............... A61F 9/00802 606/4
2015/0157406 A1 6/2015 Hipsley
2015/0157505 A1 * 6/2015 Neev ................... A61F 9/00814 606/5
2016/0183961 A1 6/2016 Hipsley
2017/0087014 A1 * 3/2017 Potter, Jr. ............ A61F 9/00781
2017/0119466 A1 * 5/2017 Hirvonen ............. A61B 18/201
2017/0231697 A1 8/2017 Hipsley
2018/0000339 A1 1/2018 Hipsley
2018/0052972 A1 2/2018 Hipsley et al.
2018/0207029 A1 * 7/2018 Herekar ............... A61N 5/0625
2019/0105200 A1 * 4/2019 Hipsley ............... A61F 9/00838
2019/0262177 A1 8/2019 Hipsley
2019/0380795 A1 * 12/2019 Tsao ....................... A61B 90/11
2020/0121389 A1 4/2020 Hipsley
2020/0185106 A1 6/2020 Hipsley et al.
2020/0391051 A1 * 12/2020 Daly .................... A61N 5/0625
2022/0031503 A1 * 2/2022 Dorin .................. A61F 9/00821

* cited by examiner

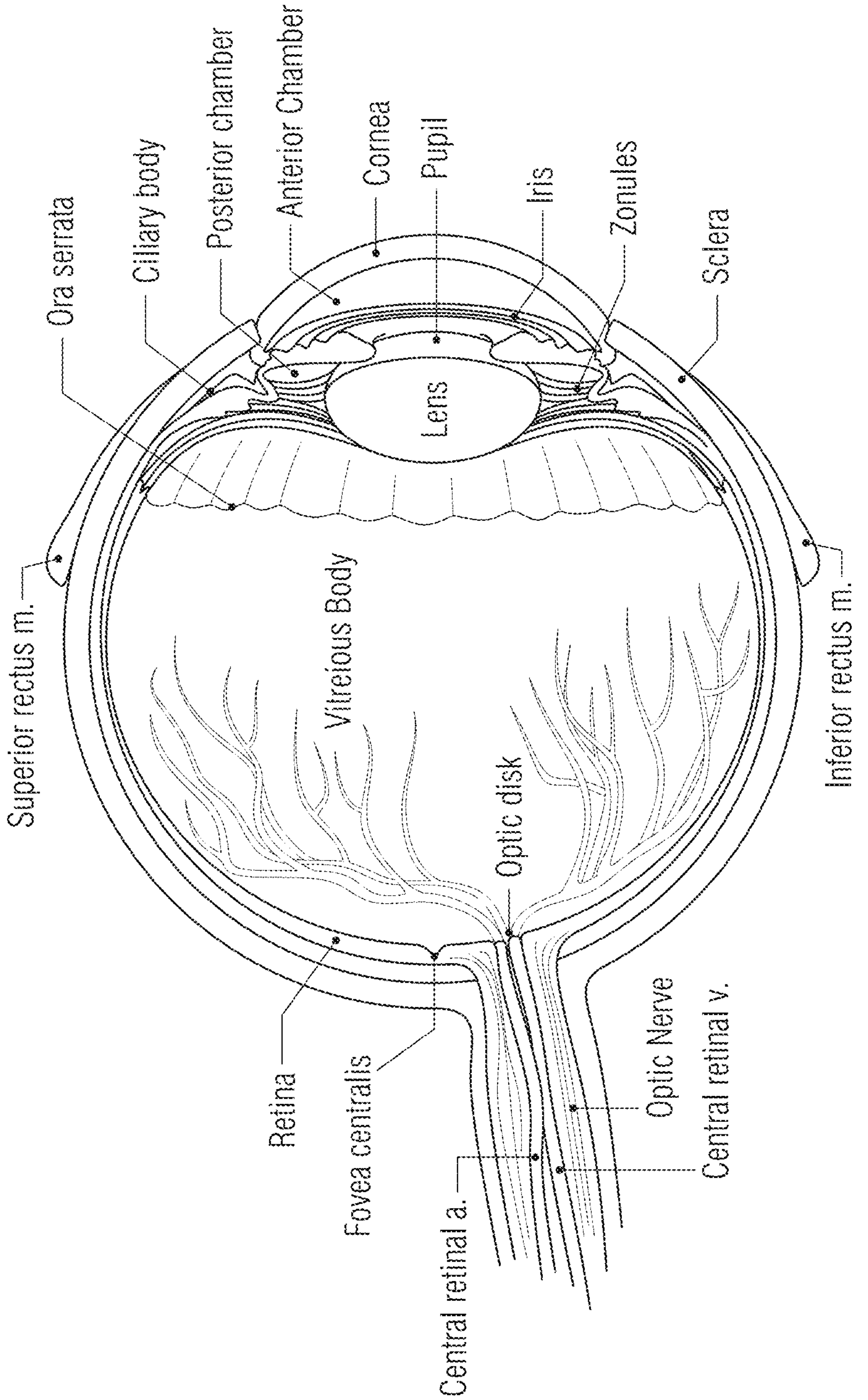
Fig. 1 : Ocular Anatomy

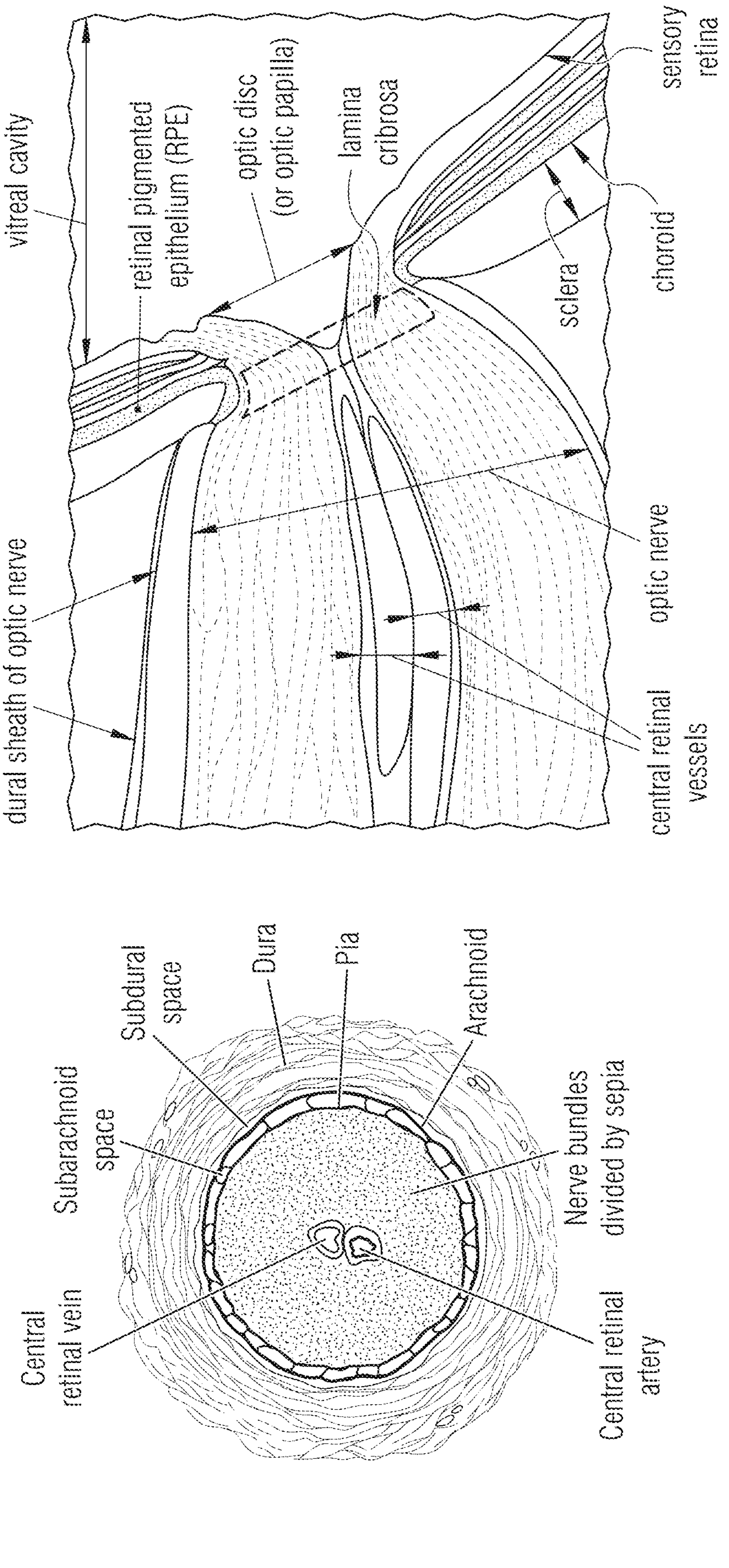
Fig. 3: Optic Nerve and Optic Disc

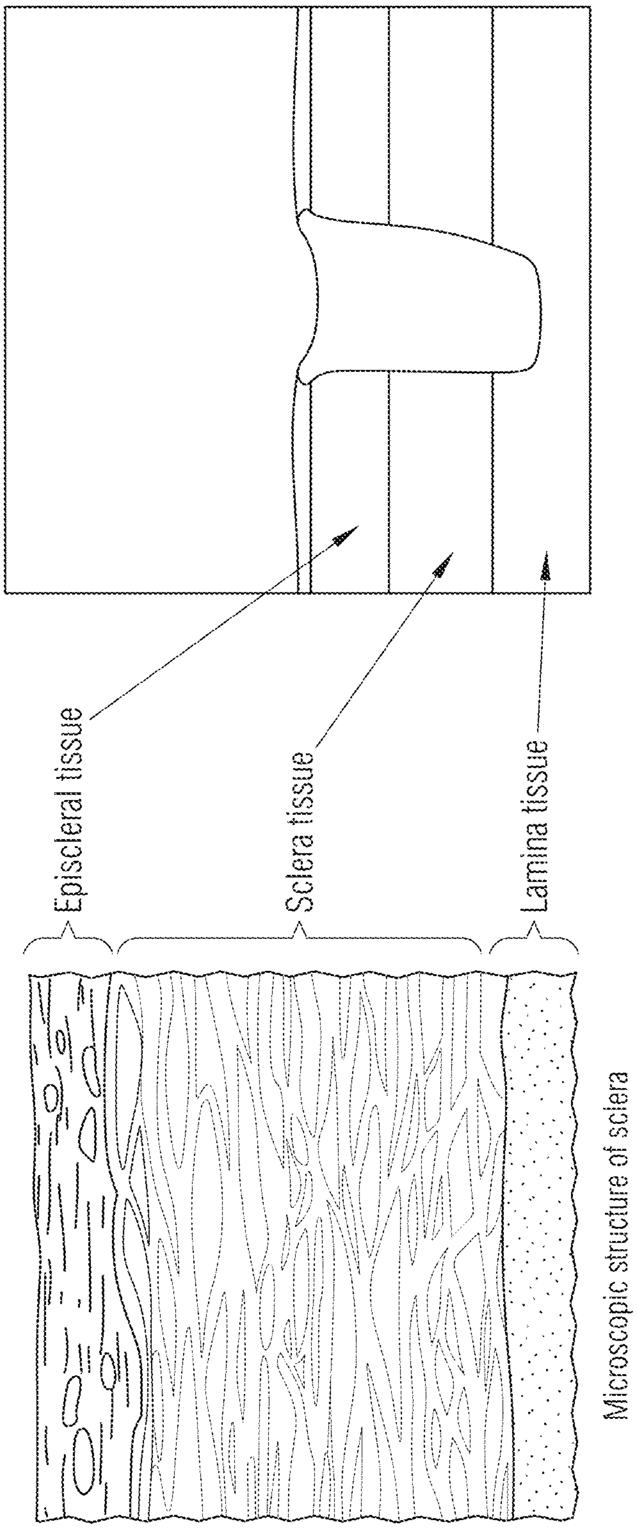
Fig. 4: Micropore & the Sclera

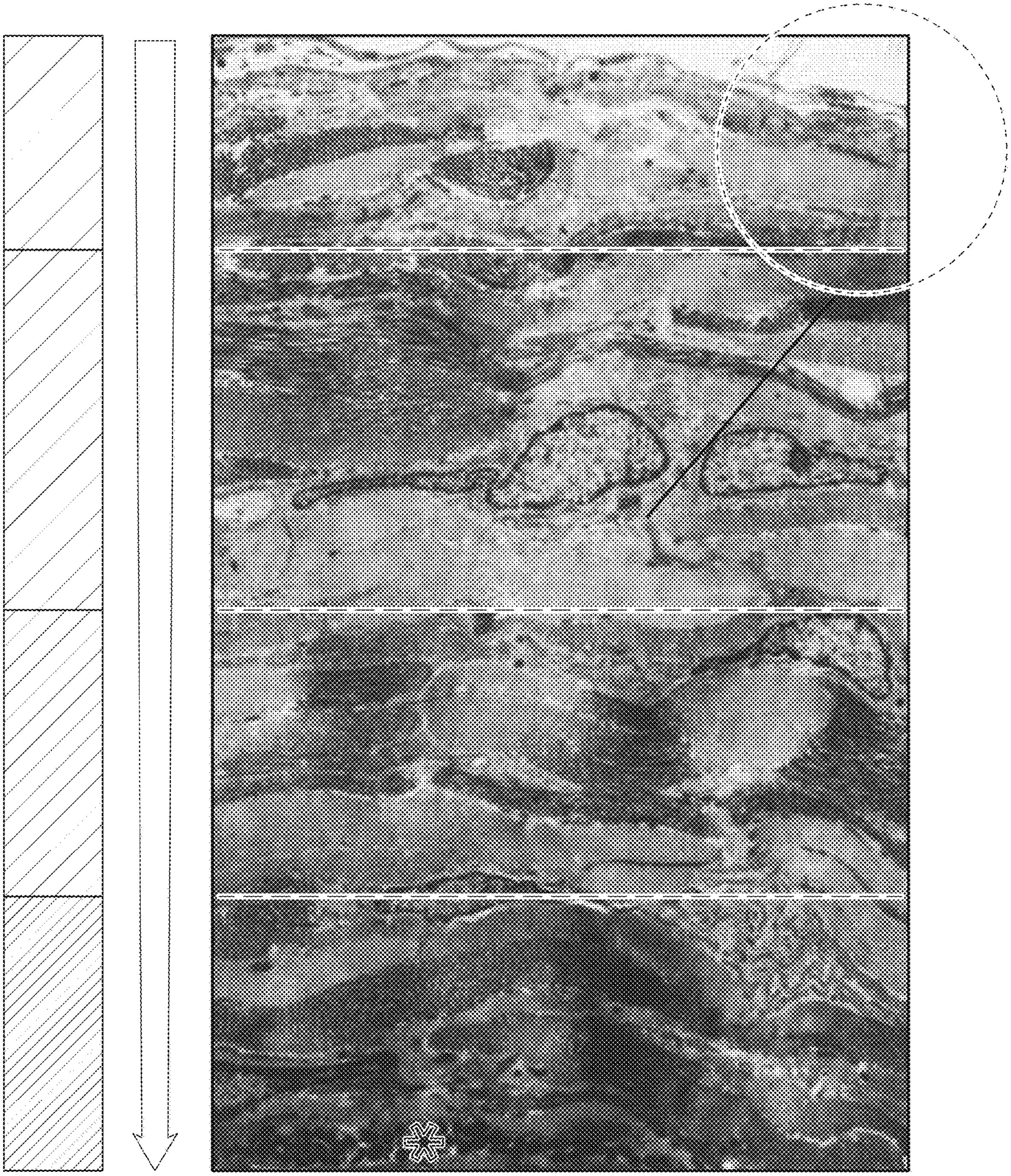

Transverse section through sclera. The lamellae forming the bulk of the sclera are denser and more irregular in outline than in the cornea. Episclera is less dense than the deeper scleral layers. The lamina fusca portion of the sclera contains some pigment (asterisk) that migrated from uvea. Sclerocytes (like keratocytes), which are swollen in the micrograph, are not as numerous as in the cornea. Rat; X 4,000

Fig. 5A: Sclera Ultrastructuree: Scleral Subsurface 3D Pore Creation approx. 400μm diameter EpiSclera

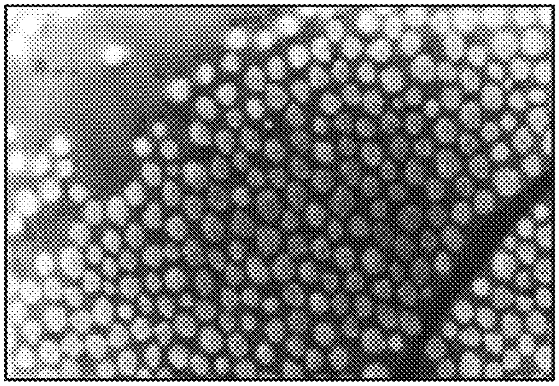

High magnification of collagen fibers in the episclera. Collagen fibers, here section transversely, are of a relatively uniform diameter albeit not as uniform as found in teh corneal stroma. Some elastin is present among the collagen. Rabbit.

Sclera Stroma (Substantia propria)

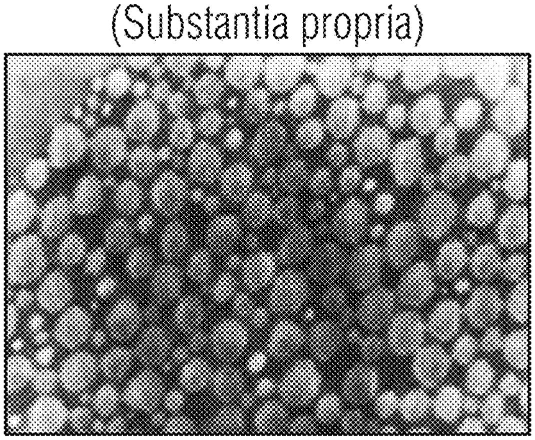

High magnification of collagen fibers in the scleral substantia propria. The transversely sectioned collagen fibers from theis scleral region show distinctly greater variation in caliber when compared to those in the episclera. Elastin is noticeable also in this part of the sclera. Rabbit.

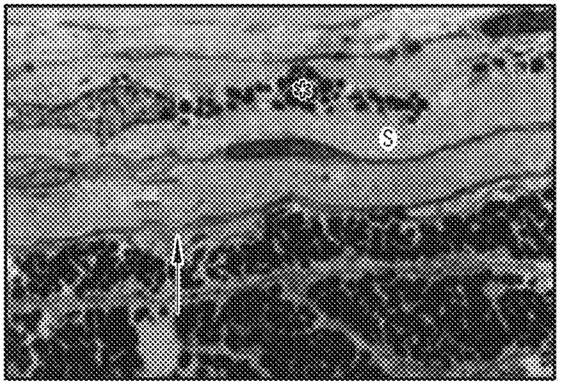

Lamina fusca

Transverse section through the scleral-choroidal interface. The lamina fusca of the sclera consists of lamellae of collagen fibers (S), sclerocytes and melanocytes (asterisk). The suprachoroid is formed of fibrocyte processes {arrow) organized in a parallel manner and melanocytes (triangle). Primate: X 5.000

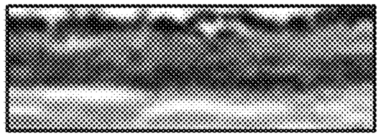

Choroid

FIG. 5B

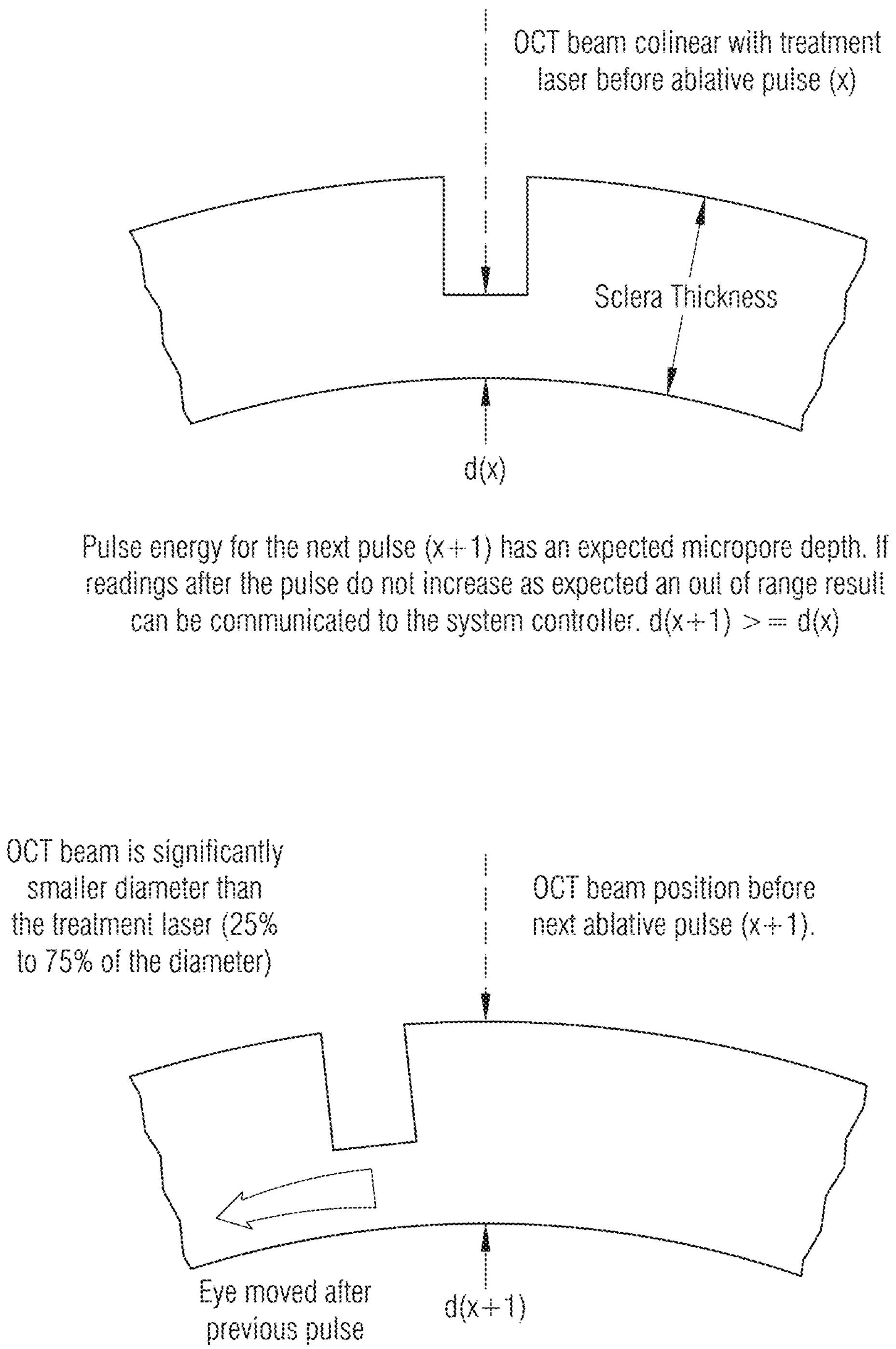
Fig. 6: Depth method to monitor eye motion between pulses of ablation

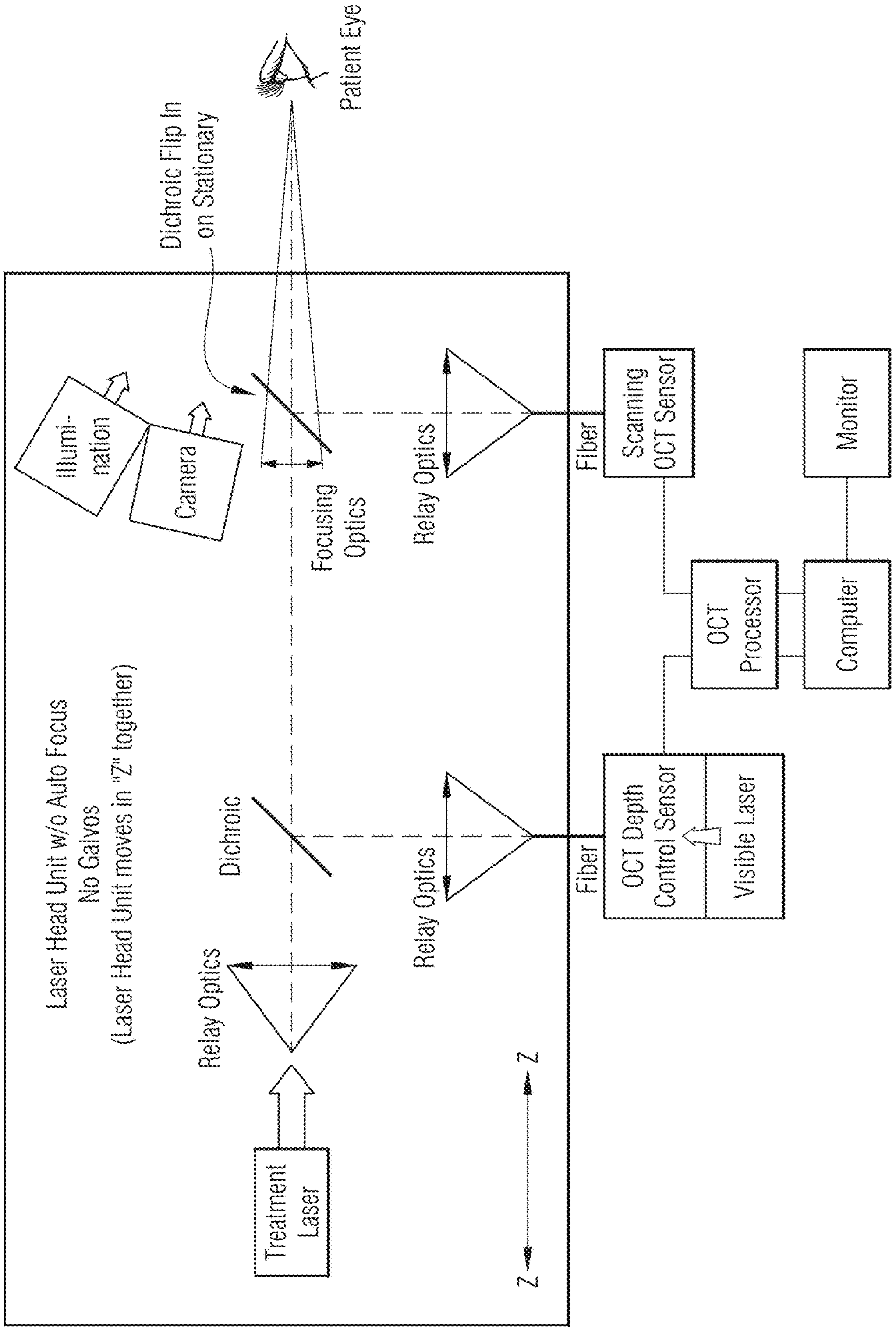
Fig. 7: System with no galvo, 5 axis Head and separate Z motion

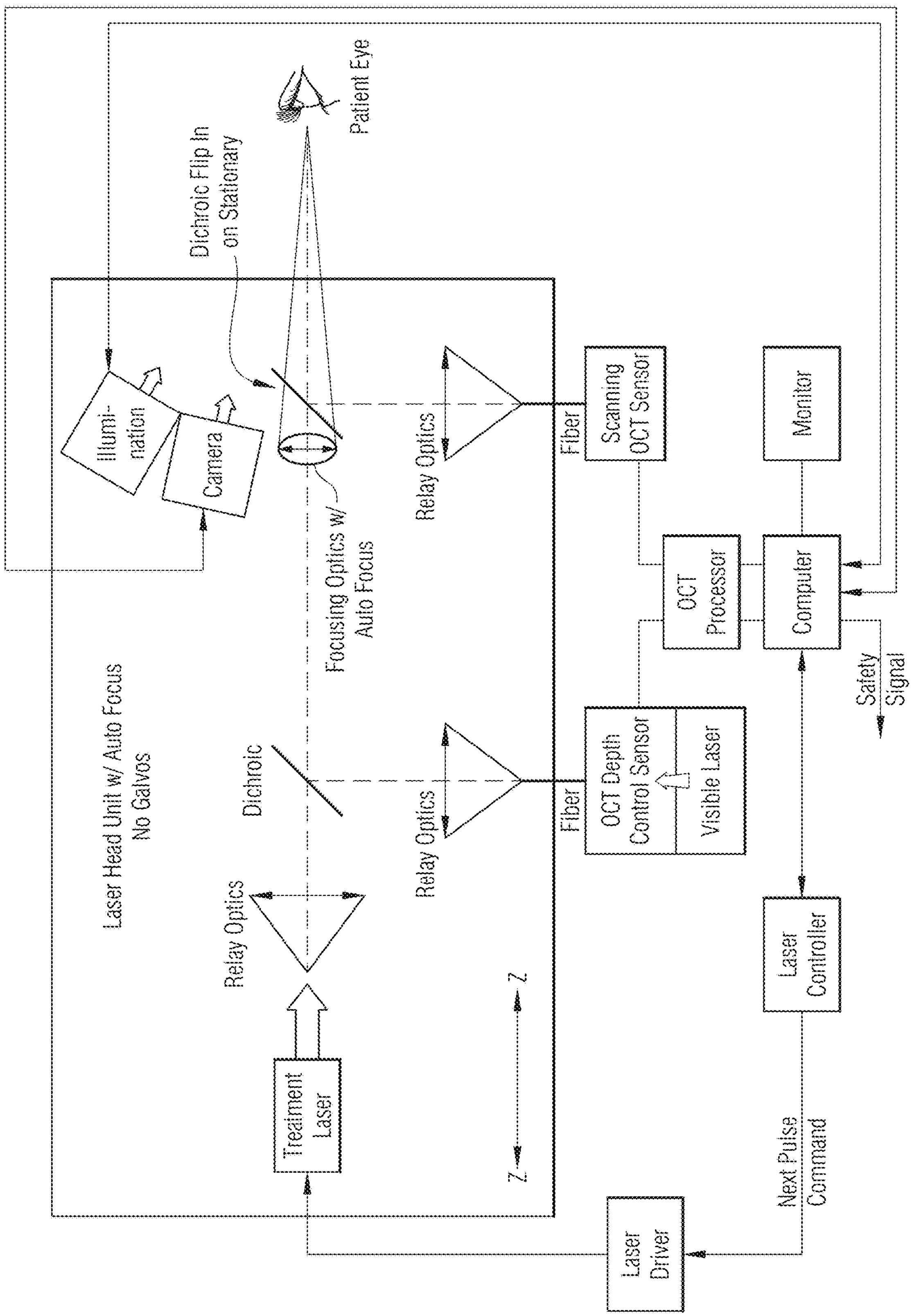
Fig. 8: Control of Laser Head with no galvo, 5 axis Head and separate Z motion

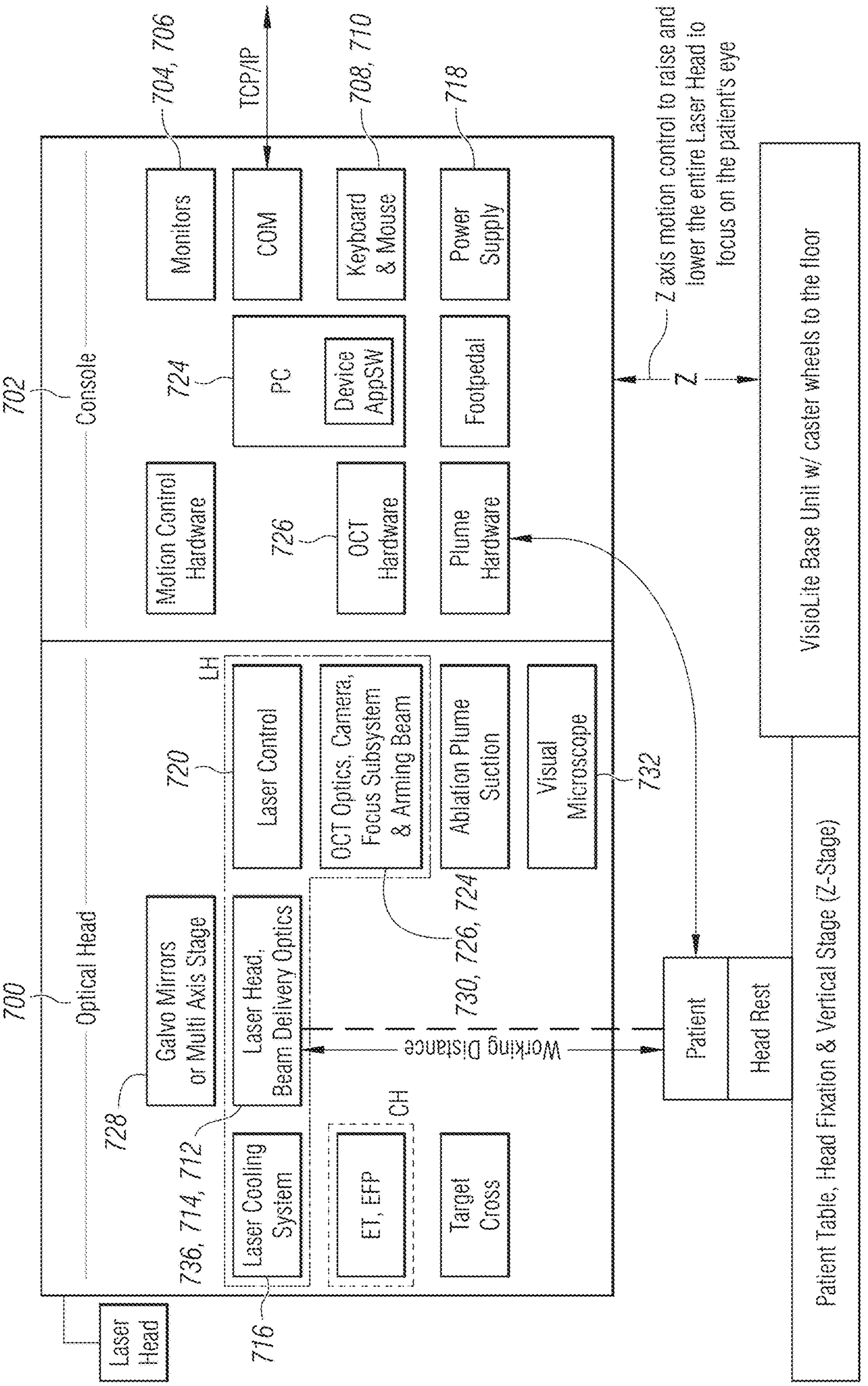
Fig. 9: System with Headrest, Z axis motion of Laser Head

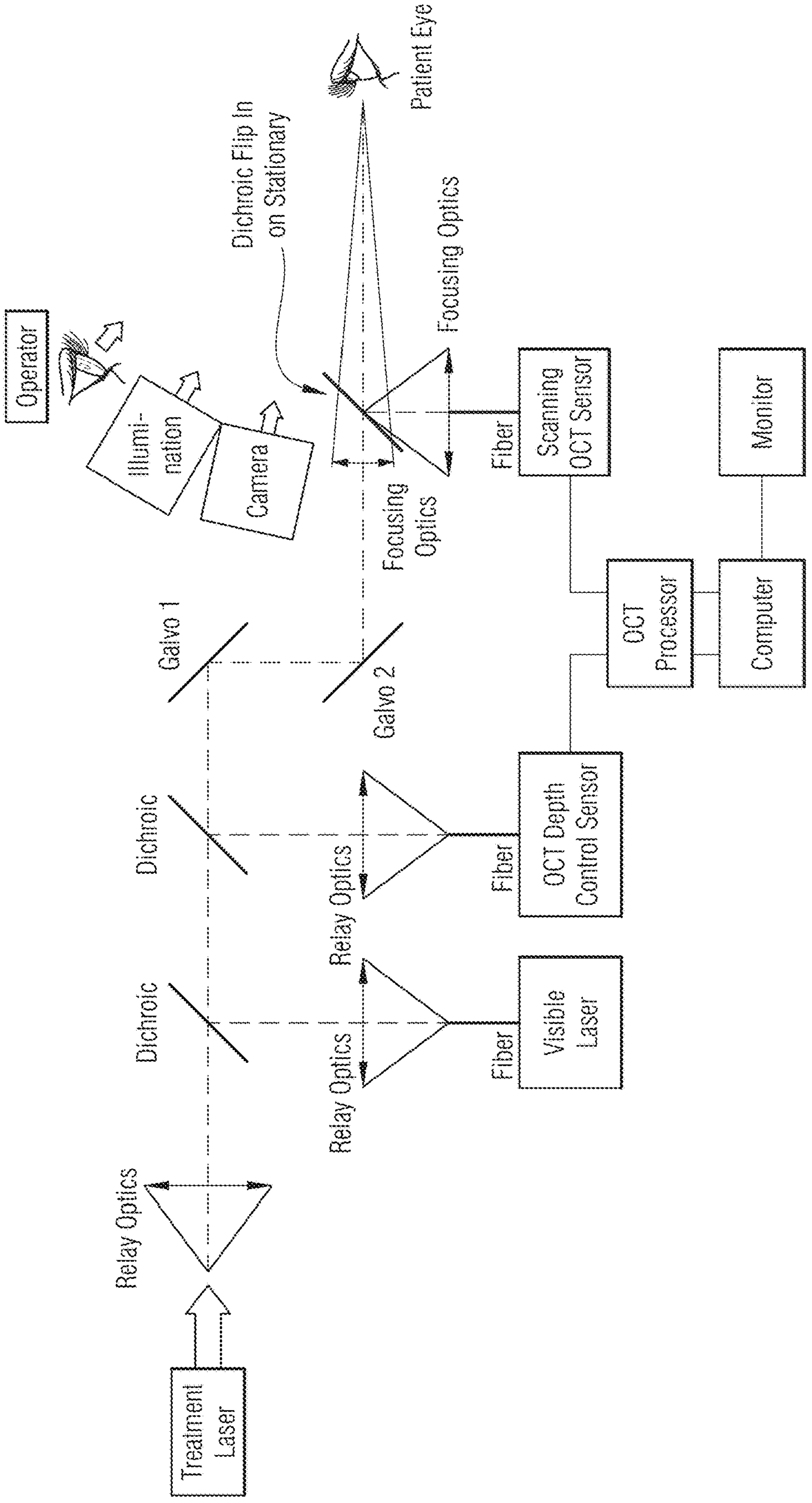
Fig. 10: System with Galvo mirrors, separate visible laser and OCT/DC fibers combined into treatment laser axis and doctor view of treatment

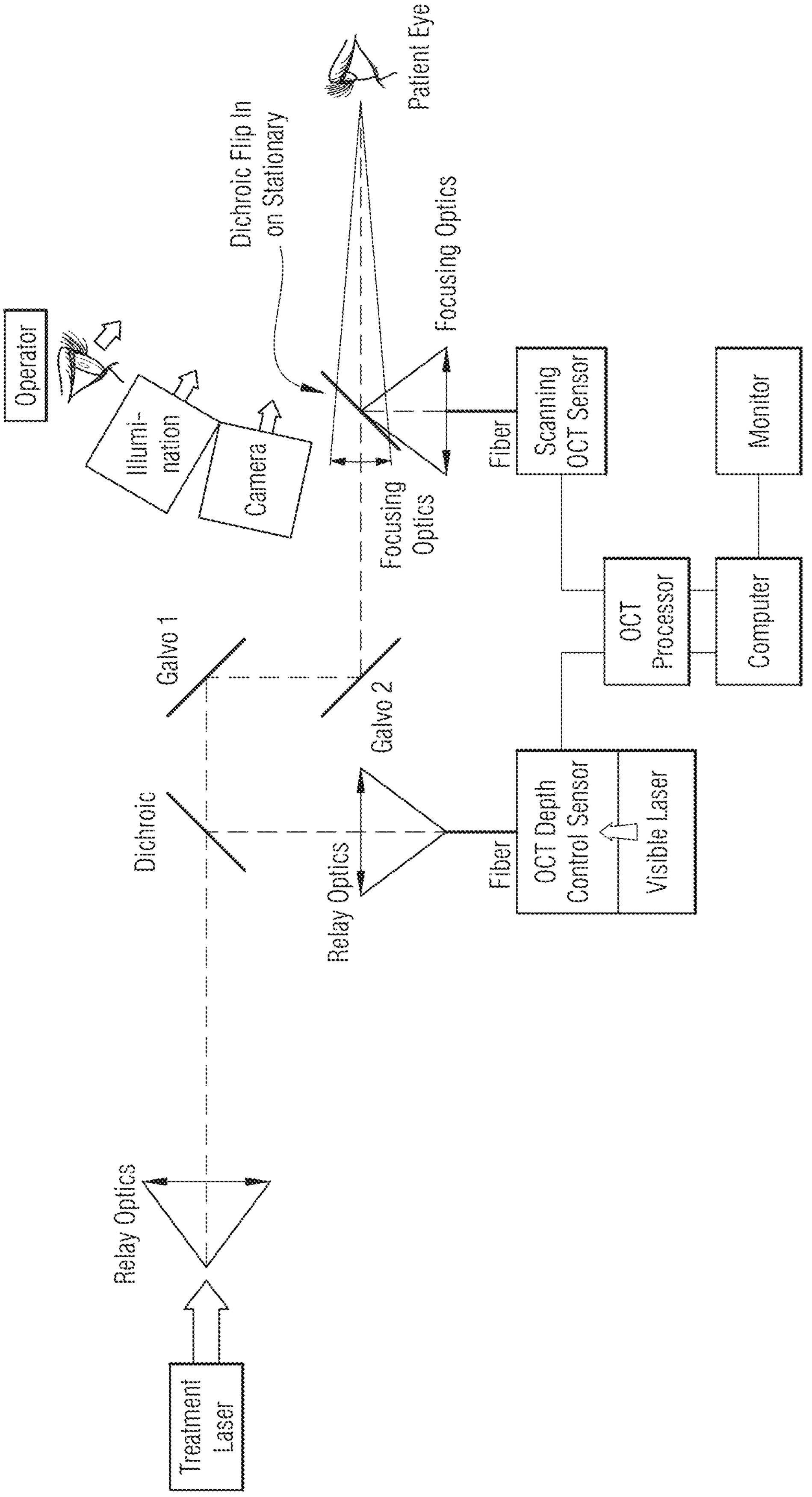
Fig. 11: System that Combines OCT/DC and Visible laser through a single fiber and shared relay lens with Treatment laser with Control and display

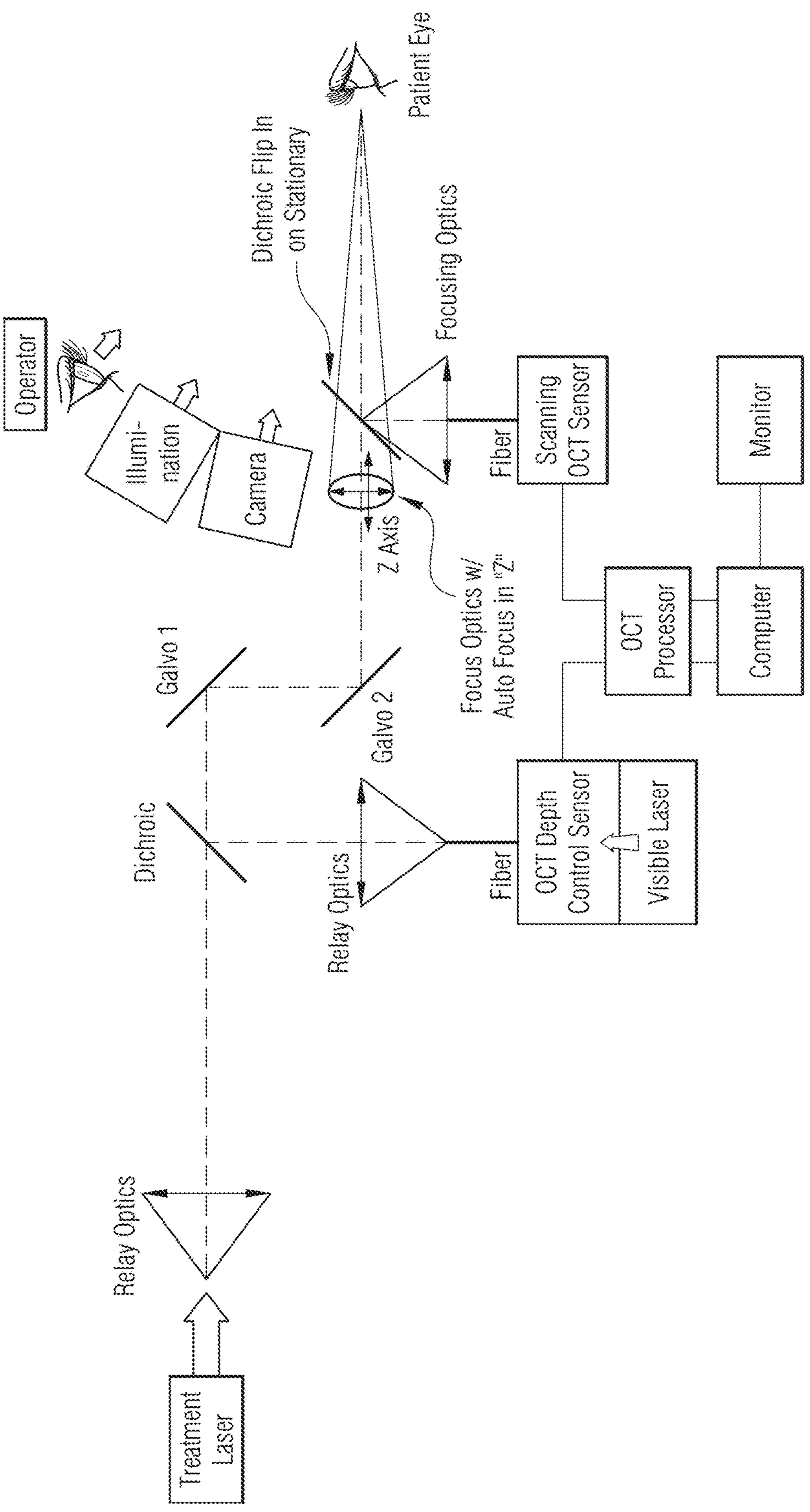
Fig. 12: Same as Fig AH but AF lens and shows dual function OCT system

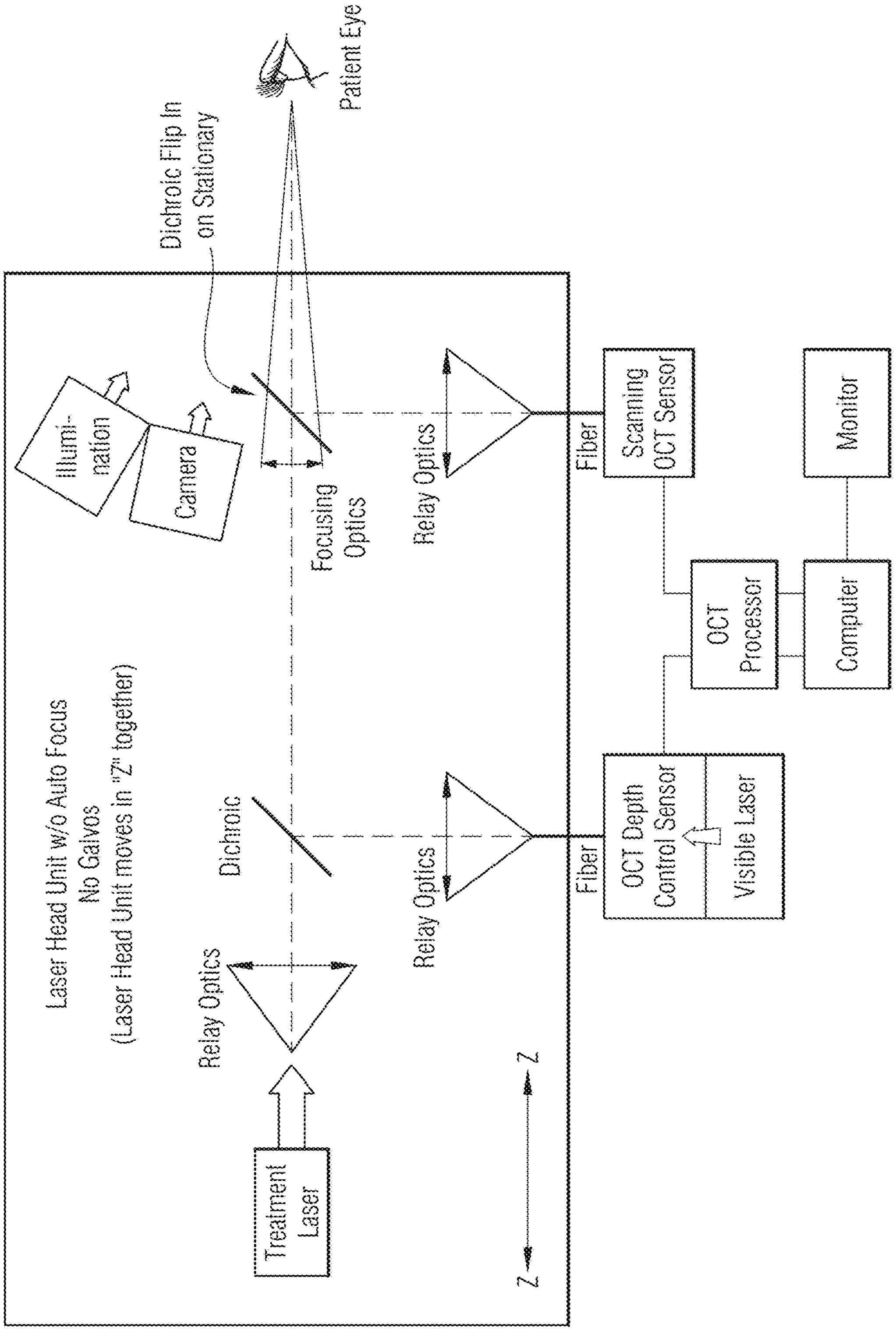
Fig. 13: Fig. AI with no galvo, 5 axis Head and separate Z motion

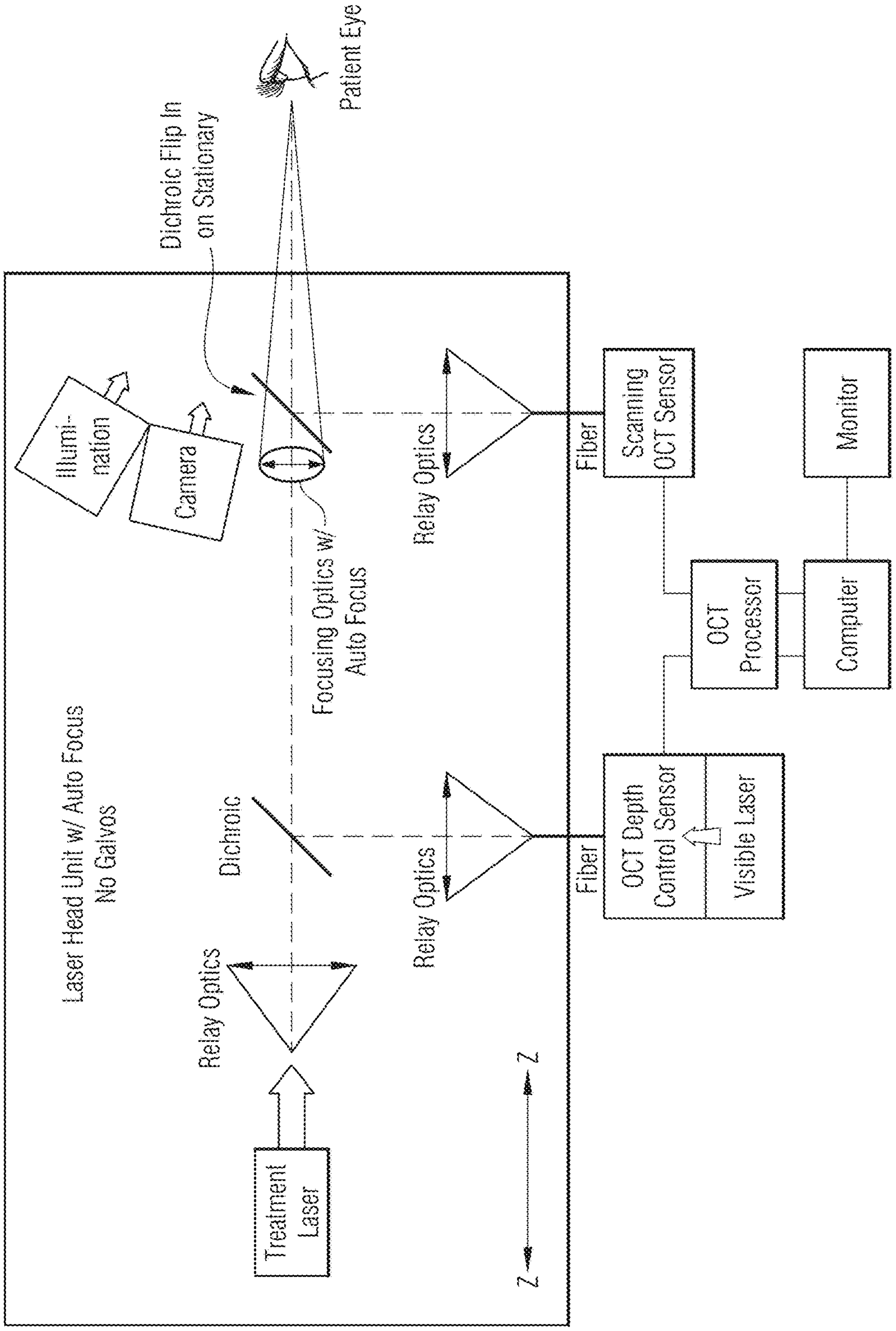
Fig. 14: Like Fig AJ but with no galvos, 6 axis with AF lens assembly

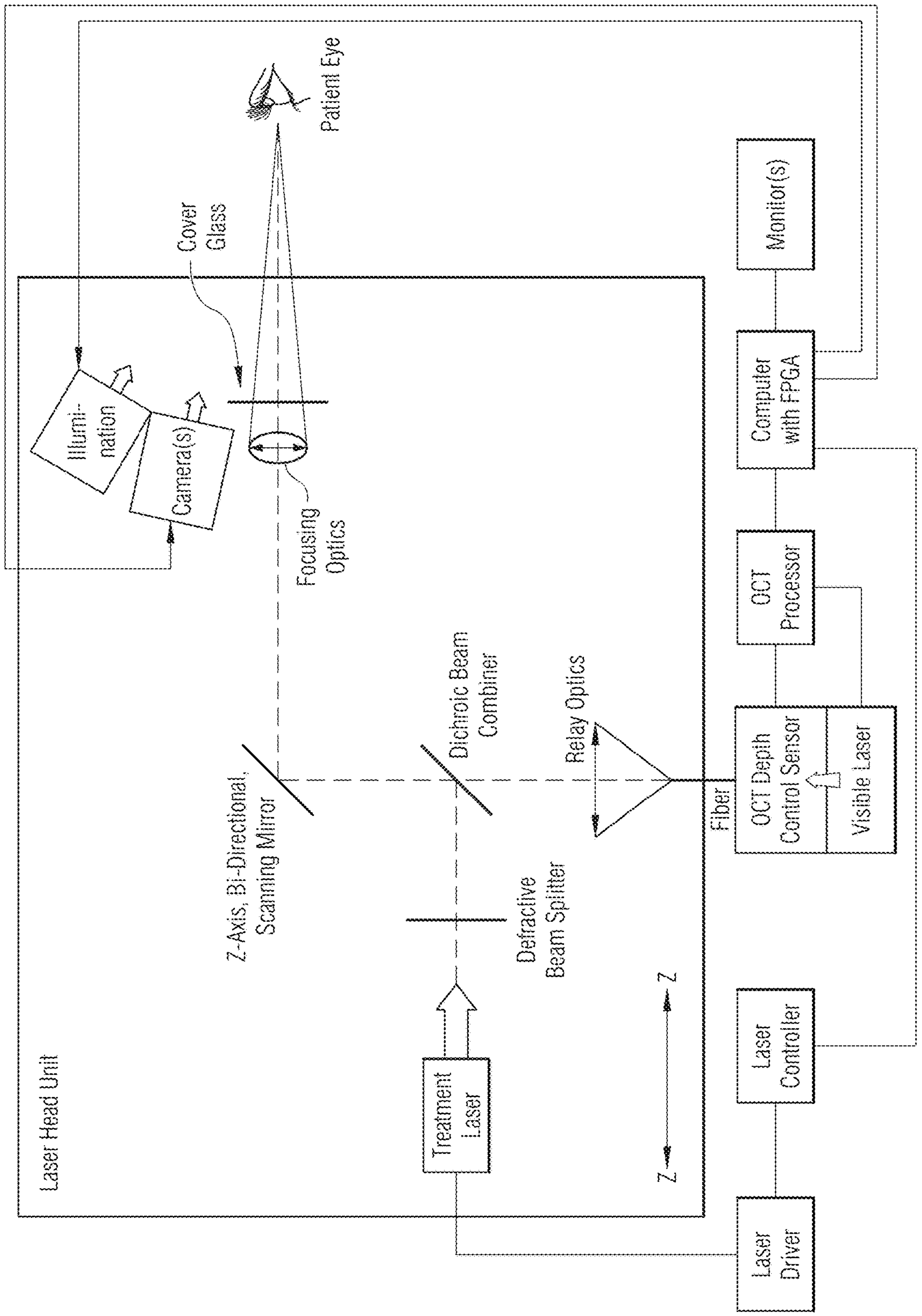
Figure 15: System with Integrated OCT Depth Control & Scanning

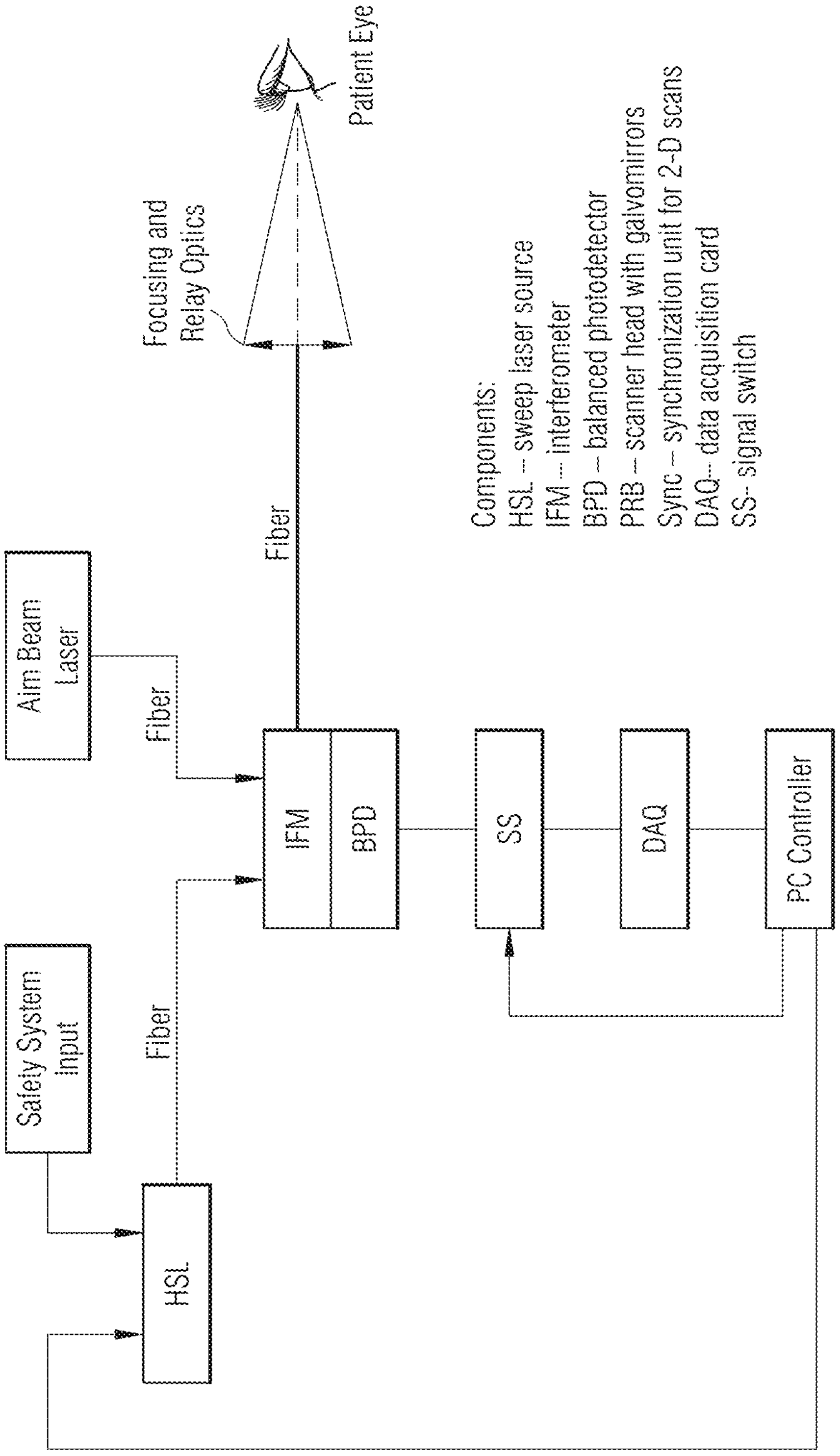
Fig. 16: OCT Control System with Depth Control with visible laser included

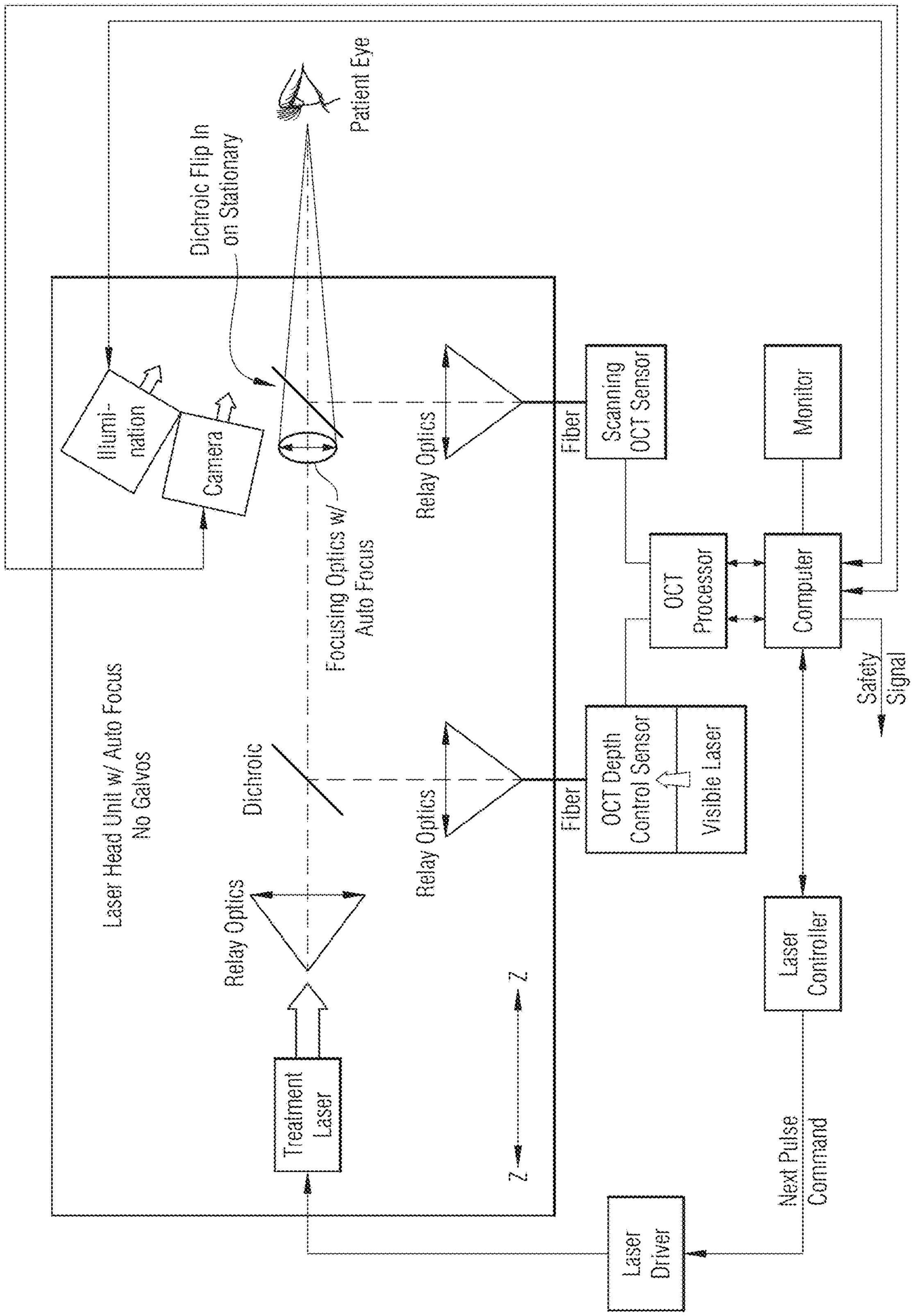
Fig. 17: Bio-Feedback System Control (OCT and/or Camera)

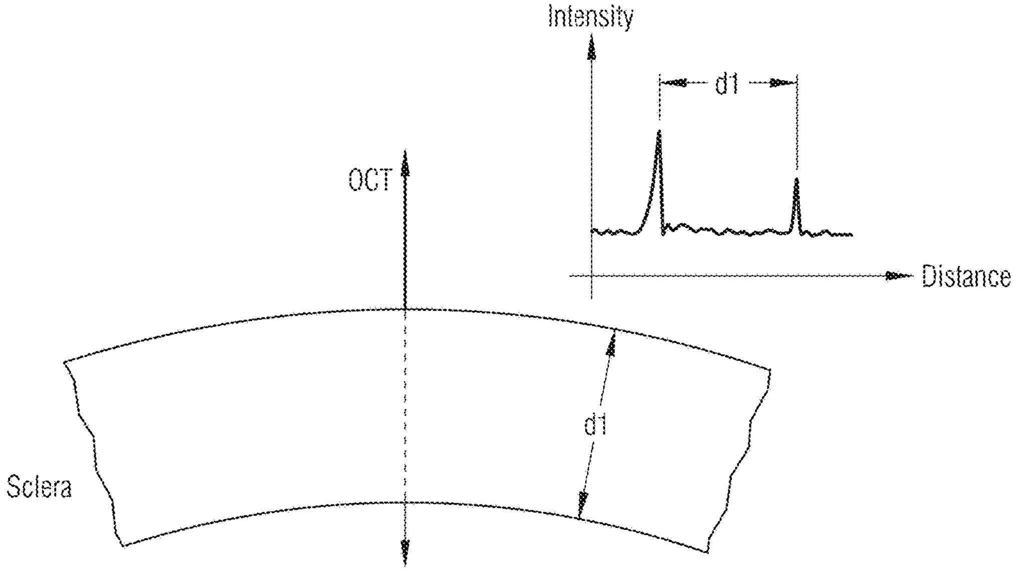

Before ablation treatment OCT signal provides top surface of eye and the inside surface of the Sclera. Sclera thickness (d1 can be calculated)

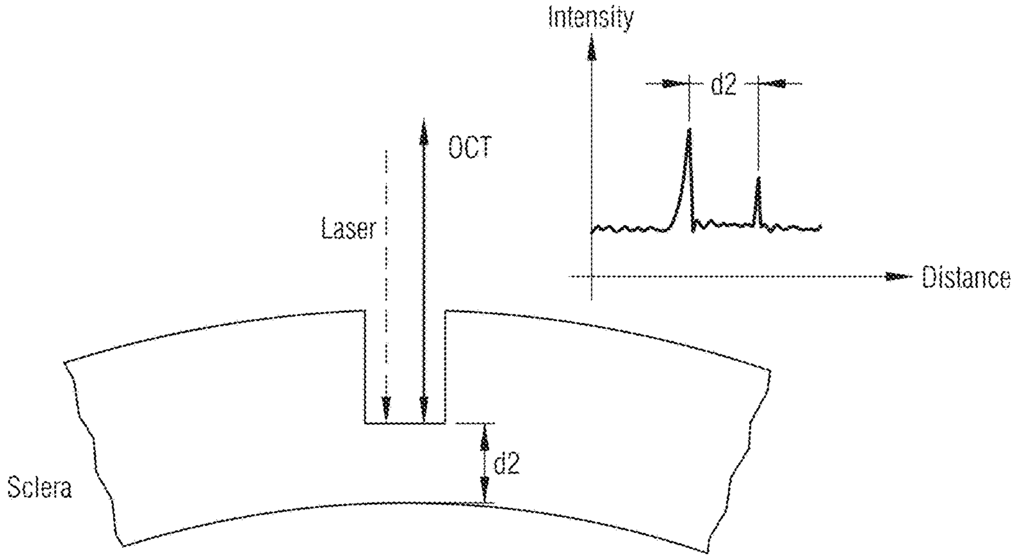

After ablation of a single laser pulse, the OCT signal provides bottom surface of the micropore and the inside surface of the Sclera. Remaining Sclera thickness (d2) can be calculated, expressed as a % of total thickness.

Figure 18: OCT Depth method to measure pore depth and scleral thickness

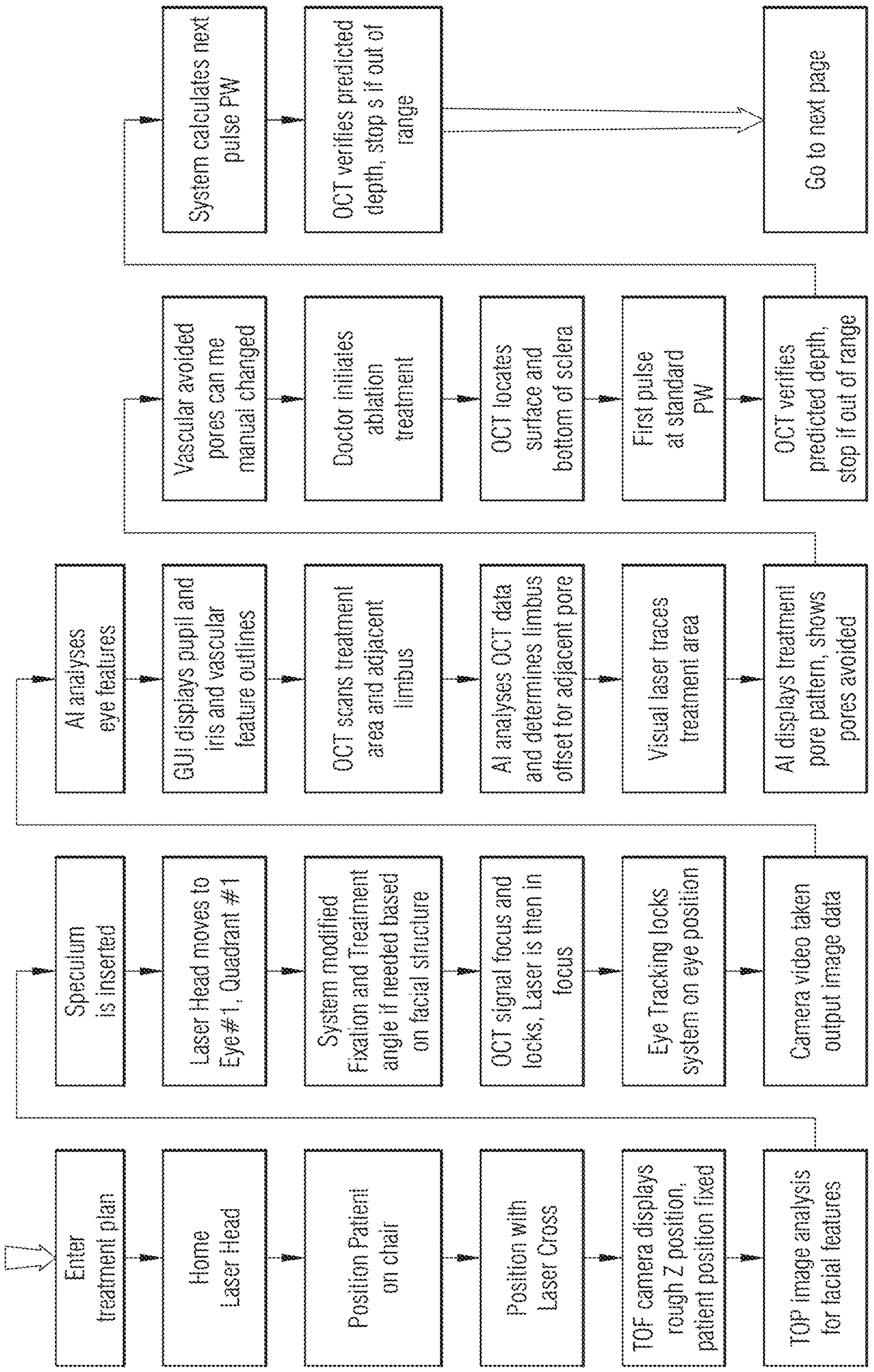
Fig. 19: Workflow process steps – pg. 1

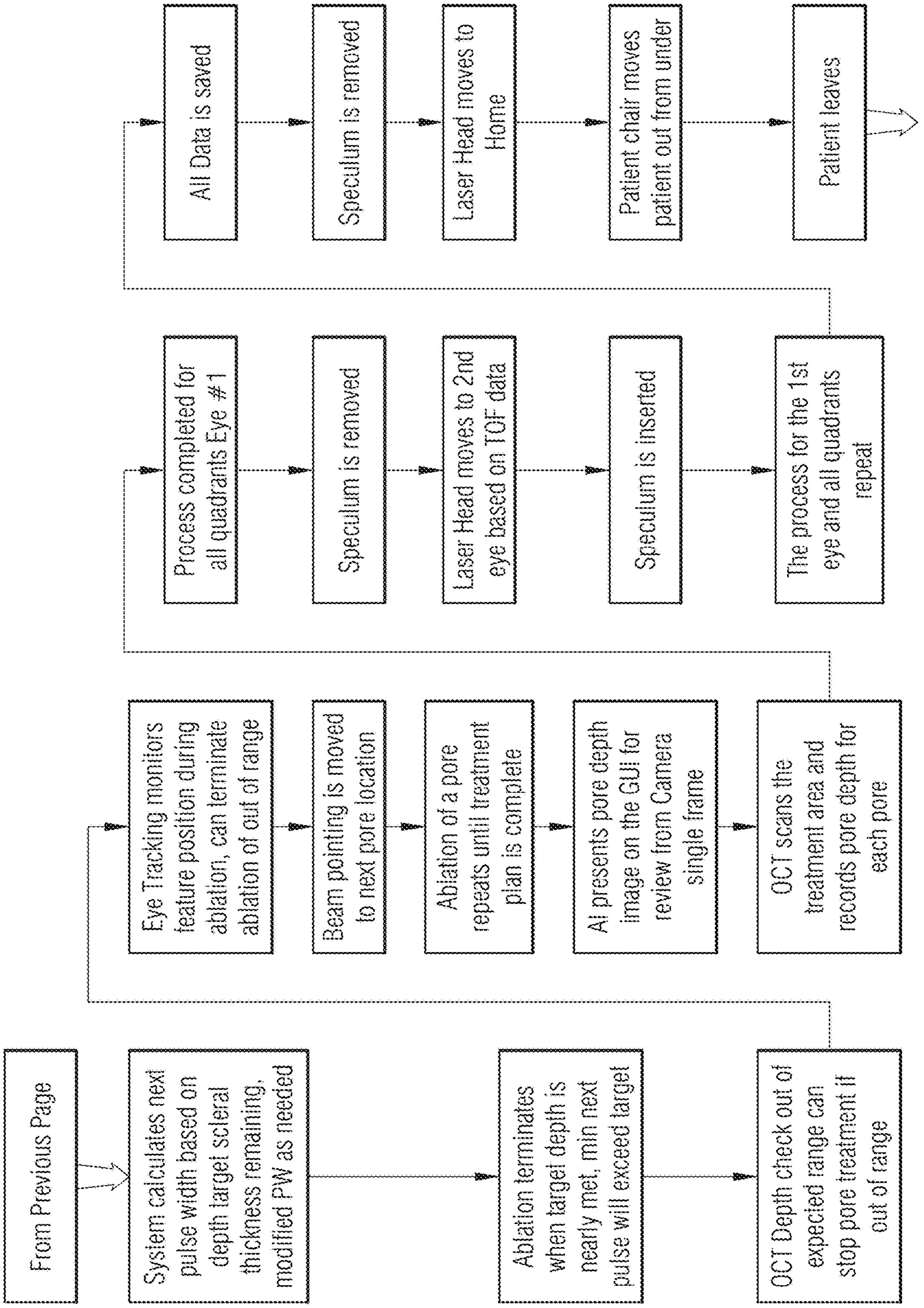
Fig. 20: Workflow process steps- pg. 2

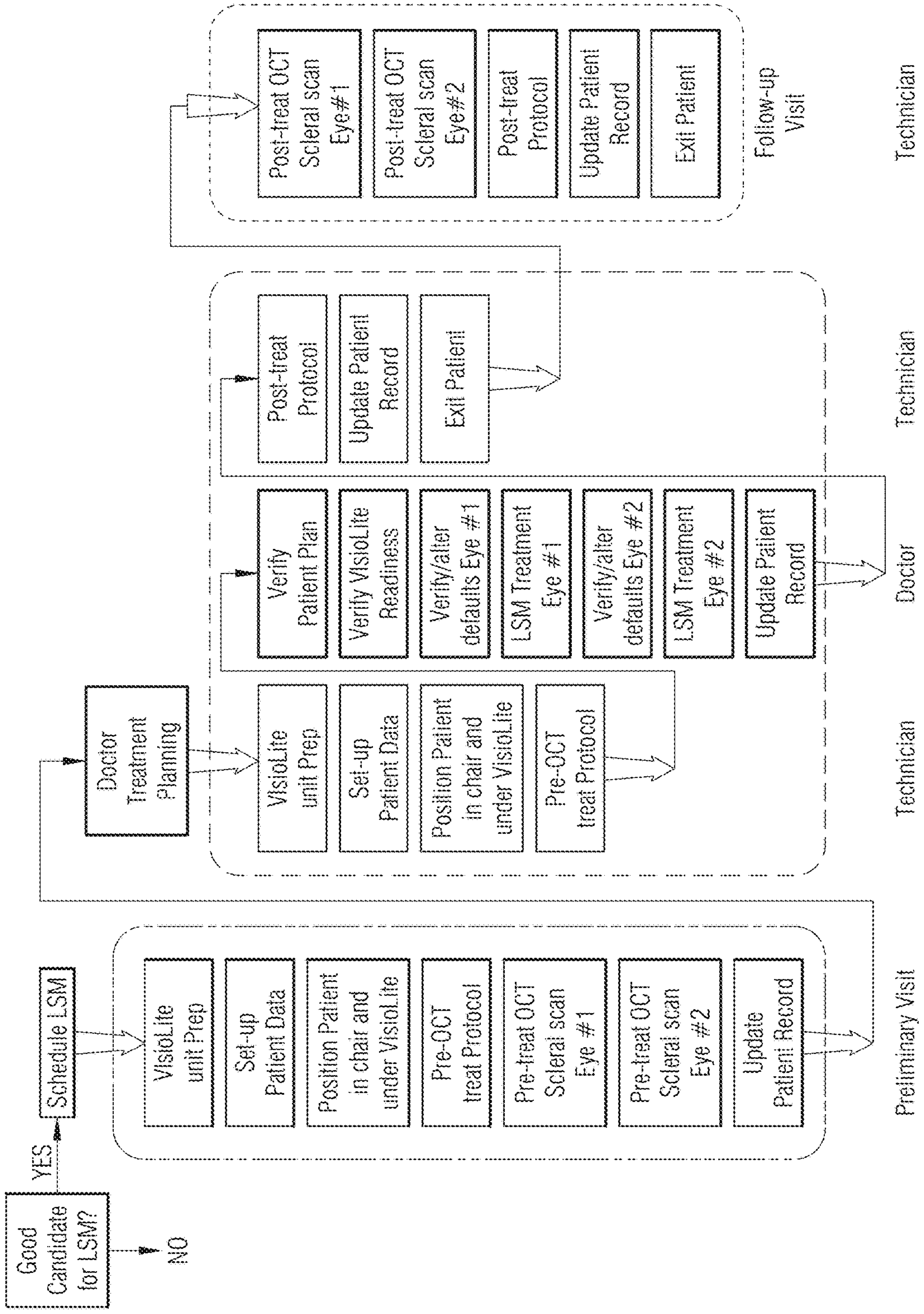
Fig. 21: Workflow Diagram including OCT & LSM pre-planning with off-line OCT scanner

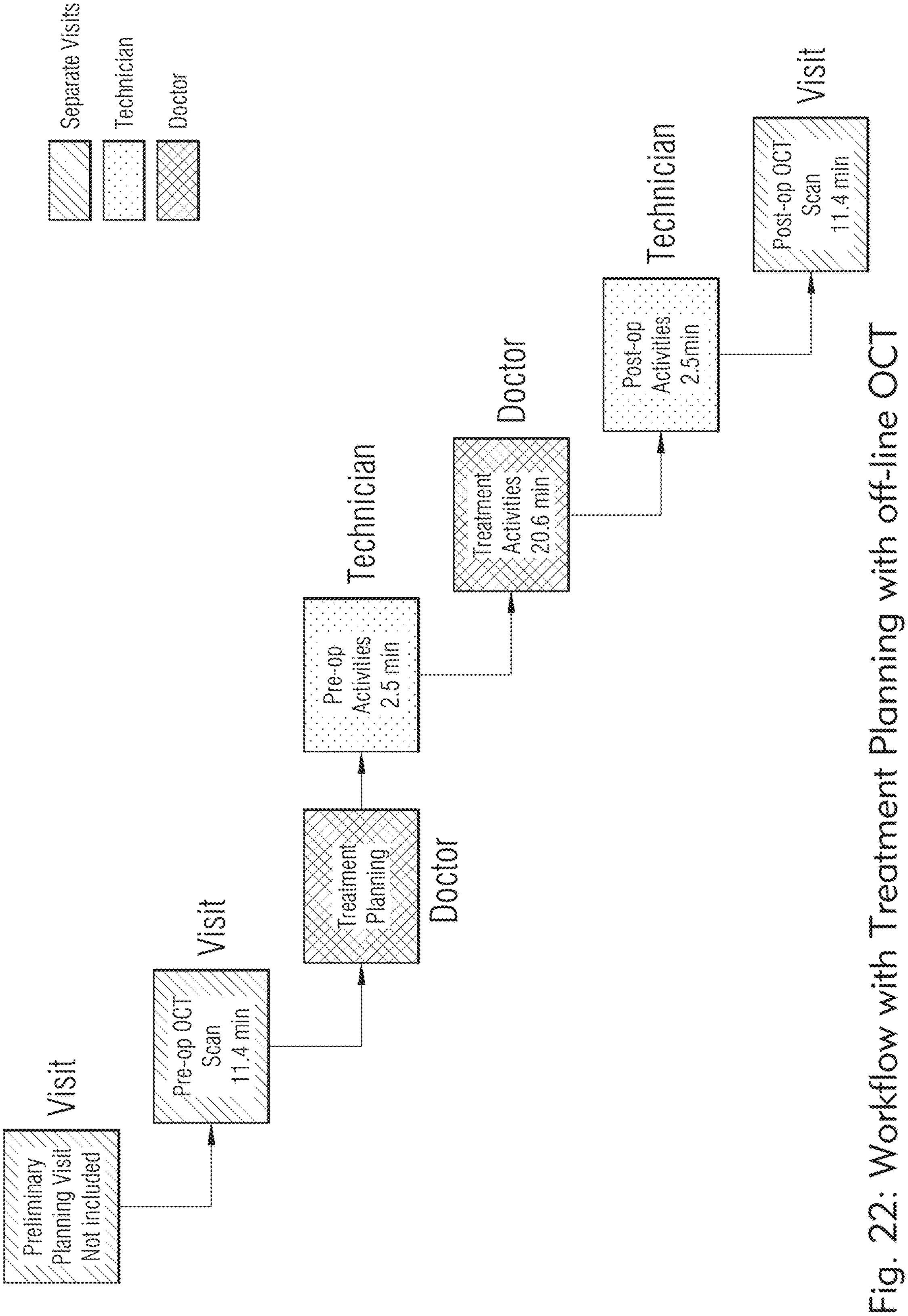
Fig. 22: Workflow with Treatment Planning with off-line OCT
(OCT scans both eyes by tech on another day)

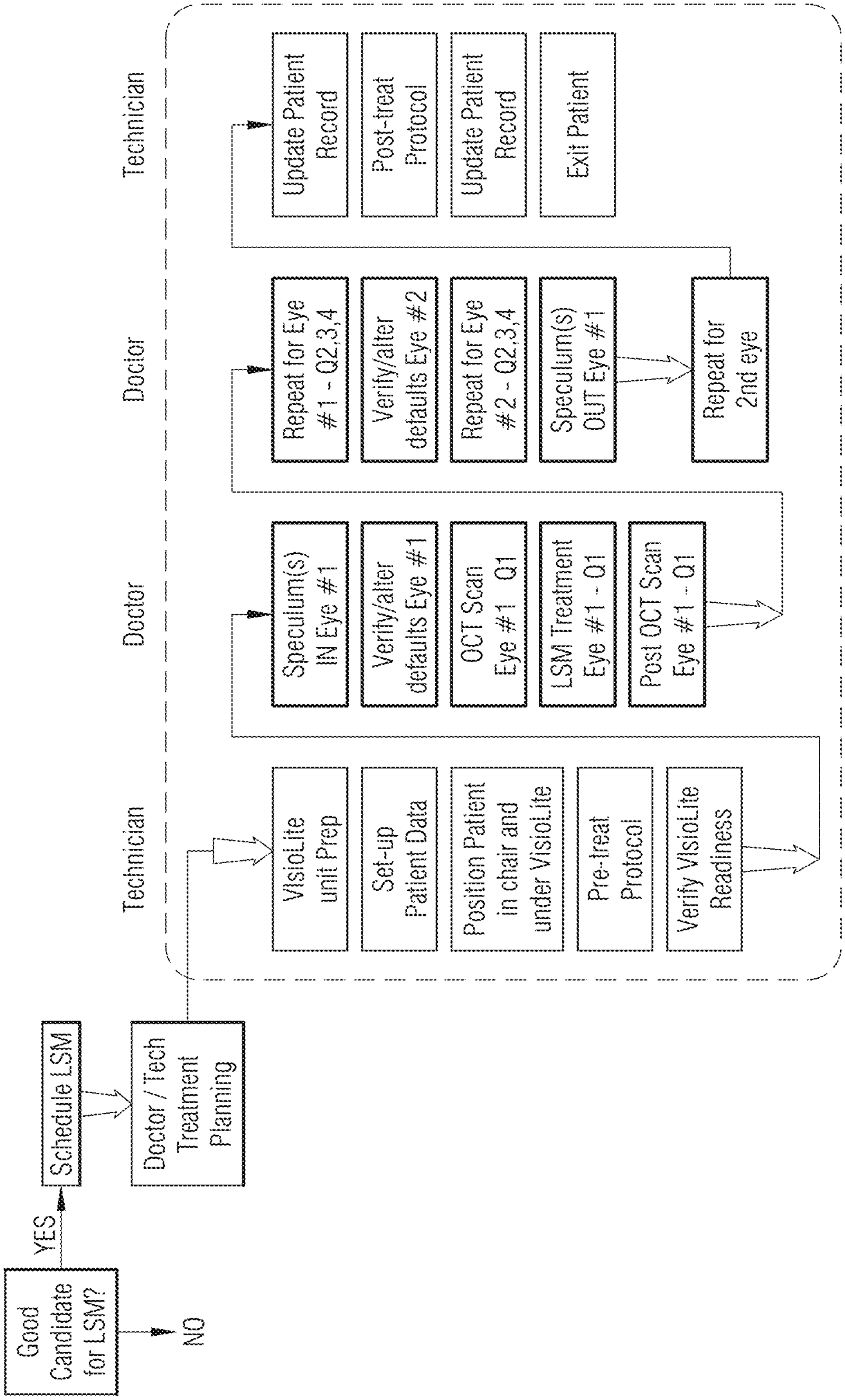
Fig. 23: Workflow Diagram including Integrated OCT Scanner

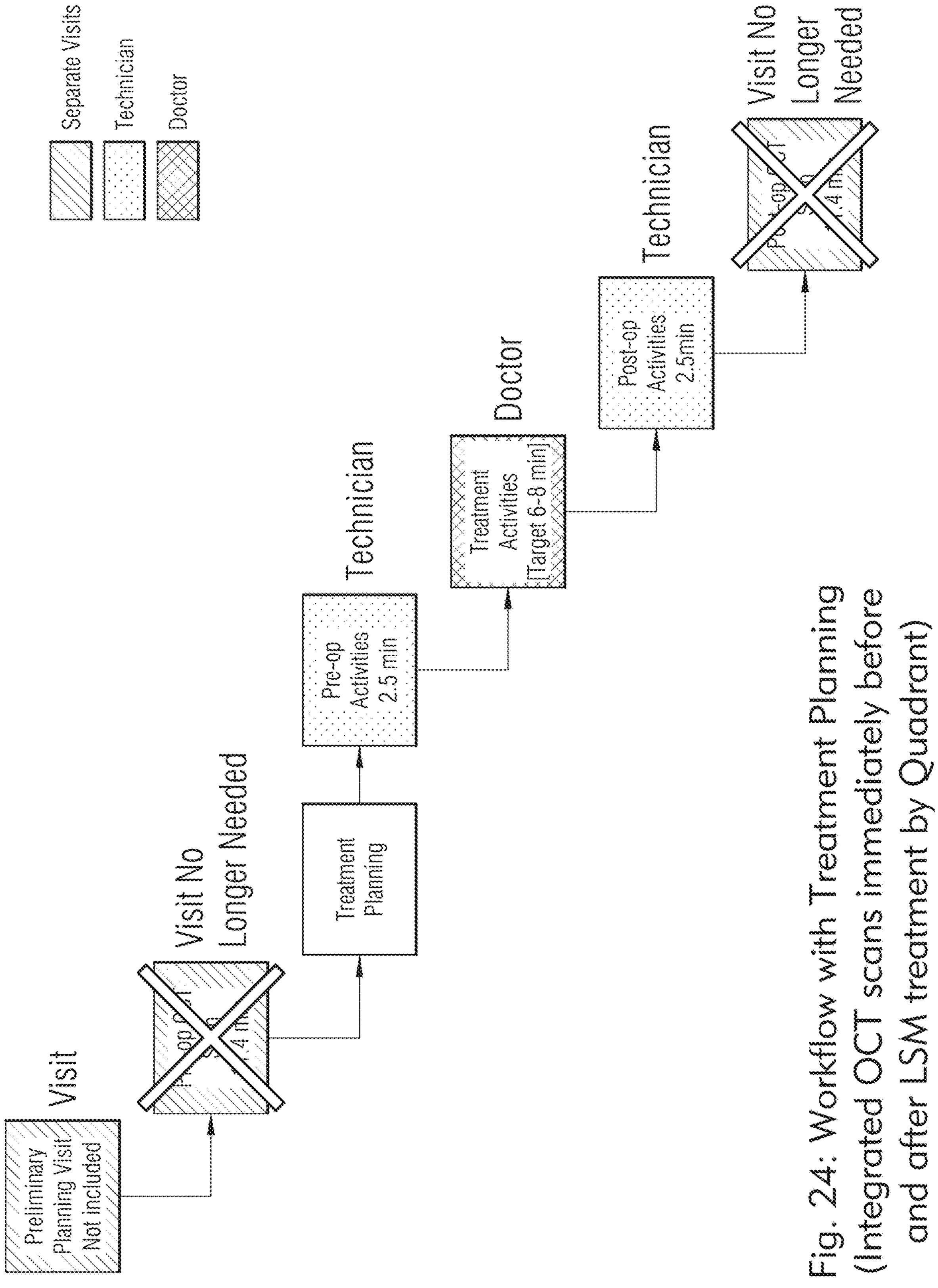
Fig. 24: Workflow with Treatment Planning (Integrated OCT scans immediately before and after LSM treatment by Quadrant)

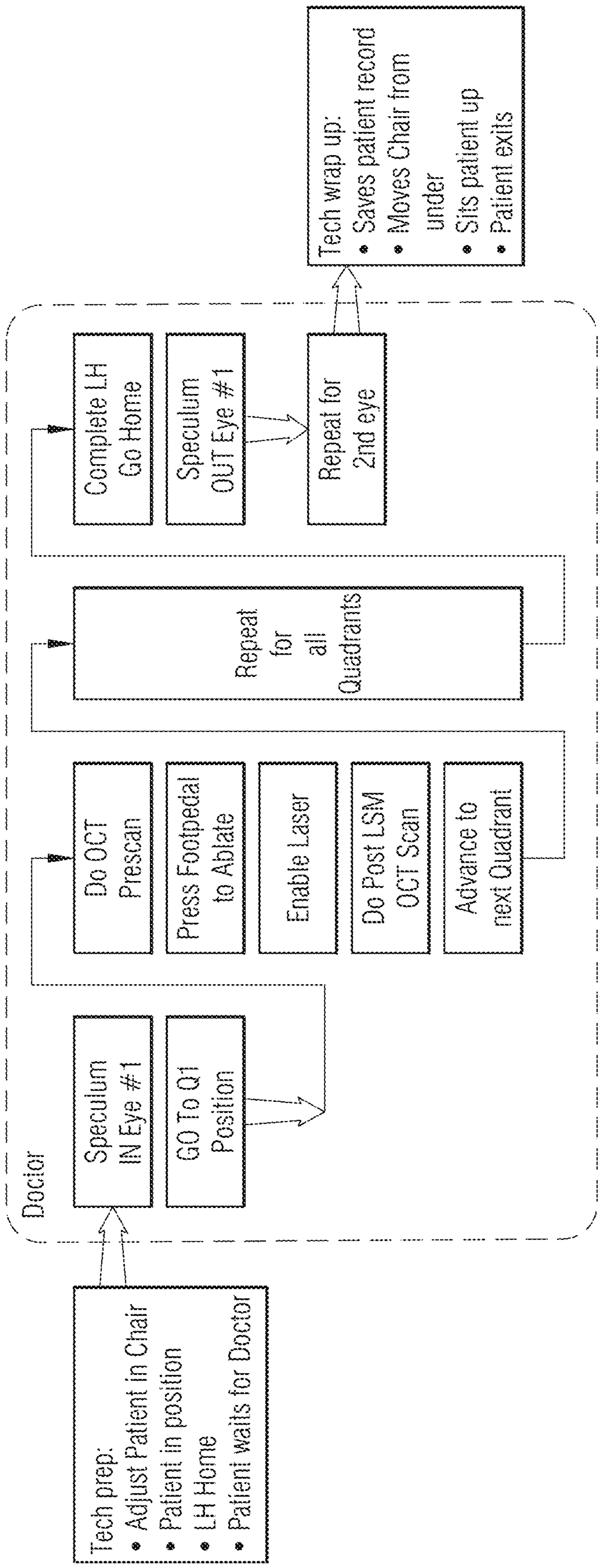
Fig. 25: Flow chart for Doctor steps in LSM treatment with Integrated OCT Scanner

Process to generate a Pore Array

| | | |
|---|---|---|
| 1. Measure the sclera thickness | >>> | Determine the required laser energy |
| 2. Calculate the energy splitting | | The laser train pulse length (100% thickness: 50%, 75%, 87.5%) |
| 3. Measure the eye movement by feature tracking (RBG + Aim + Adjust) | | |
| 4. the laser train length (3 pulses) | >>> | The eye should be steady to 25 μm over |
| 5. Switch-on the pupil tracking (IR light) | >>> | Safety is active (25 μm tol. / no adjust) |
| 6. Apply the laser pulse and measure the remaining depth by OCT. | | With the first pulse the depth should be close to the therapeutic window (~50%) |
| 7. Adjust the pulse length | >>> | Compare data of 5. to reach 75% |
| 8. The go back to 4. till 75% is reached | | |
| 9. Pupil detection is running at all times | >>> | |
| 10. Switch-off the pupil tracking (IR light) | >>> | Safety function may not be active |
| 11. Move to the next pore position (RGB + Aim+ Adjust) | | Based on the information of the feature tracking & the modulated aiming beam. |
| 12. Go back to 1. until the array is done | >>> | |

Fig. 26: Flow diagram for Pore Array Generation

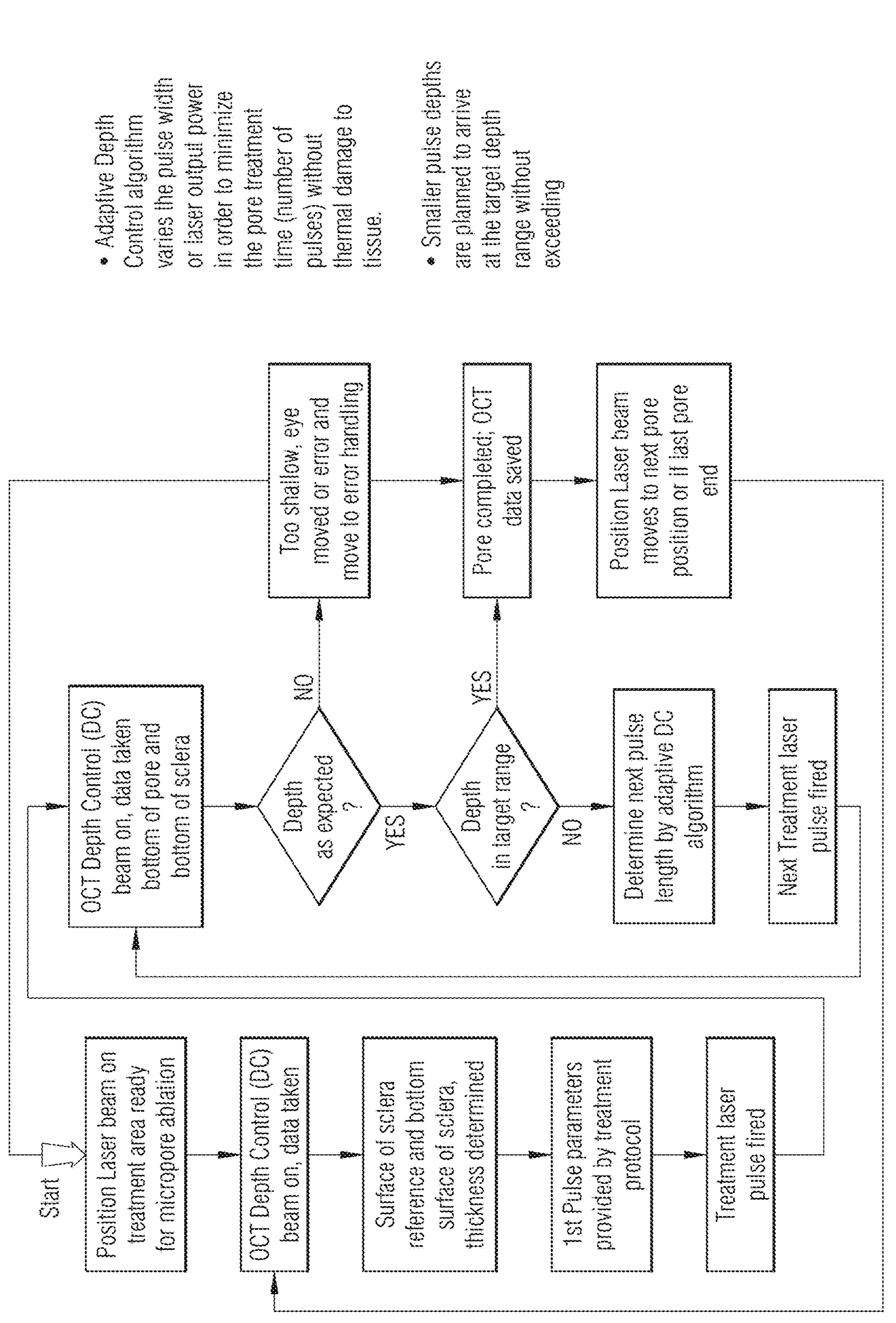
Fig. 27: Method of OCT/DC Adaptive control and OCT/DC tracking eye motion

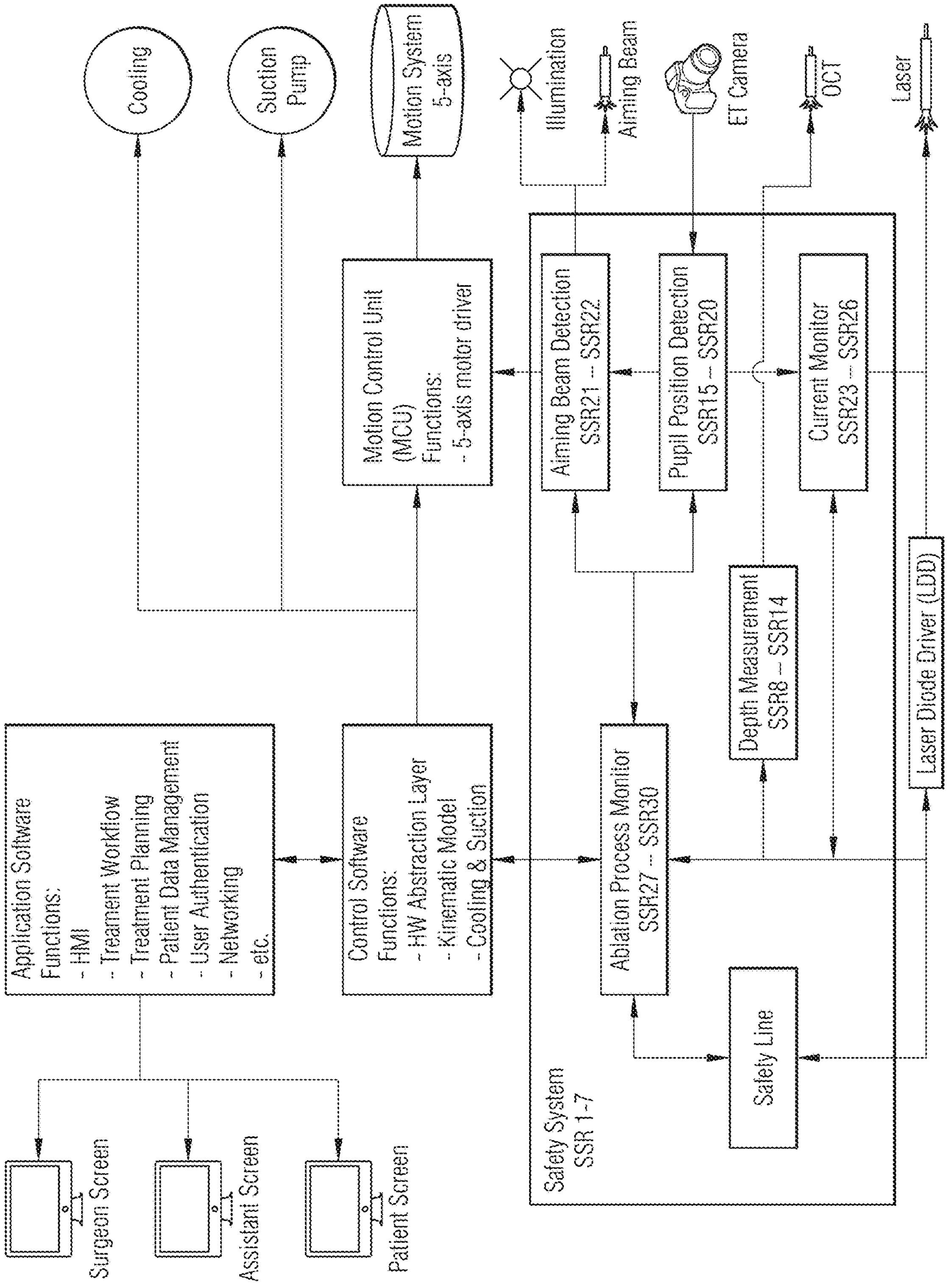
Fig. 28: System block diagram integrating sub-systems and FPGA w/ safety controls

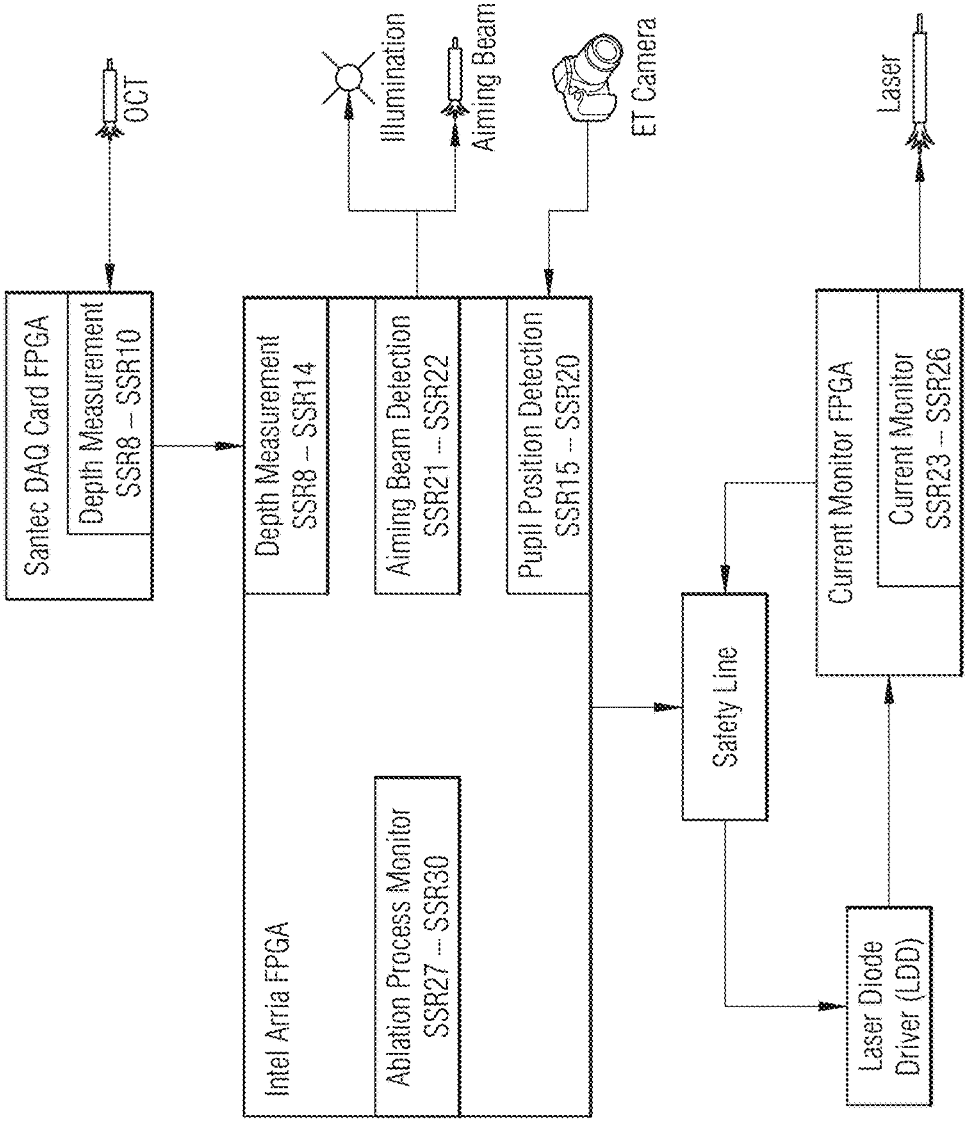
Fig. 29: System block diagram integrating sub-systems and FPGA w/ safety controls

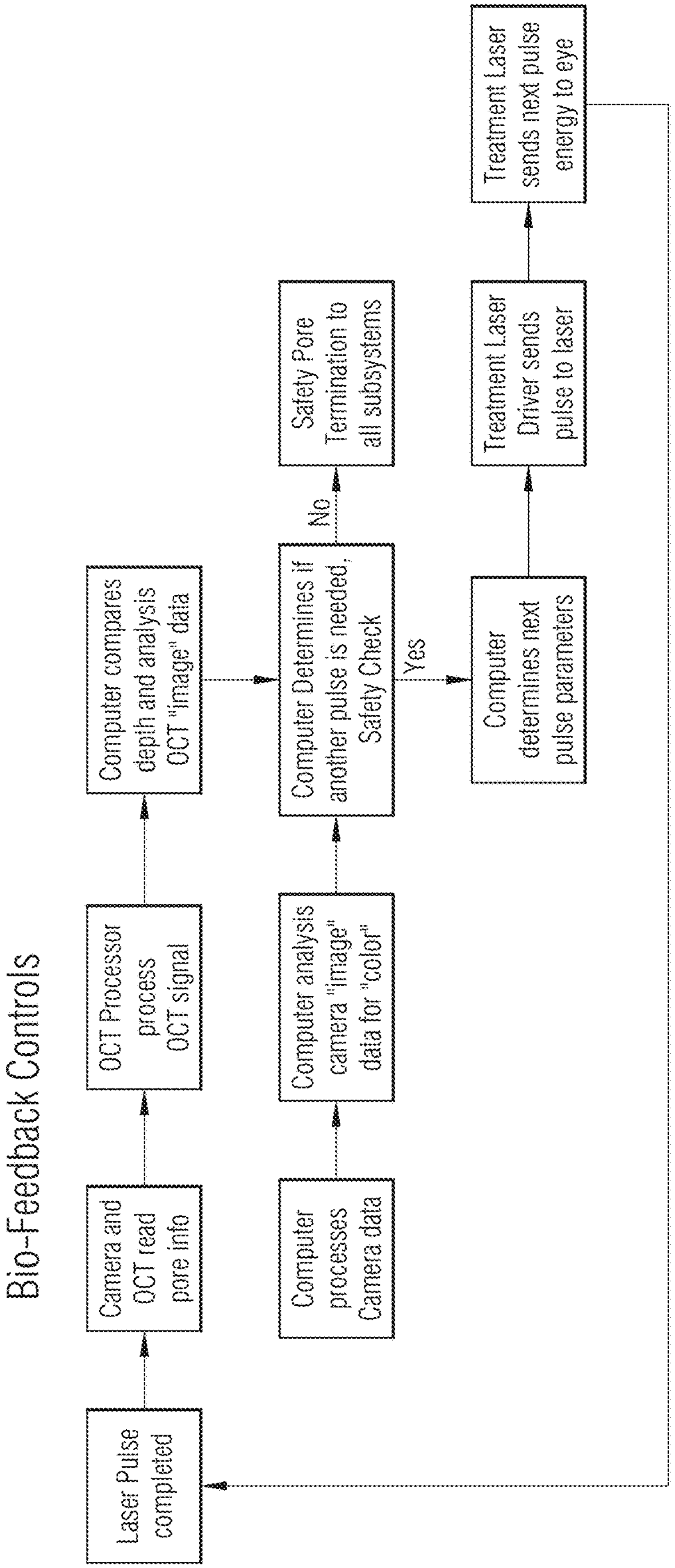
Fig. 30: Bio-Feedback Controls

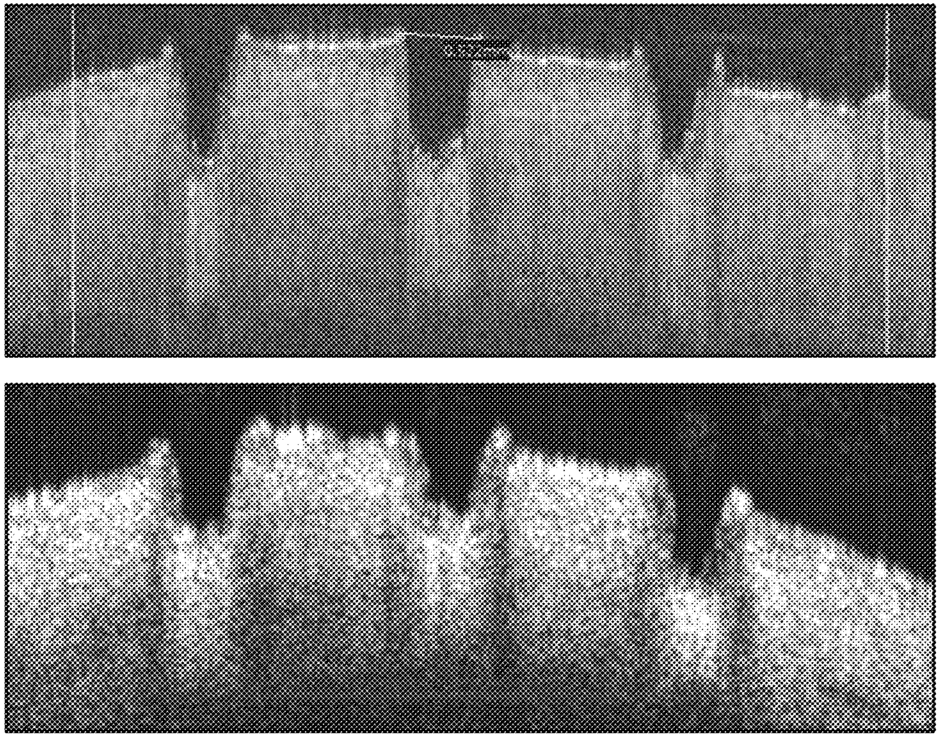
Fig. 31: OCT/DC (single line scan) over micropores to create OCT data and images

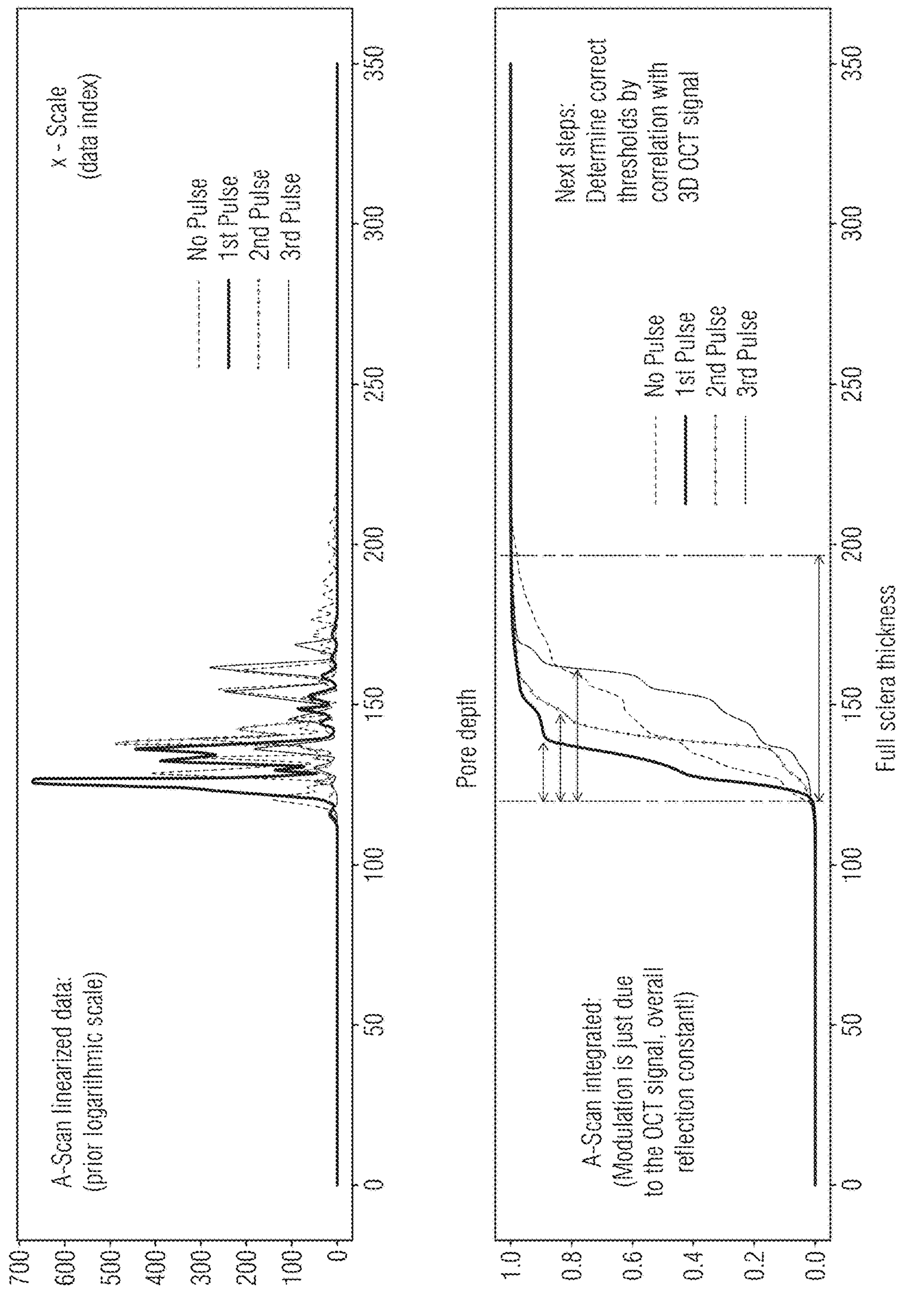
Fig. 32: Porcine Eye: 3 pulses - d=0.36 mm: A-Scan (Processed data)

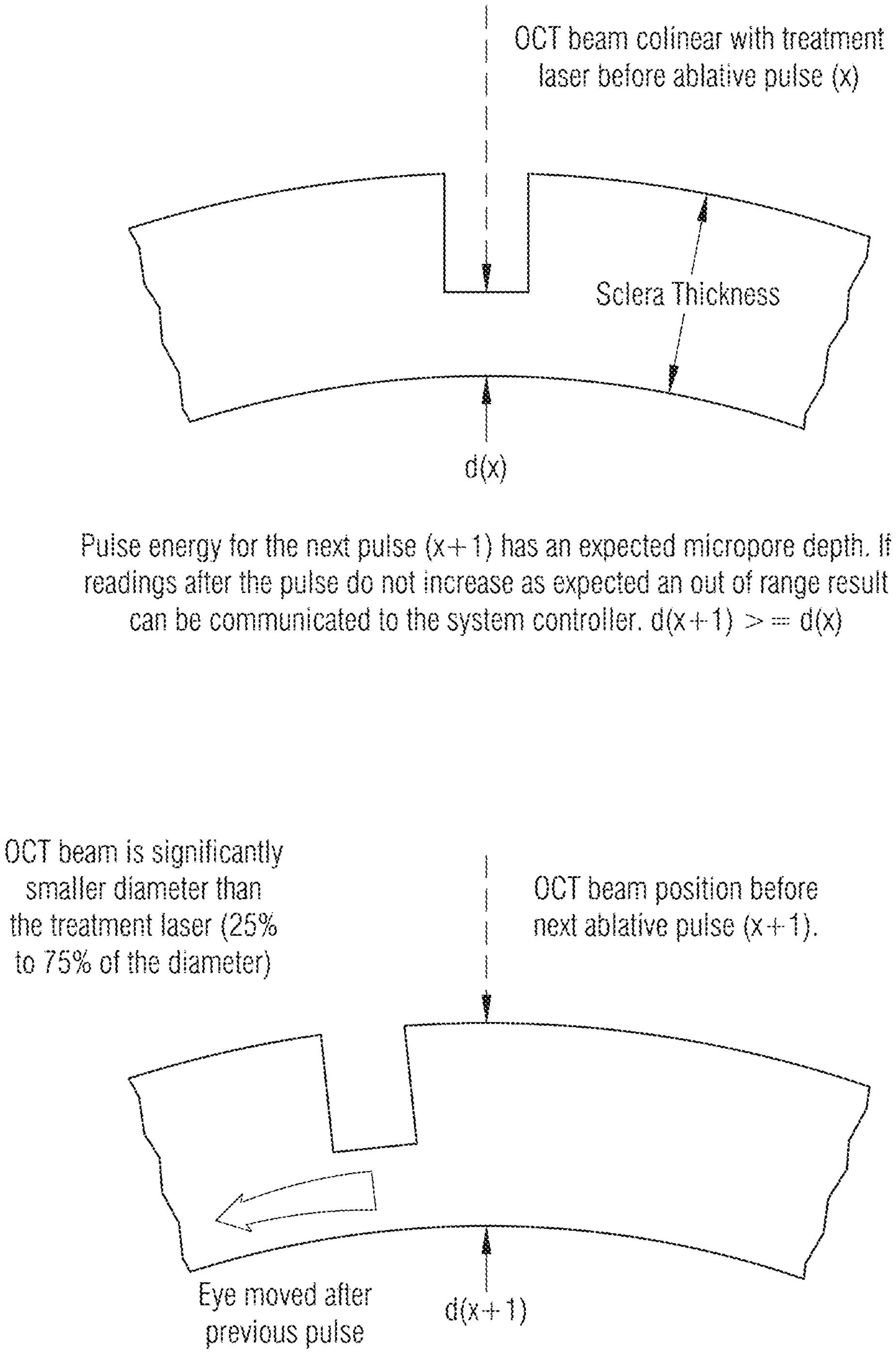
Fig. 33: OCT Depth method to monitor eye motion between pulses of ablation

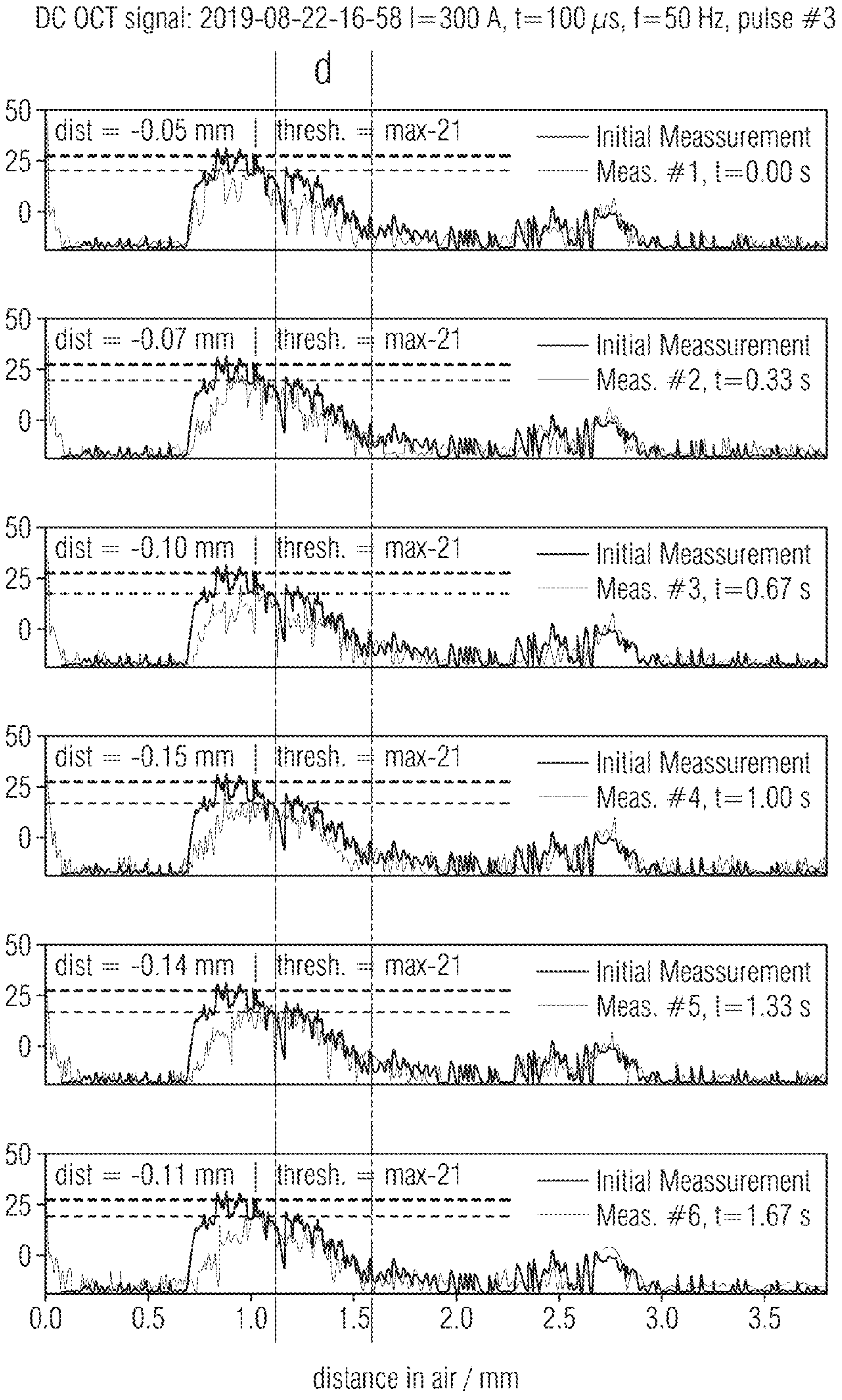
Fig. 34A: OCT Depth Control Signal with Porcine Eye: 3 pulses - d=0.36 mm: A-Scan (Unprocessed data)

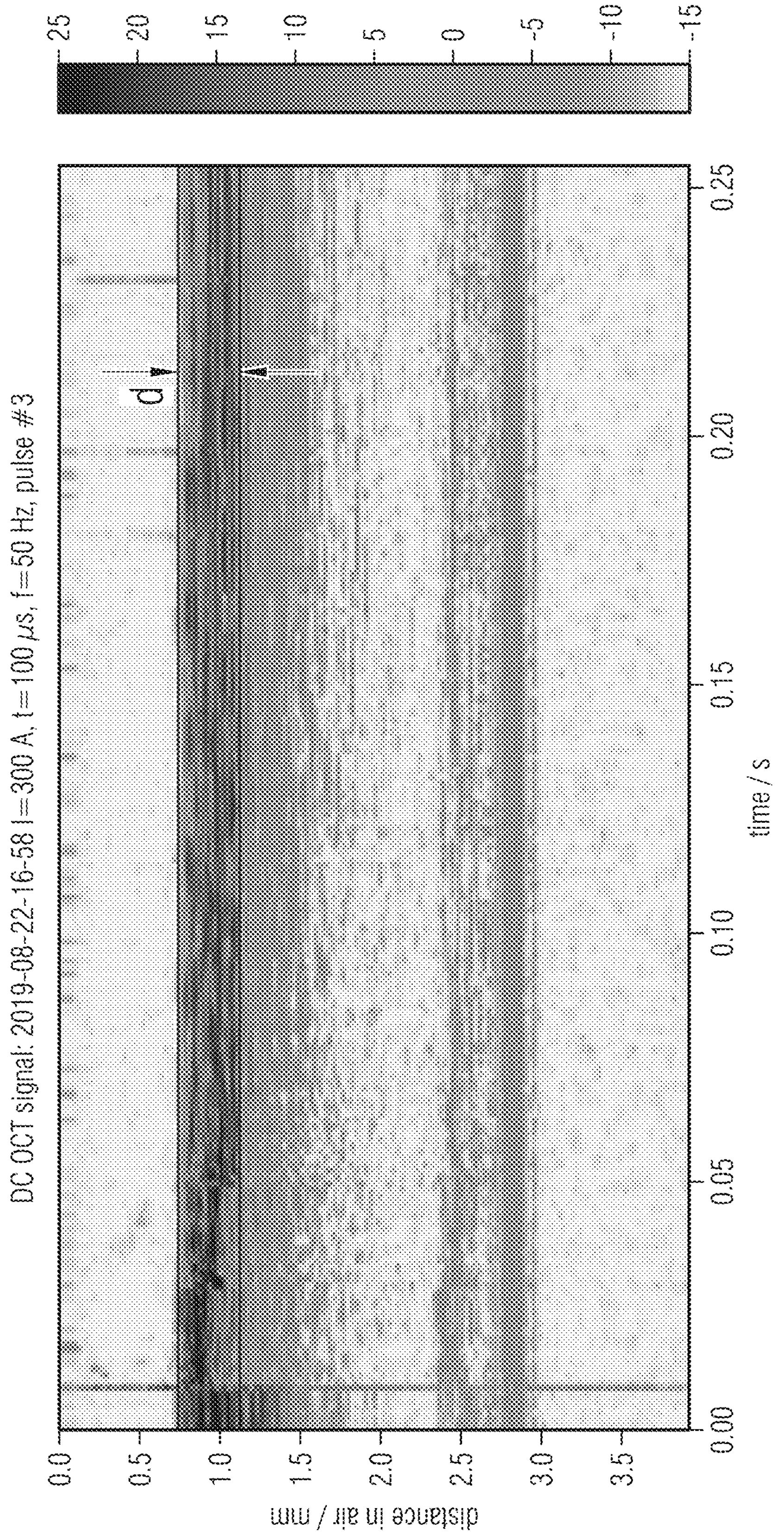
Fig. 34B: OCT Depth Control Signal with Porcine Eye:
3 pulses - d=0.36 mm: A-Scan (Unprocessed data)

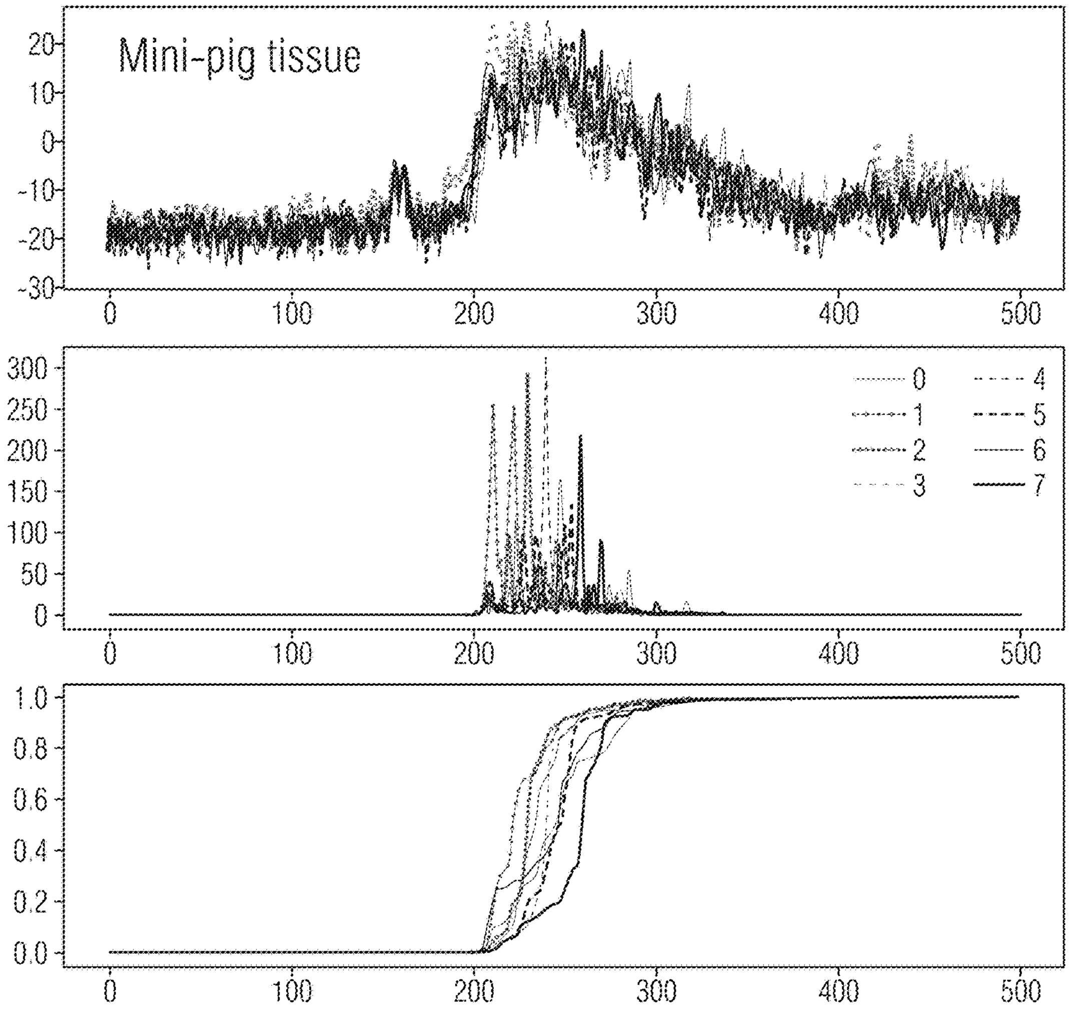
Fig. 35A: Depth Control Signal Analysis: Tissue from humans and other animals do not behave the same, an alternate algorithm must be used

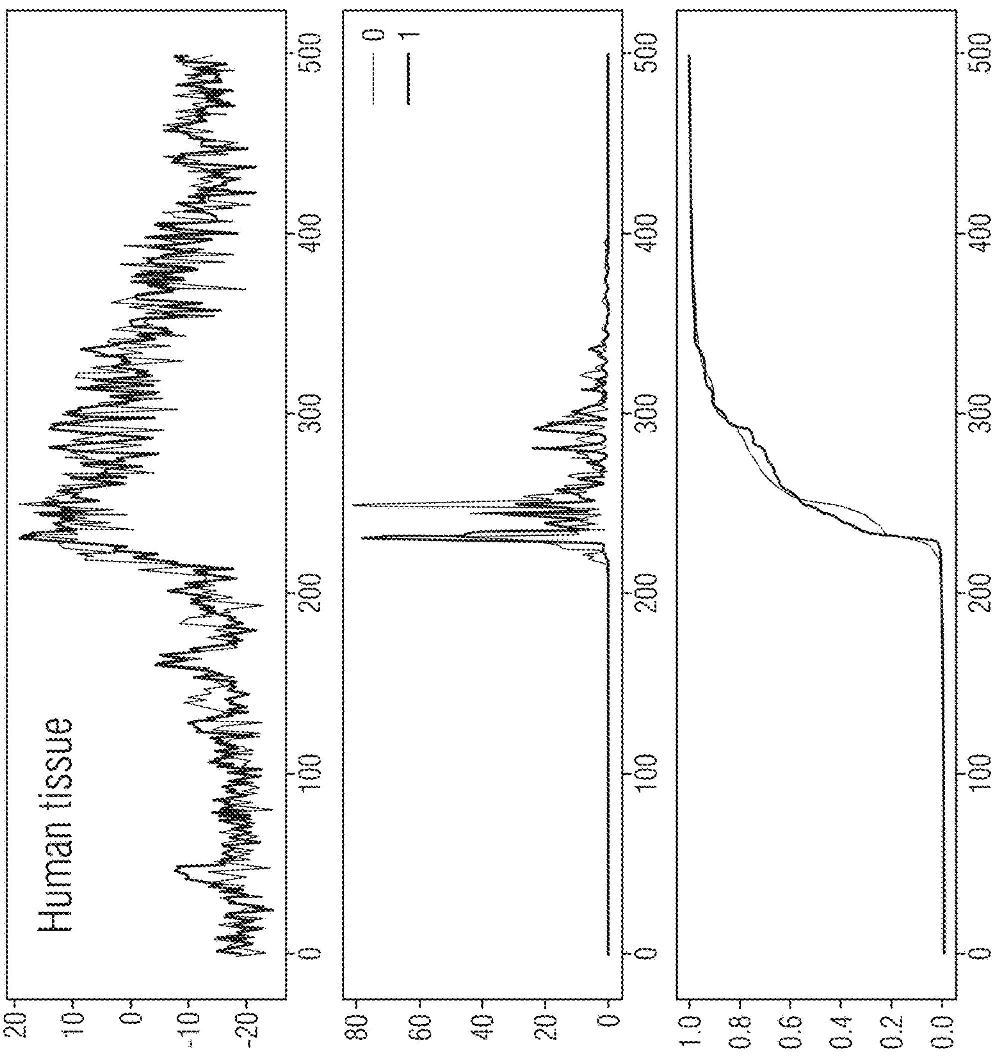
Fig. 35B: Depth Control Signal Analysis: Tissue from humans and other animals do not behave the same, an alternate algorithm must be used

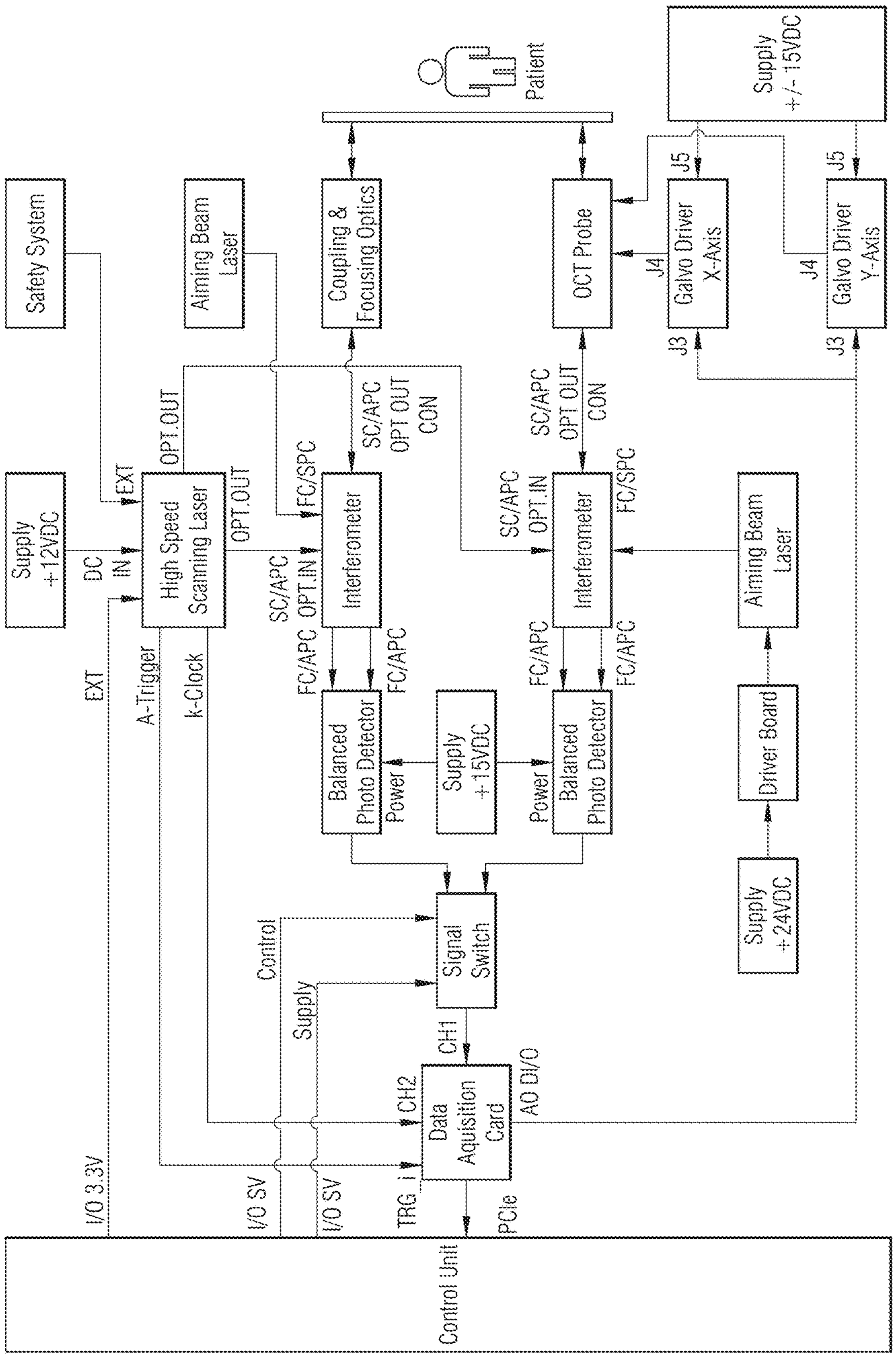
Fig 36: Control diagram of the Off-line (Dual) OCT Scanner

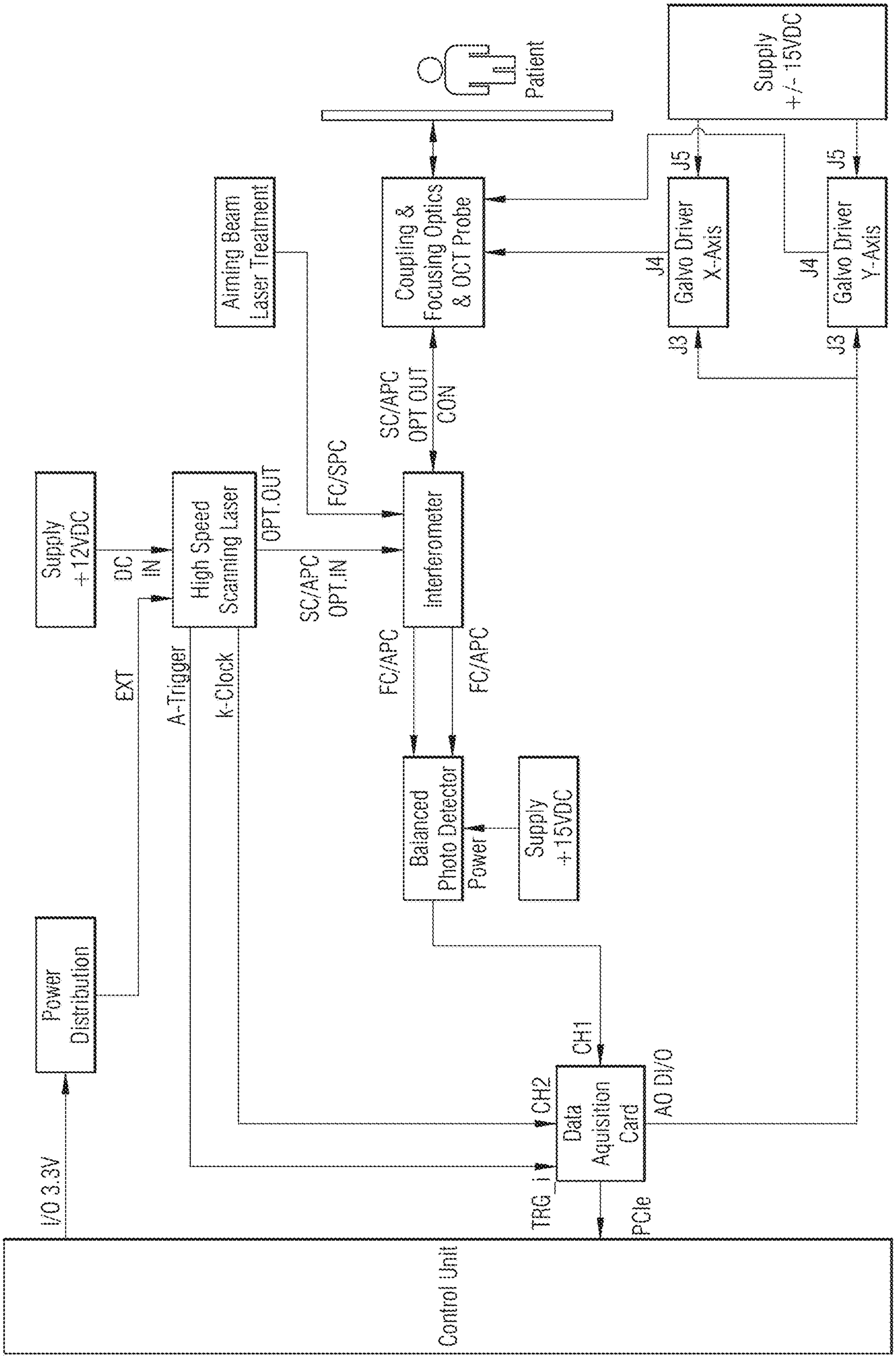
Fig. 37: OCT Architecture with Integratd Scanner

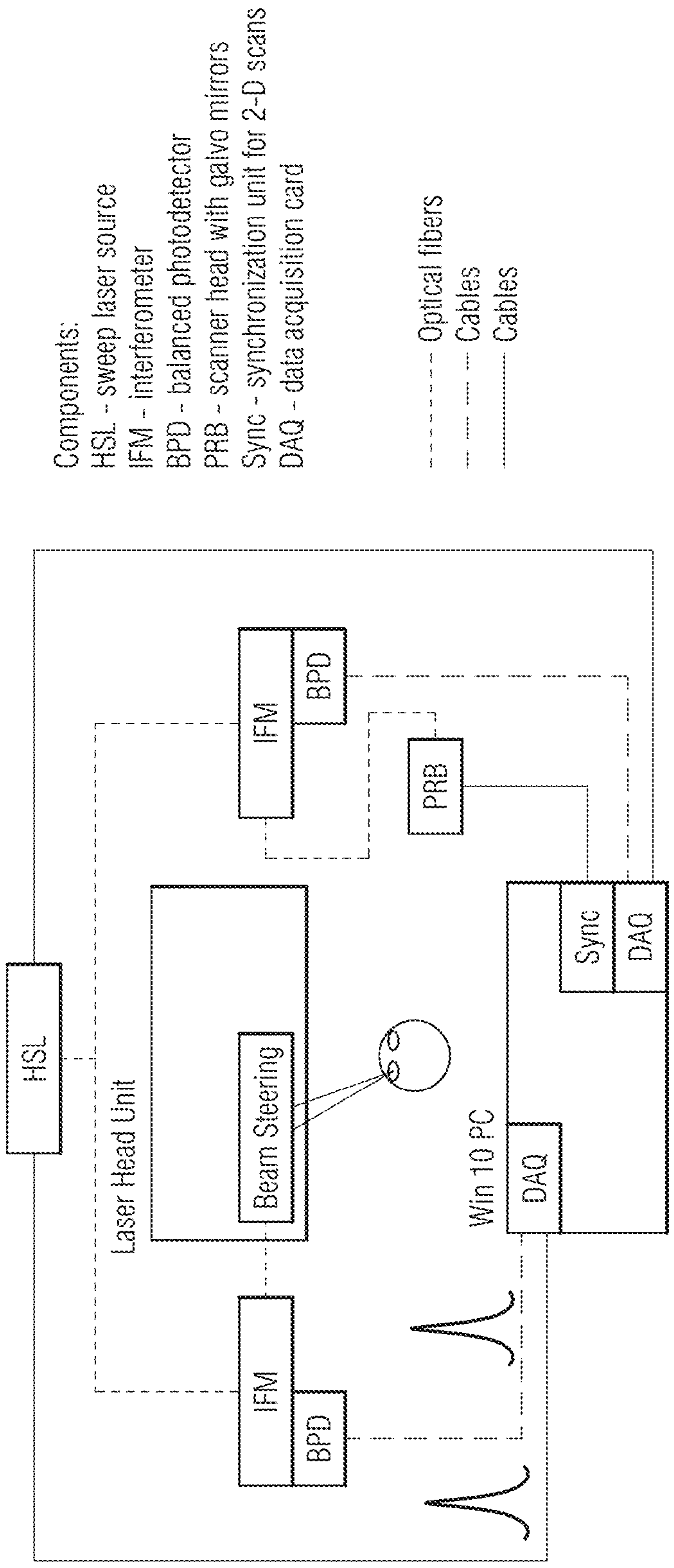
Fig. 38: Oct System Configuration for Depth Control and Laser ablation procedure

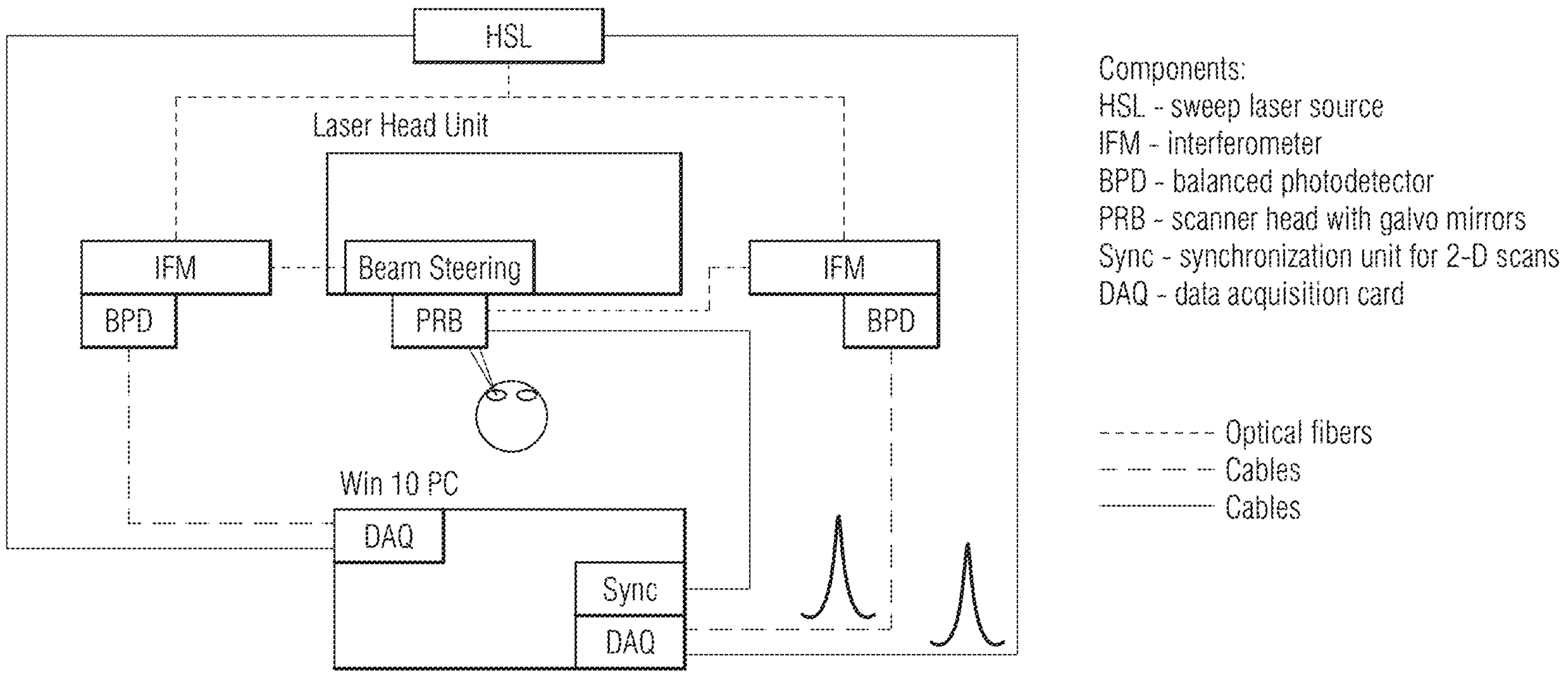
Fig. 39: OCT System Configuration for depth control and Laser ablation procedure that share dual purpose internal components, IFM and DAQ

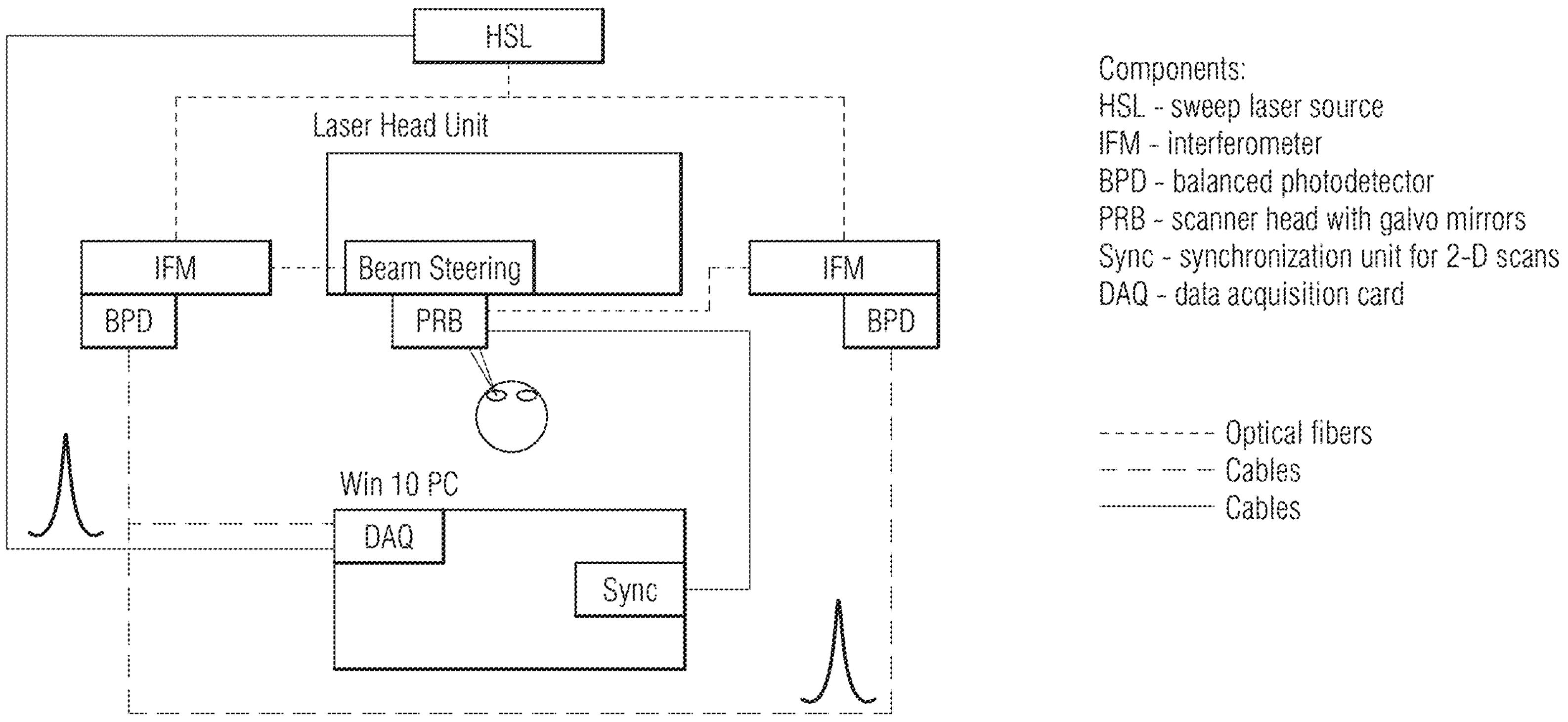
Fig. 40: OCT System Configuration for depth control and Laser ablation procedure with additional shared dual purpose internal components, IFM and DAQ

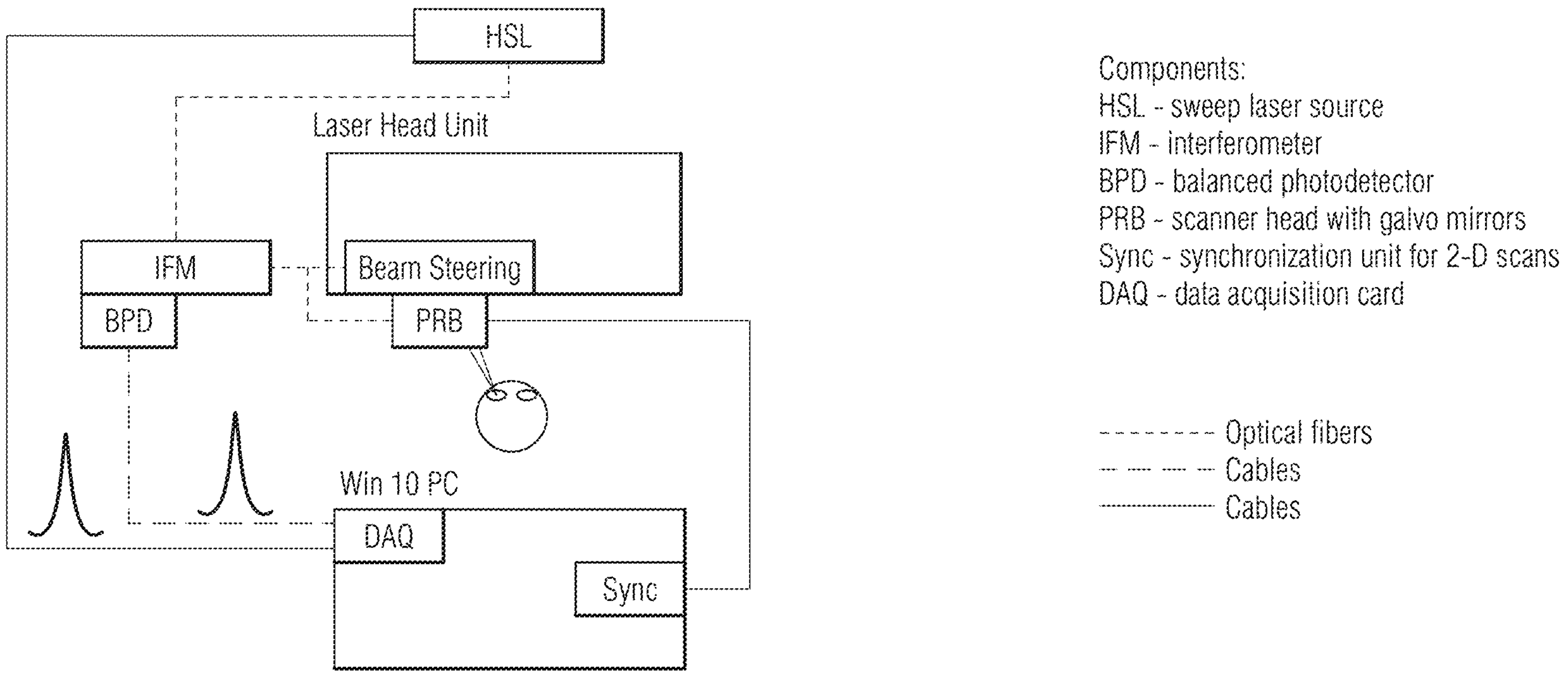
Fig. 41: OCT System Configuration for depth control and Laser ablation procedure with additional shared dual purpose internal components, IFM and DAQ

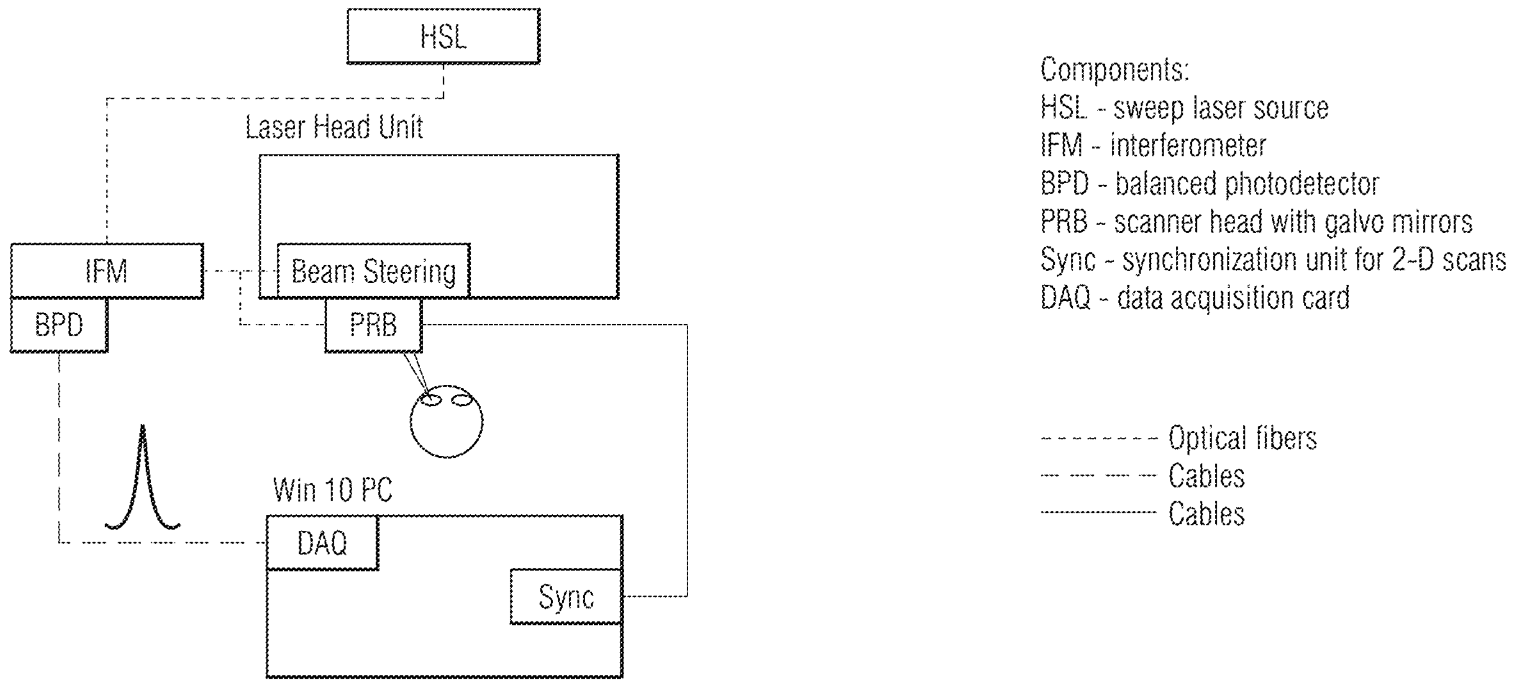
Fig. 42: OCT System Configuration for system with scanning mirror where OCT Depth Control and Scanning is done with the same OCT sensor and a scanning mirror

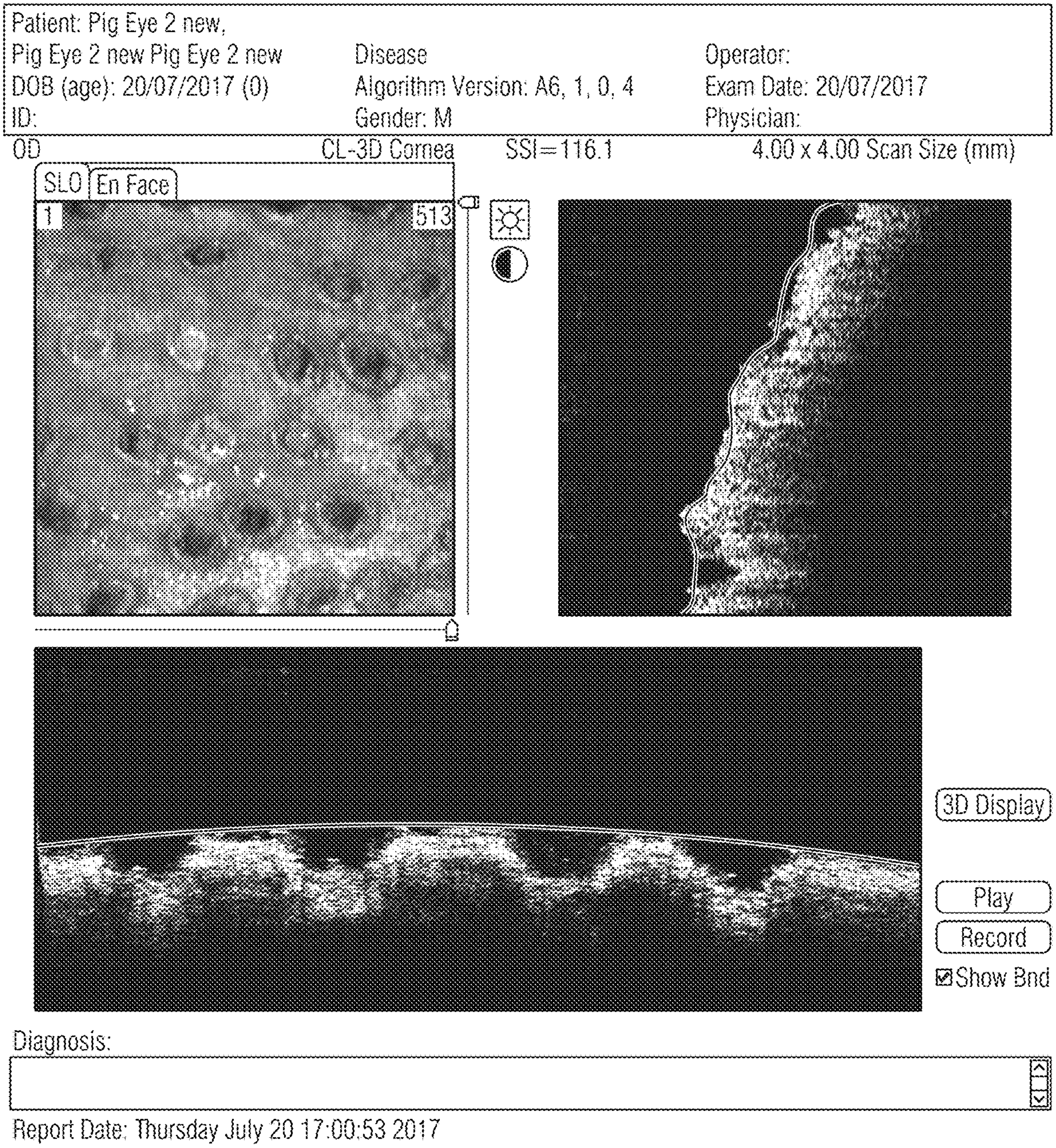
Fig. 43A: Scanning OCT image

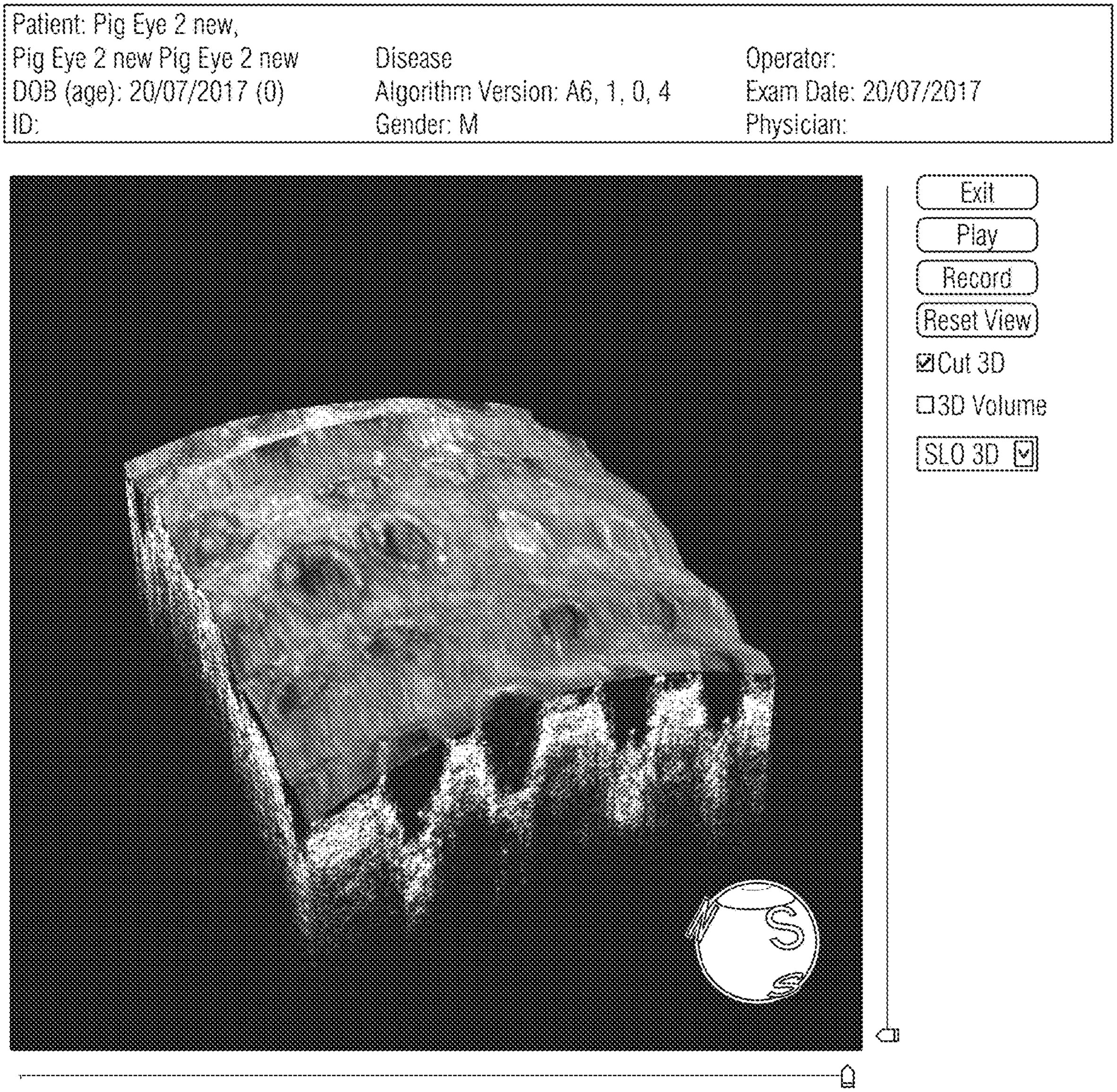
Fig. 43B: Scanning OCT image

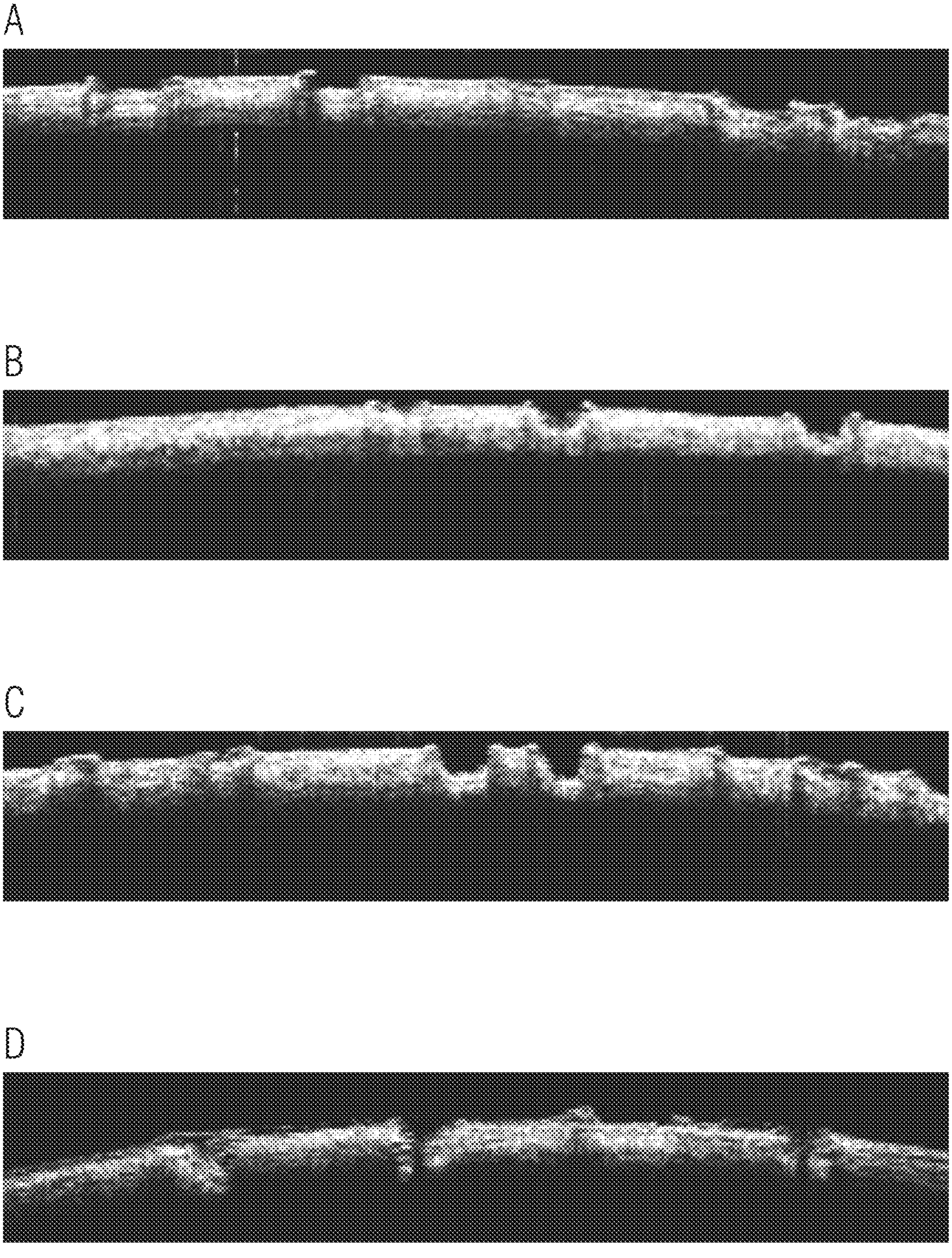
Evaluation of the depth of laser ablation by ASOCT.
The margin of the scleral micropores was clearly visible.
Fig. 44: OCT of Micropores

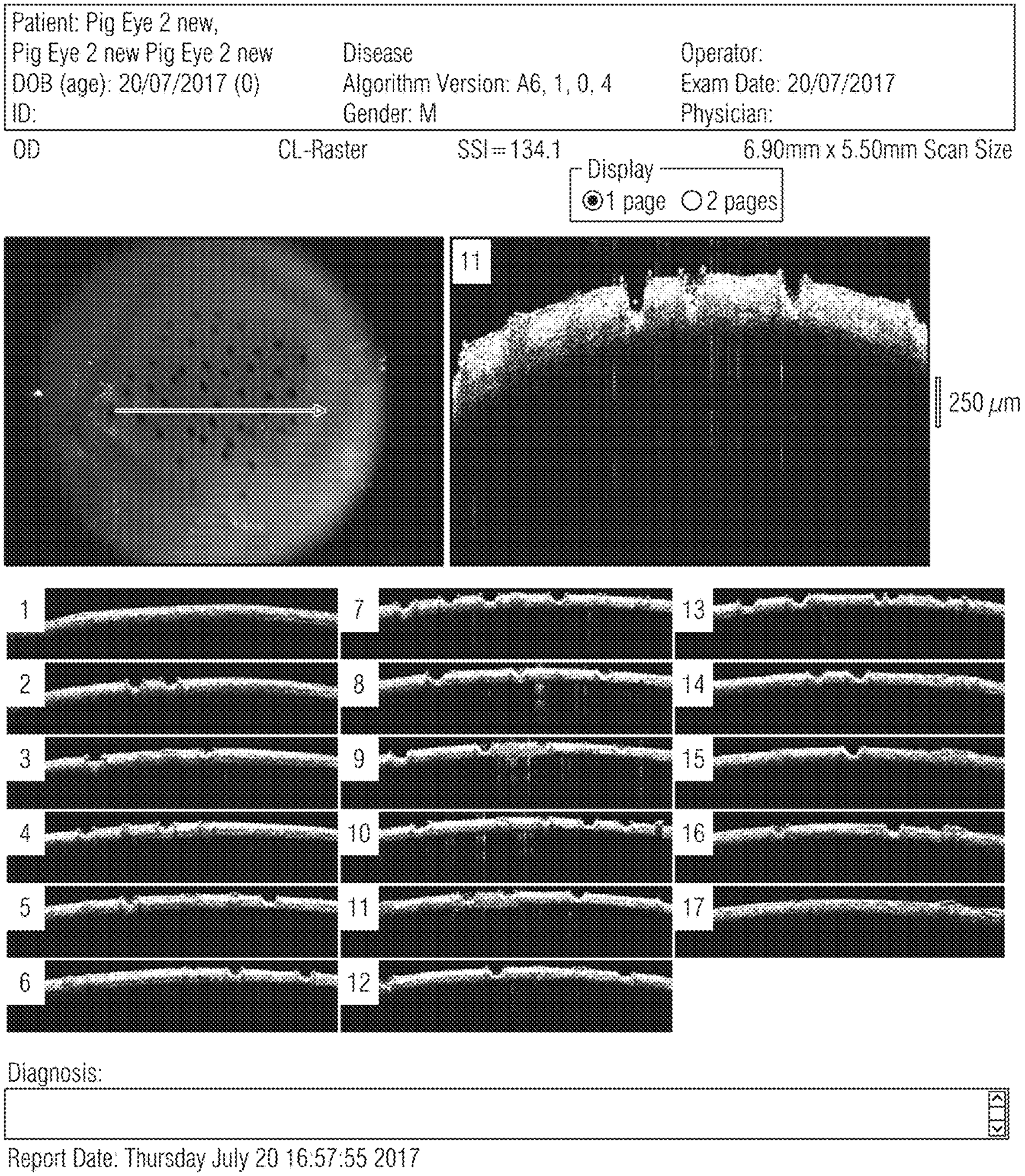
Treatment protocol:
8ppp @ 10% density;
5x5 array
Average Thickness Sclera: 400um
Average Depth of Micropore: 185um
Depth Ratio: 46%
Fig. 45: OCT Depth Measurement

| | | |
|---|---|---|
| Patient: Monkey 5246, | | |
| PLEASE LASER OD 7ppp, OS 8ppp | Disease | Operator: |
| DOB (age): 21-07-2017 (0) | Algorithm Version: A6, 1, 0, 4 | Exam Date: 20/07/2017 |
| ID: | Gender: M | Physician: |
OS CL-Line SSI=82.2 8.00mm Scan Length
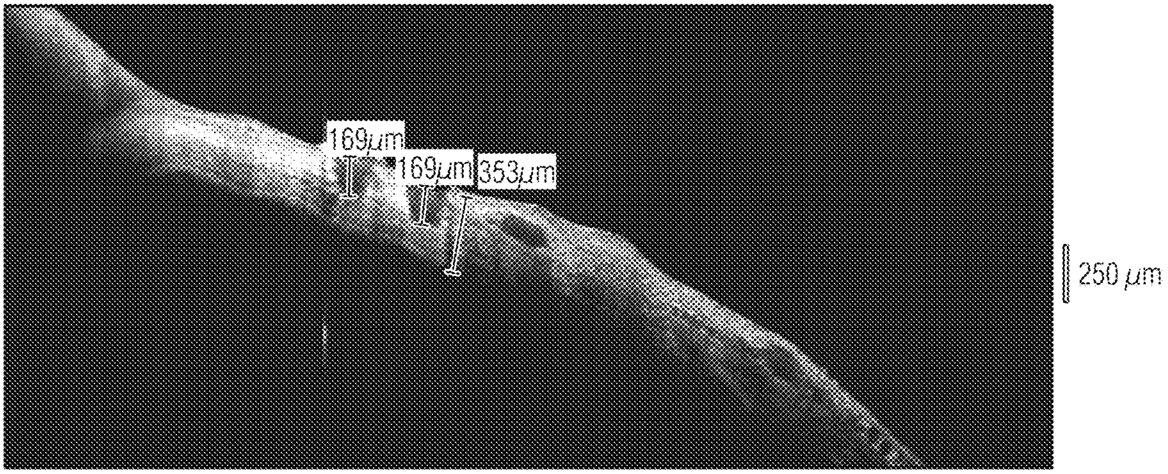
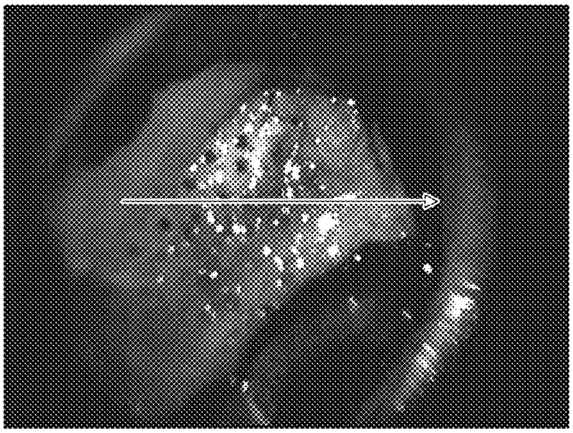
# of Averages: 32
Average
No Average
Diagnosis:
Report Date: Tuesday August 01 13:57:29 2017
Fig. 46: OCT images showing depth of Micropores Eye Tracking system capable of:
- the pupil, iris, vessels and sclera detection DNN Network
- Feature tracking with focus on features in the iris and pupil only
- Automatic detection of eye-centers with TOF and automatic zoom on eye to be treated by Moveable Mirror
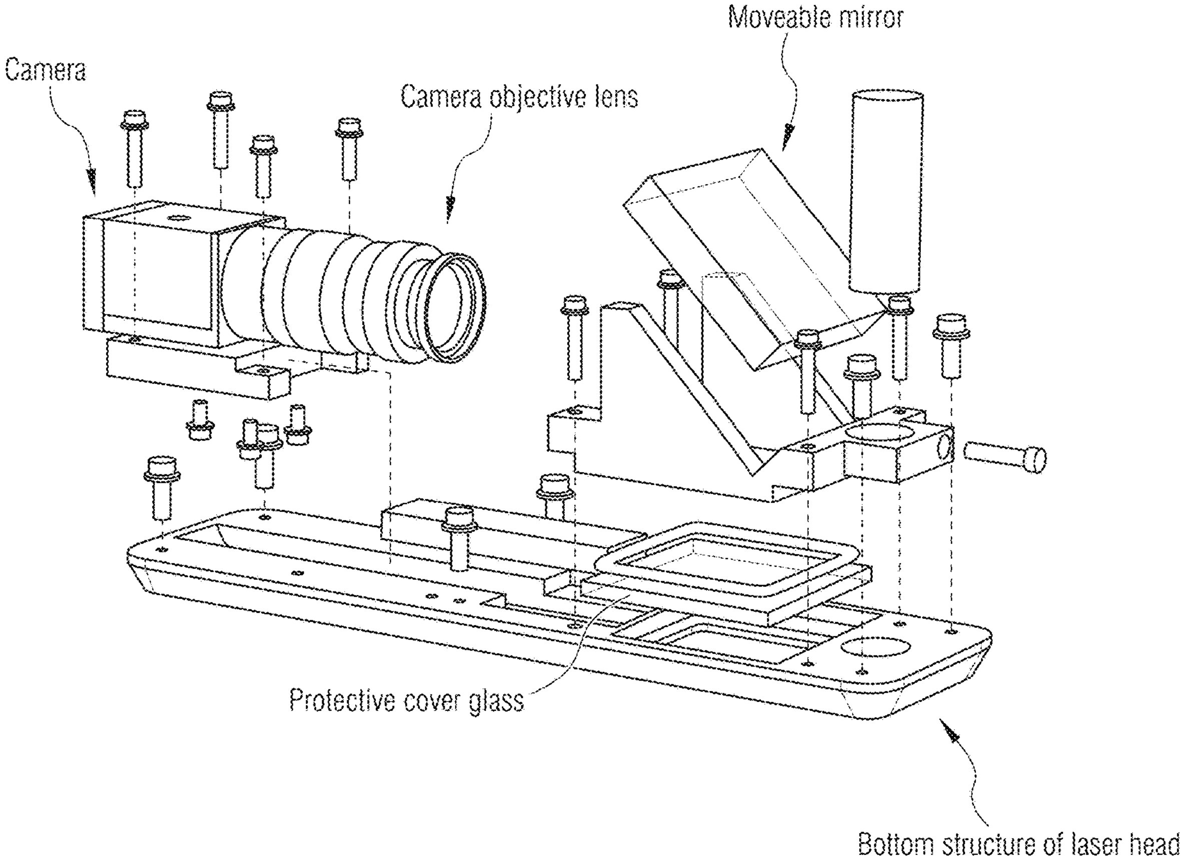
Fig. 47: Eye tracking architecture

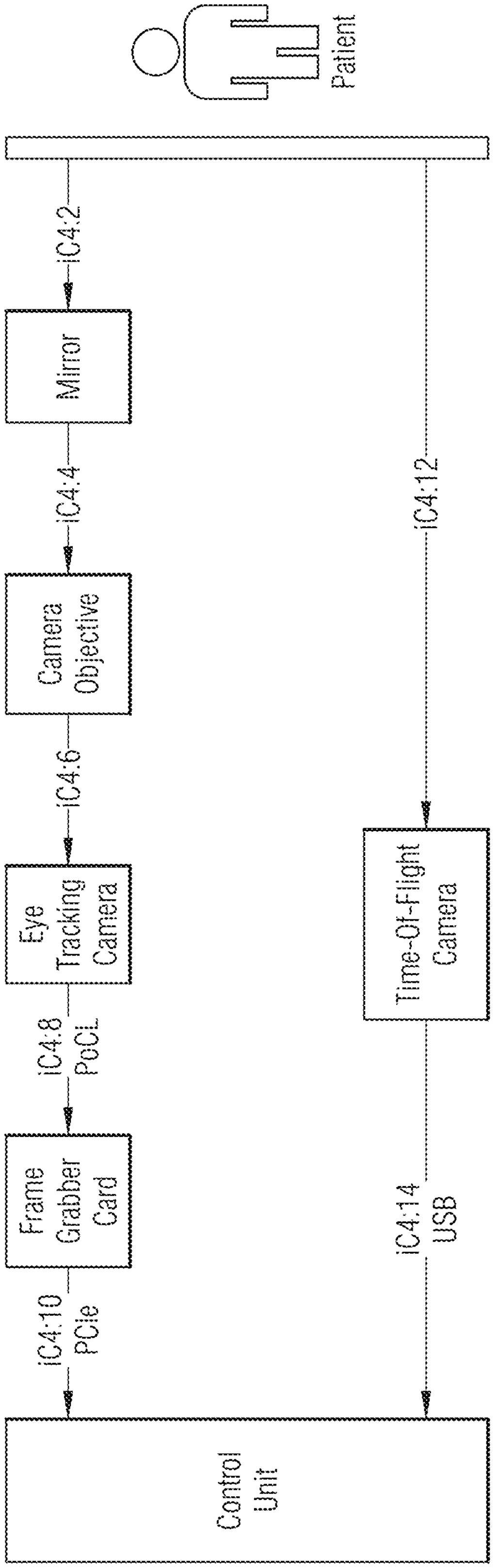
Fig. 48: Eye tracking process diagram

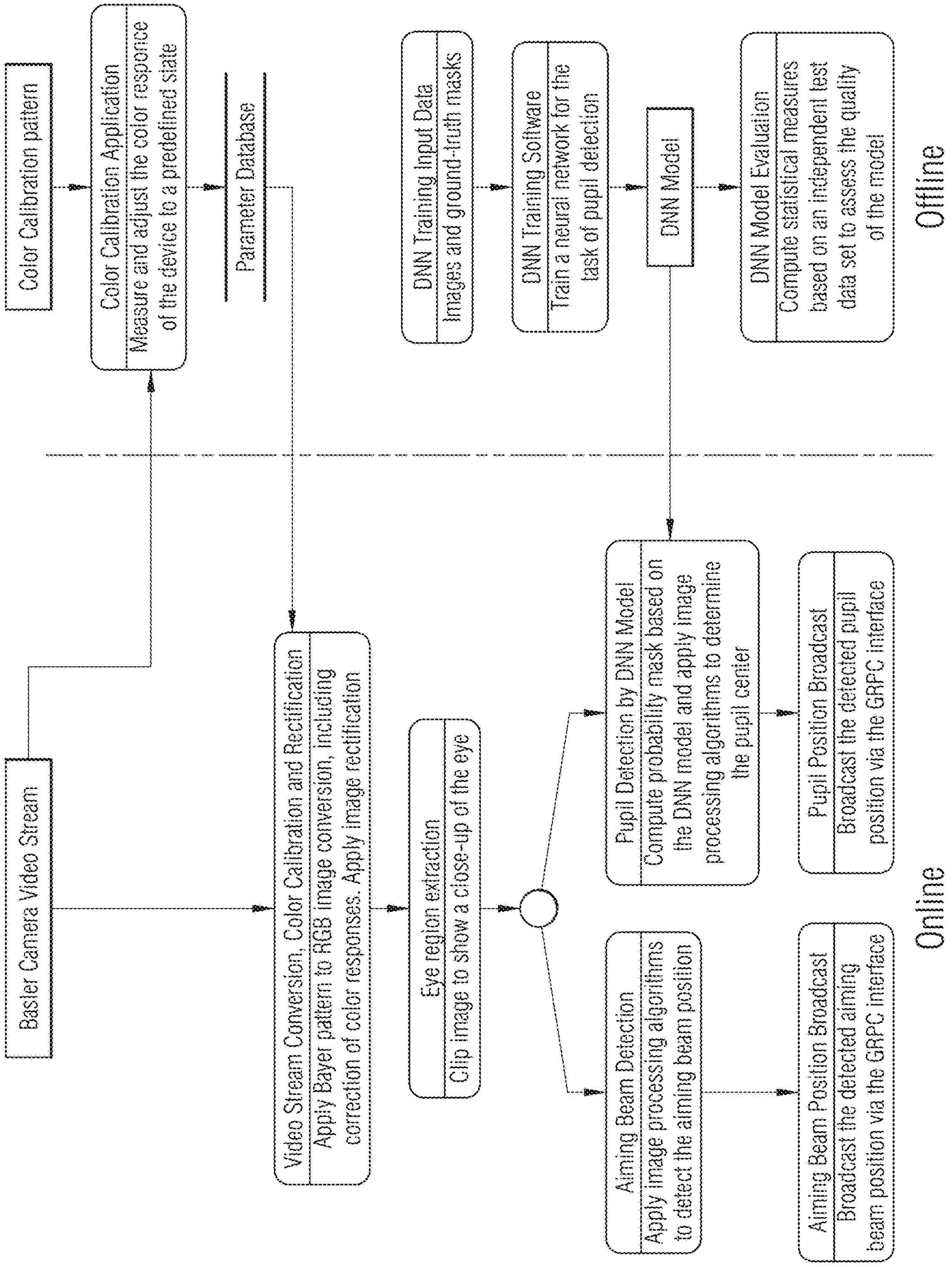
Fig. 49: Eye tracking process diagram

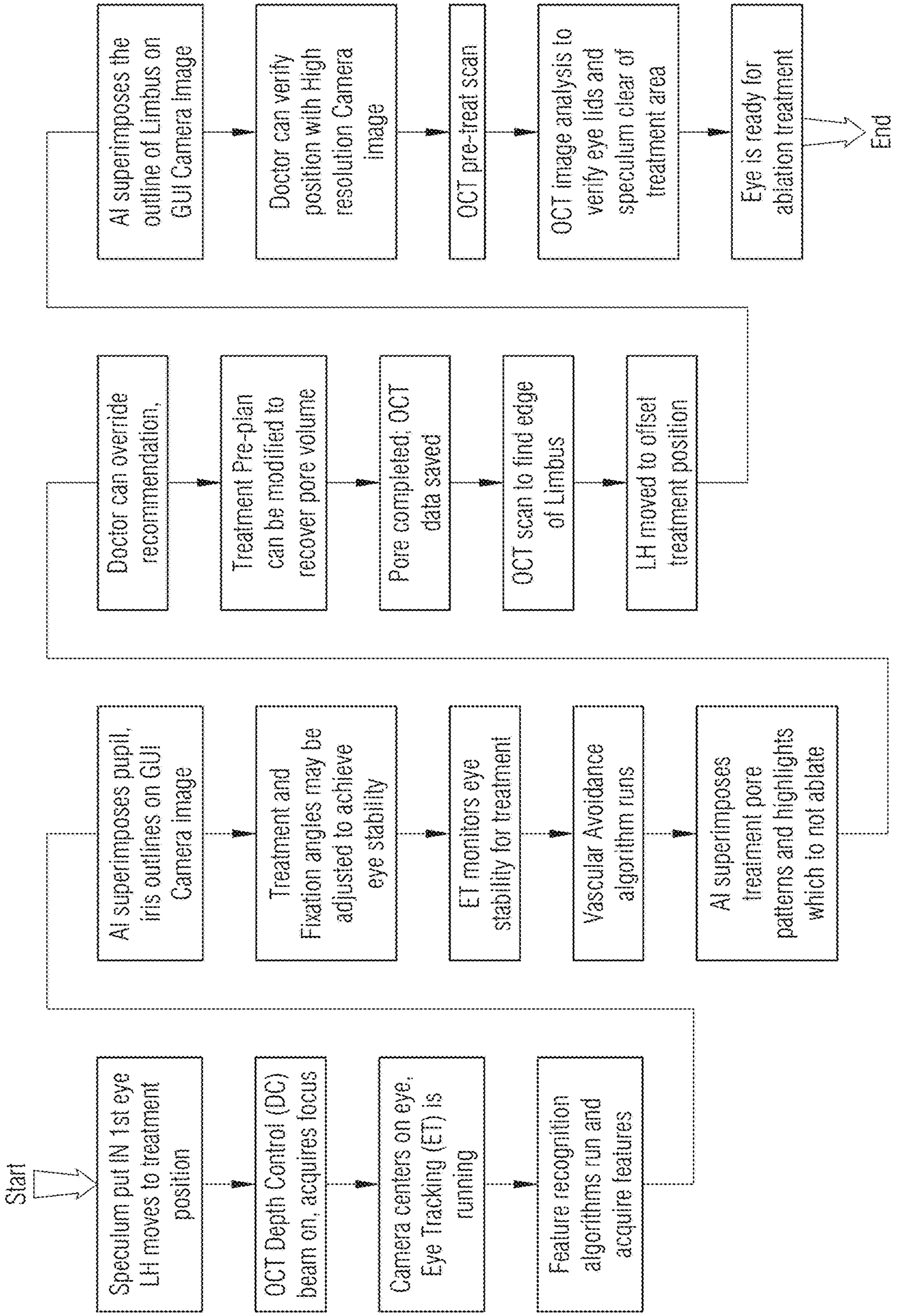
Fig. 50: Method for Feature Recognition and Treatment Position alignment to AT Limbus

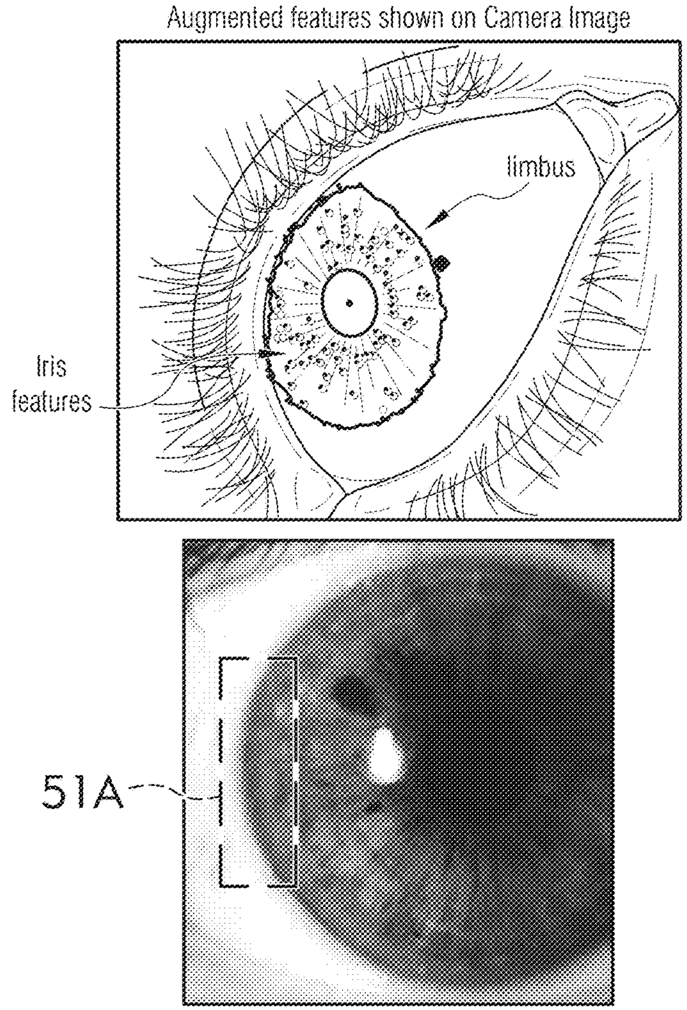
Fig. 51: Feature recognition of the AT limbus highlighted through AI analysis and shown as an overlay to the camera image
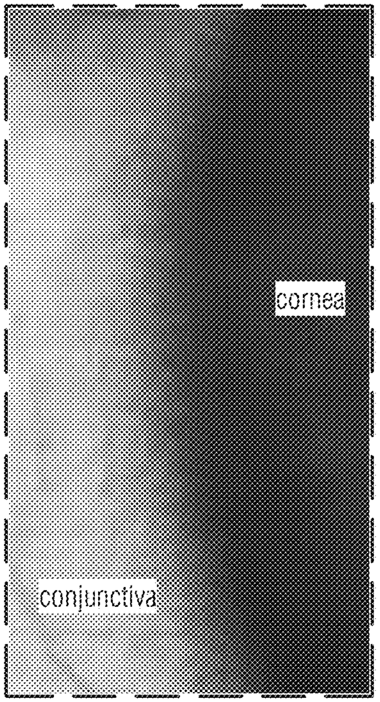
Fig. 51A

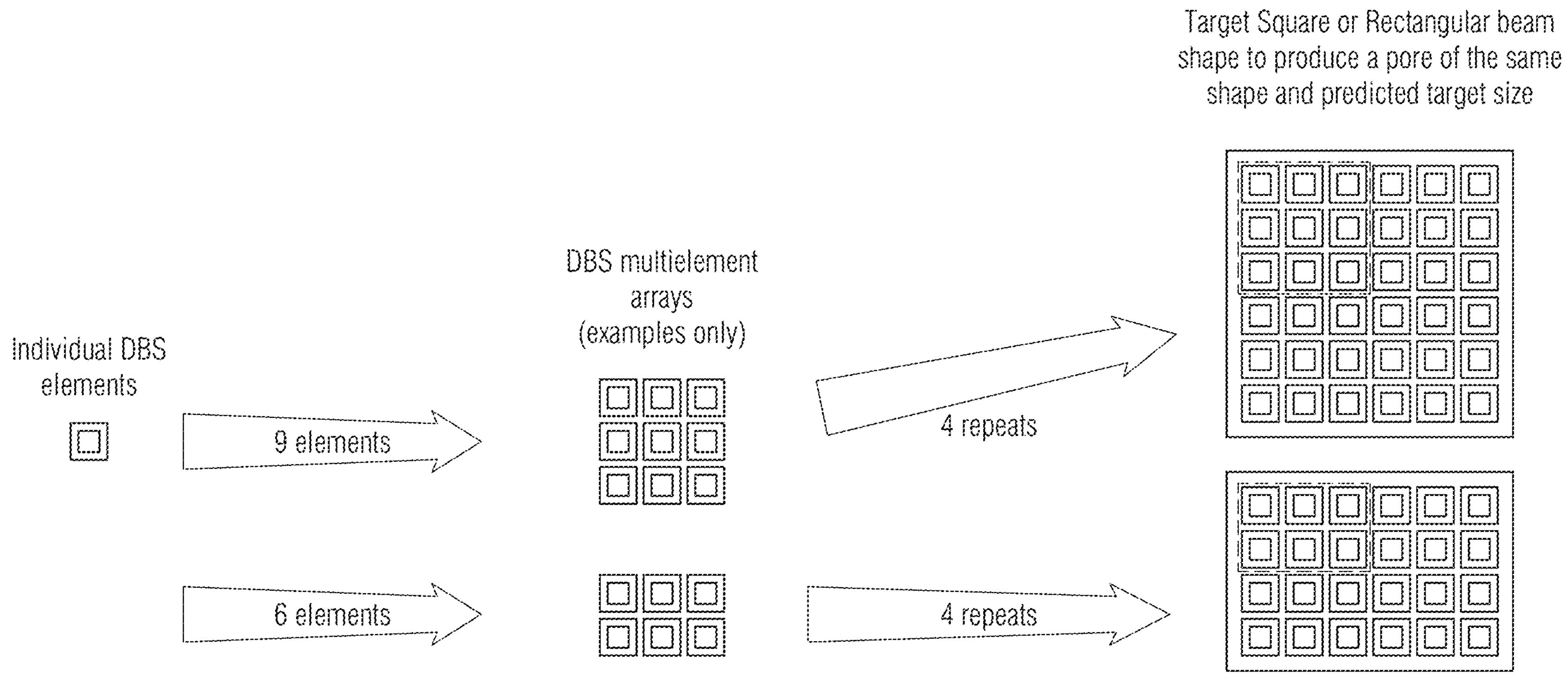
Fig. 52: Design Concept to create a plurality or size and shaped pores through multiple exposures using a DBS First Pore Shold be Between Midlimbal Line and Posterior Limbal Border, and over Schlemm's Canal

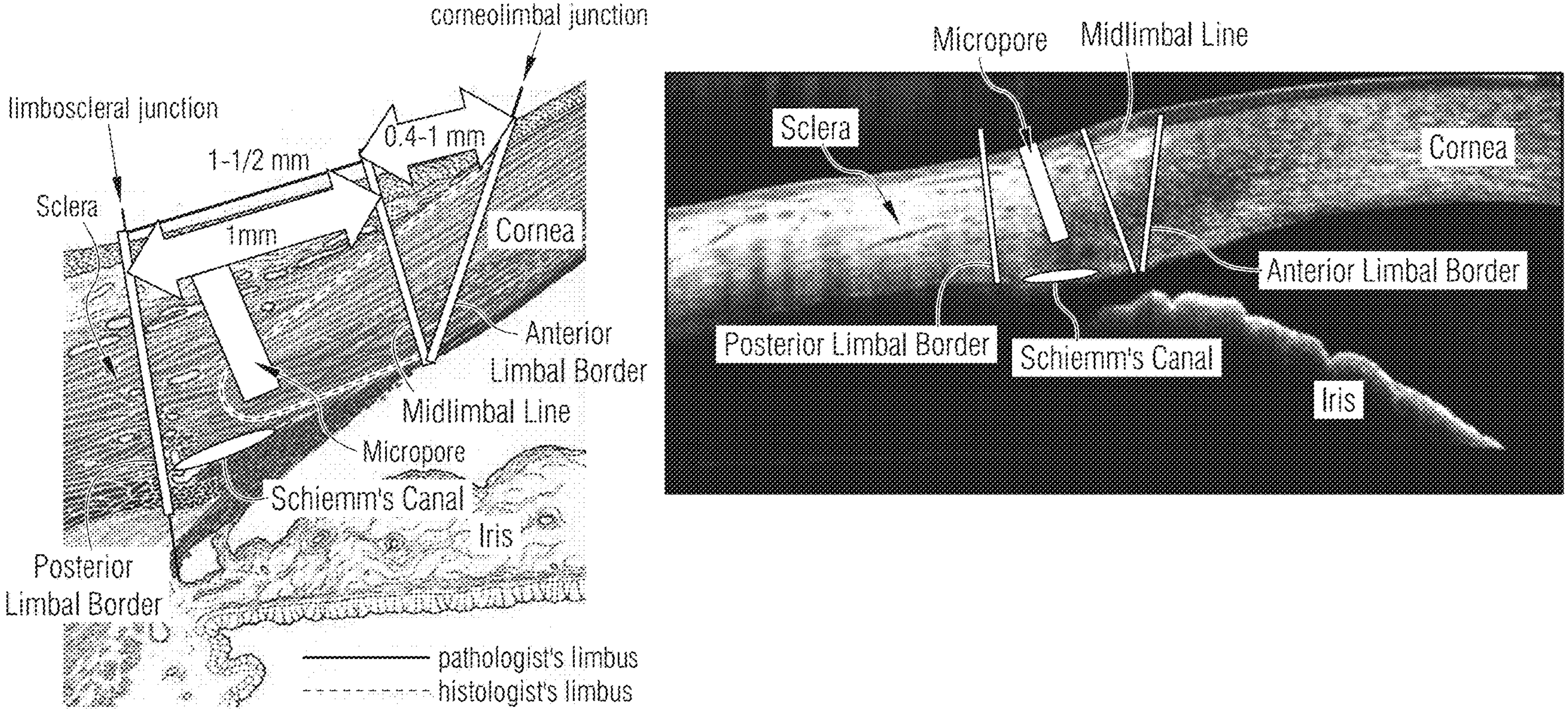

Proposed elastic fiber organisation in the limbal region. Translucent green: Trabecular meshwork. Solid green: Trabecular meshwork insertion. Gold: Elastic limbal region with concentrated elastic fiber sheets. Most elastic fibers appear to emanate from this region and extend across the posterior stroma. Continuous elastic sheets are represented by solid gold lines; transition of sheets to fibers is represented by dashed hold lines. Blue: Descemet's membrane. (Modified from Hogan et al)39. (For interpretation of the references to colour in the figure legend, the reader is referred to the web version of this article.)

Retina

Fig. 53: Treatment Positioning relative to Anatomical Limbus

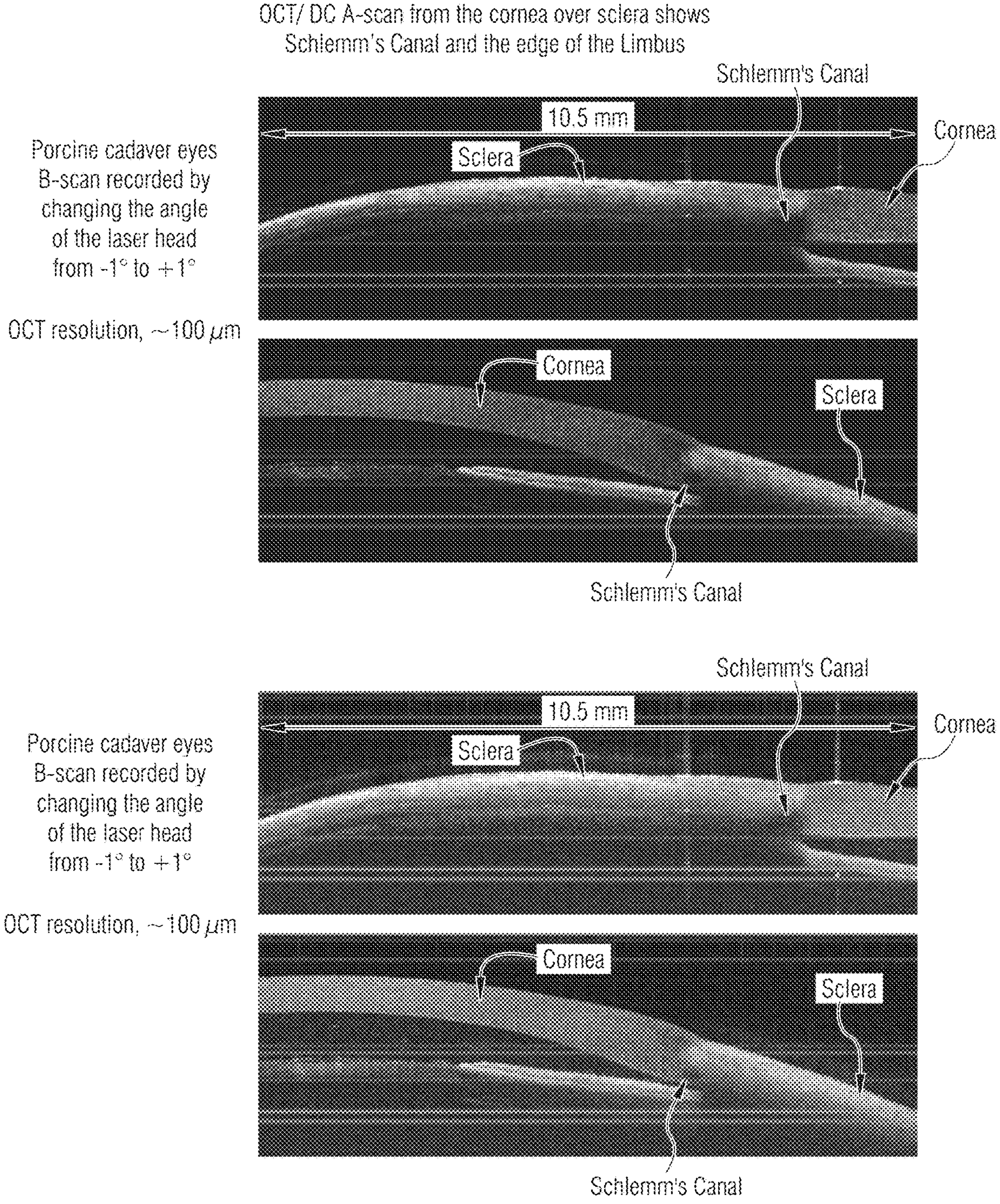
Fig. 54: OCT/ DC A-scan from the cornea over sclera shows Schlemm's Canal and the edge of the Limbus at 2 resolutions

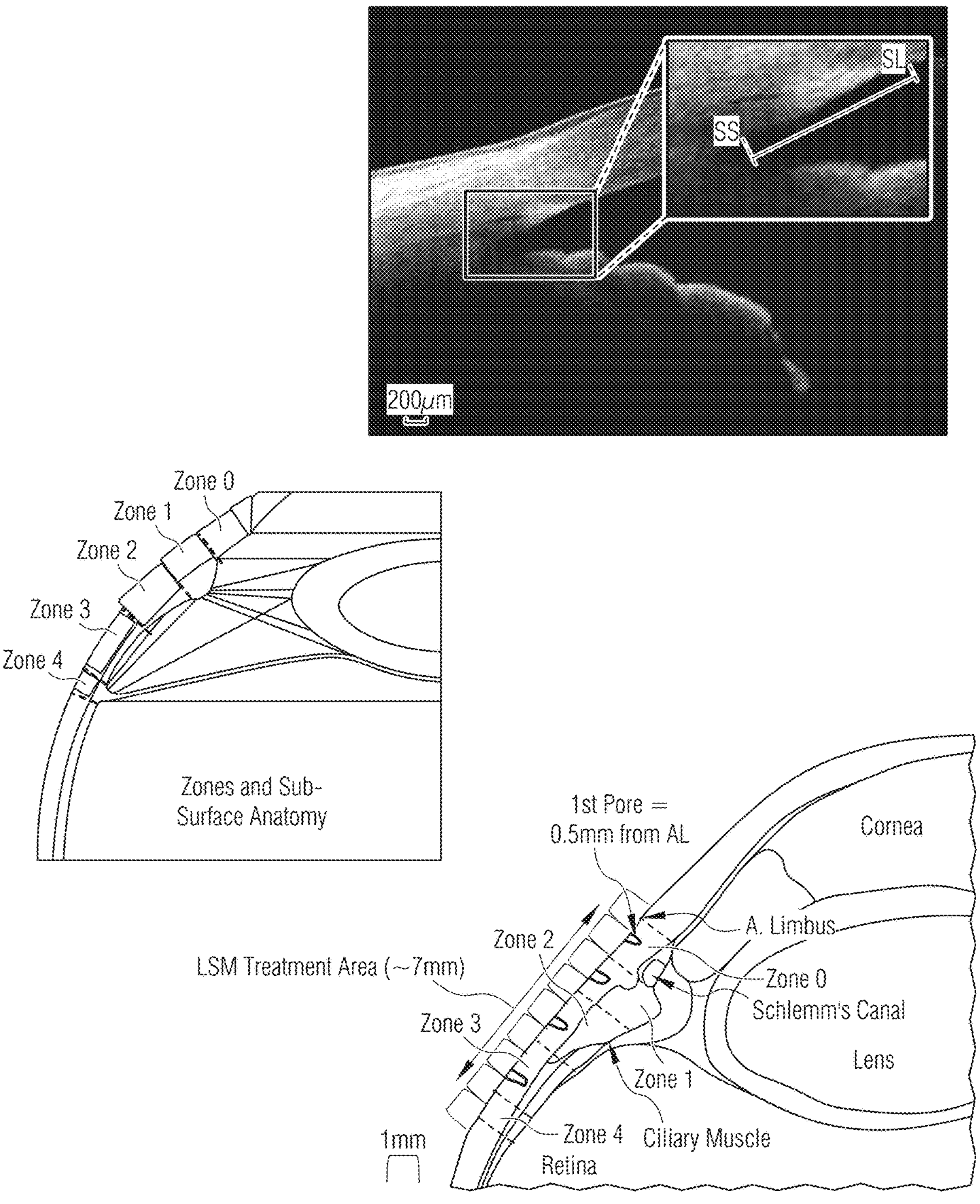
Fig. 55: Treatment position relative to Schlemm's Canal and Anatomical limbus

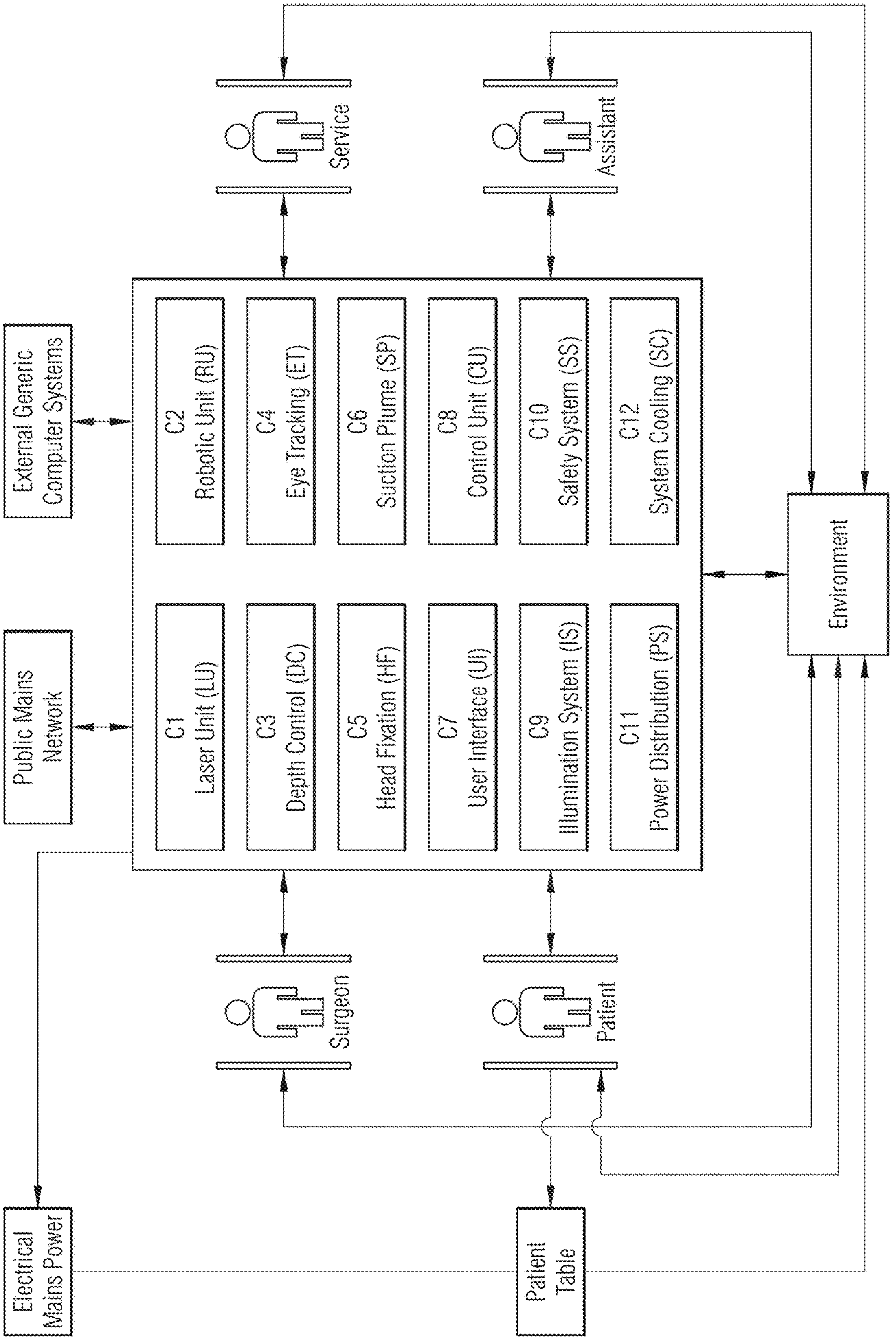
Figure 56: User / System architecture diagram

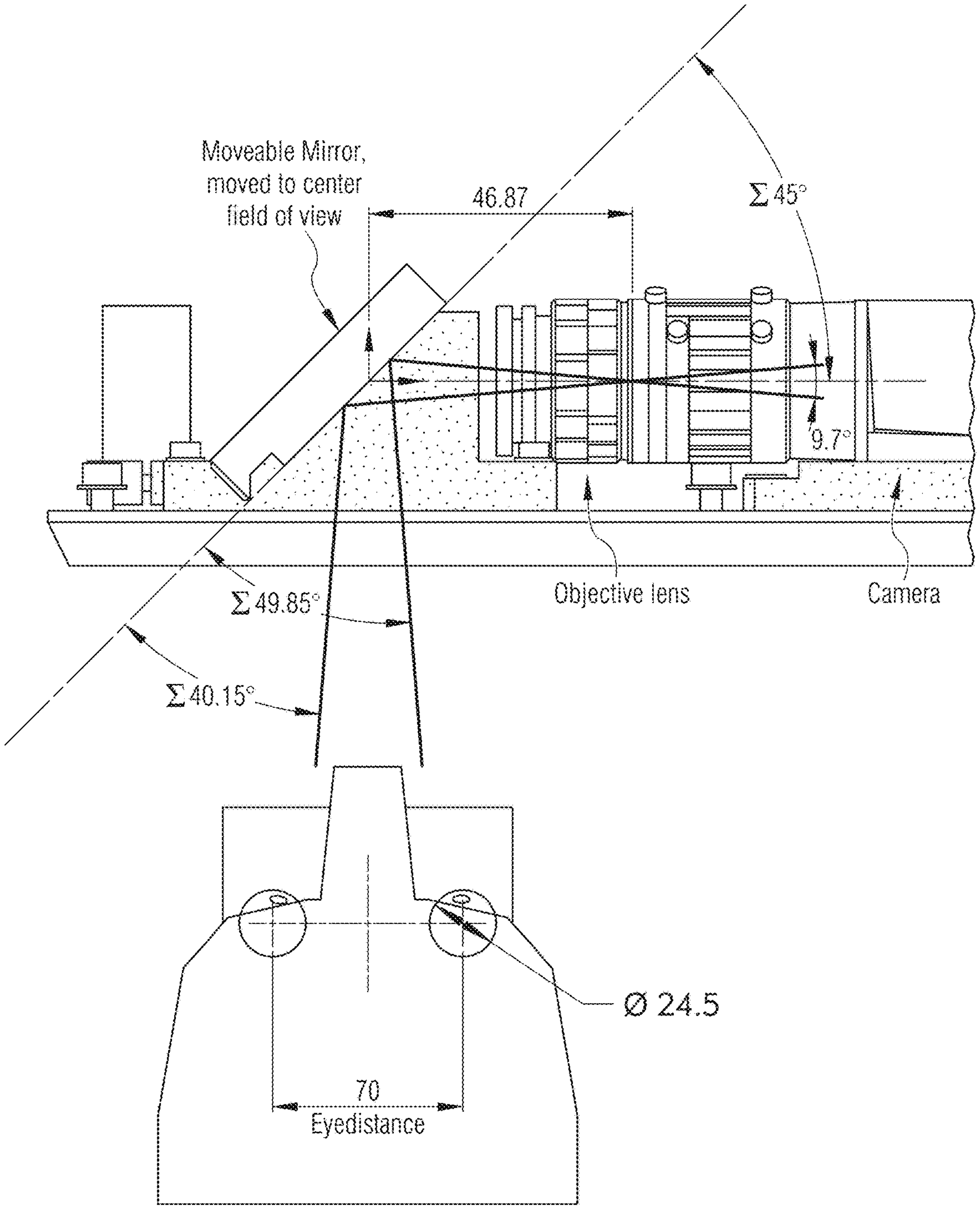
Fig. 57: High Magnification Camera System with mirror

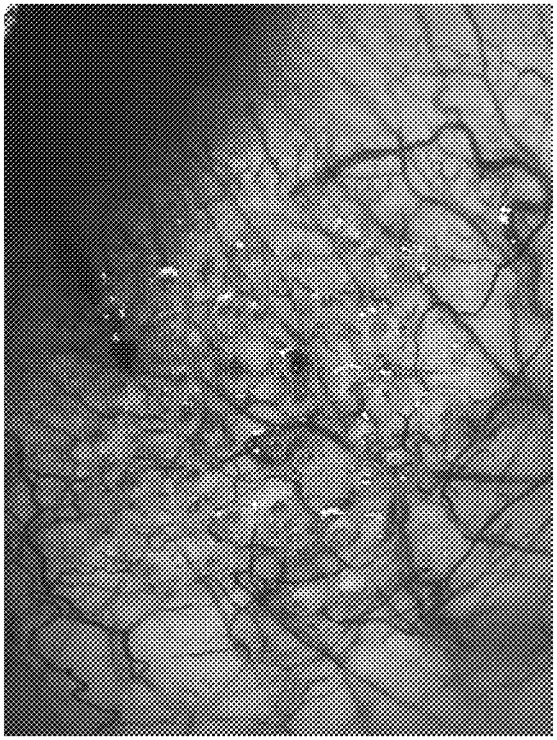
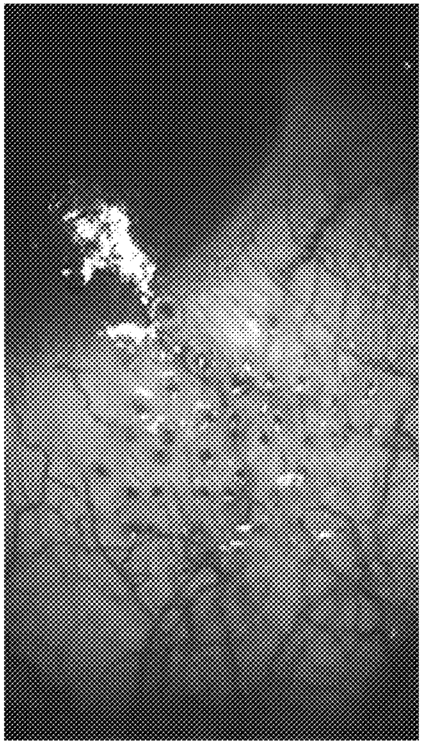
Magnification factor = 0.4 x–2.4 x
Zoom ratio 1 : 6
Resolution: 1,680 x 1,050
Fig. 58: Microscope quality camera images at a higher magnification and resolution for inspecting treatment area and manual treatment positioning

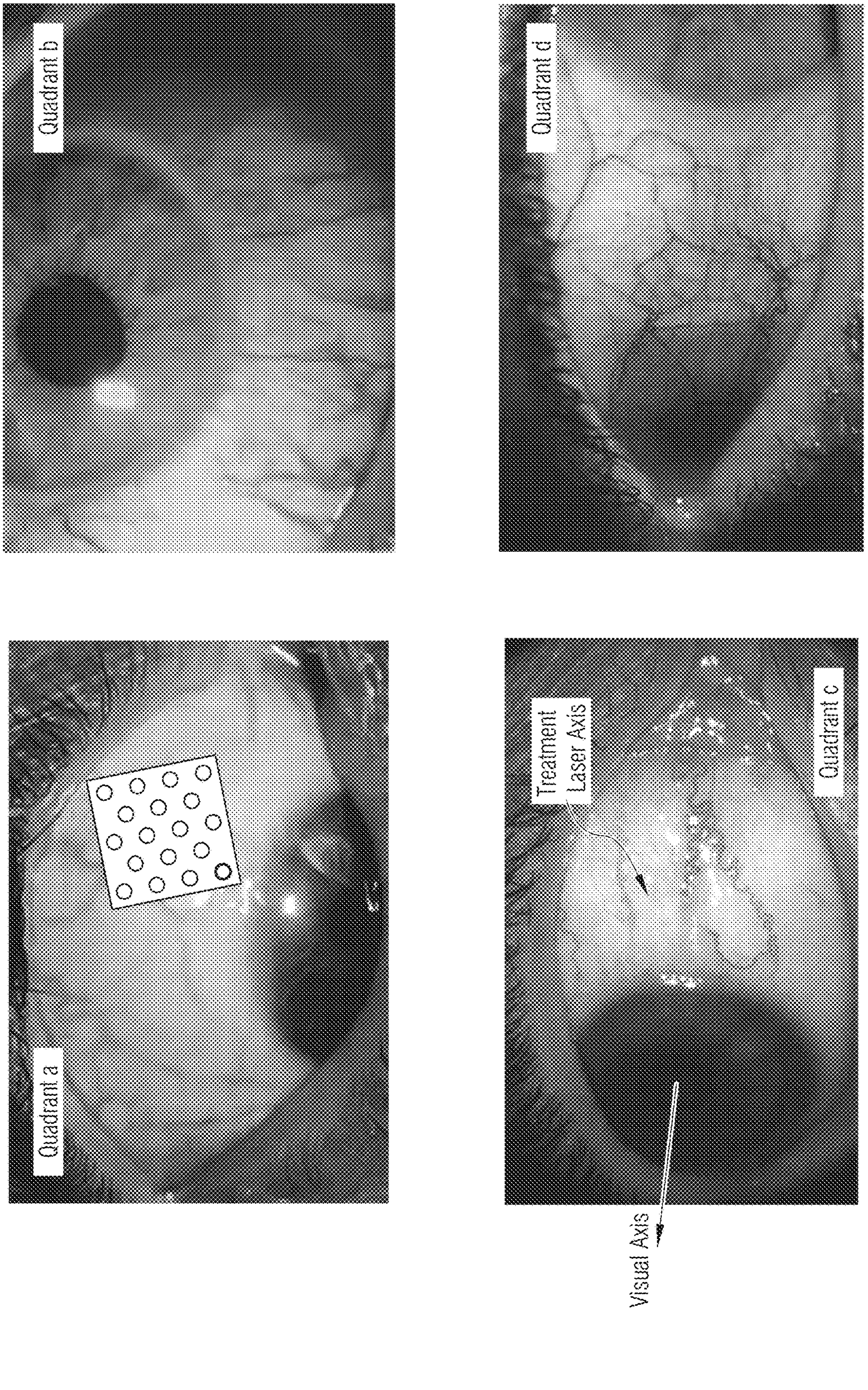
Fig. 60: Extreme eye movements by Off-Axis Scanning laser, beam NOT coincident with the visual axis or the pupil Planning with static image

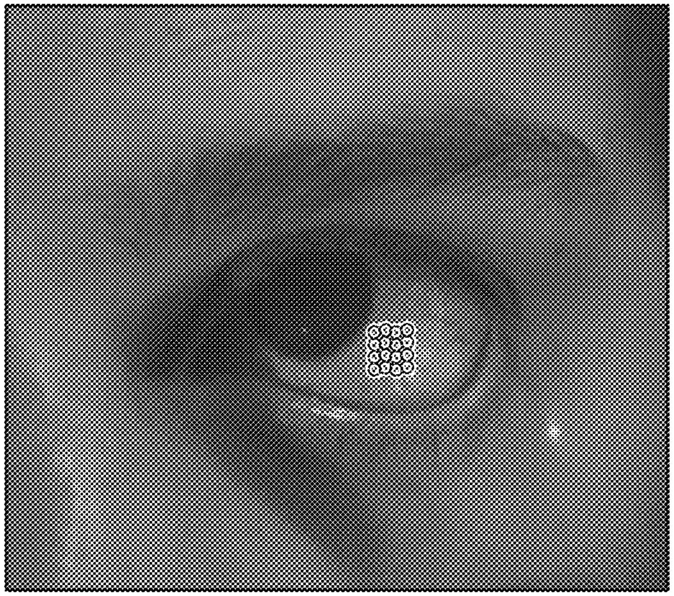

Planning could be done by means of:
- Manual pointing the laser so the projected treatment pattern positioned to limbus
- Also could be done automatically based on OCT scan for limbus and then position to it.
- The doctor could have the ability to modify automatic positioning Feature detection in static image

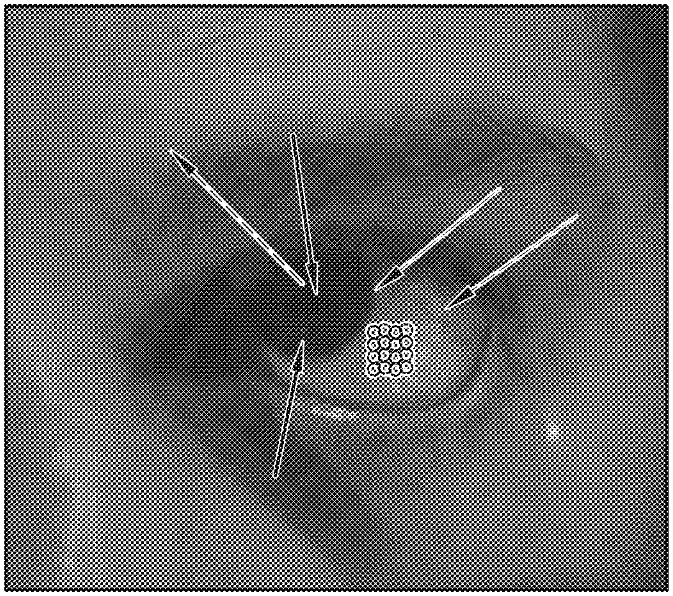

Planning could be done by means of
Feature detection from static Camera images:
- Modification of Planning position could be altered
- Individual pores deleted from plan based on vascular features
- The doctor could have the ability to modify automatic positioning Fig. 61A: Methods for Treatment Positioning and Anatomy Avoidance Feature detection in live image Transformation from static to live image

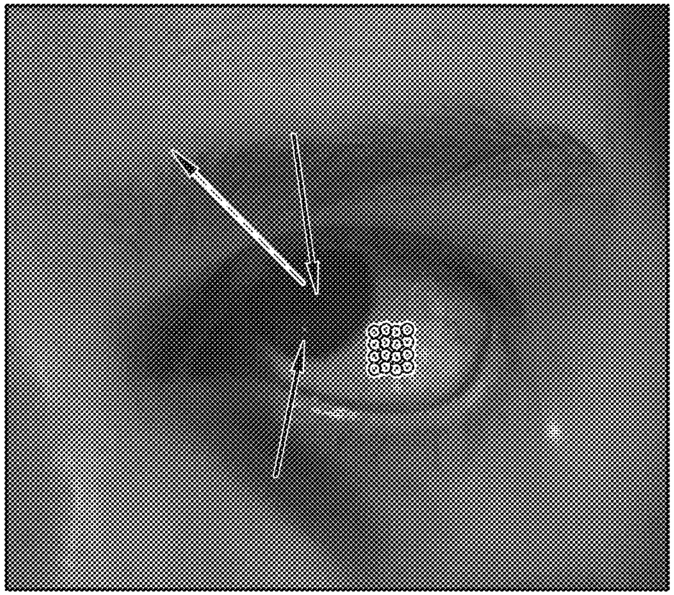

Planning could be done by means of
Feature detection from static Camera images:

- Modification of Planning position could be altered
- individual pores deleted from plan based on vascular features
- The doctor could have the ability to modify automatic positioning

- Transformation, scale and align all coordinate systems

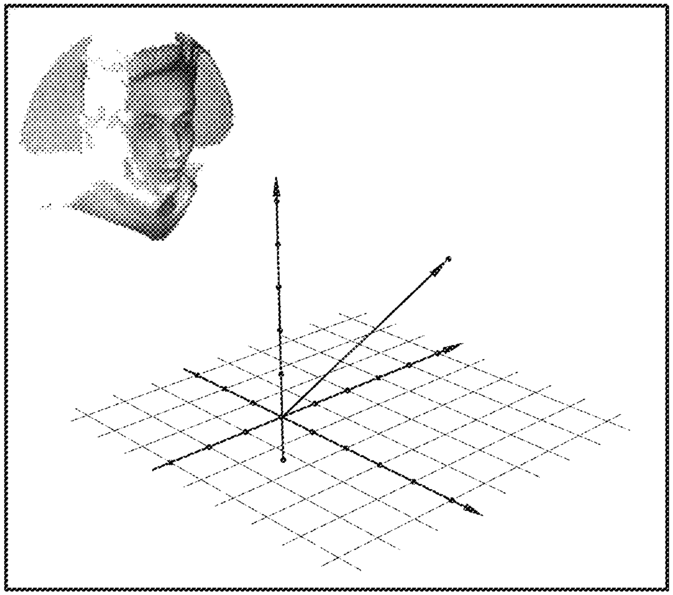

COORDINATE SYSTEMS FOR CAMERA IMAGE, TOF CAMERA IMAGE, AND GUI TREATMENT POSITION SIMULATION IMAGE ARE SCALED AND POSITIONED TO A COMMON GLOBAL POINT

Fig. 61B: Methods for Treatment Positioning and Anatomy Avoidance

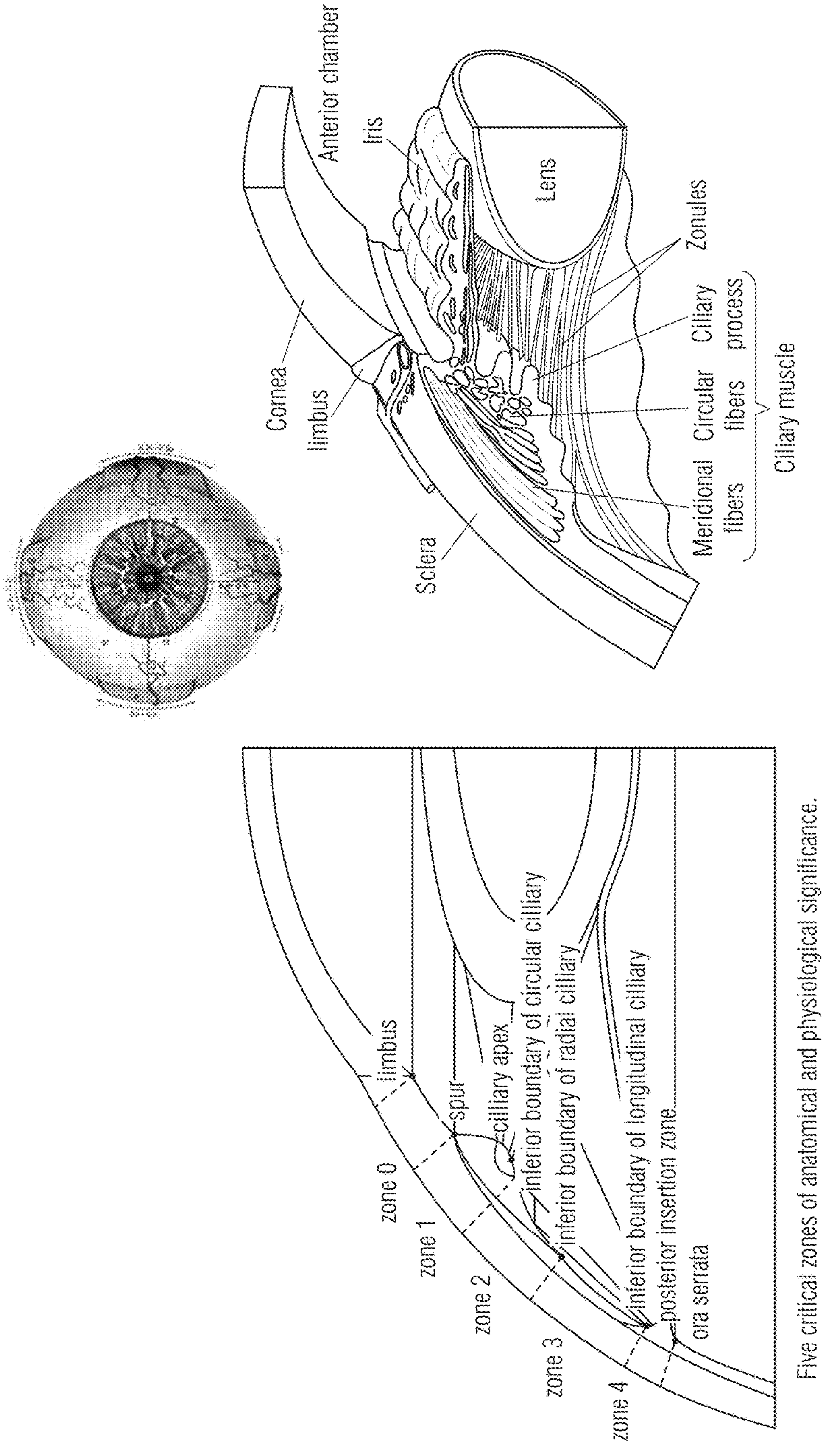
Fig. 67: Anterior Segment 5 Critical Zones

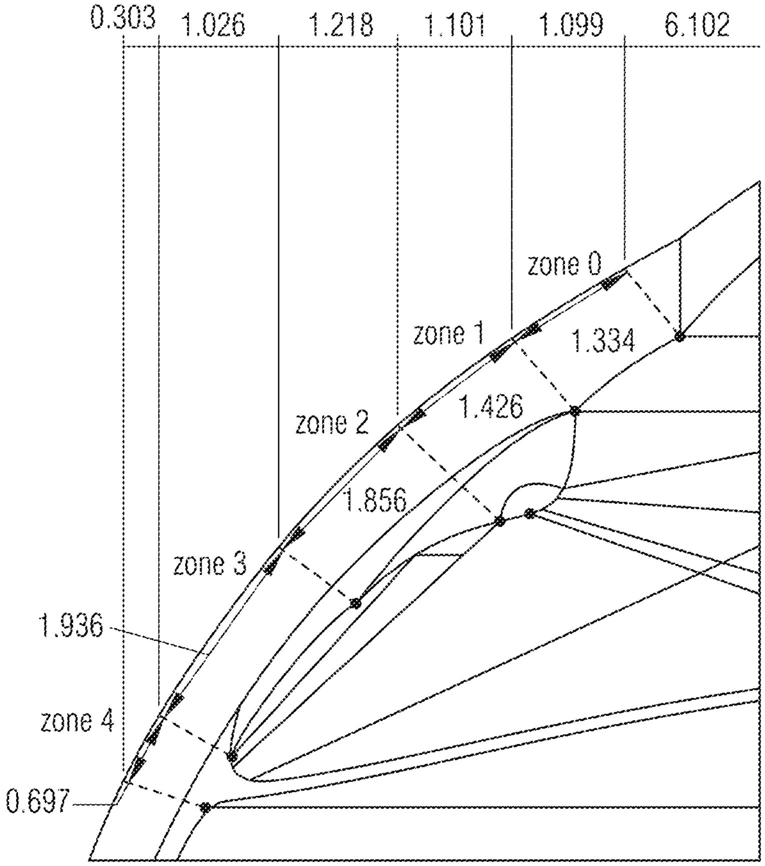

Five critical zones of anatomical and physiological significance.

- Zone 0) 0.0-1.3mm from anatomical limbus (AL); distance from the AL to the superior boundary of Schlemm's canal/scleral spur/ciliary muscle;
- Zone 1) 1.3-2.8mm from AL; distance from the sclera spur to the inferior boundary of the circular muscle;
- Zone 2) 2.8-4.7mm from AL; distance from the inferior boundary of the circular muscle to the inferior boundary of the radial muscle;
- Zone 3) 4.7-6.6mm from AL; inferior boundary of the radial muscle to the superior boundary of the posterior vitreous zonule zone; and
- Zone 4) 6.6-7.3mm from AL; superior boundary of the posterior vitreous zonule zone to the superior boundary of the ora serrata.

Fig. 68: 5 Critical Anterior Zones

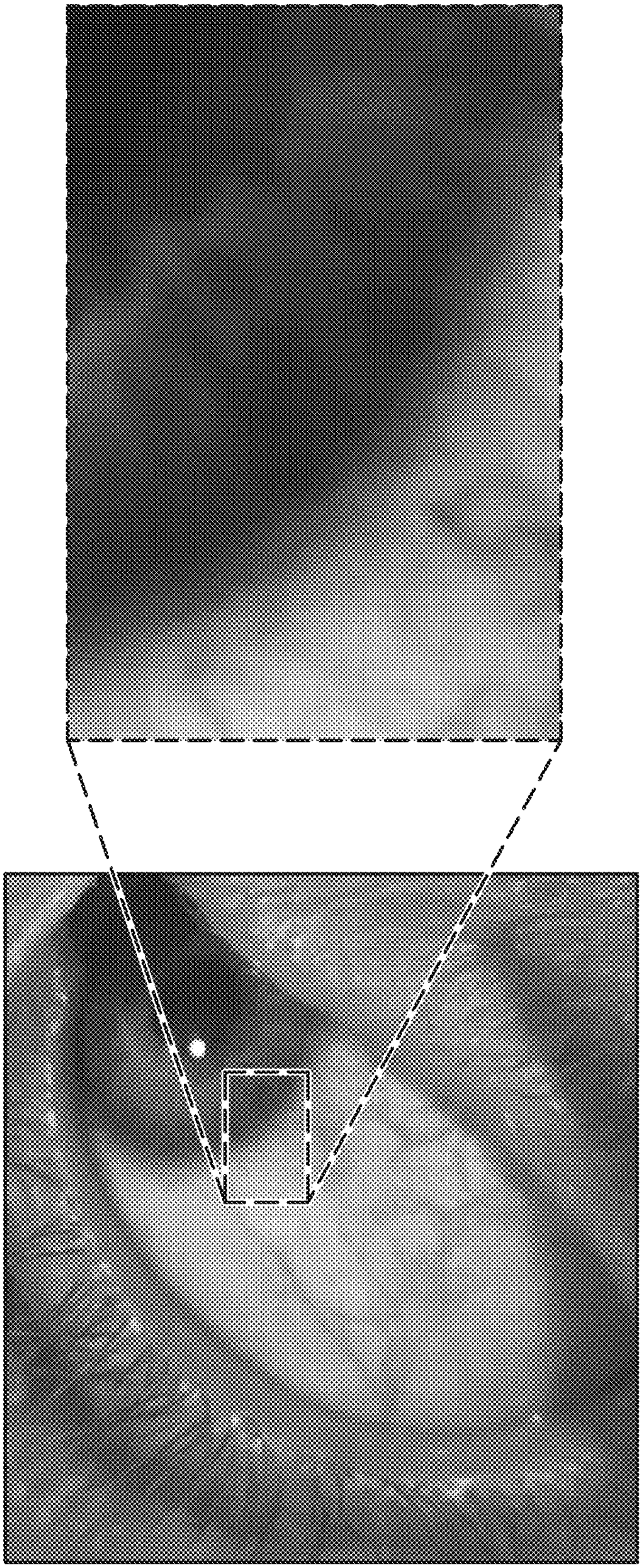
Fig. 69: Camera image on GUI shows High Resolution - Zoom Feature to show anatomical limbus as reference for Treatment Positioning

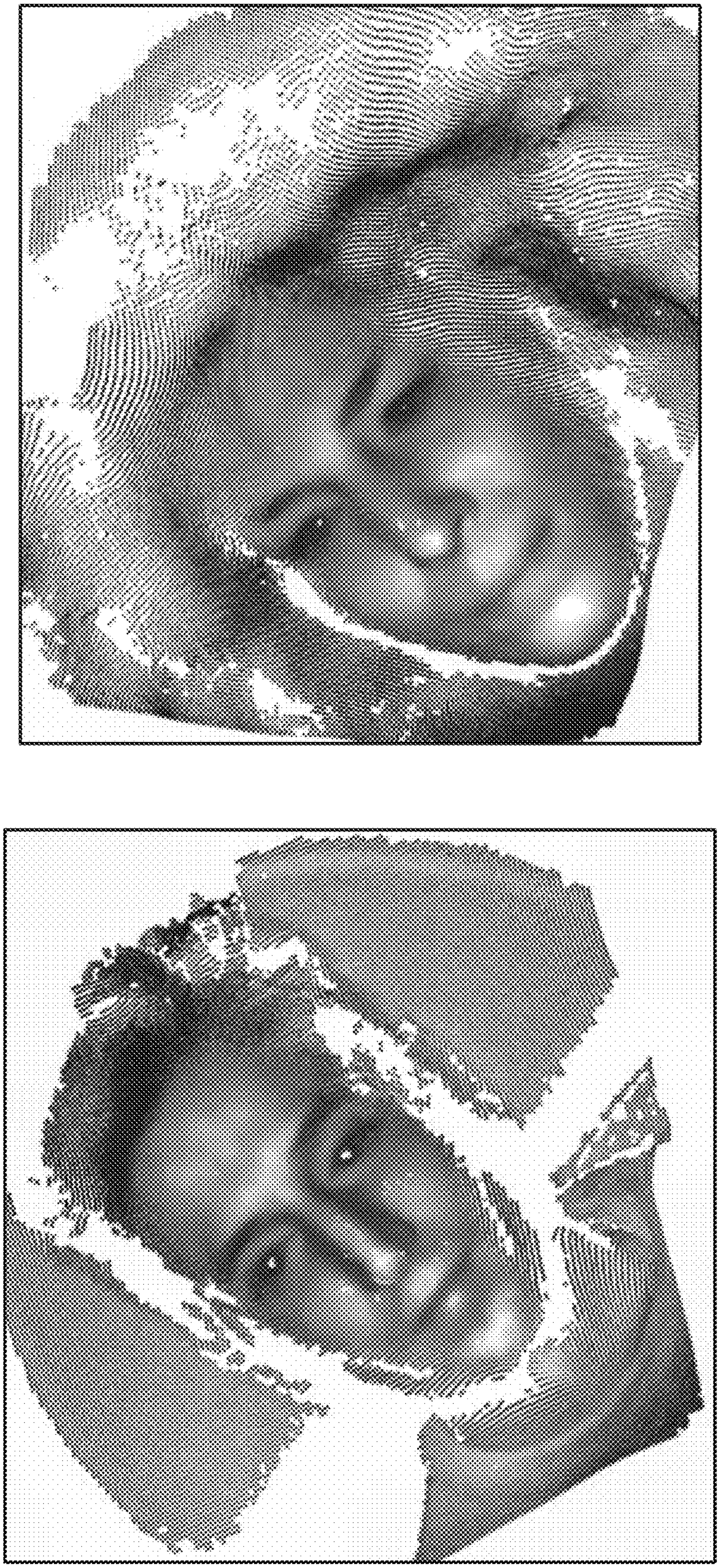
Fig. 70: TIME OF FLIGHT (TOF) camera images for positioning of the patient for treatment under the Laser Head

- Semi-Automated
- Non-Contact
- Treatment <10 min
- Real Time Depth Control
- Real Time OCT Imaging
- Innovative Eye Tracking
- Superior Safety Fig. 72: System with Patient Chair – rolling table or pivoting table or chair Fig. 73: Laser Head positions for each quadrant around facial features Fig. 74: Underside of the Laser Head System showing:
Camera(s), Illumination Sources, Laser Cross and TOF Camera Fig. 75: Bottom view of the Laser Head complete Fig. 76: System with Ablation Plume Removal Fig. 77: Treatment laser and Eye Fixation System Fig. 78: Laser Head System Motions in No Galvo system Fig. 79: Swivel and Translation motions Fig. 80A: Off Axis Laser Head positions for 1 eye Fig. 80B: Off Axis Laser Head positions for 1 eye

| Eye position | Treatment Angle [°] | Pitch [°] | Yaw [°] | x-Axis [mm] | Swivel [°] | Z-Axis [mm] |
|---|---|---|---|---|---|---|
| Eye right Q1 77mm | 28 | 62.58 | -5.89 | 136.99 | 56.18 | 297.94 |
| Eye right Q2 77mm | 28 | 62.3 | -4.27 | 190.69 | 143.06 | 297.95 |
| Eye right Q3 77mm | 28 | 62.3 | -4.27 | 190.69 | 216.94 | 297.95 |
| Eye right Q4 77mm | 23 | 67.71 | -5.83 | 109.99 | 301.09 | 310.83 |
| Eye left Q1 77mm | 28 | 62.58 | -5.89 | 136.99 | 123.82 | 297.94 |
| Eye left Q2 77mm | 28 | 62.3 | -4.27 | 190.69 | 36.94 | 297.95 |
| Eye left Q3 77mm | 28 | 62.3 | -4.27 | 190.69 | 323.06 | 297.95 |
| Eye left Q4 77mm | 23 | 67.71 | -5.83 | 109.99 | 238.91 | 310.83 |
| Eye right Q1 55mm | 25 | 65.3 | -3.98 | 127.1 | 53.58 | 305.98 |
| Eye right Q2 55mm | 28 | 62.17 | -3.19 | 182.02 | 141.02 | 297.96 |
| Eye right Q3 55mm | 28 | 62.17 | -5.19 | 182.02 | 218.98 | 297.96 |
| Eye right Q4 55mm | 16 | 74.5 | -4.00 | 76.49 | 300.86 | 324.75 |
| Eye left Q1 55mm | 25 | 65.3 | -3.98 | 127.1 | 126.42 | 305.98 |
| Eye left Q2 55mm | 28 | 62.17 | -3.19 | 182.02 | 38.98 | 297.96 |
| Eye left Q3 55mm | 28 | 62.17 | -3.19 | 182.02 | 321.02 | 297.96 |
| Eye left Q4 55mm | 16 | 74.5 | -4.01 | 76.49 | 239.14 | 324.75 |
| Max. Difference: | | 62.17 | +5.89 | 114.2 | - | 26.81 |
| | | 74.5 | -5.89 | - | - | - |

See Fig E1 for definition of Pitch, Yaw and Swivel Angles and dimensions shown are for reference only Fig. 81: Details Eye Position per quadrant and treatment angles shown in Figure E1

Fig. 82: Laser Focal and Angular Positions in relation to the top of the eye for off-axis treatment Fig. 84: Laser subsystem to combined treatment laser with fiber based OCT/DC Fig. 85: Laser Subsystem with fixed focus and a small DBS Fig. 86: Using DBS to alter size and shape of beam Fig. 87: Beam profiles for DBS with 150/150 divergent beam

- Attached to handheld suction devise
- Doctor attaches and hold position for treatment
- The glass could be protective from treatment wavelength emissions Fig. 88: Eye Docking Accessory

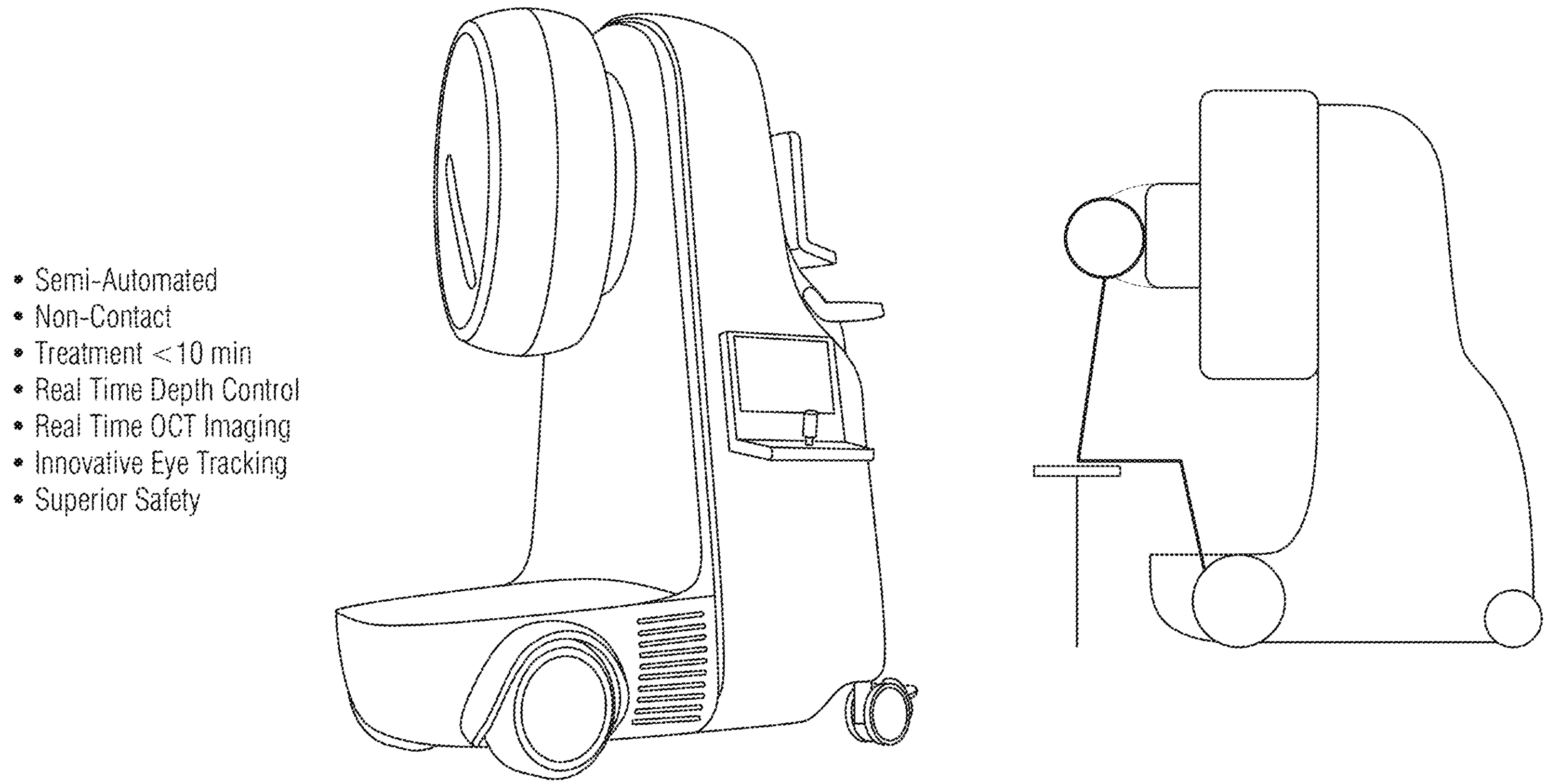
Fig. 90: AVG Product Concept System with patient in the sitting position

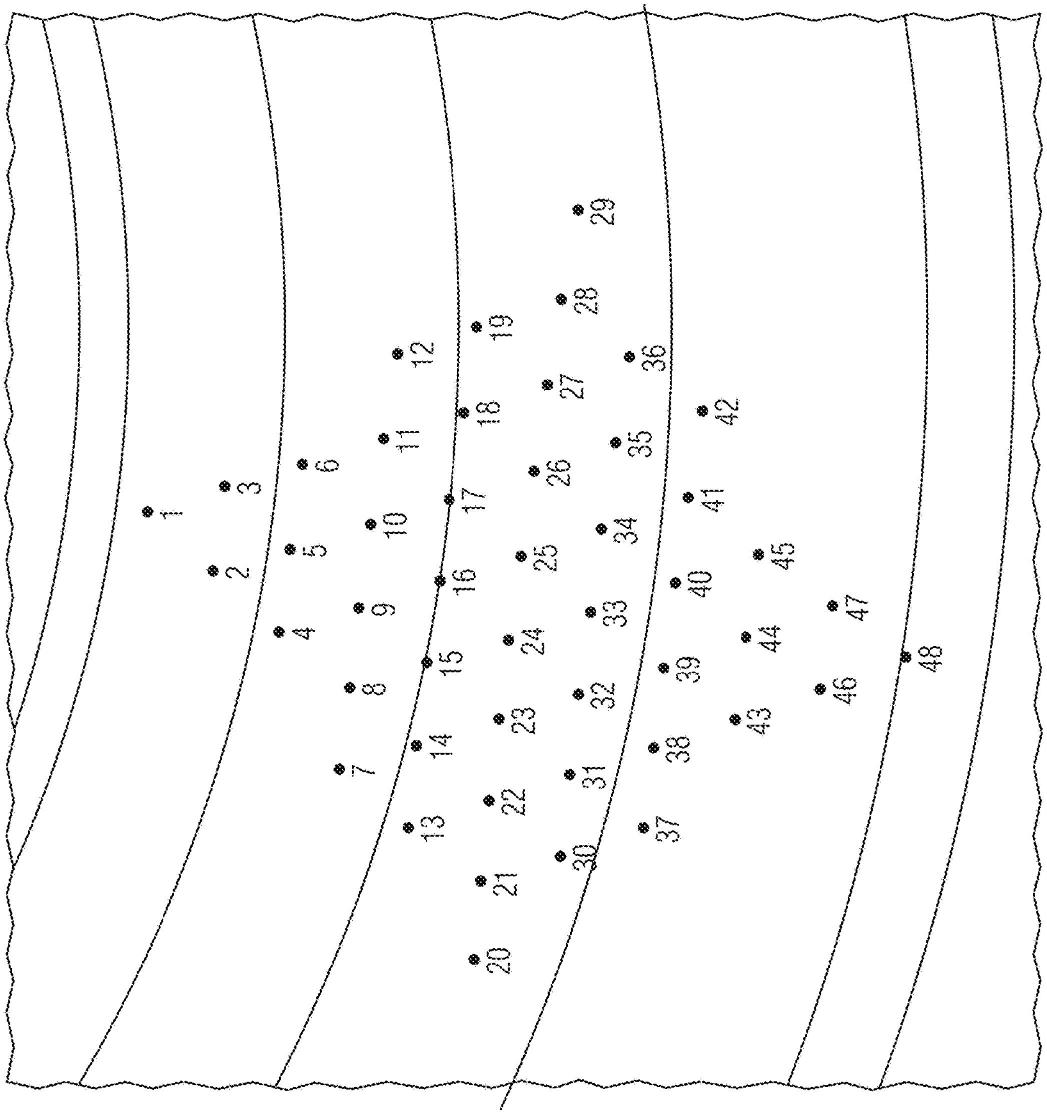
Fig. 91: View of treatment area and numbered micropore treatment order

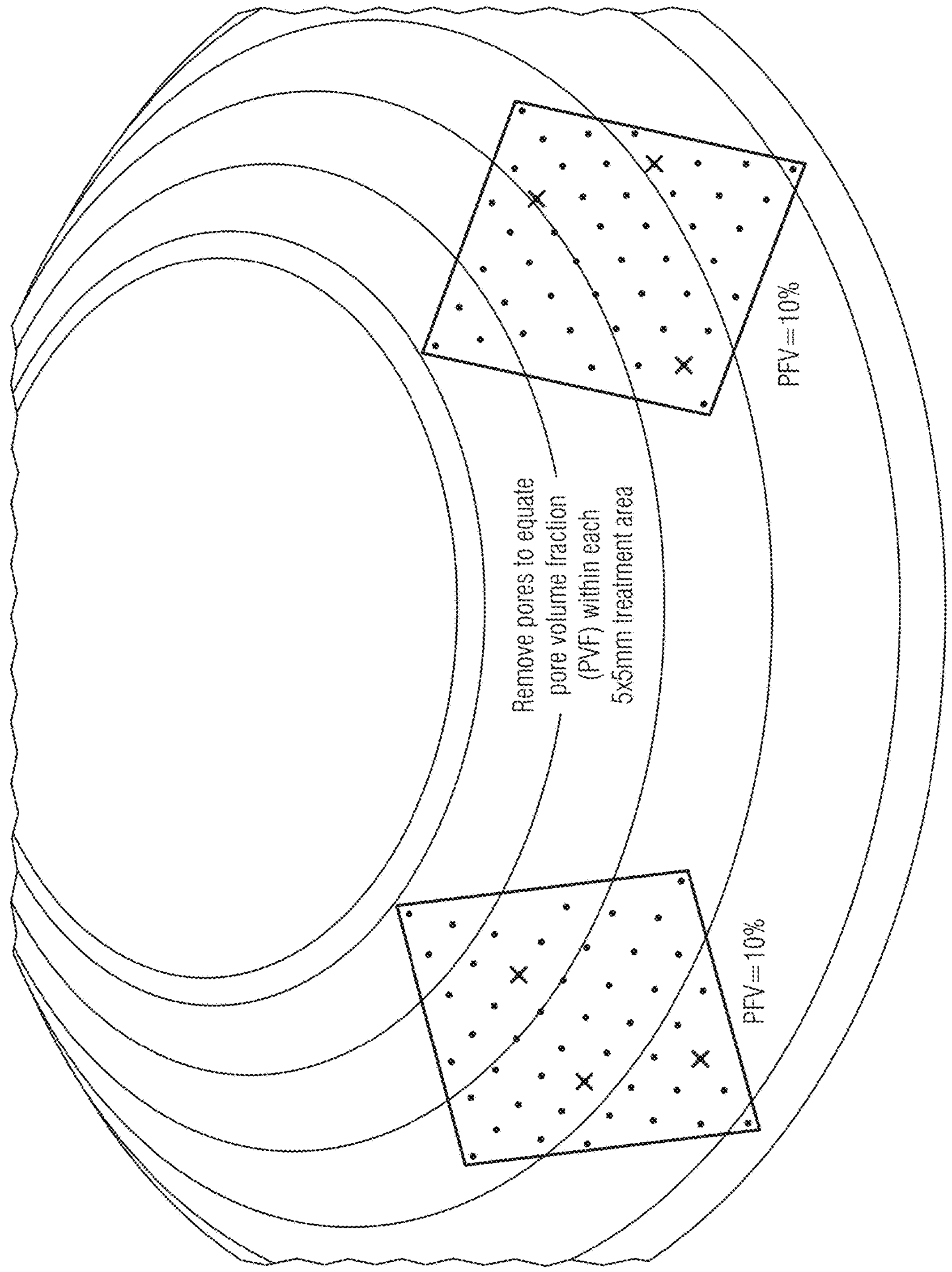
Fig. 92: View of treatment area and zones on eye globe

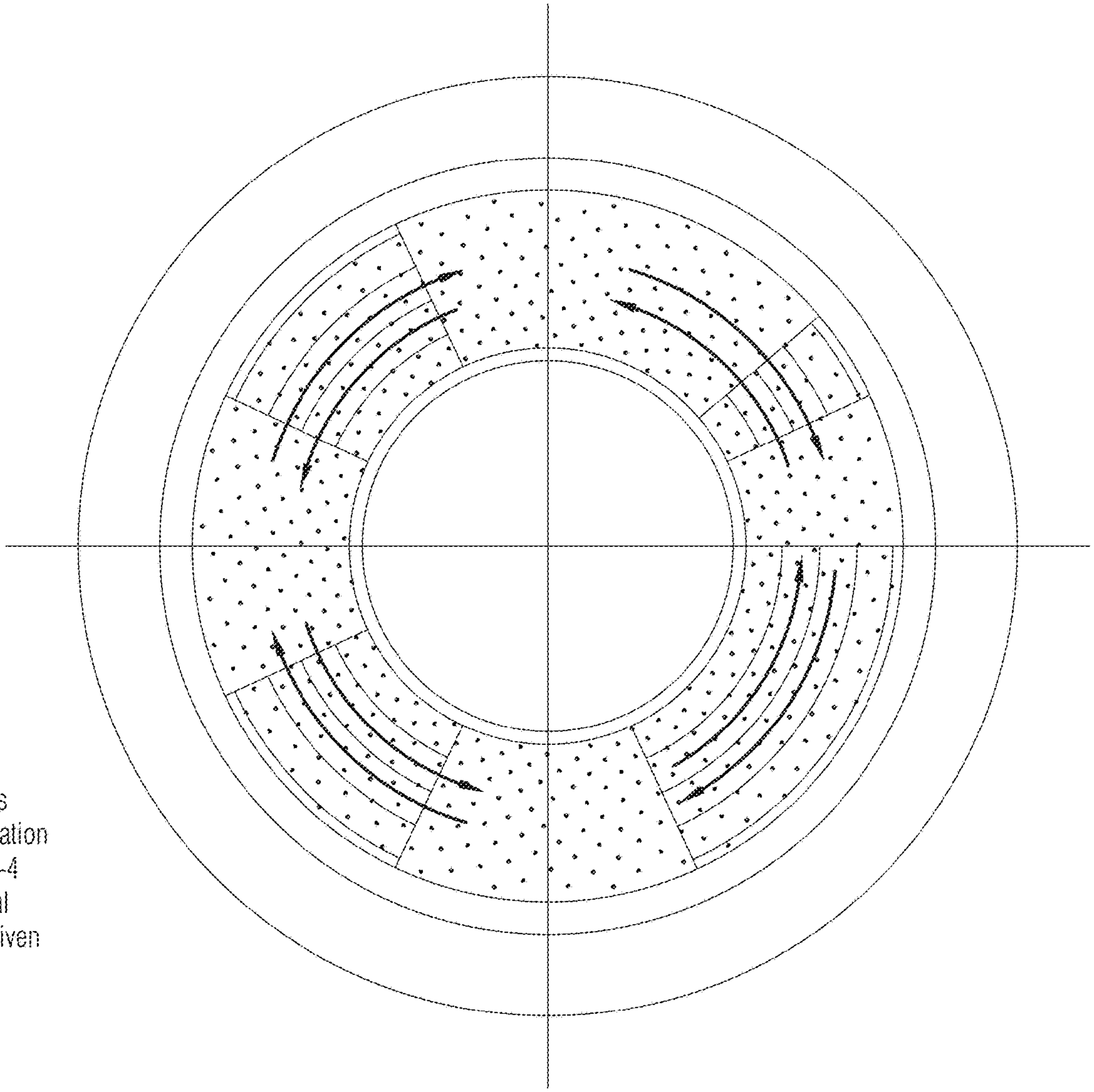
Up to 12 treatment segments could cover 360 degrees rotation around the Limbus, Zones 1-4 that end up treating the spiral micropore locations in the given treatment area
Fig. 93: New Modified Fig 2K-18 Treatment areas for 360degree treatments

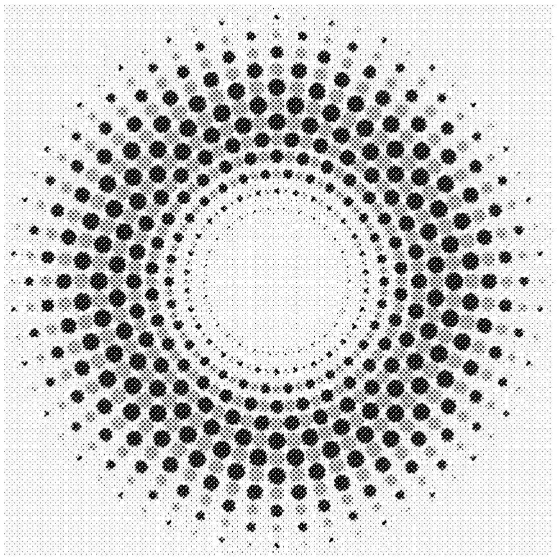
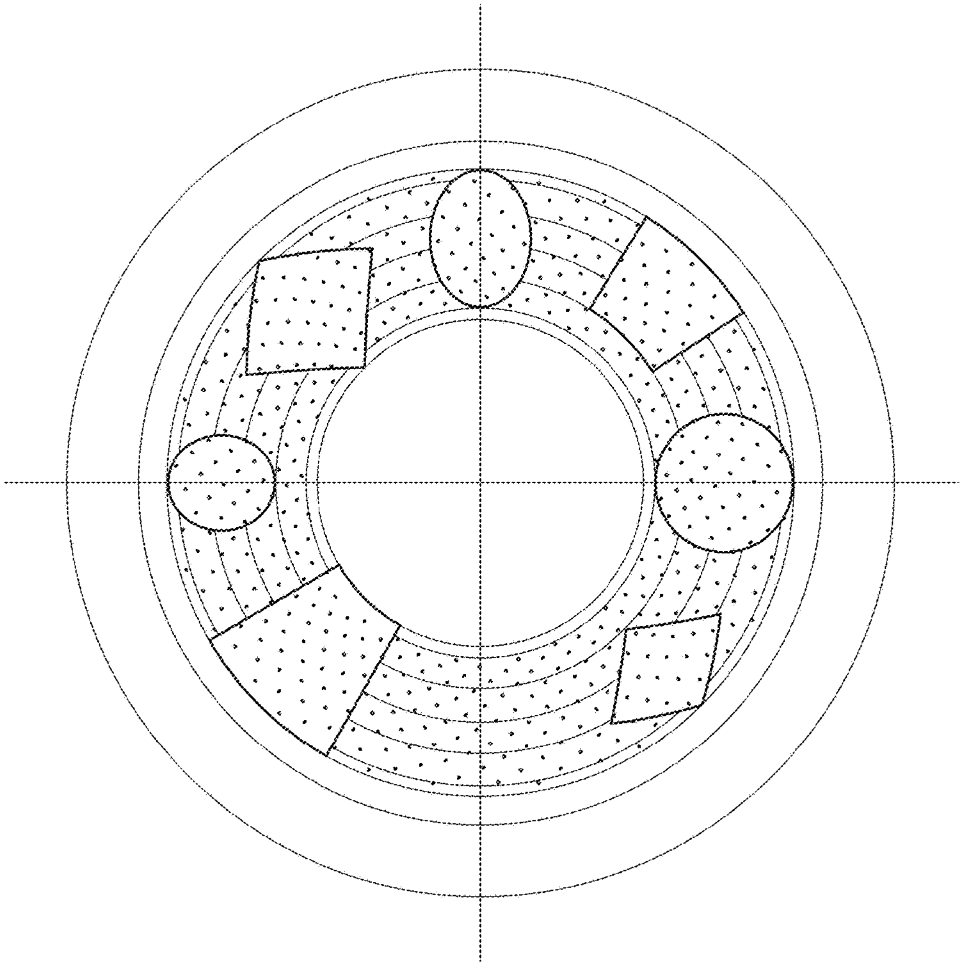
Patterns pre-defined to sum up to a spiral or other 360deg treatment pattern.
Predefined by order, # of pores and pore locations in the pattern
Fig. 94: Golden Spiral created from individual treatment patterns – pattern formation is one pass CW/ one pass CCW for the portion of the pattern in quadrant. Density related

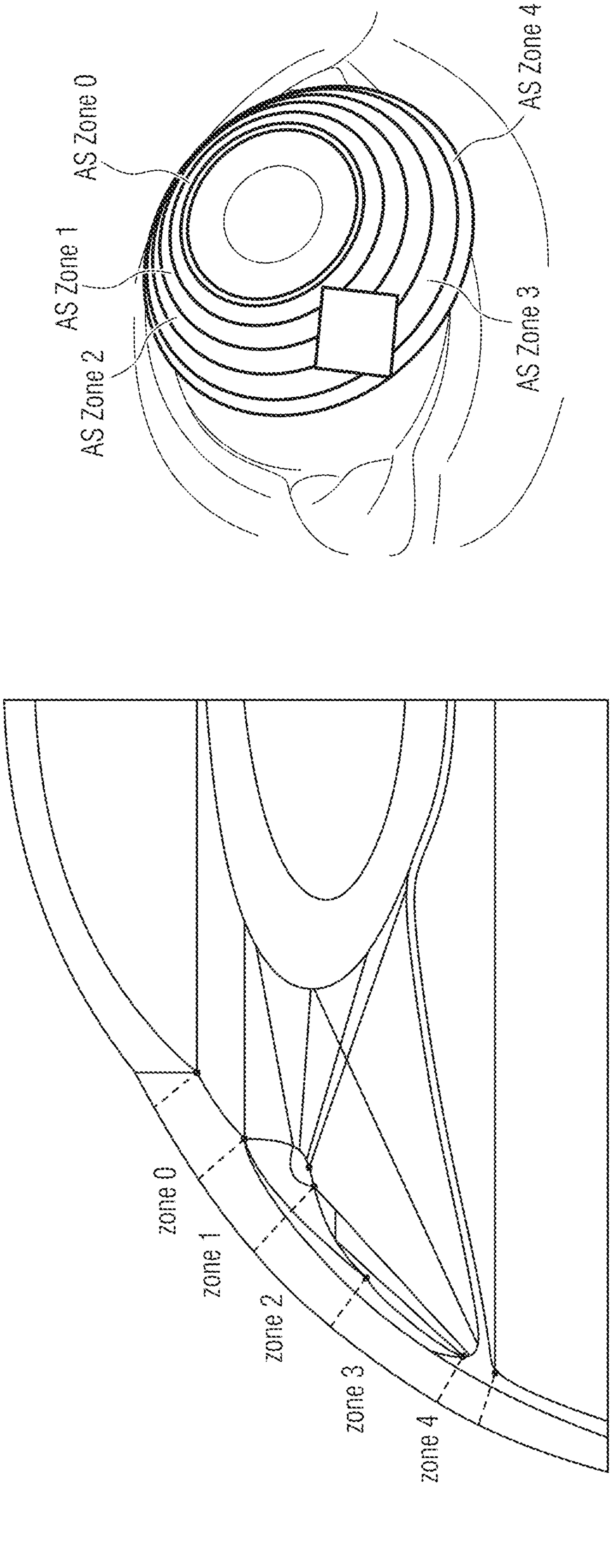
Fig. 95: Anterior Segment 5 Critical Zones

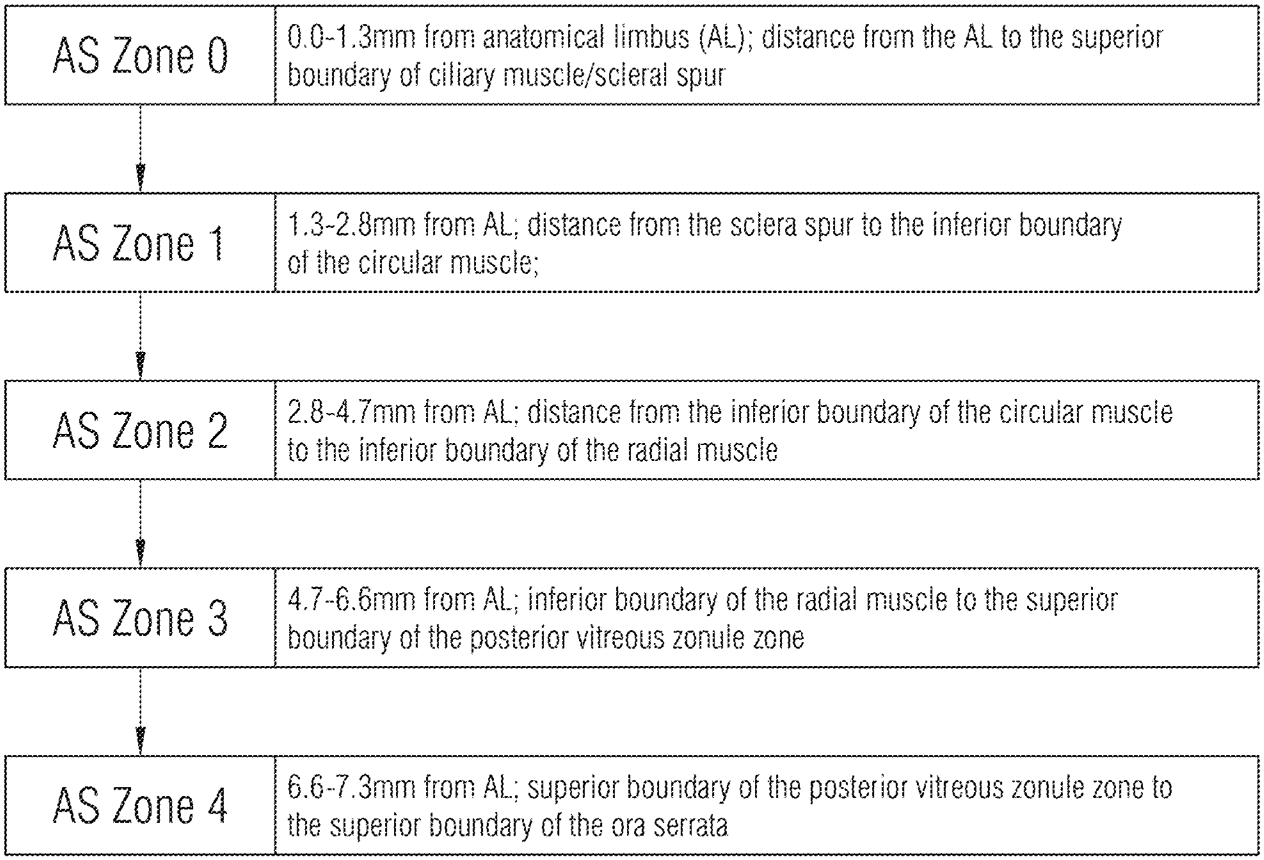
Fig. 96: Anterior Segment Zone Descriptions

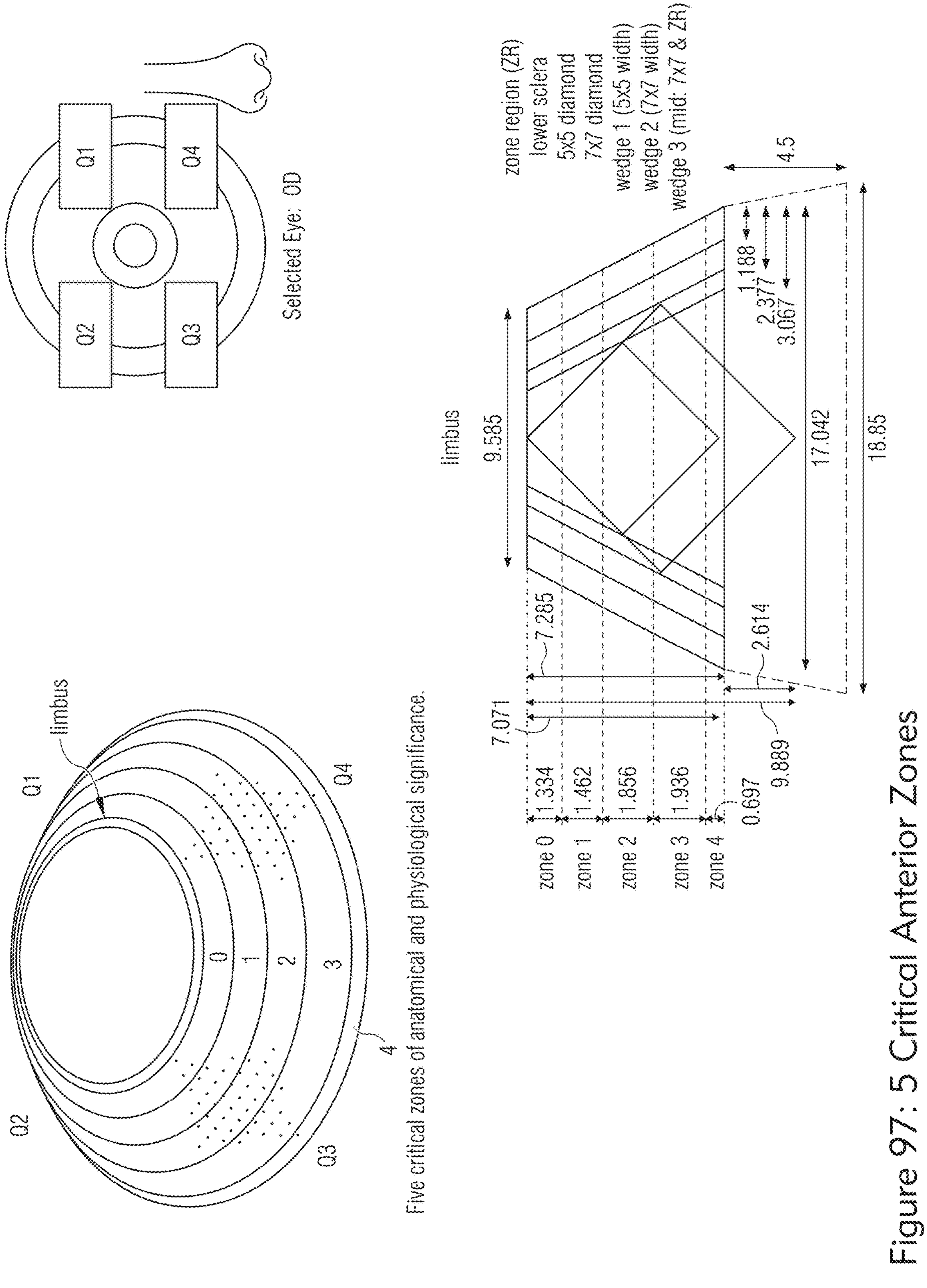
Figure 97: 5 Critical Anterior Zones

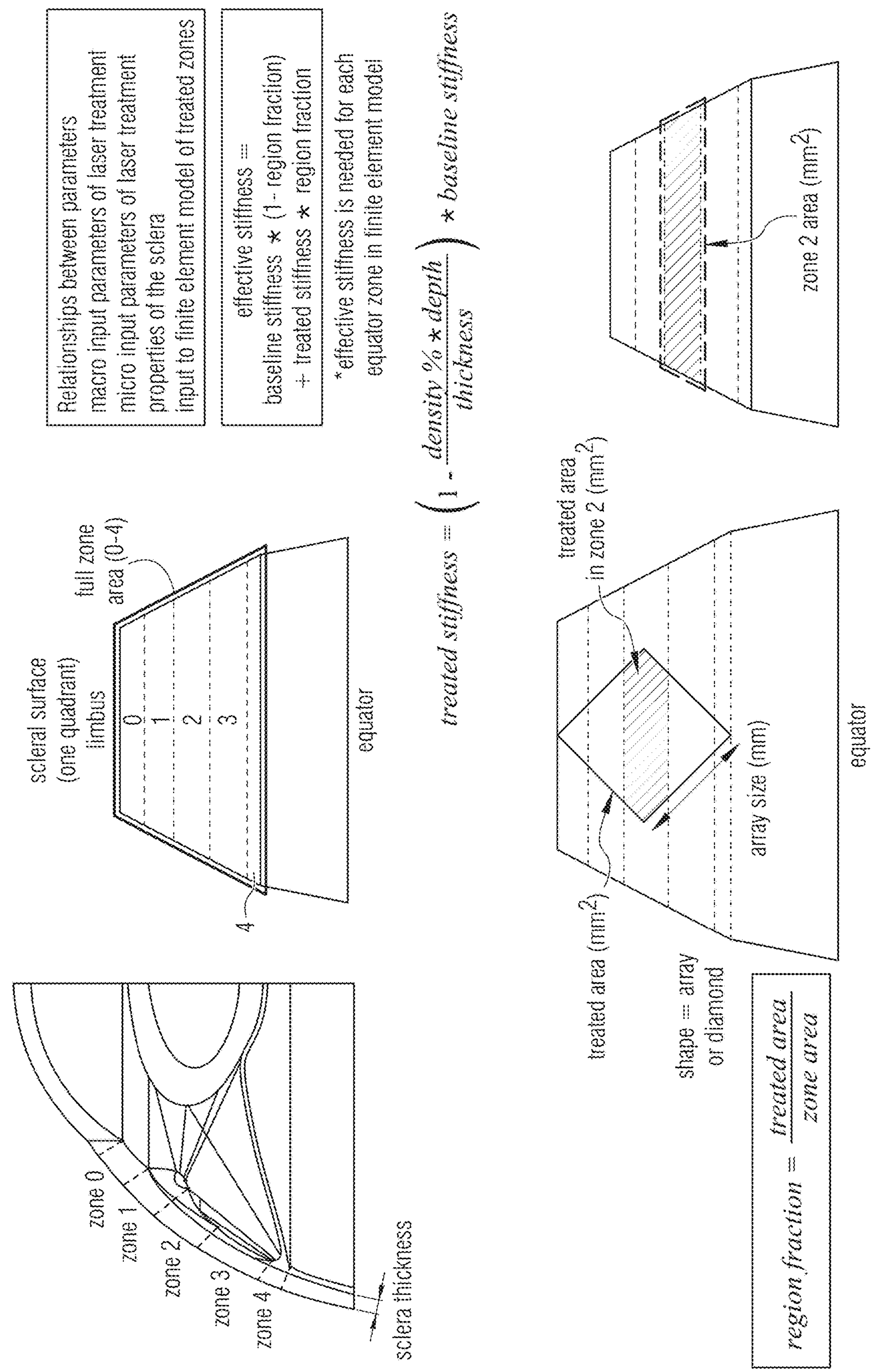
Fig. 98: Macro parameter definitions for Anterior Zones

<u>baseline simulation:</u> original model of healthy accommodation with "old" sclera

- stiff starting sclera: modulus of elasticity (E) = 2.85 MPa, equivalent to ~50 years old
- tight attachment between the sclera and the ciliary/choroid
- All other parameters changed (ciliary activation, stiffness of other components, etc.

<u>shape treatment simulations:</u> baseline model with regionally "treated" sclera stiffness

- treated different area shapes (w/o changing attachment)? treated stiffness: modulus of elasticity (E) = 1.61 MPa, equivalent to ~30 years old*
- effective stiffness in each zone determined by amount of shape area in each zone

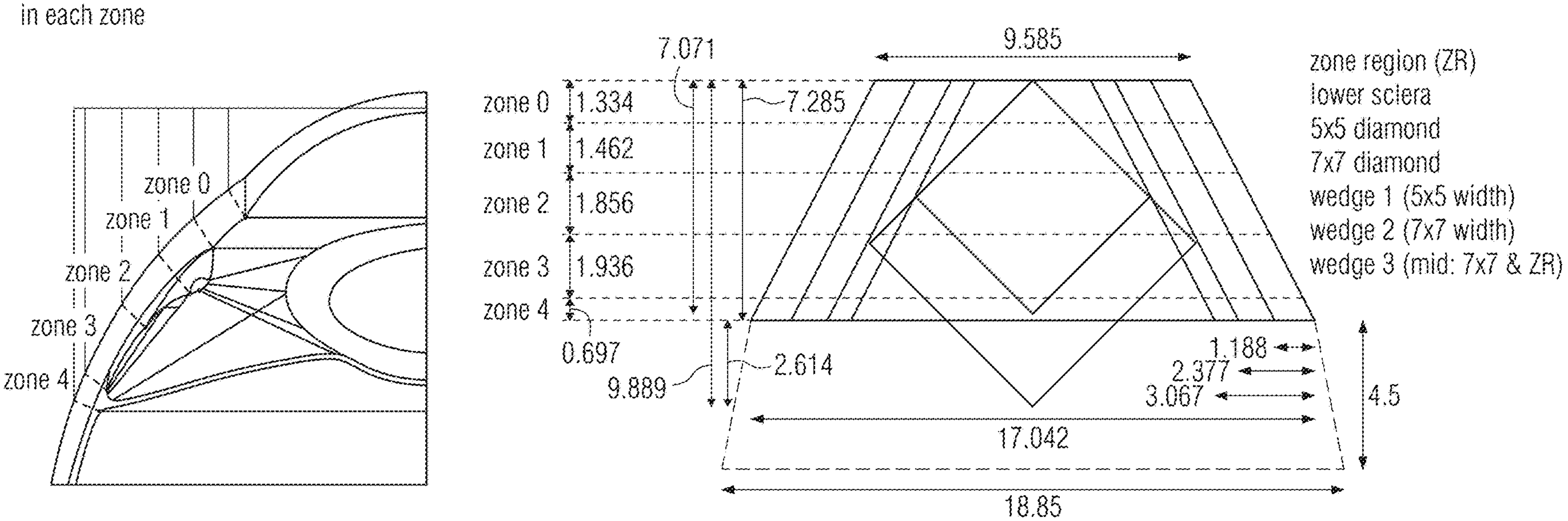

Fig. 99: Different treatment region shapes applied to one sclera Anterior zone quadrant with reference to 5 critical zones

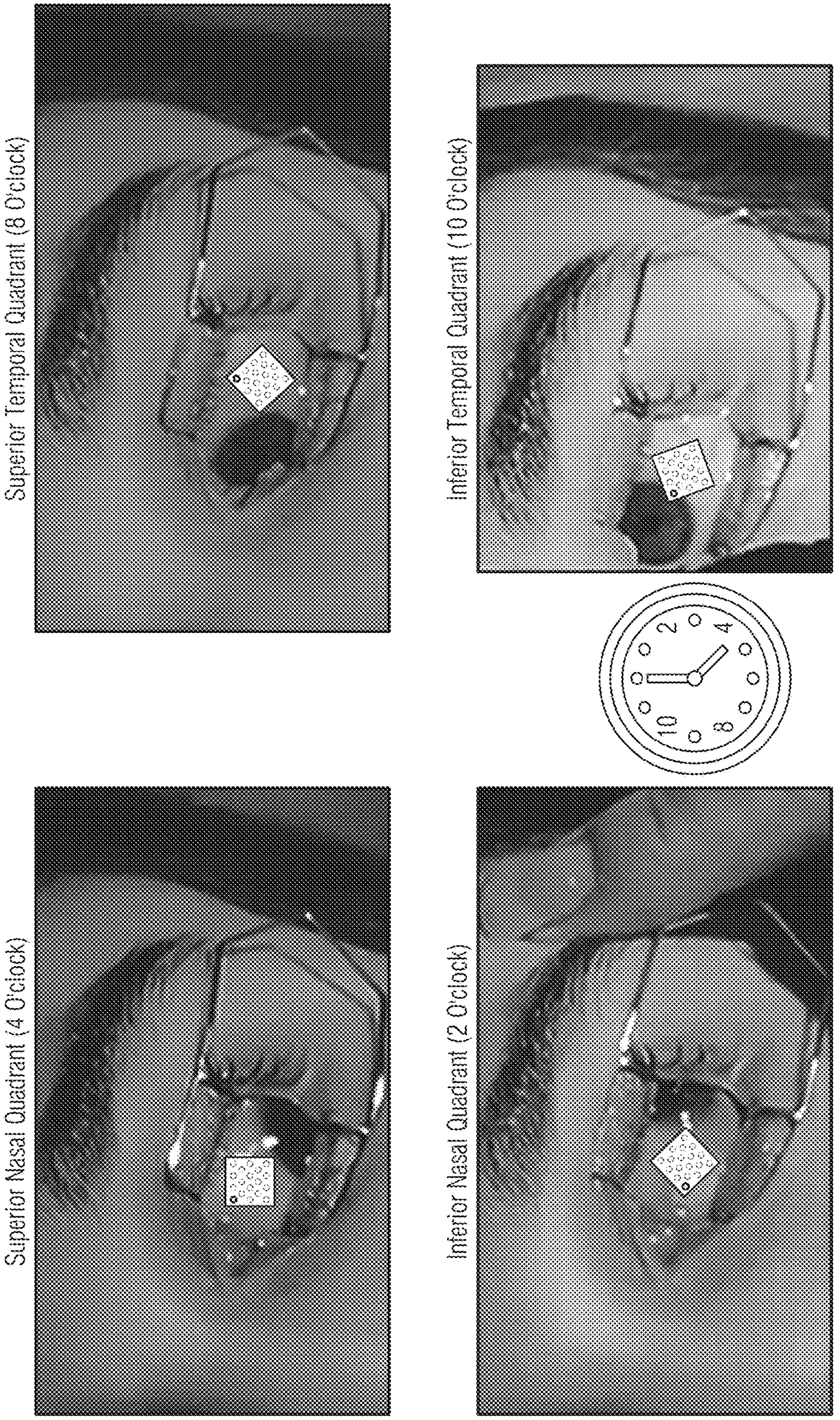
Fig. 100: Four Quadrant Treatment Positions for right eye referenced around the limbus

Figure 101:
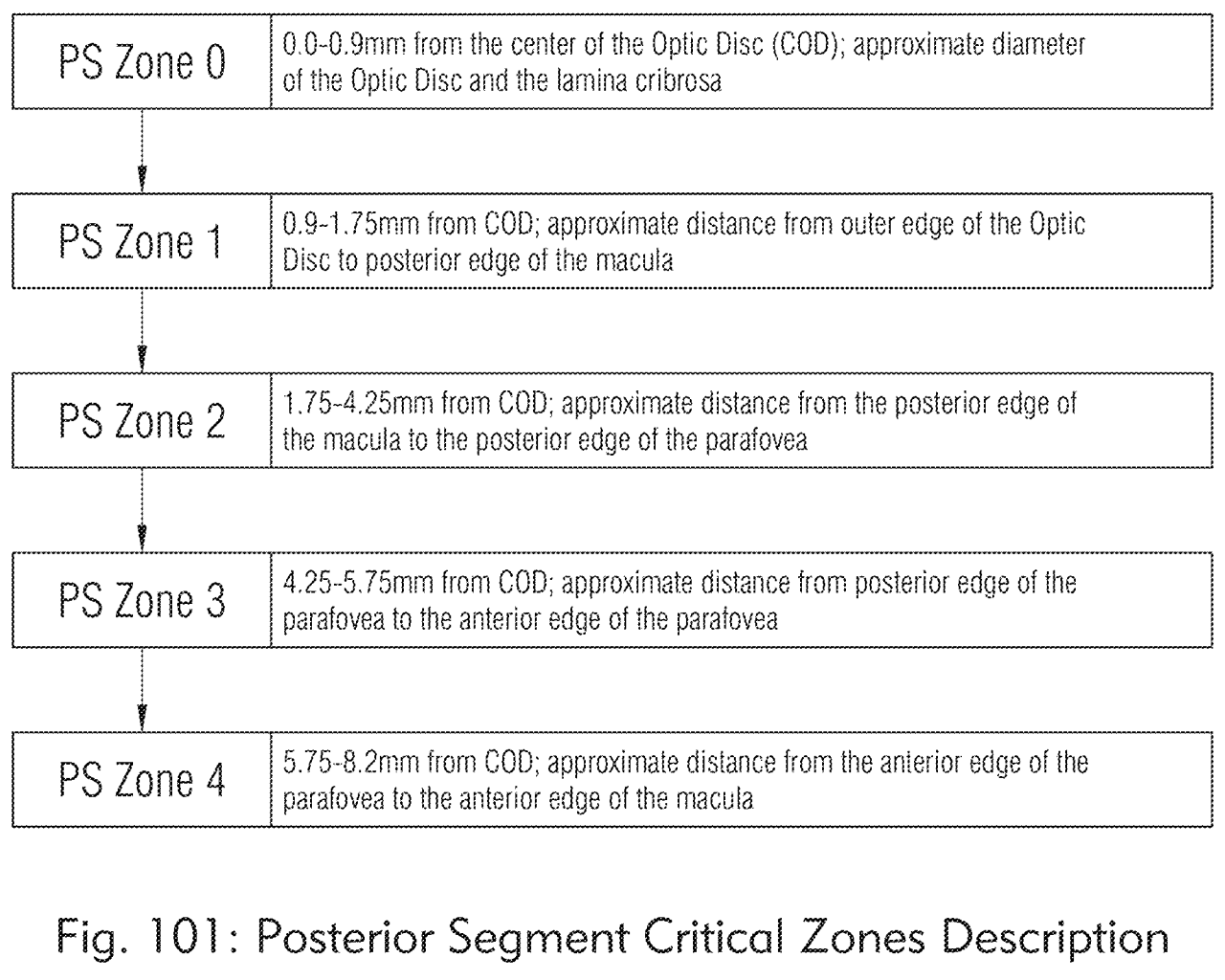

| | |
|---|---|
| PS Zone 0 | 0.0-0.9mm from the center of the Optic Disc (COD); approximate diameter of the Optic Disc and the lamina cribrosa |
| PS Zone 1 | 0.9-1.75mm from COD; approximate distance from outer edge of the Optic Disc to posterior edge of the macula |
| PS Zone 2 | 1.75-4.25mm from COD; approximate distance from the posterior edge of the macula to the posterior edge of the parafovea |
| PS Zone 3 | 4.25-5.75mm from COD; approximate distance from posterior edge of the parafovea to the anterior edge of the parafovea |
| PS Zone 4 | 5.75-8.2mm from COD; approximate distance from the anterior edge of the parafovea to the anterior edge of the macula |

Fig. 101: Posterior Segment Critical Zones Description

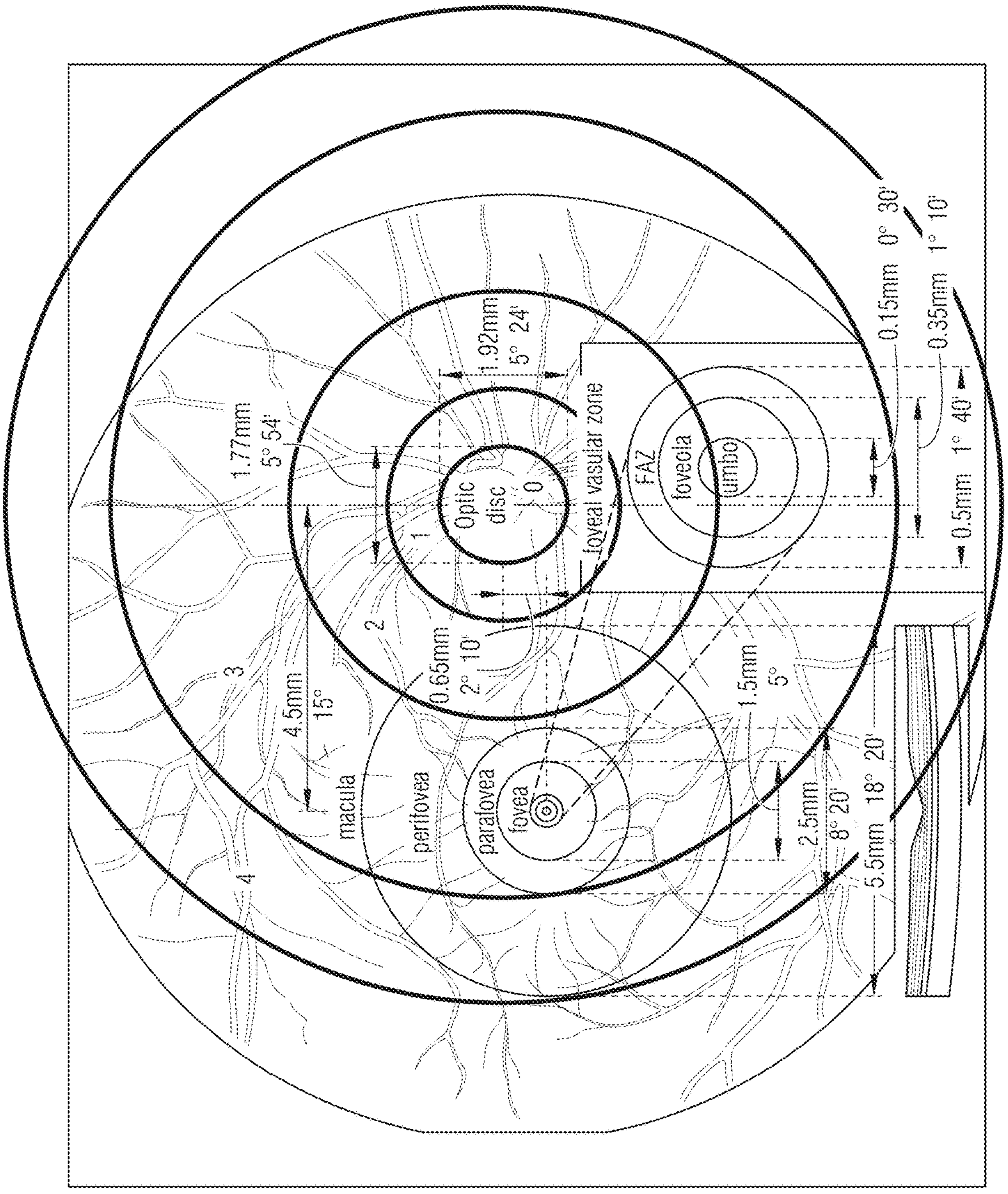
Fig. 102: Posterior Segment 5 Critical Zones

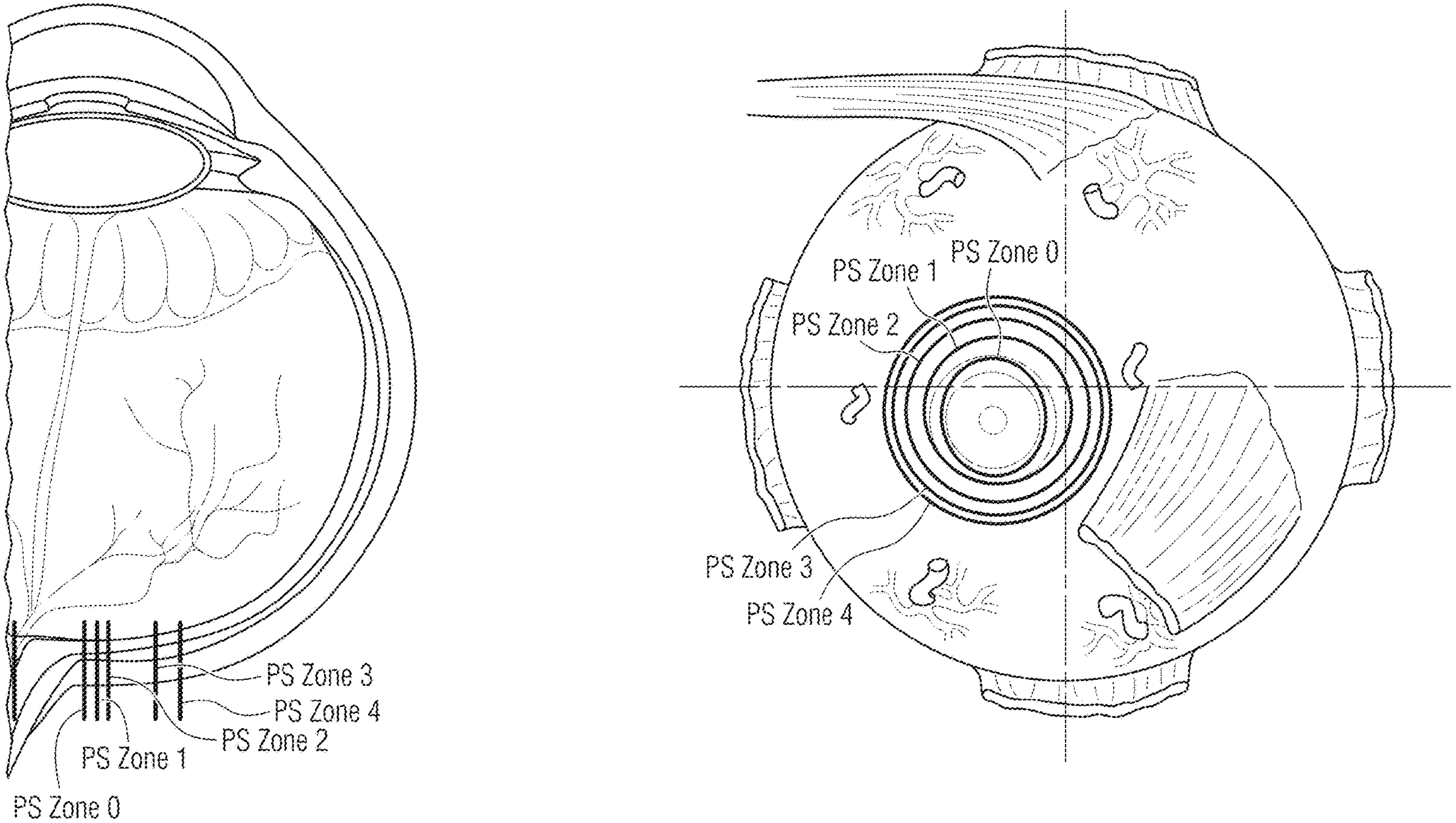

Drawing of the posterior eye. T, temporal; N, nasal. The optic nerve (a) with its central vessels and surrounding meningeal sheaths is seen. Its center is located 3 mm nasal and 1 mm inferior to the posterior pole of the eye. Surrounding it are the short posterior ciliary arteries and nerves. The approximate position of the macula is at x. Along the horizontal meridian, which bisects the eye, are the long posterior cili ary arteries and nerves (b). The exits of four vortex veins are shown, one for each quadrant (c). The curved, oblique insertions of the superior oblique ( d) and inferior oblique (e) muscles are seen. The cut ends of the four rectus muscles are at f. (Hogan M, Alvarado J, Weddell J: Histology of the Human Eye—An Atlas and Textbook. Philadelphia: WB Saunders, 1971:51)

Fig. 103: Posterior Segment 5 Critical Zones

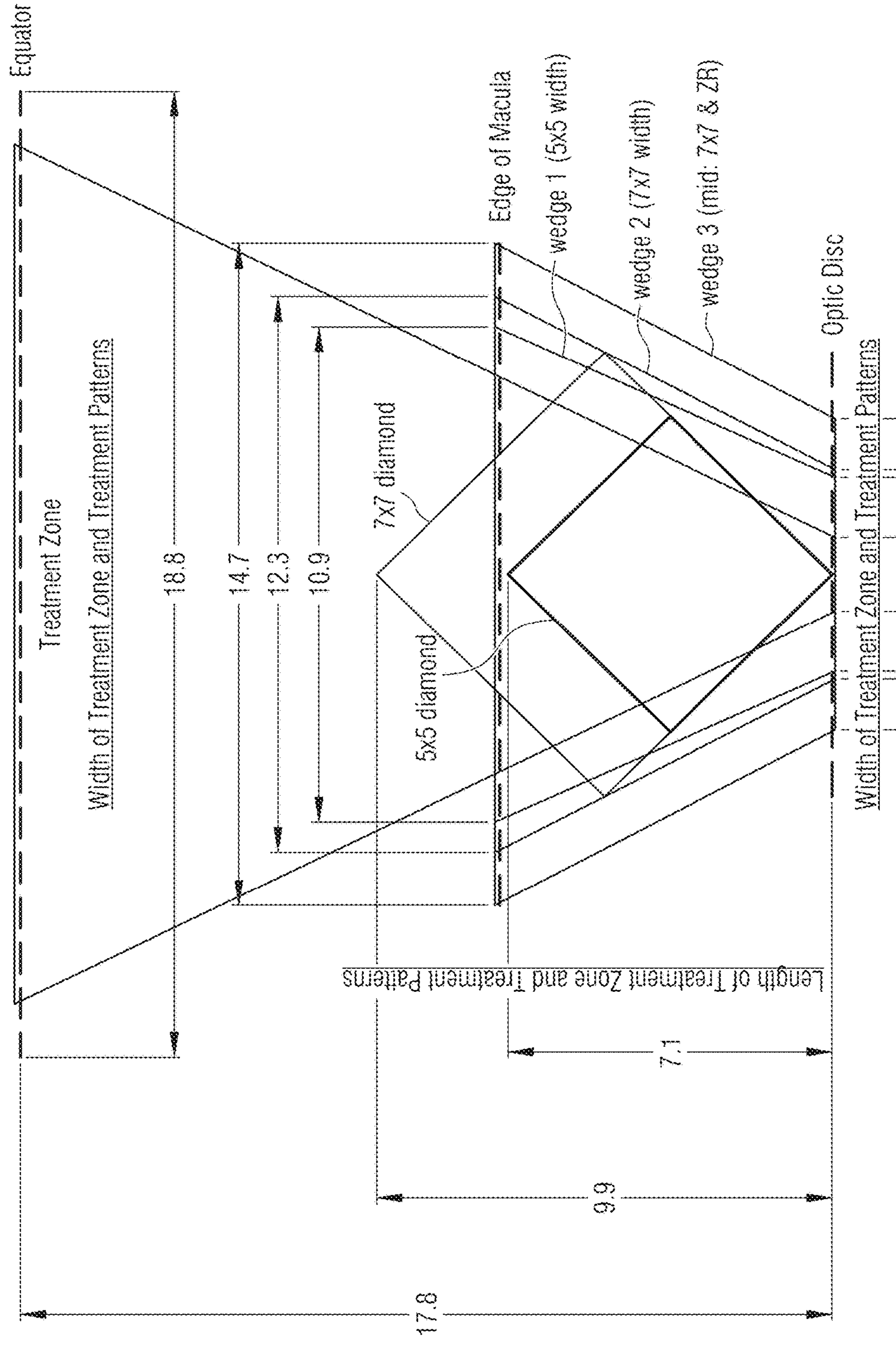
**Dimensions are to scale (1cm = 1mm) and in mm
**Assuming 4 quadrants for treatment
Fig. 104: Plurality of Treatment Zone Posterior Treatment Patterns

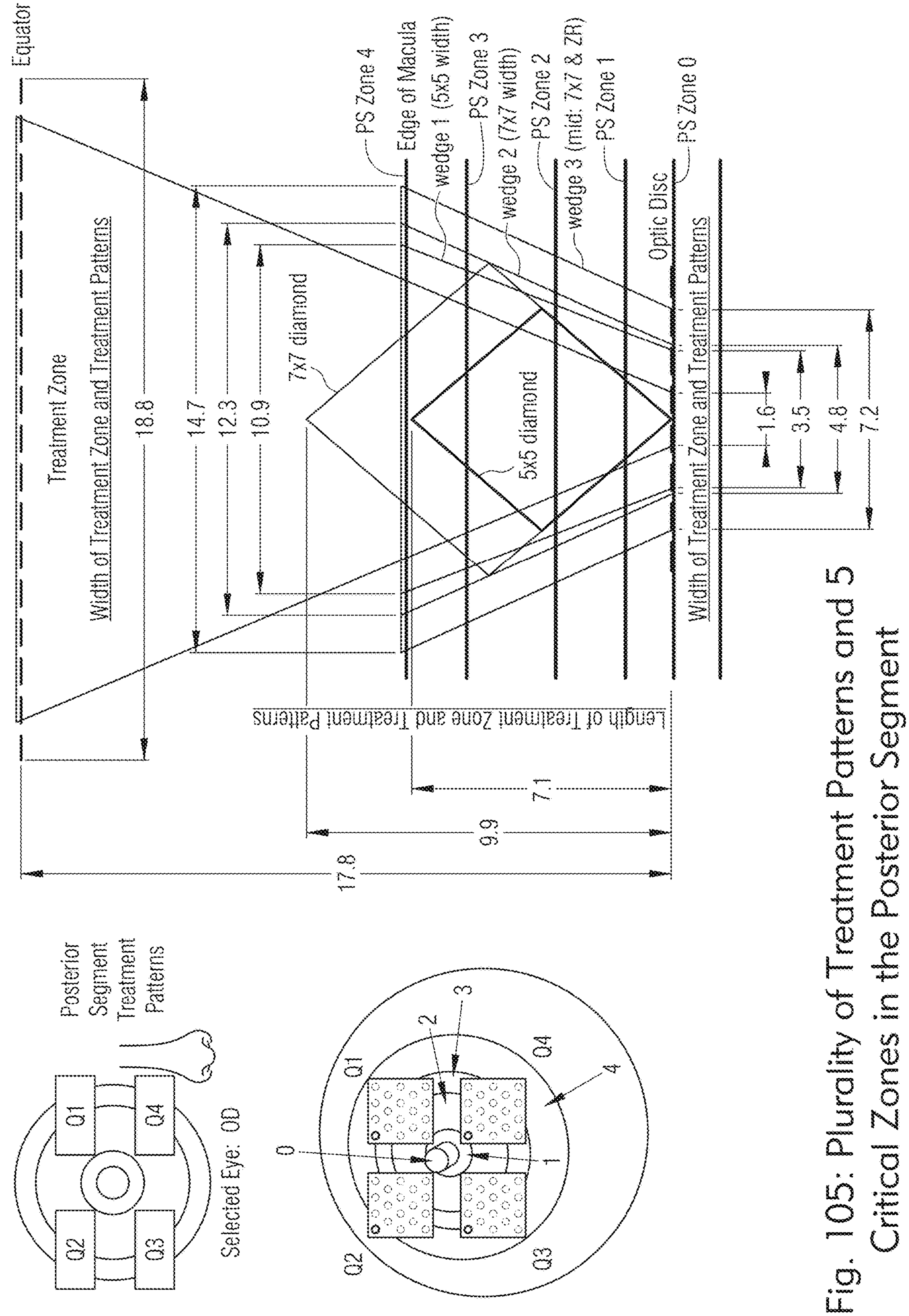
Fig. 105: Plurality of Treatment Patterns and 5 Critical Zones in the Posterior Segment

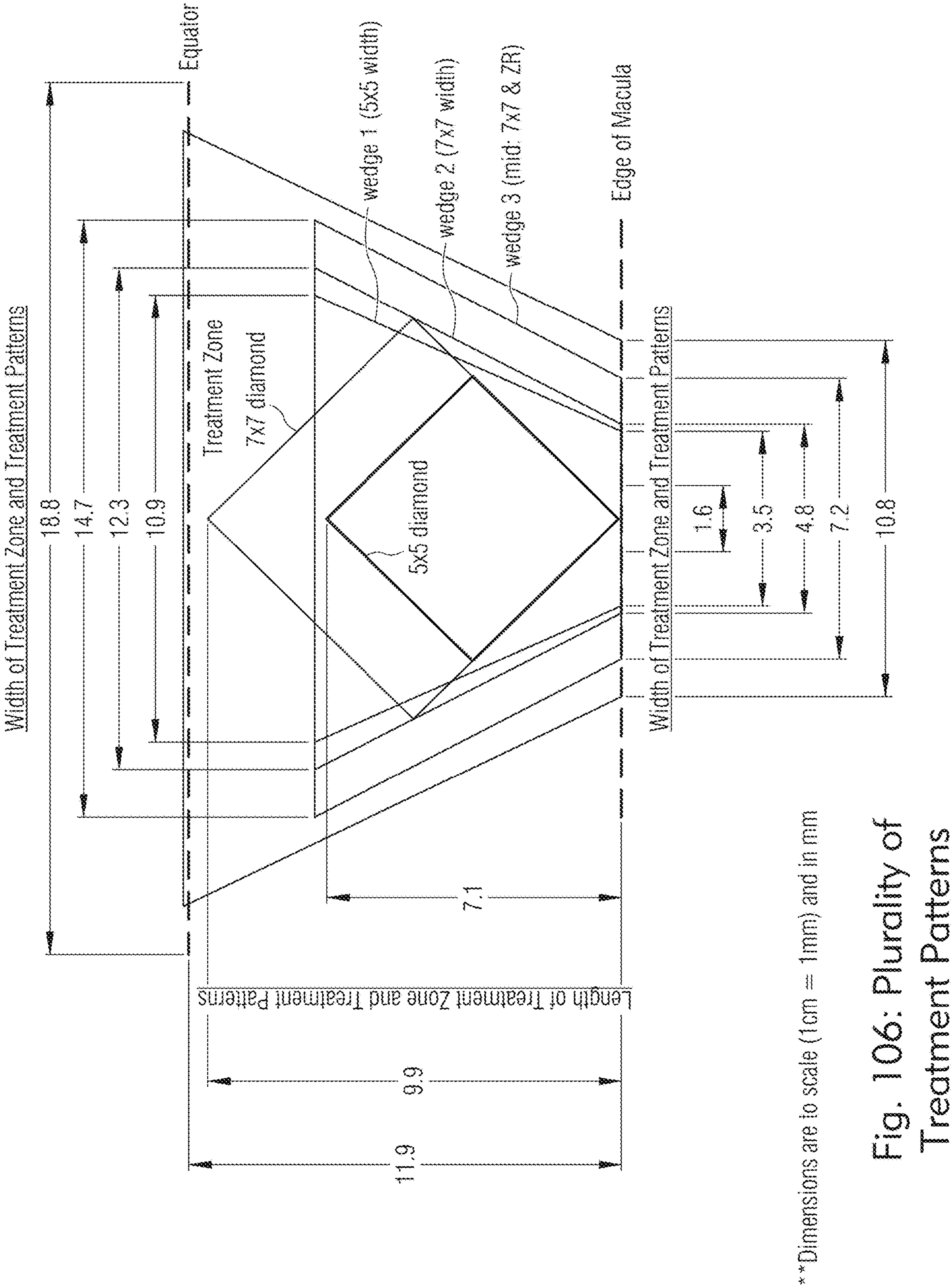
**Dimensions are to scale (1cm = 1mm) and in mm
Fig. 106: Plurality of Treatment Patterns Relationships between parameters
macro input parameters of laser treatment
micro input parameters of laser treatment
properties of the sclera
input to finite element model of treated zones

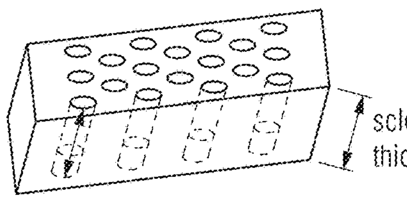

depth (mm)
→ depends on pulse per pore $$depth\ \% = \frac{depth}{thickness}$$

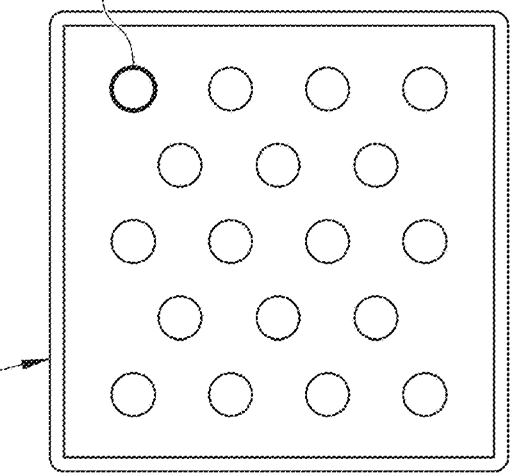

$$density\ \% = \frac{\#\,pores \star spot\ size}{treated\ area}$$

pore volume fraction = treated volume occupied by pores, i.e. sclera volume removed by the laser $$pore\ volume\ fraction = \frac{total\ pore\ volume}{treated\ volume} \approx \frac{density\ \% \star depth}{trhickness} = density\% \star depth\%$$

$$treated\ stiffness = (1 - pore\ volume\ fraction) \star baseline\ stiffness$$

$$treated\ volume = treated\ area \star thickness$$

$$total\ pore\ volume = spot\ size \star \#\,pores \star depth \approx density\ \% \star treated\ area \star depth$$

$$effective\ stiffness = (1 - region\ fraction \star pore\ volume\ fraction) \star baseline\ stiffness$$

Fig. 107: micro parameter definitions

- A cone (or truncated cone) is 1/3 the volume of a cylinder (square or circle)
- To achieve the same pore volume fraction with a cone:
  - Increase pore depth
  - Increase pore surface area
  - Increase number of pores
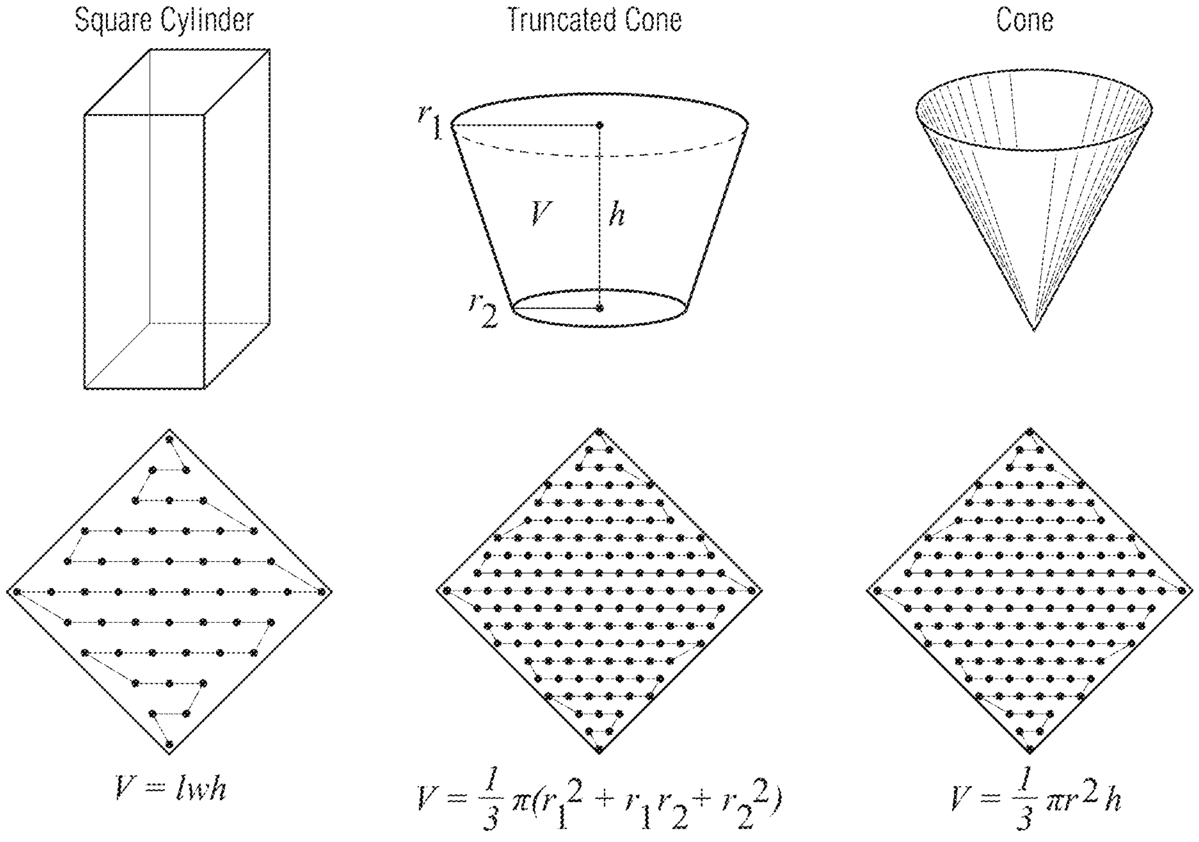
Fig. 108: Pore Volume Fraction Depends on Shape

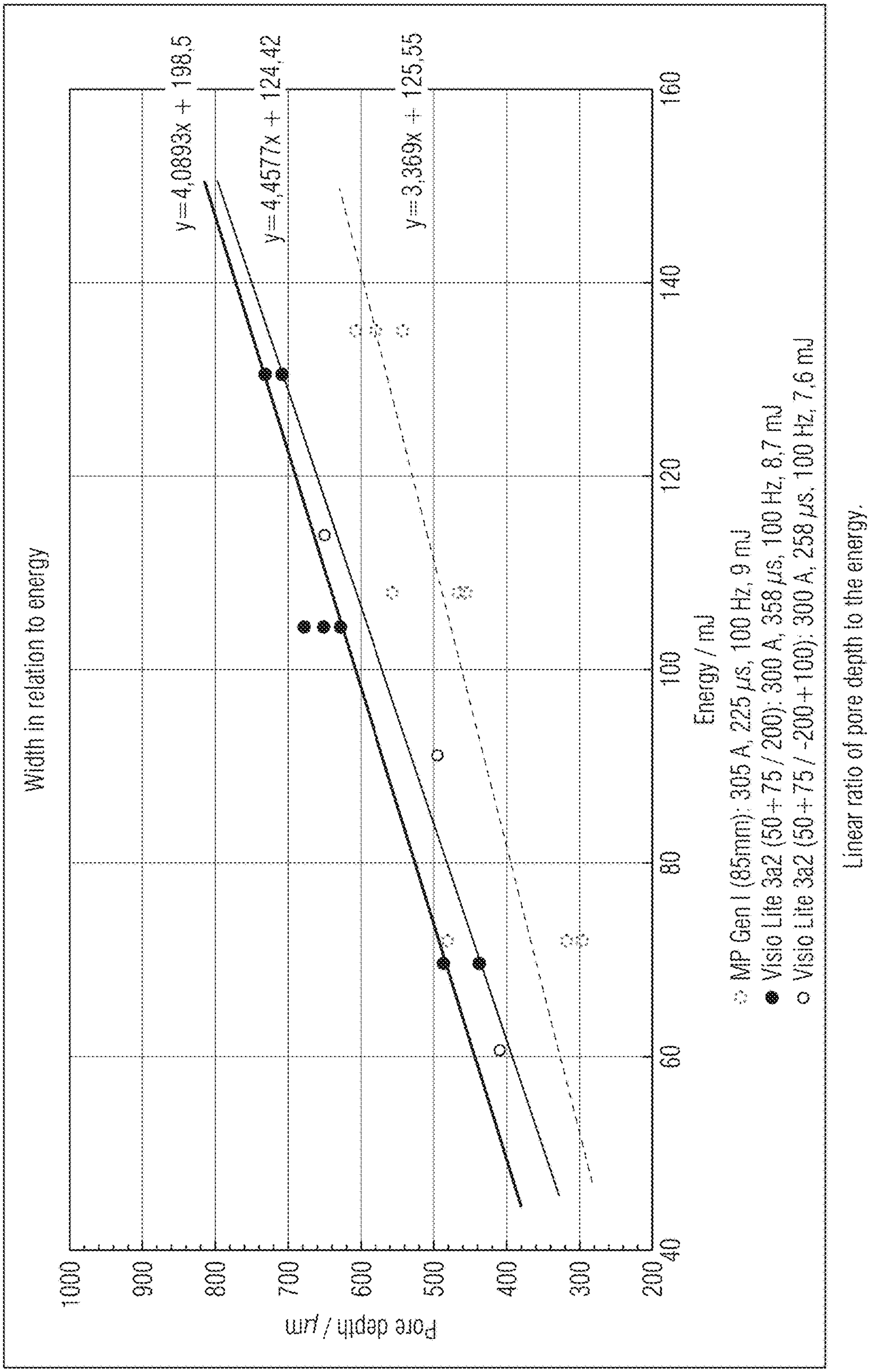
Fig. 109: Pore depth plotted in relation to total energy per pore

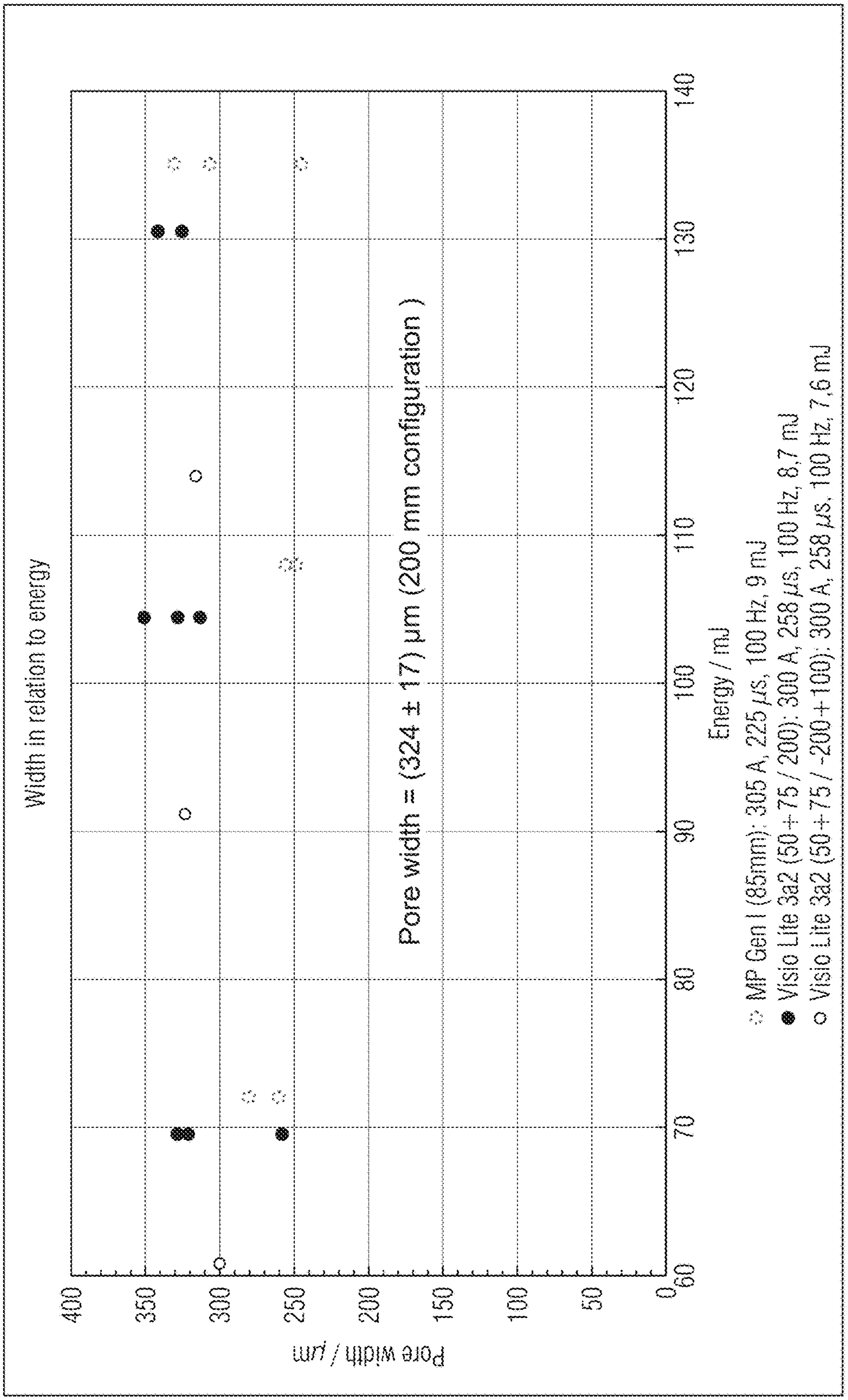
Pore Cross section size (width or diameter) stays the same when increasing the energy per pore.
Fig. 110: Pore width plotted in relation to total energy per pore

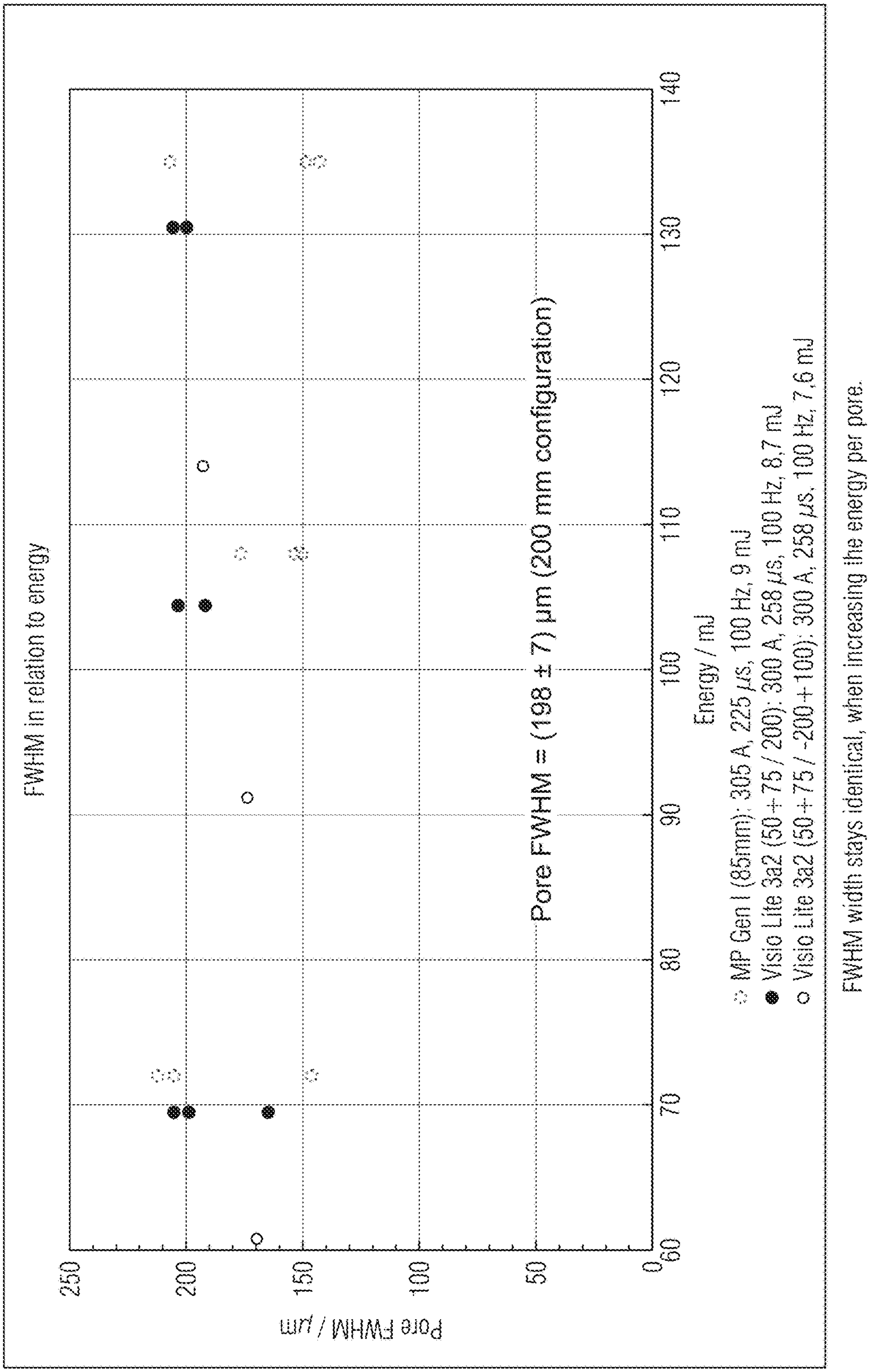
Fig. 111: Pore FWHM plotted in relation to total energy per pore

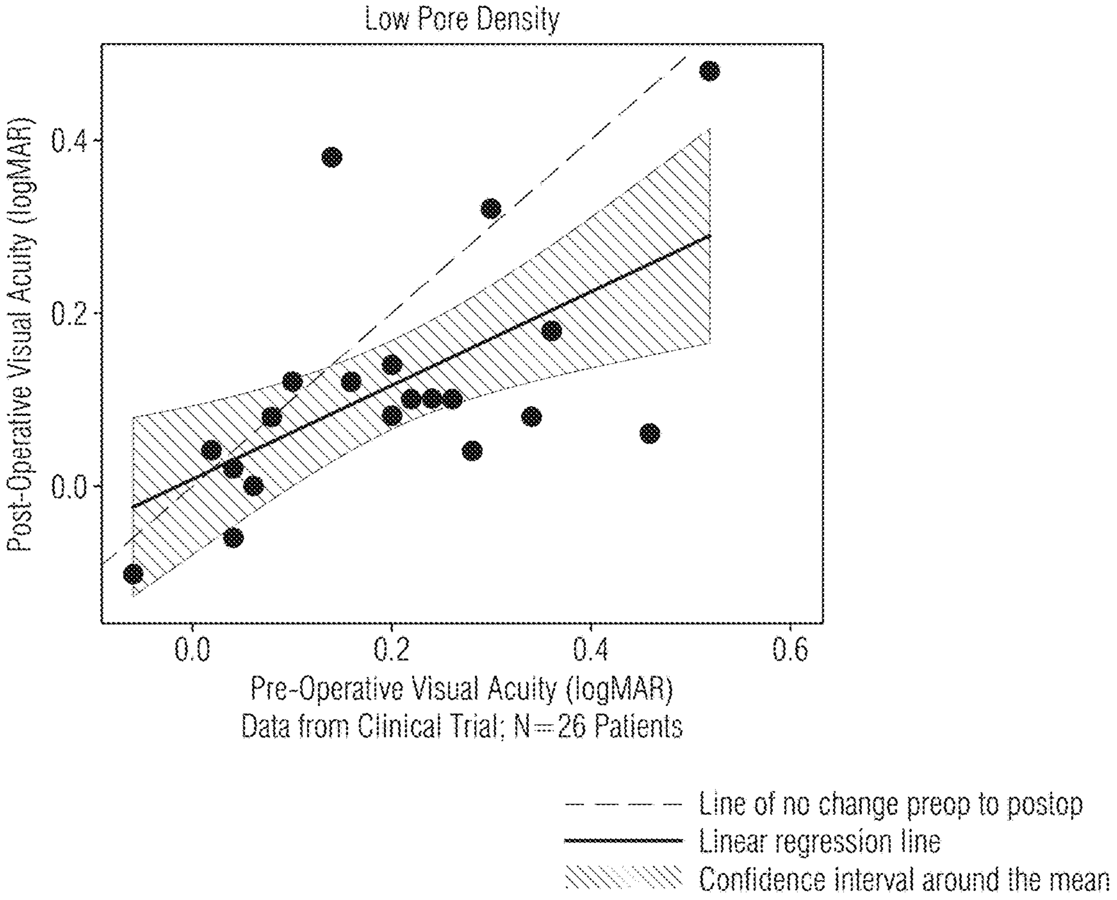
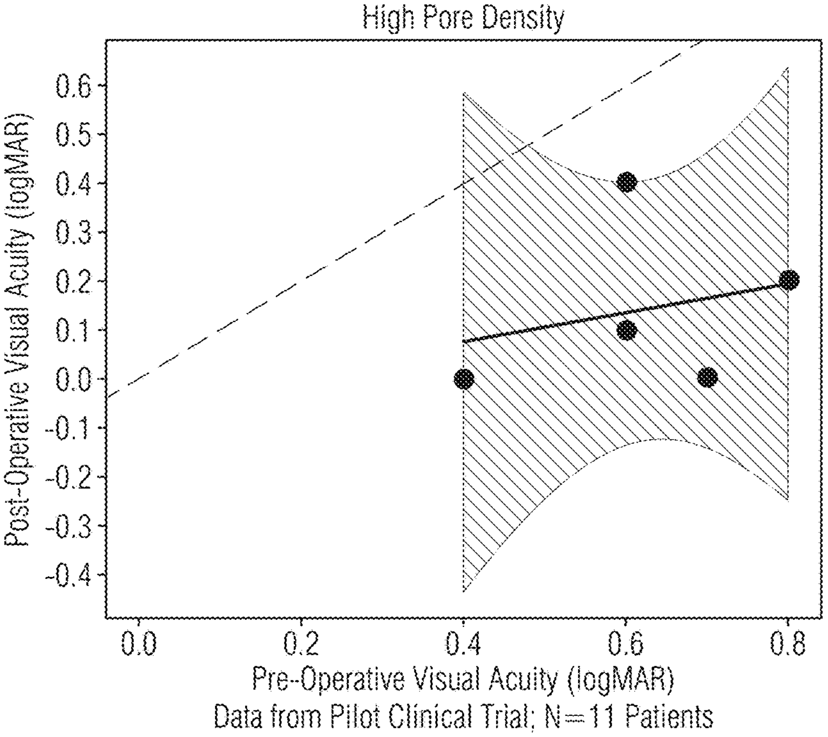
Fig. 112 - Visual Accuity Comparisons

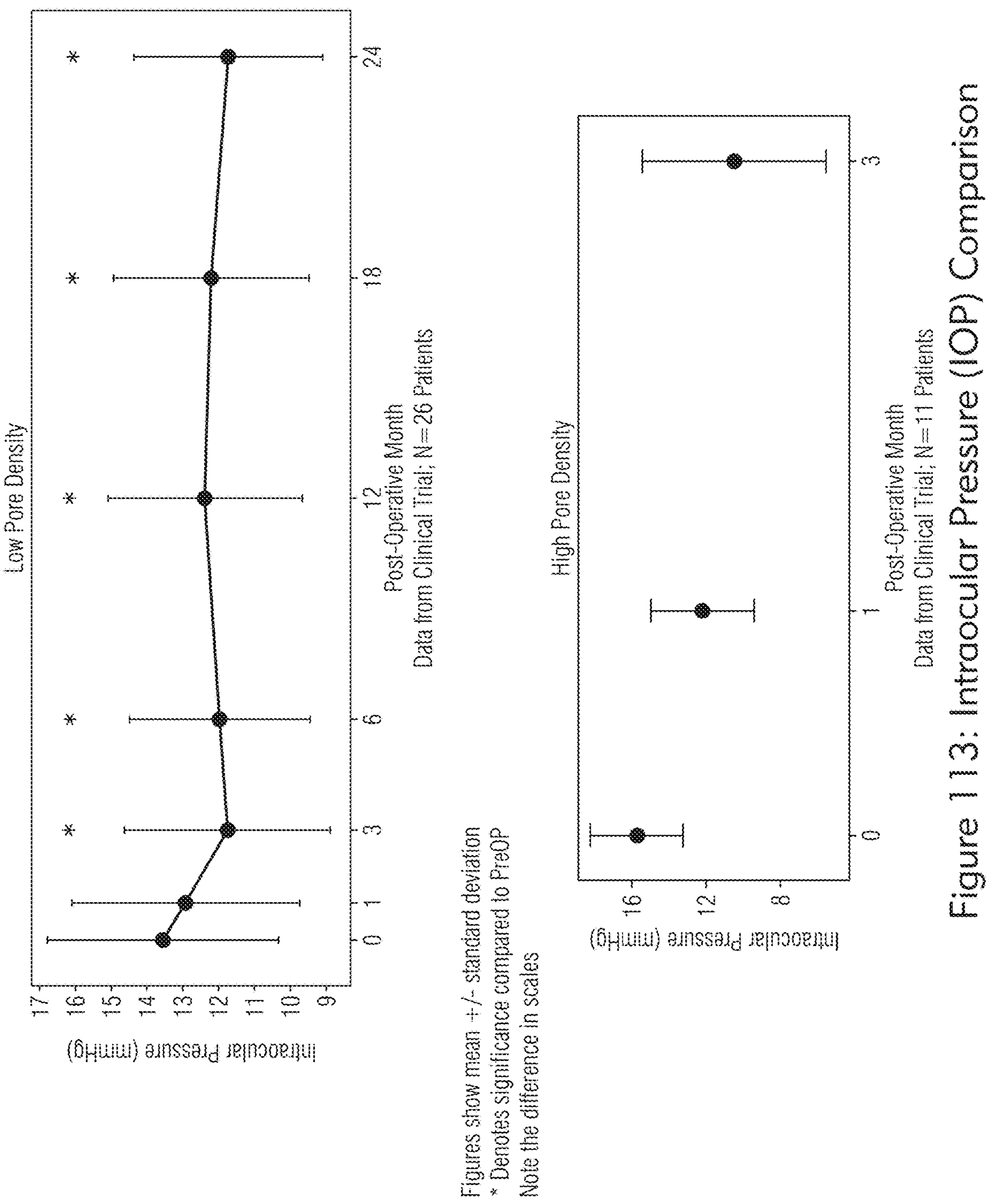
Figure 113: Intraocular Pressure (IOP) Comparison (Clinical Trial; N=21 Patients)
- Binocular UNVA 95% > 20/40
- Binocular UIVA 100% > 20/40
- Binocular UDVA 100% > 20/40
- No loss of BCVA
- Average Lines of improvement 1.5 (Range 1-4)
- IOP average decrease of 2mmHg

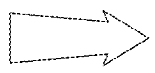

(Clinical Trial; N=5 Patients)
- Binocular UNVA 100% > 20/40
- Binocular UIVA 100% > 20/40
- Binocular UDVA 100% > 20/40
- No loss of BCVA
- Average Lines of improvement 4.5 (Range 2-8)
- IOP average decrease of 5mmHg Figure 114: Compare Innovation Improvement in Visual Acuity and IOP

• Hoya: Low Pore Density
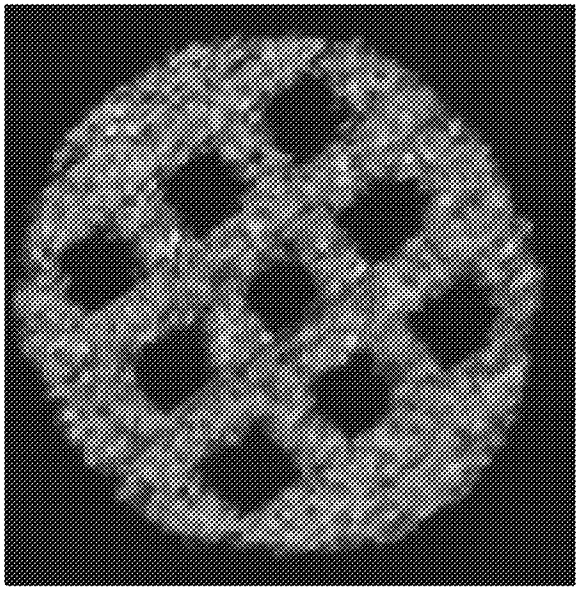
• ( High Pore Density)
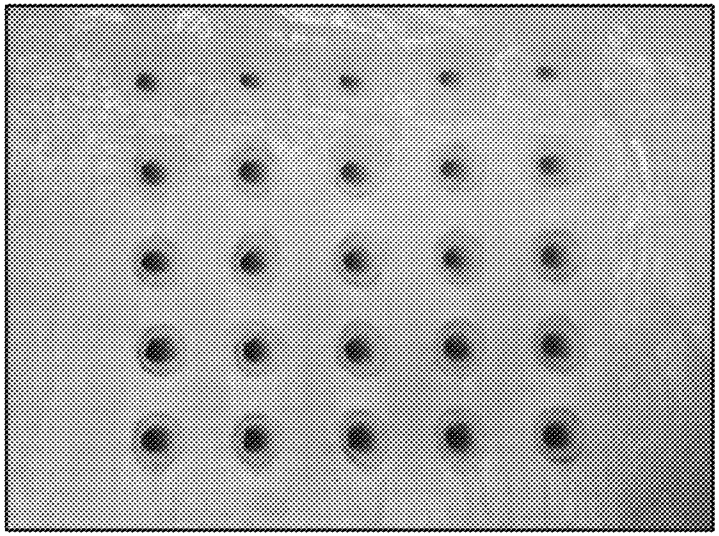
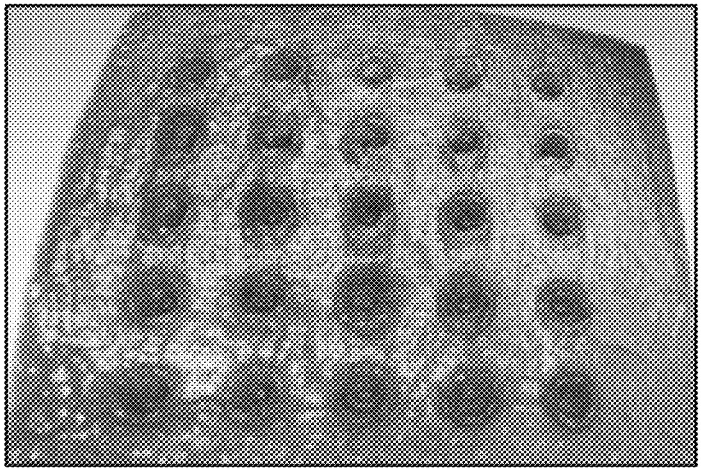
Figure 115: Hoya Low Density System vs High Density

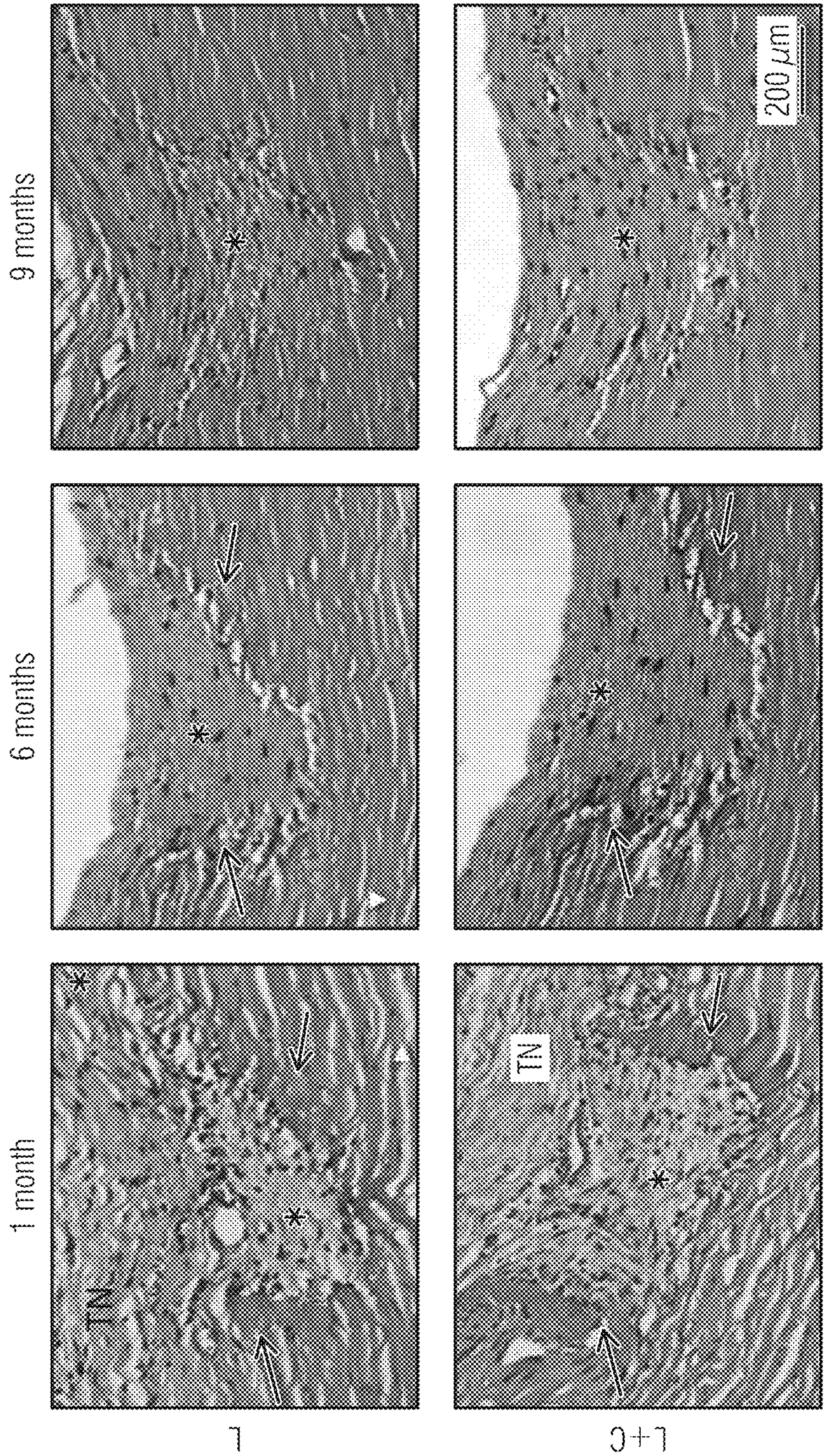
Fig. 116: Histology of Micropores

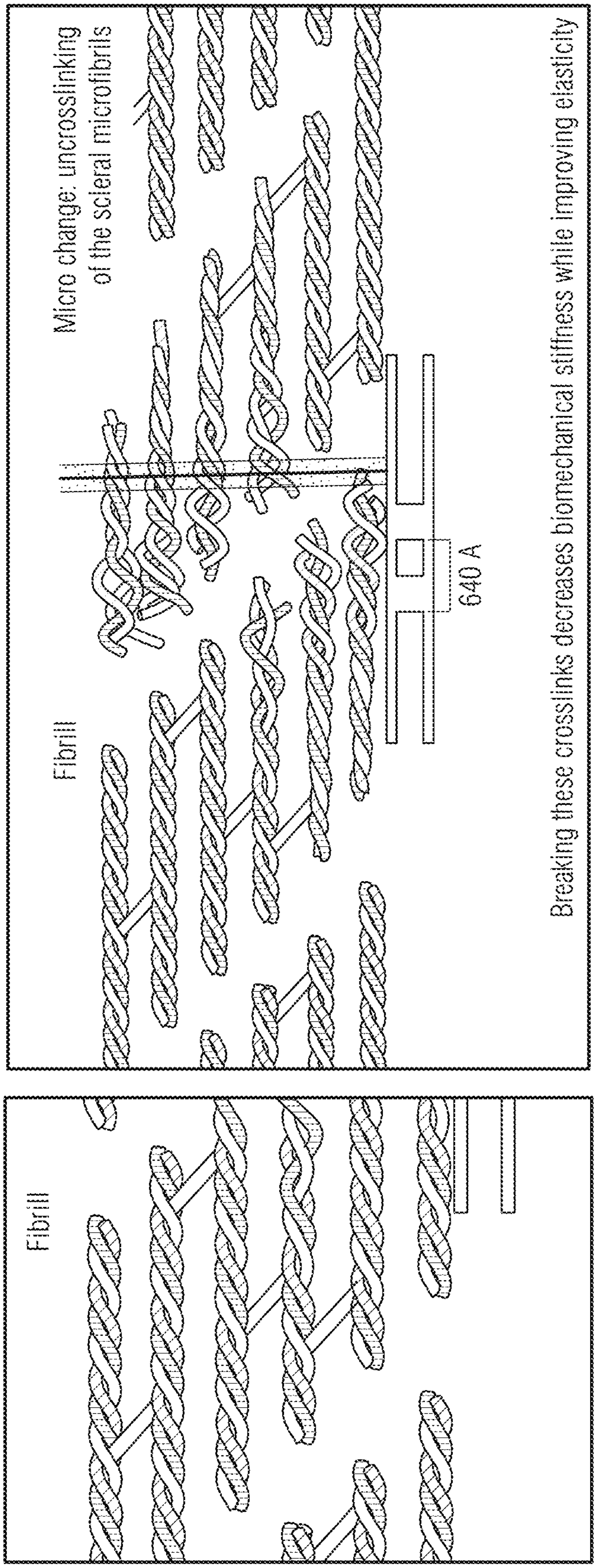
Fig. 117: Un-crosslinking: Breaking of Bonds ⟶
Decreased Biomechanical Stiffness (Compliance)

Treatment laser beam ablation of individual pores
Un-crosslinking is breaking bonds in microfibrils and fibrils. It weakens tissue or allows tissue to be more compliant.
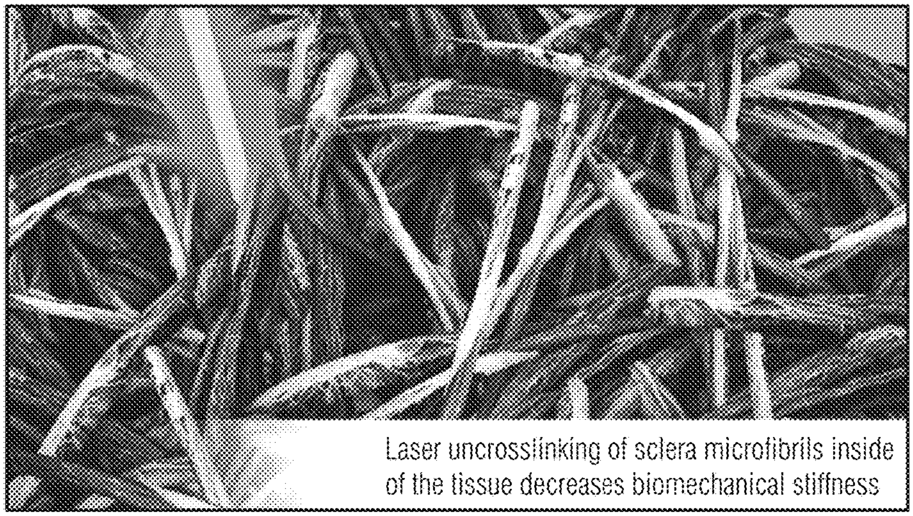
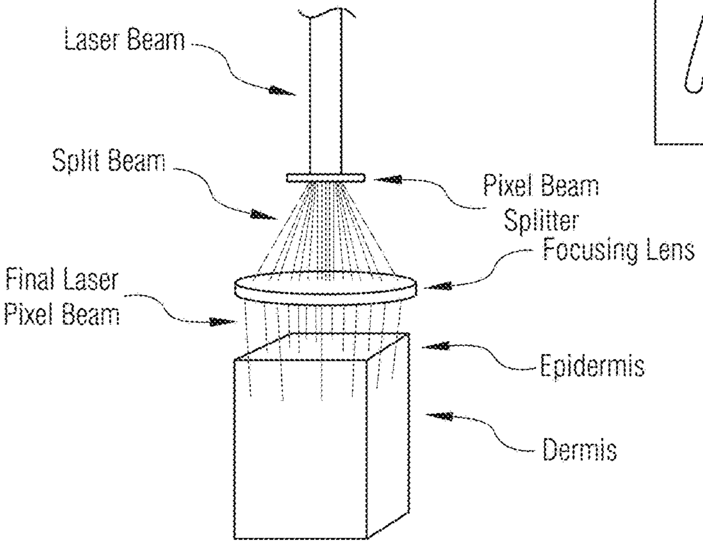
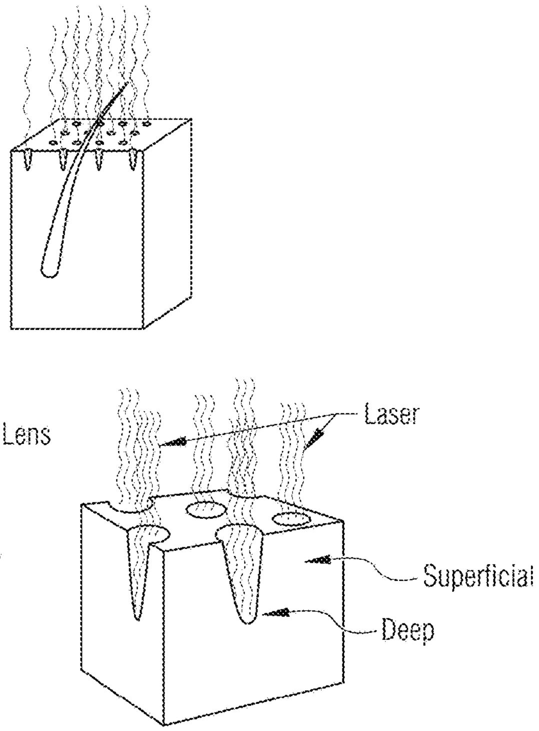
Fig. 118: Laser Un-crosslinking Scleral Fibrils & Microfibrils

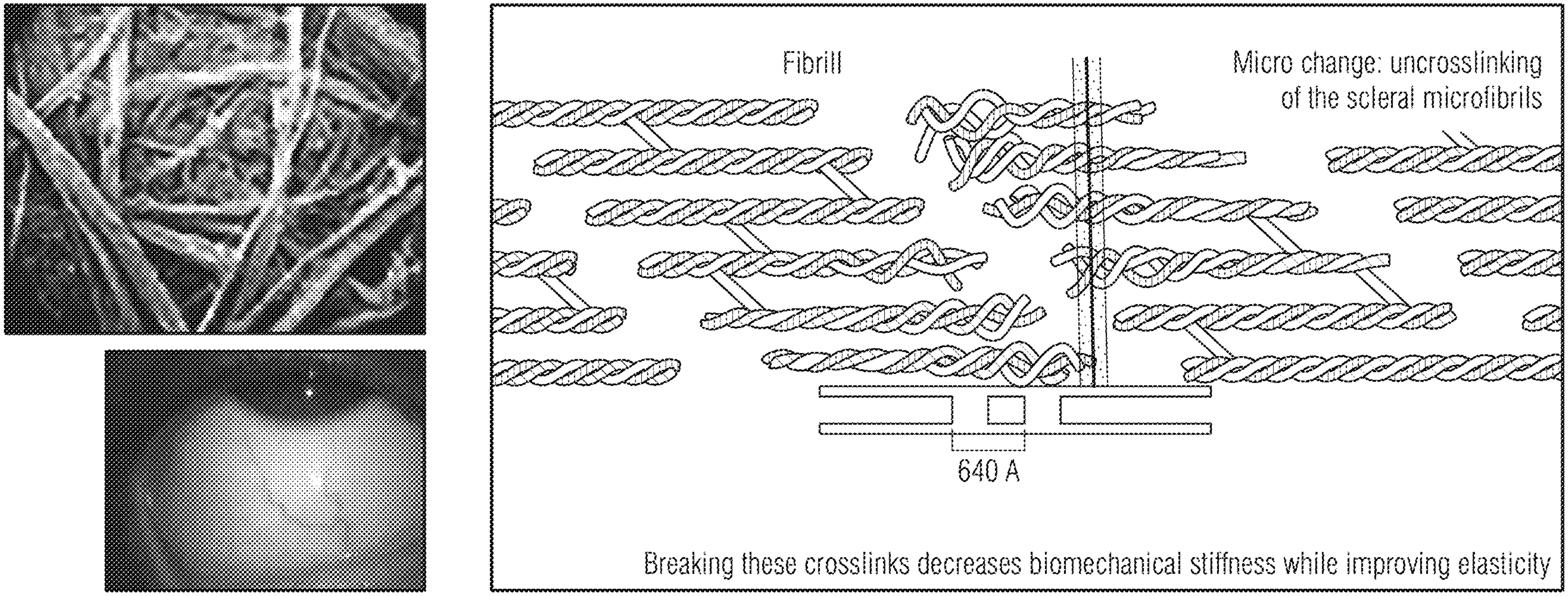
Fig. 119: Laser Scleral Microporation:
SubSurface Bond Breaking maybe change word from 'subsurface ablation" to "subsurface bond breaking" within the pore cylinder. Uncrosslinking Breaking Bonds ⟶ Decreased Biomechanical Stiffness

- In the simplest view the motion control moves the treatment laser as shown on slide 21 around the patient's eye on the surface of a dome.
- The dome is positioned in the x, y and z axis to align with the initial micropore position of the treatment protocol and then step around the dome to the next micropore position.
- The x, y and z axis is not changed over the treatment of one quadrant but will need to be modified for another quadrant.

Dome with Laser Head Unit optical axis pointing to center of the treatment area

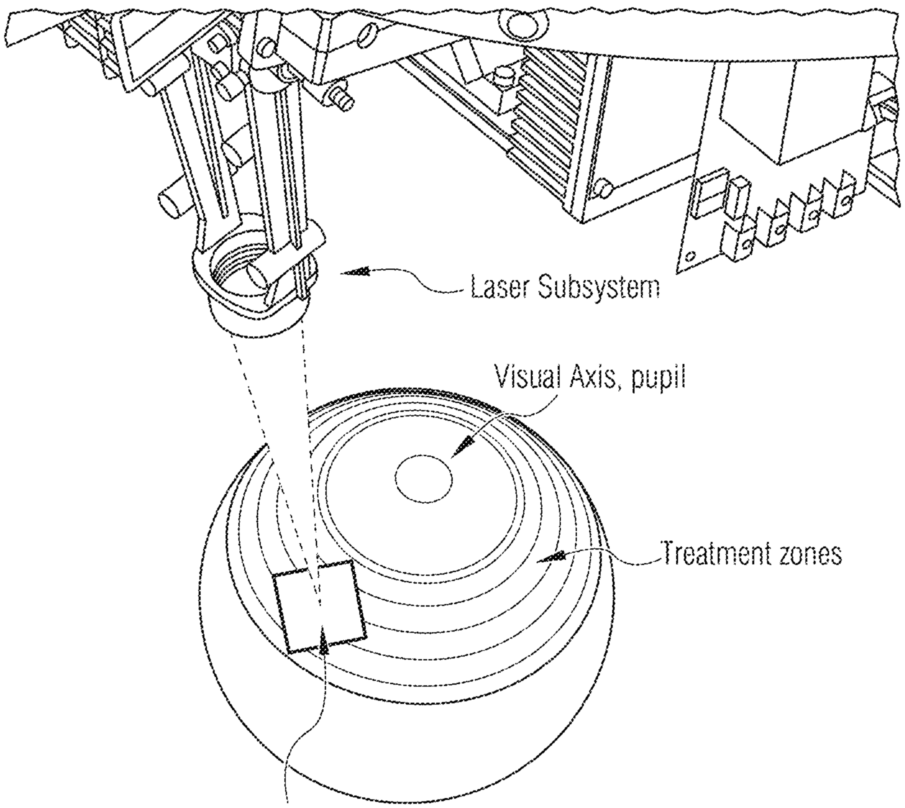

Figure 120: Treatment Dome Off Axis Laser pointing Concept

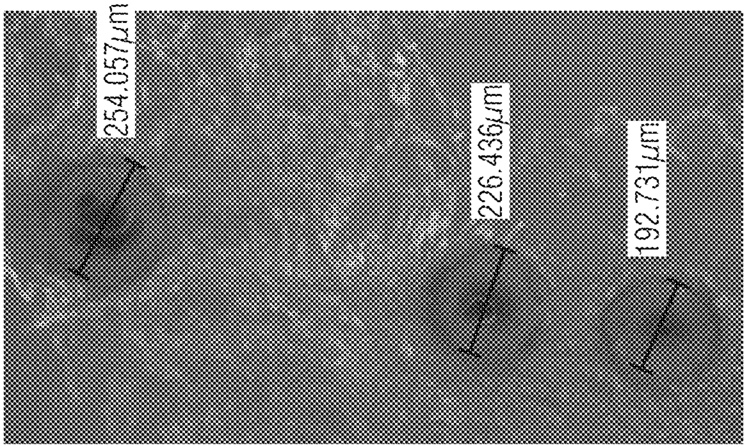
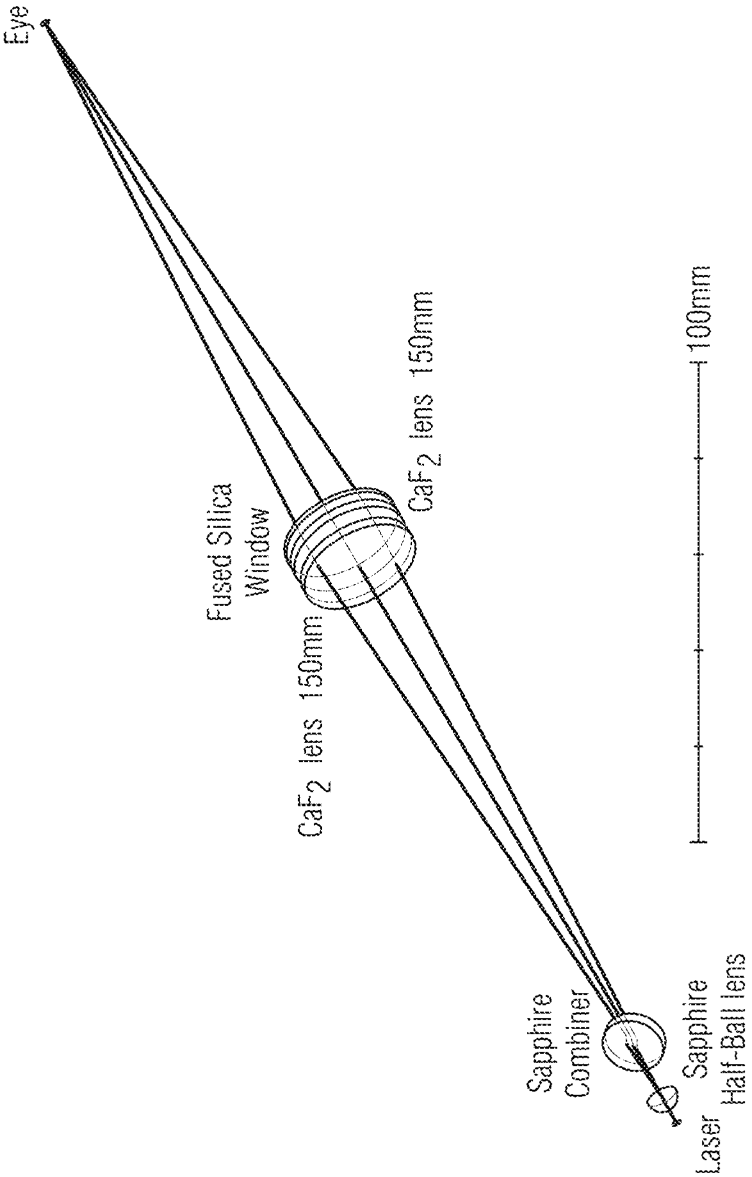
Fig. 121: Optical configuration - Spherical $CaF_2$: 150/150

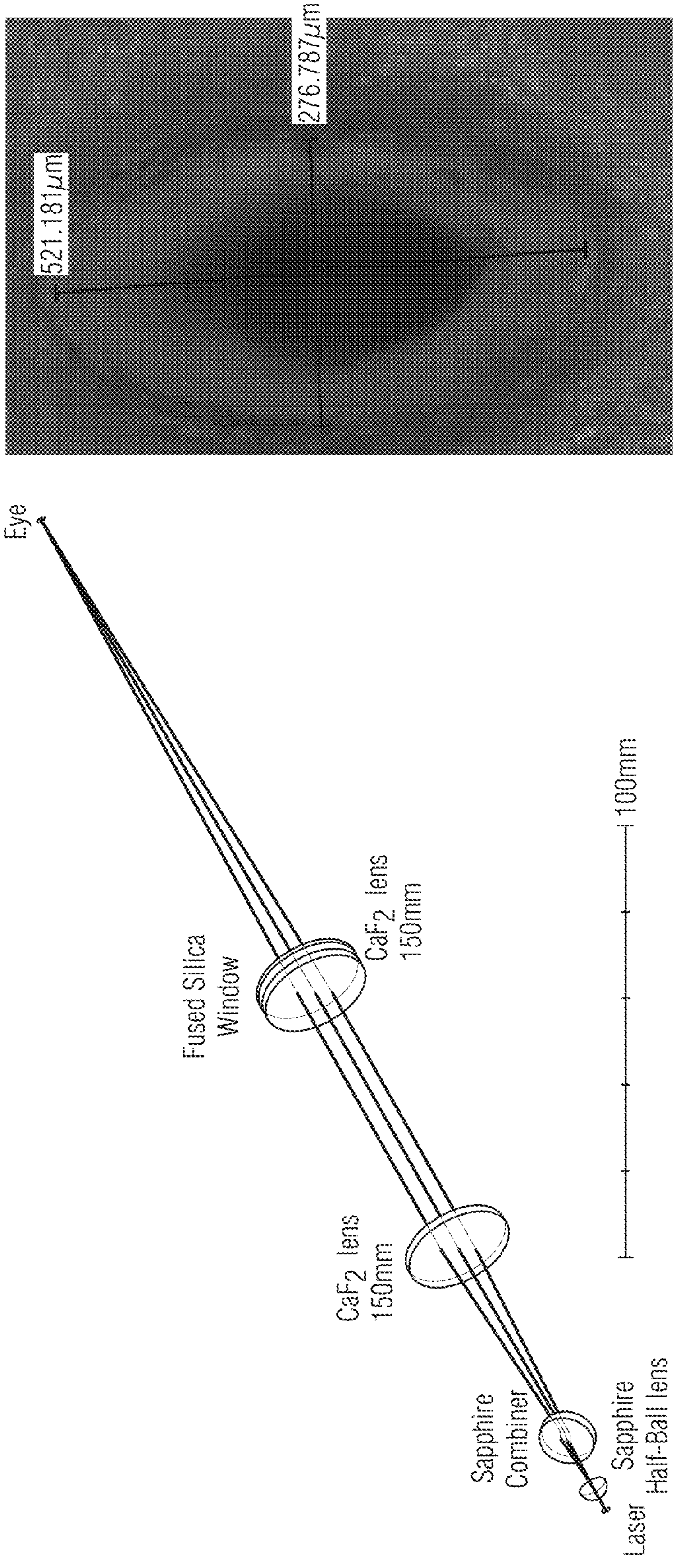
Fig. 122: Optical configuration - Increased focus size: Spherical $CaF_2$ : 75/150

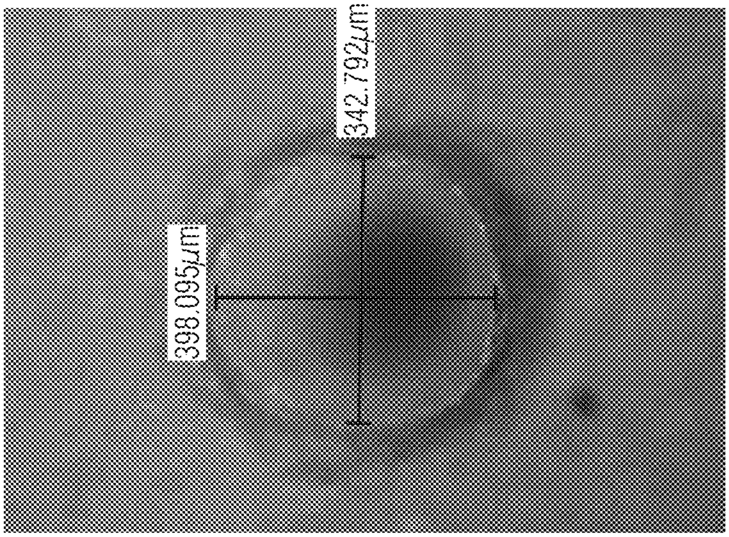
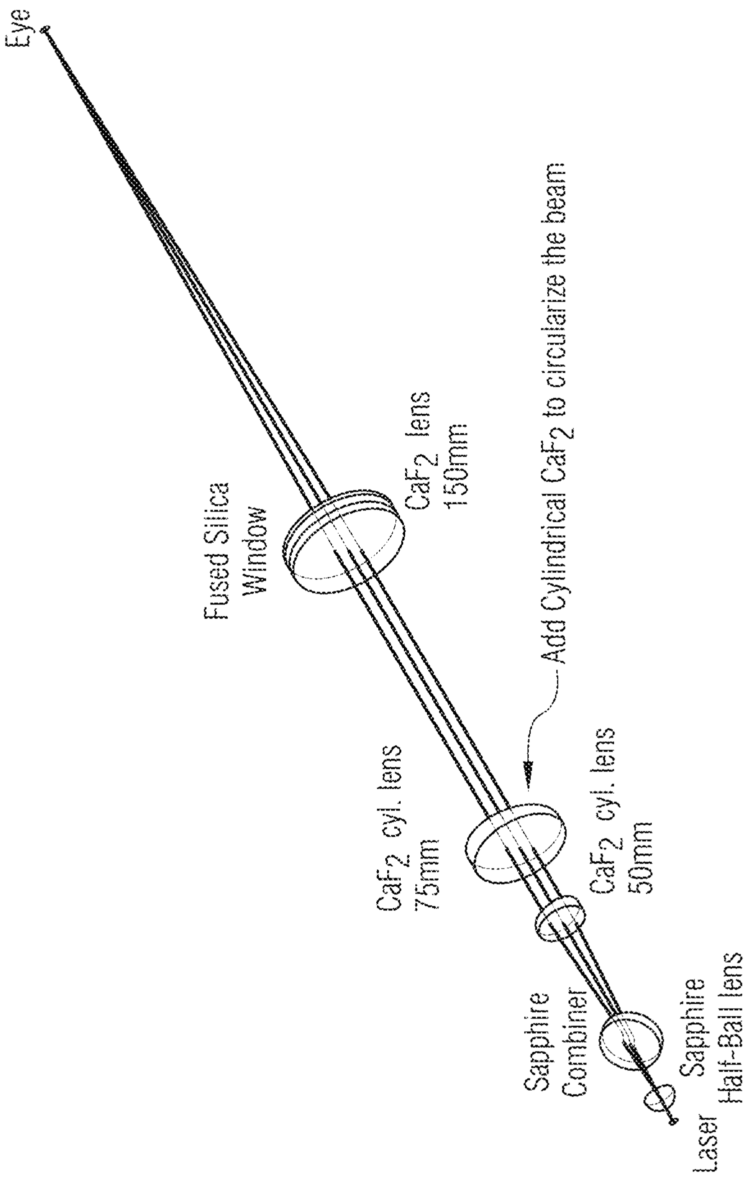
Fig. 123: Optical configuration - Circularization of the focus: Cylindrical $CaF_2$ : 50/75/150

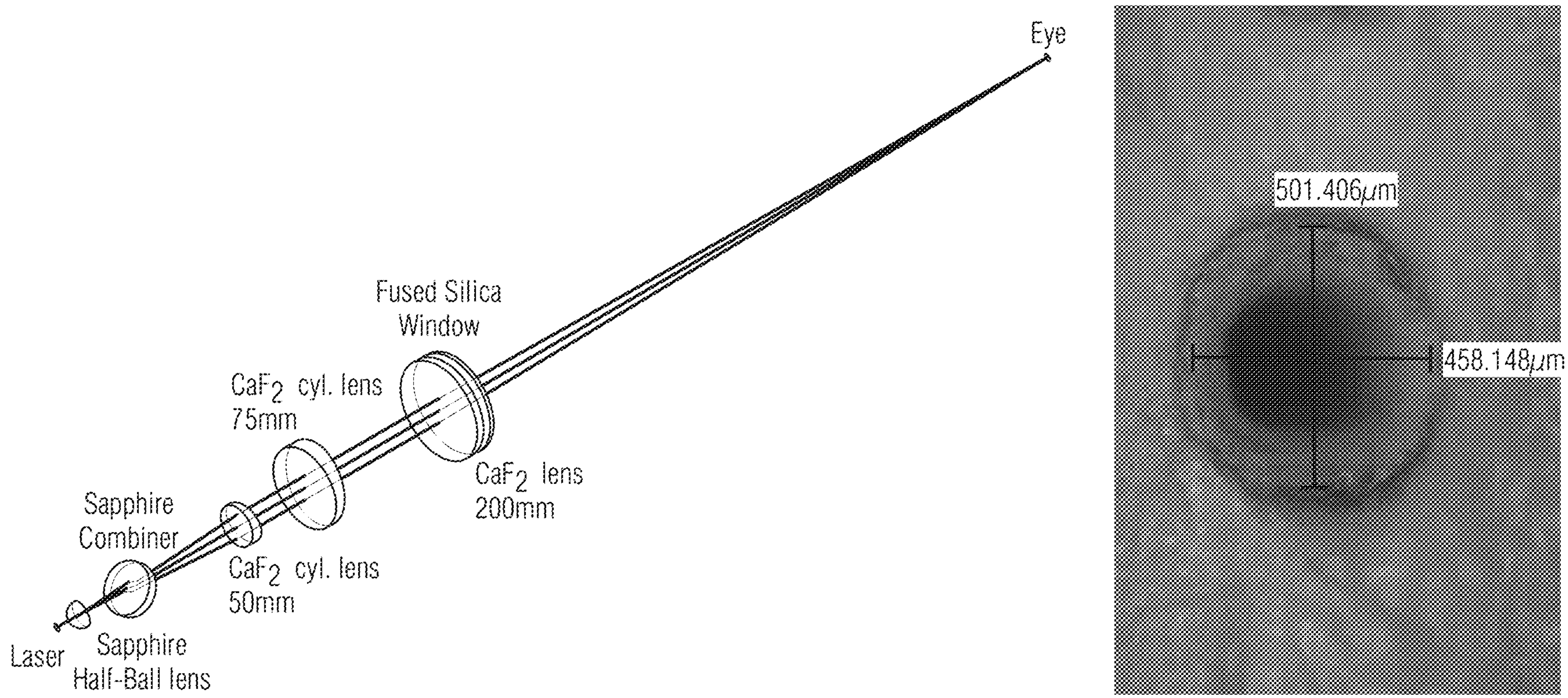
Fig. 124: Circularization & Increase of the beam focus: Cylindrical $CaF_2$ : 50/75/200

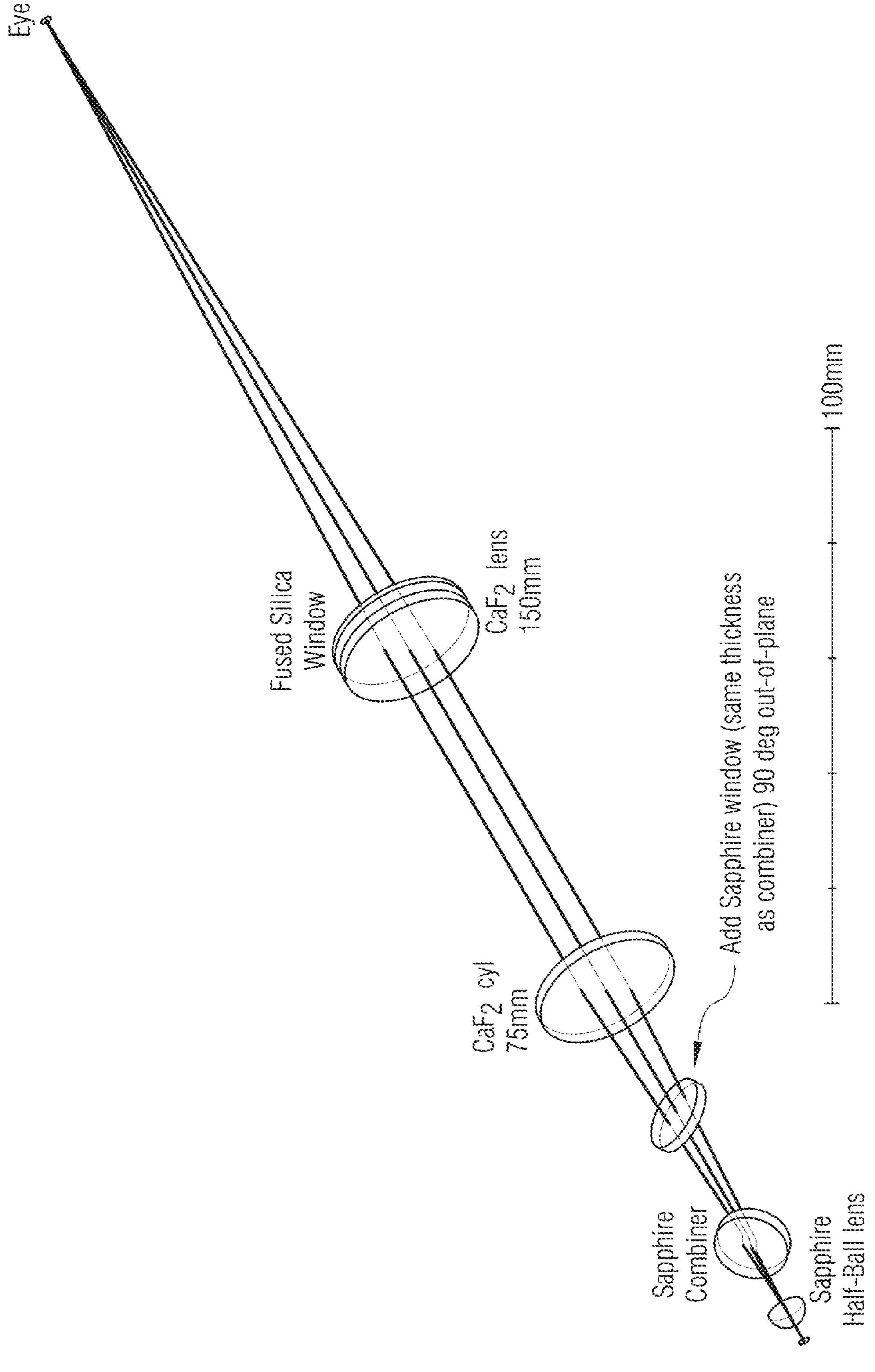
Fig. 125: Alternative concept with polarization correction window added Required Performance:
| | |
|---|---|
| • Mechanical scanning angle | ~ 2° (full angle) |
| • Angle required for 60 μm step | ~ 420 μrad |
| • Required line speed for 2° mech. | > 50 Hz |
| • Required lines for 10 x 10 mm2 | ~160 line scans |
| • Speed for a full scan | < 4 seconds |
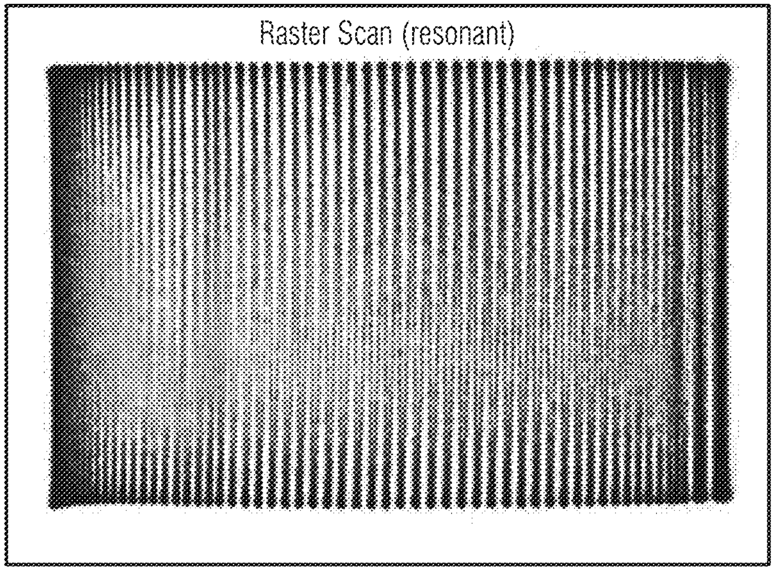
Fig. 126A: Optical System with Scanner Mirror capabilities - one axis is operated RESONANT (MR-15-30)

| | | |
|---|---|---|
| Actuator Type | 4-Quadrant (2 axis, bi-directional) | |
| Mechanical tilt angle DC | ±25 X axis; ±25 Y axis | ° |
| Mechanical tilt angle dynamic | ±25 X axis; ±25 Y axis | ° |
| Mirror diameter | 15 | mm |
| Center of rotation to mirror surface | 1.3 | mm |
| External diameter | 35.4 | mm |
| Height | 14.5 | g |
| Weight | 29.3 | ppm/°C (Max) |
| Scale drfit | T.B.D | μrad/°C (Max) |
| Zero drift | 25 | μrad |
| Resolution (closed loop) | <5 | μrad |
| Repeatablility RMS (typical) | 30-100 | Hz |
| Full scale bandwidth | 20 | |
| Sine wave (+25°) | | Hz |
| Small signal badwidth (<+0.1°) | 350 | ms |
| Large angle step response (20° step) | 7.5 | ms |
| Small angle step response (0.1° step) | 1.4 | |

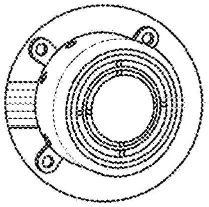

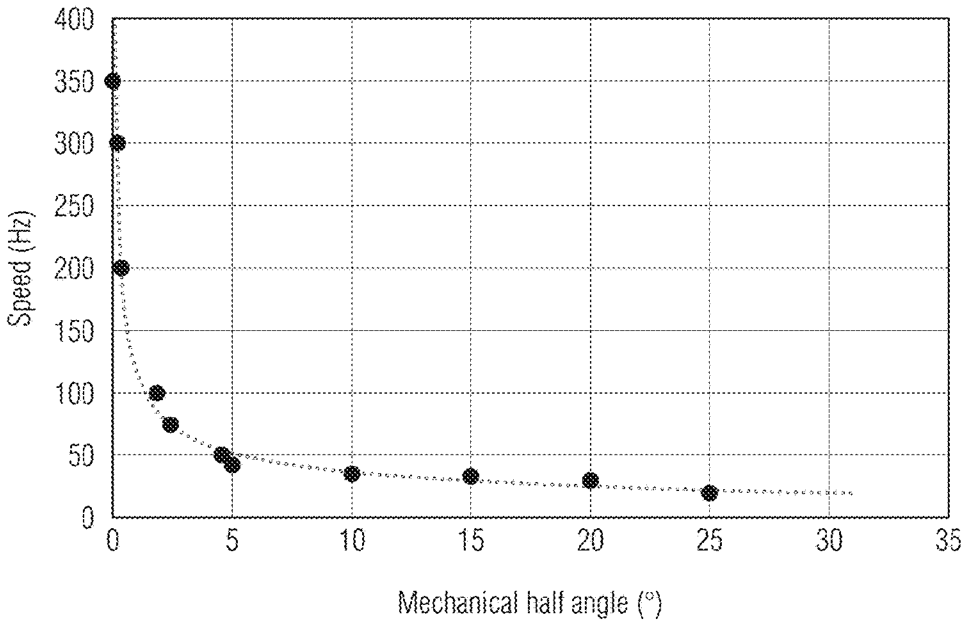

Fig. 126B: Optical System with Scanner Mirror capabilities - one axis is operated RESONANT (MR-15-30)

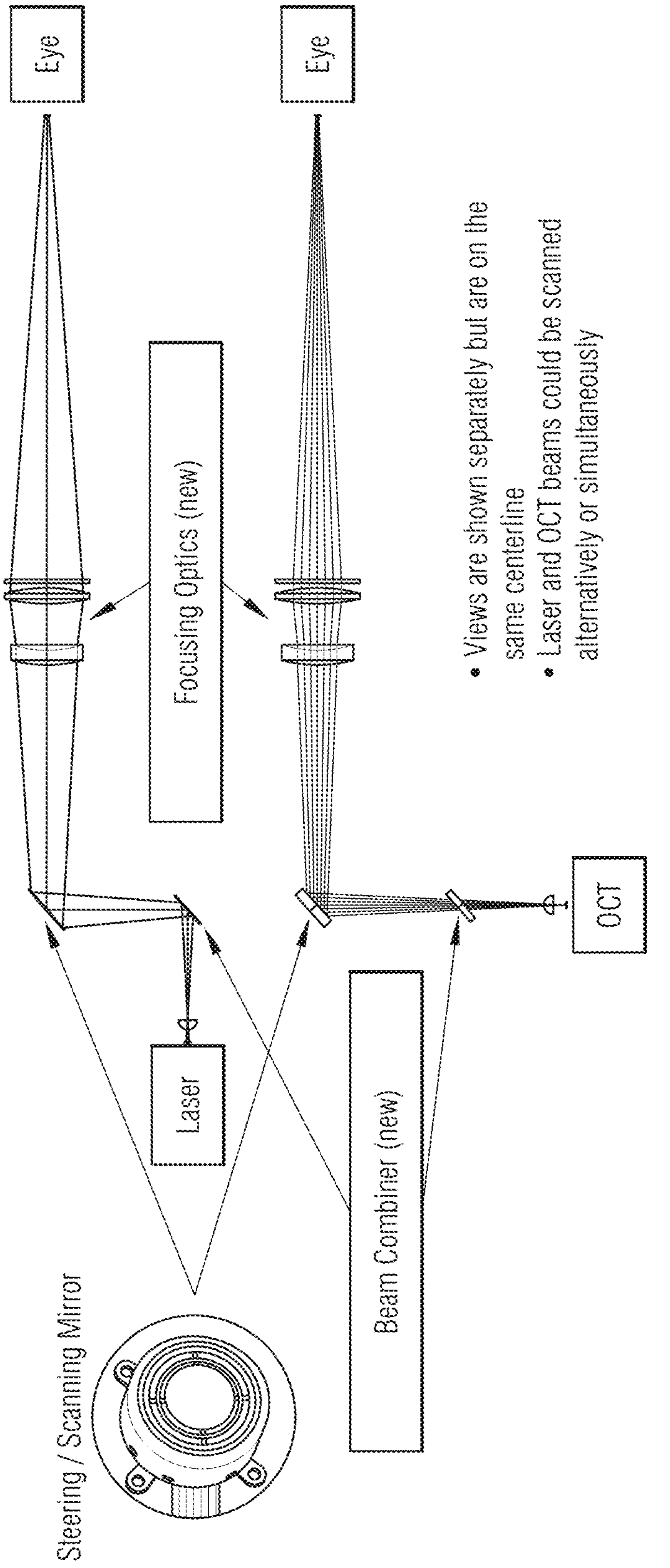
Fig. 127: System with scanning mirror , 5 axis Head, separate Z motion and Real-time OCT/DC with beam splitter

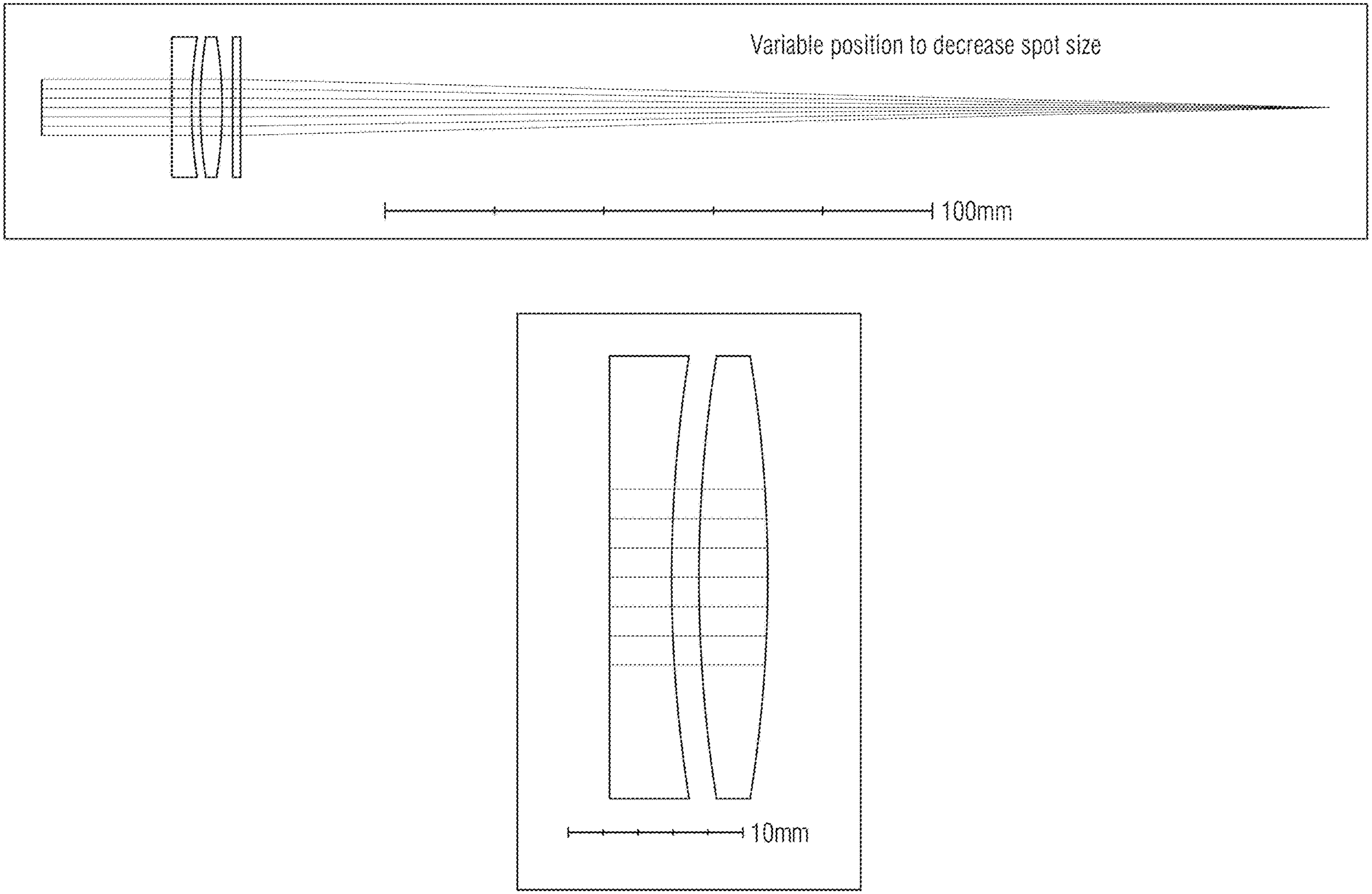
Fig. 128: Optical System with Doublet with overall focal length of 200 mm and 300μm beam diameter

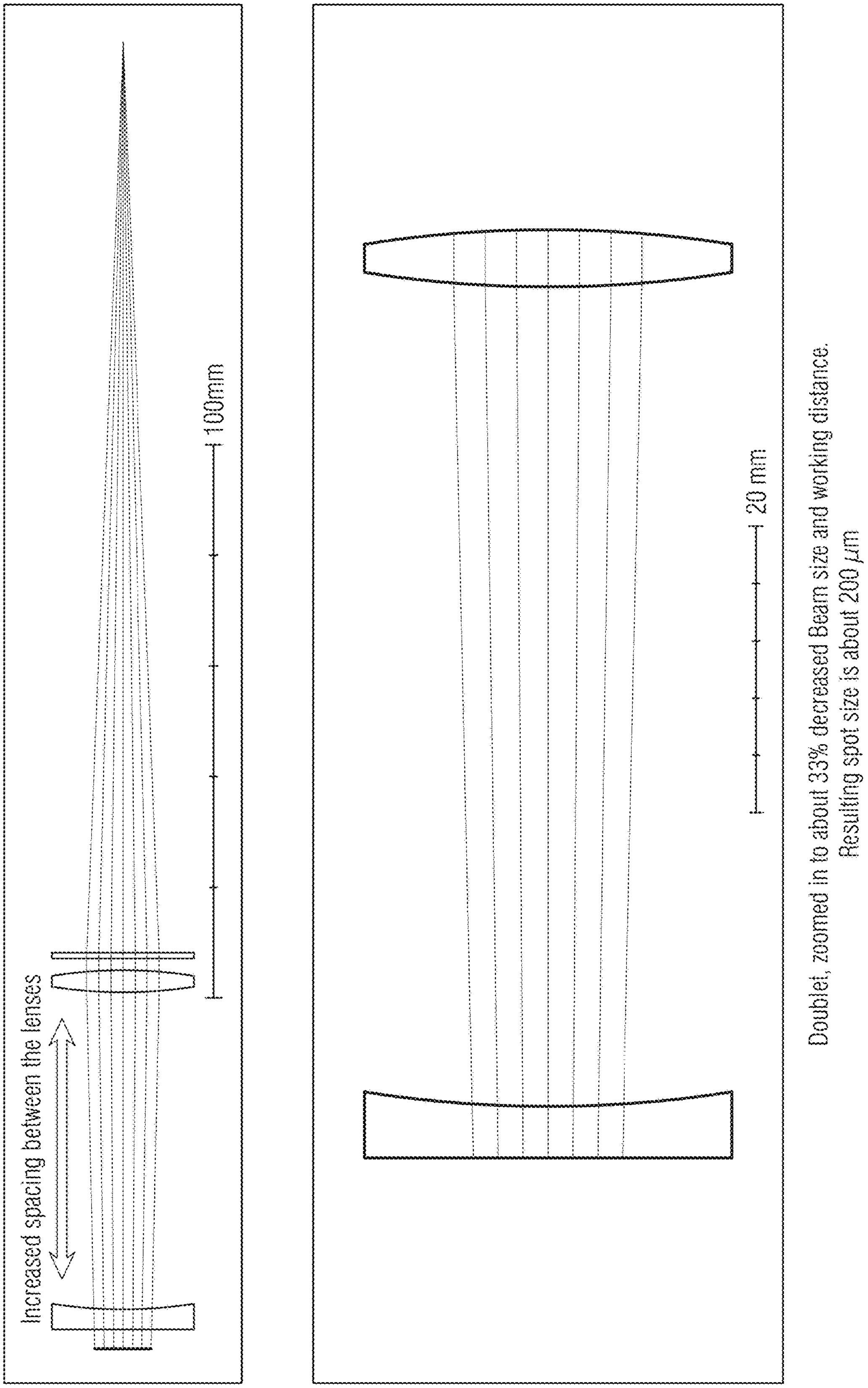
Fig. 129: Optical System with doublet for zoom spot size with overall focal length of 200 mm and 200μm beam diameter

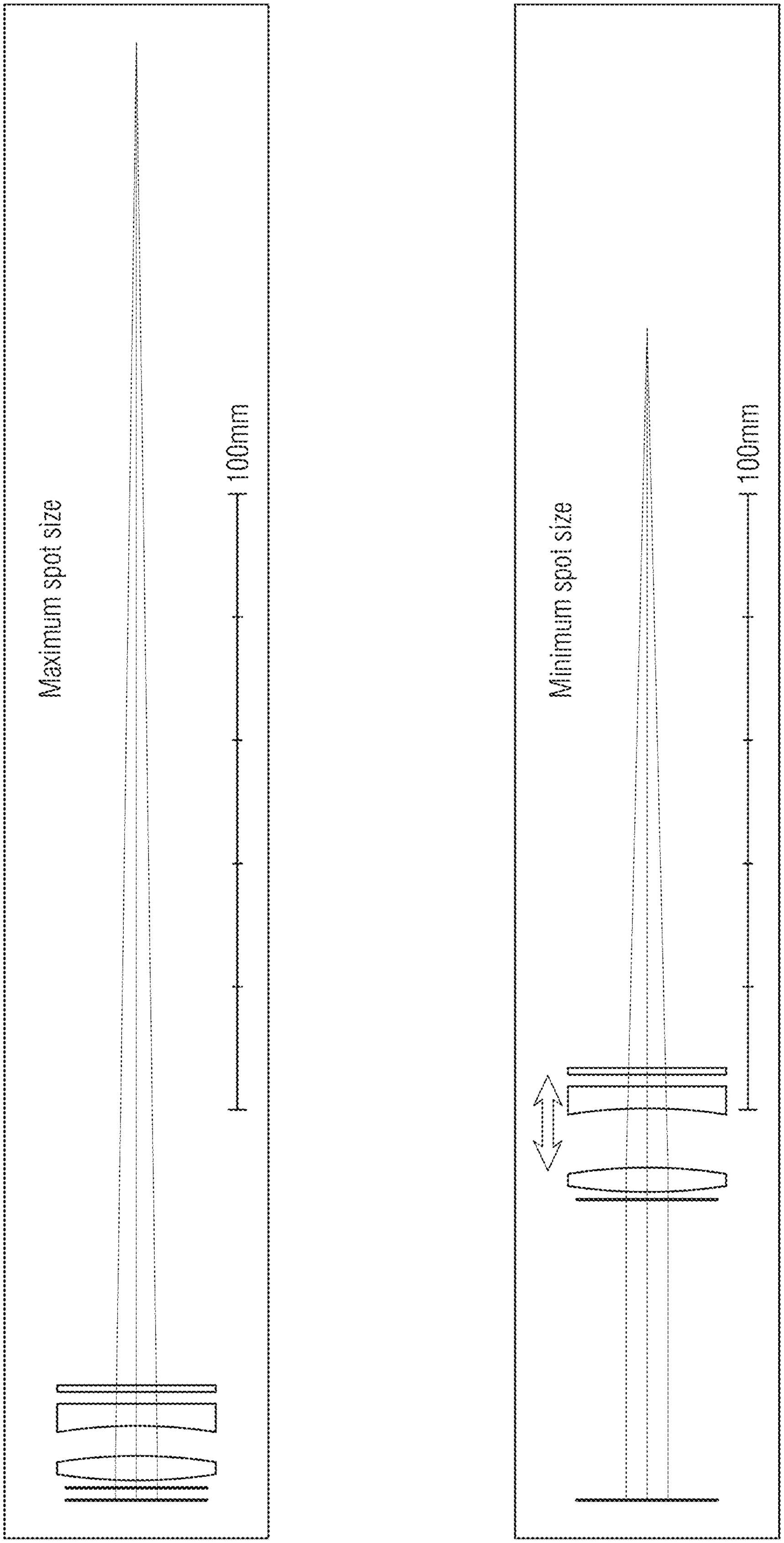
Focusing (75 mm) / Defocusing (-100 mm) 100% = 484 $\mu m$
Resulting spot size is adjustable from 580 $\mu m$ (120%) to 460 $\mu m$ (95%).
Fig. 130: Optical System with adjustable larger spot size

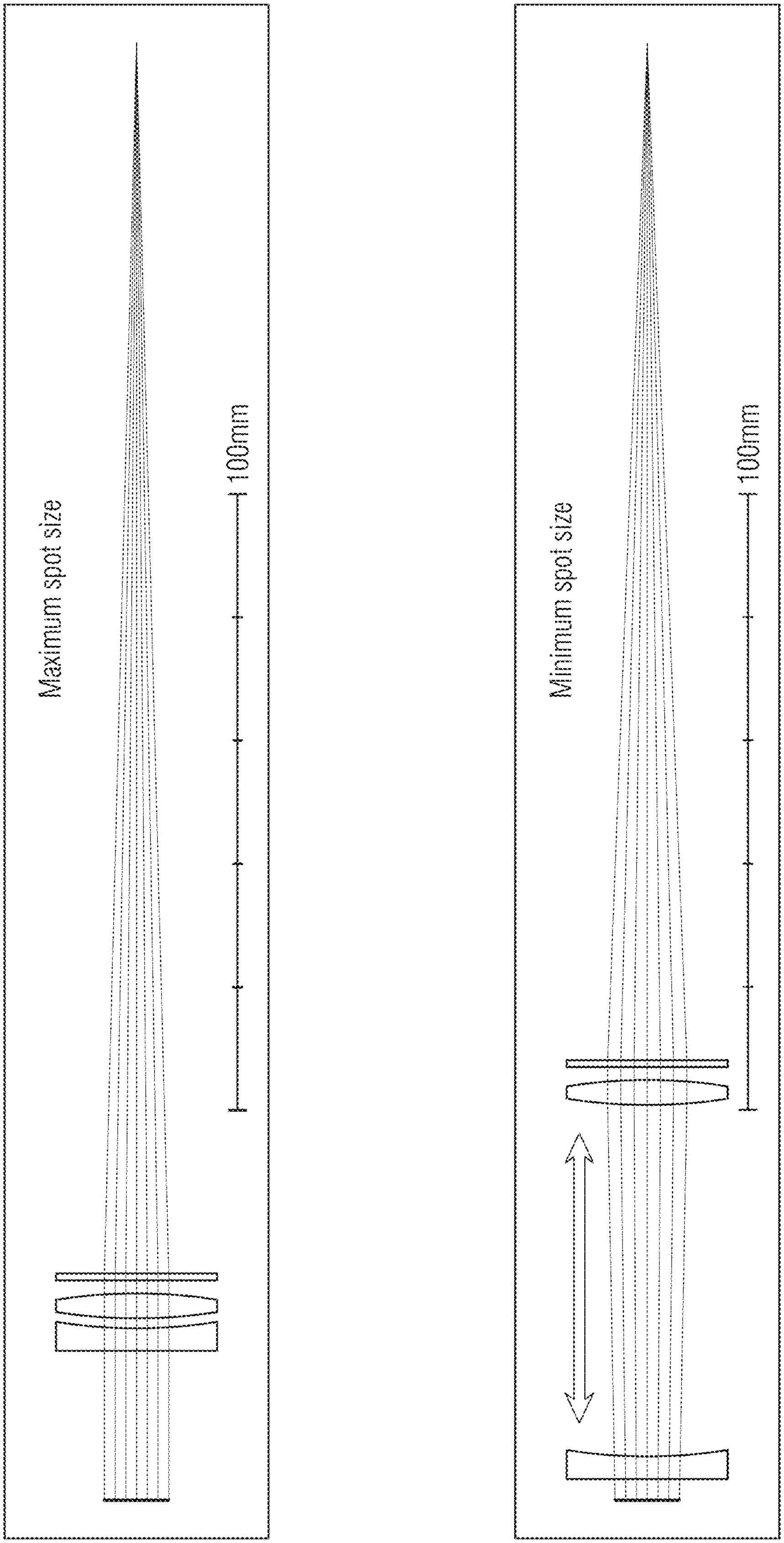
Defocusing (-200 mm) / Focusing (100 mm) 100% = 484 $\mu m$
Resulting spot size is adjustable from 474 $\mu m$ (98%) to 314 $\mu m$ (65%)
Fig. 131: Optical System with doublet for a adjustable small beam size of 314$\mu m$

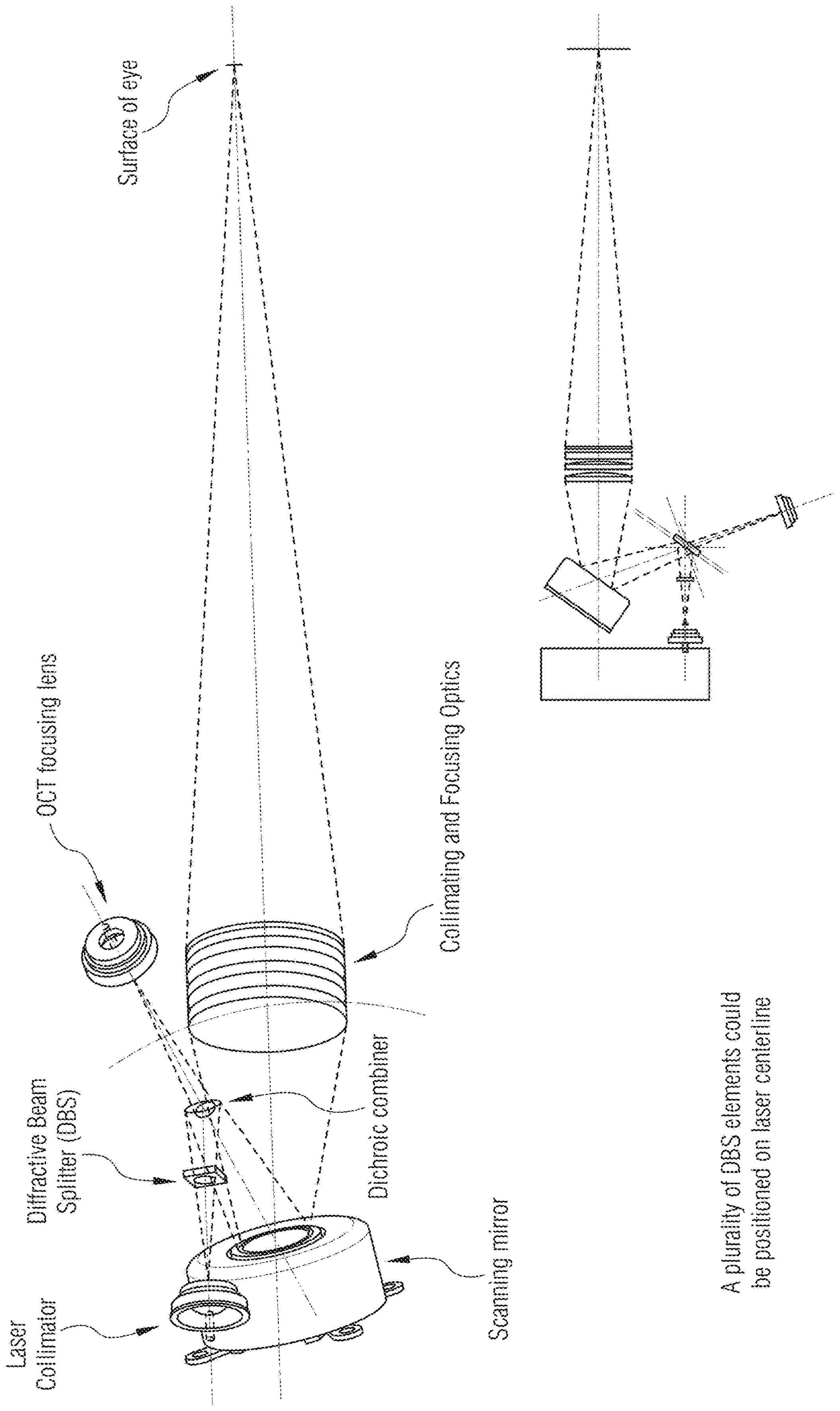
Fig. 132: Optical Design for Integrated OCT scanner

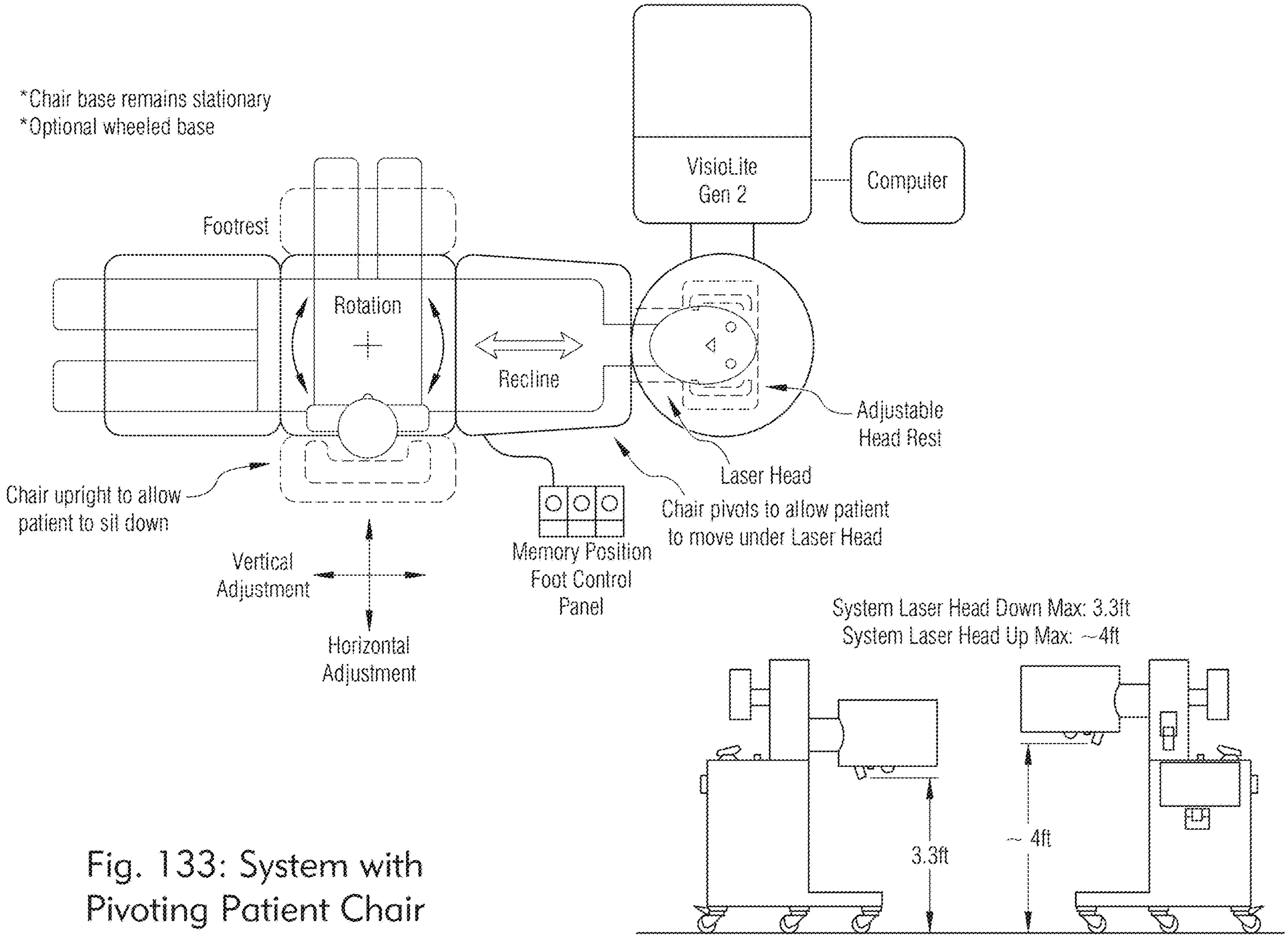
Fig. 133: System with Pivoting Patient Chair

- The Helmet could be mounted on the headrest in a chair or table
- Headrest could be mounted to the VisioLite System an provide positive locational feedback to the System.
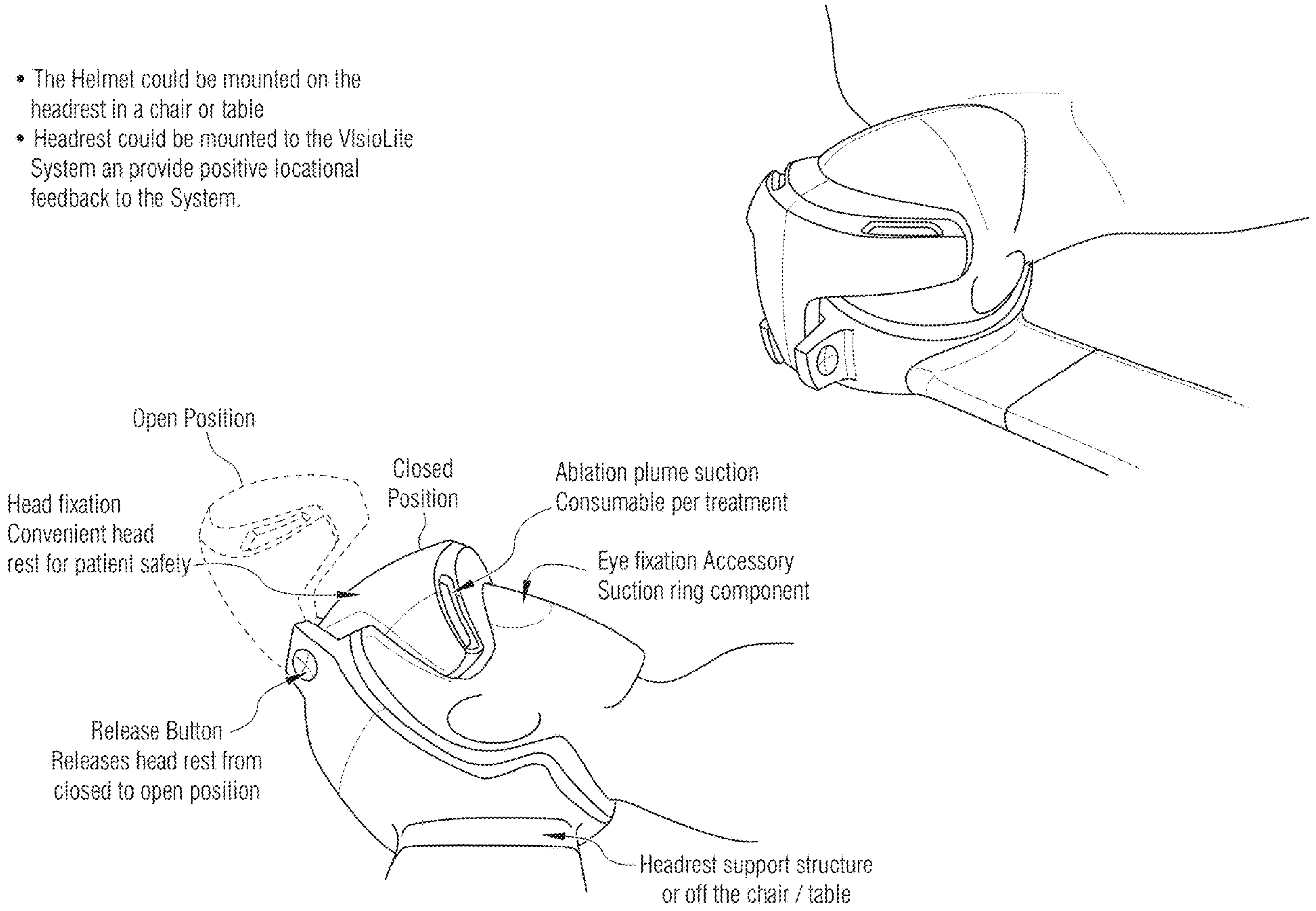
FIG. 134: The Helmet / Headrest with integrated Plume nozzle

- The Headrest could serve to assist in holding the patient's head and eye still in preparation and during treatment
- The Headrest could mount at the end of the treatment table or to the VisioLite unit.
- The headrest could be moved up and down to rough align the patient's eye in the Z axis
- The headrest could mold the ablation plume suction in position next to the quadrant being treated as positioned by the Doctor
- The headrest could also serve as a mounting location for the automated optional eye docking mechanisms

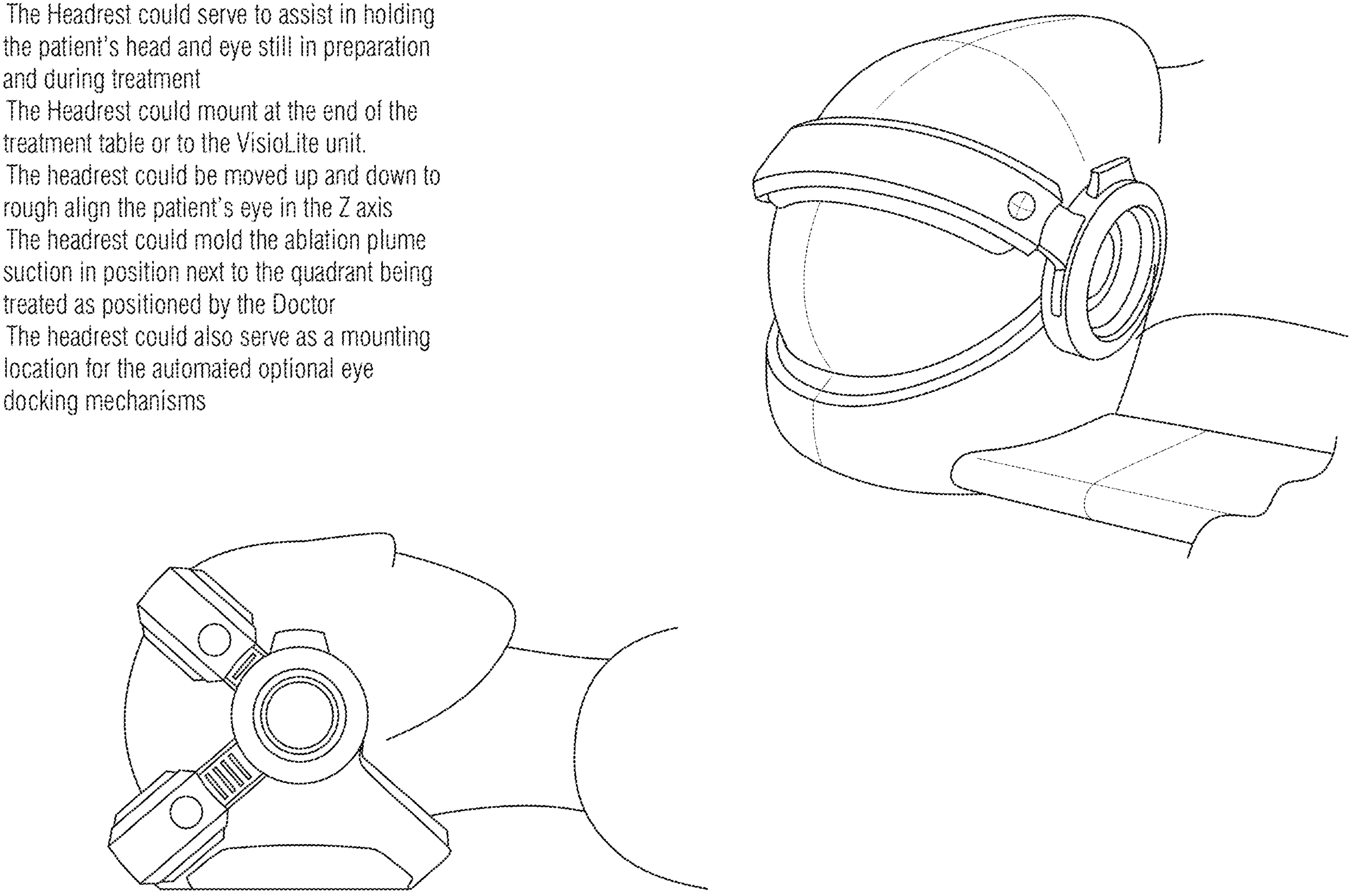

FIG. 135: Concepts for Headrest and Helmet

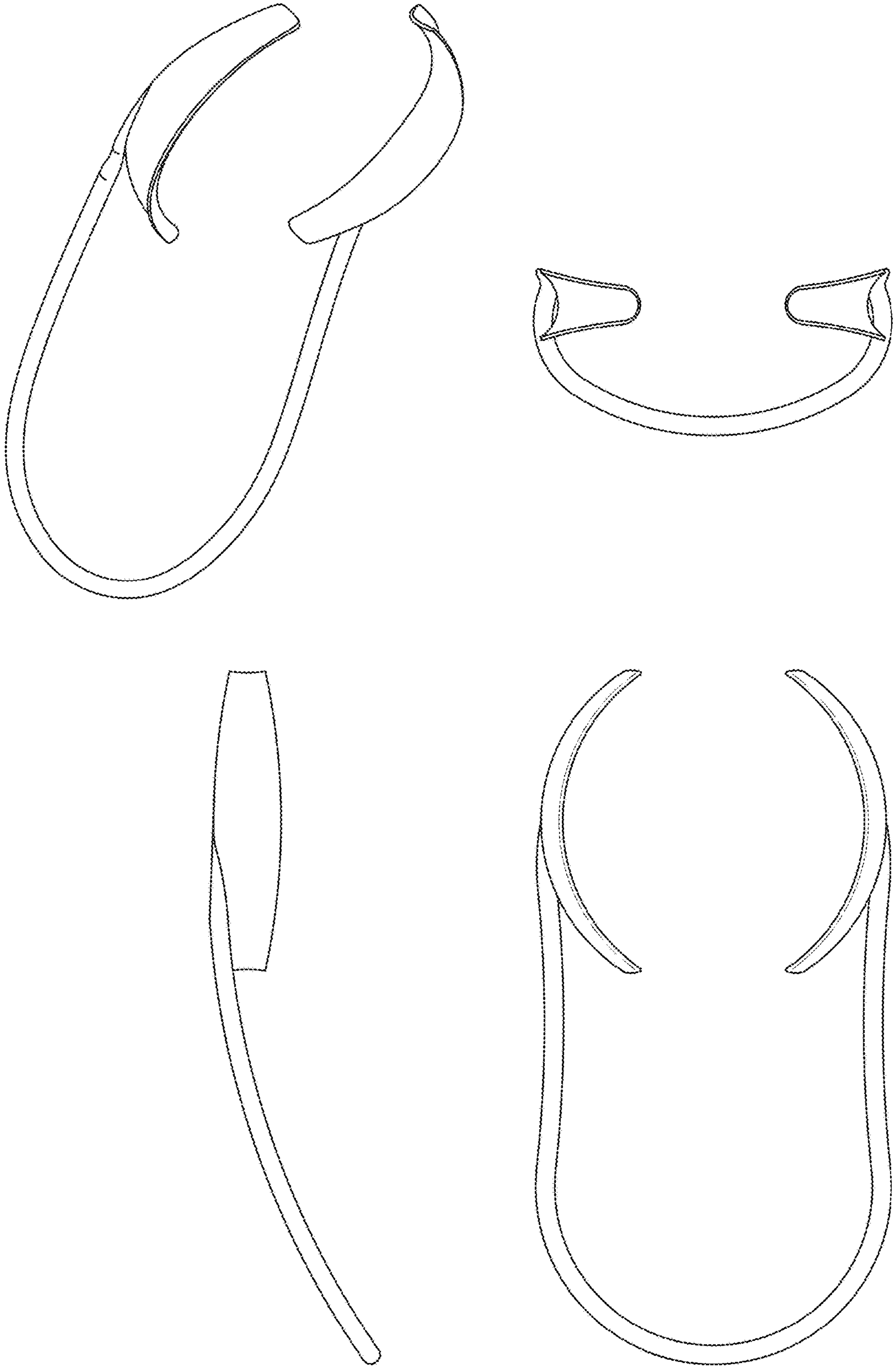
Fig. 136: Speculum

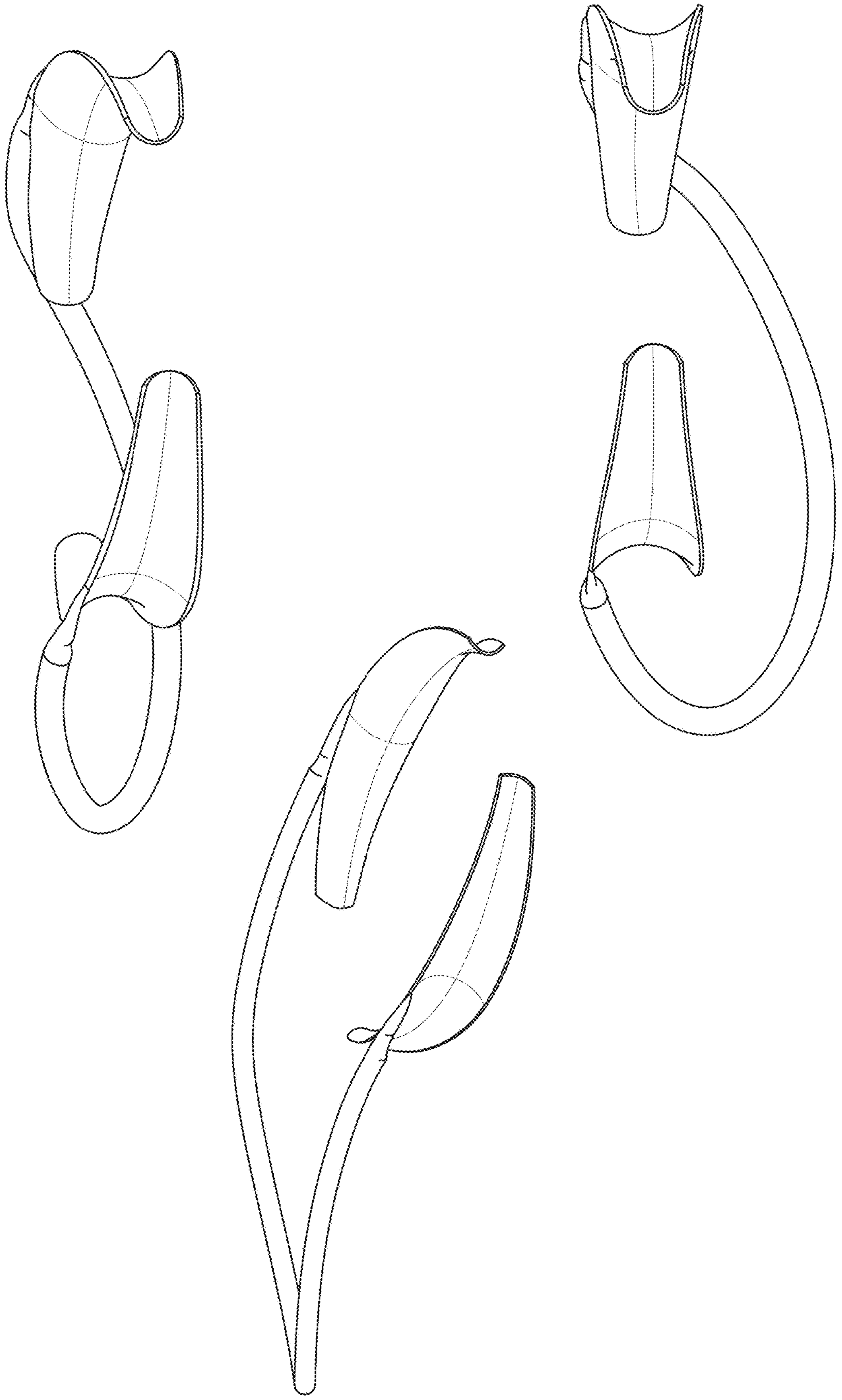
Fig. 137: Disposable Speculum with Silicone Overlay

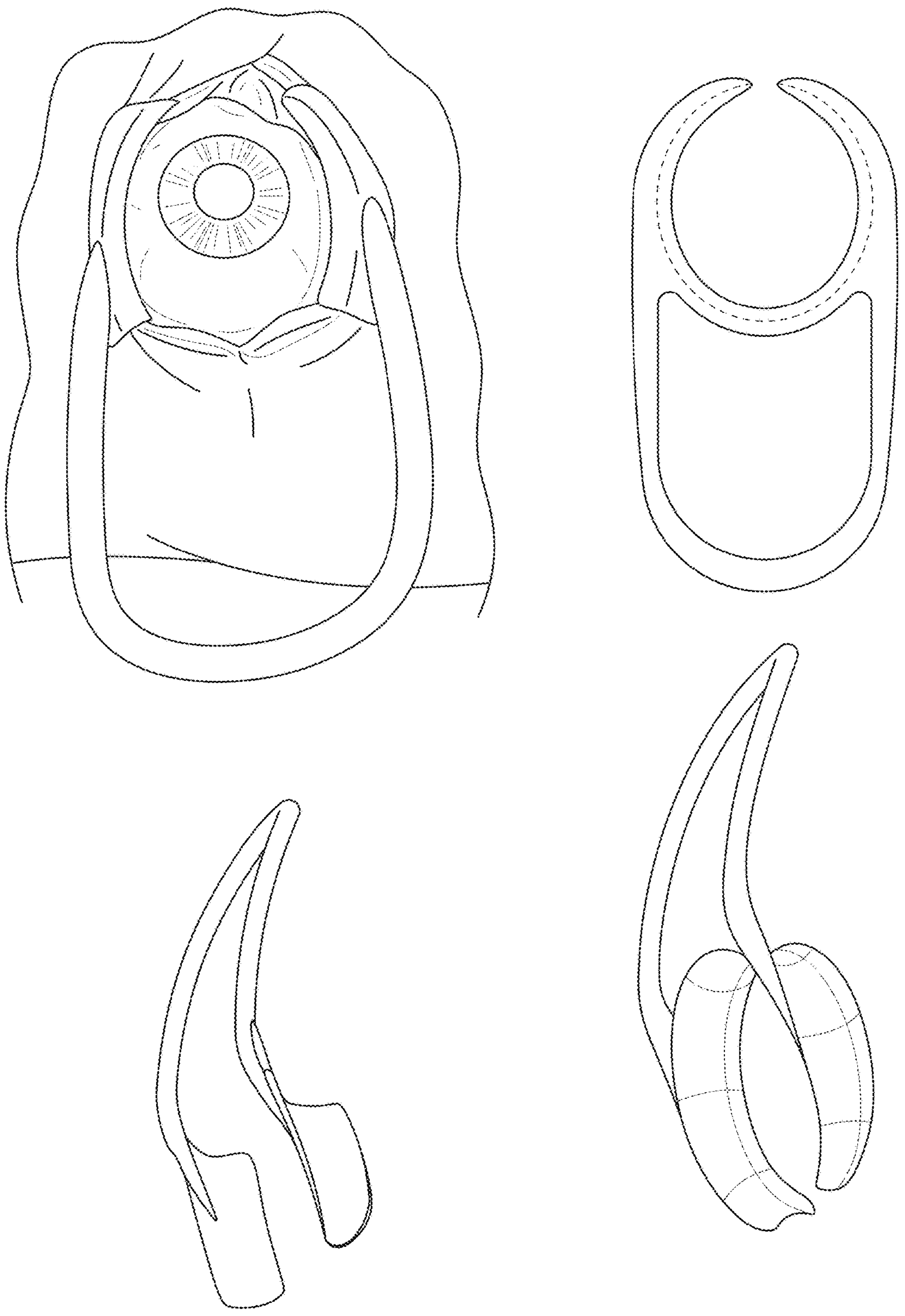
Fig. 138: Speculum

Table 2
Thickness ($\mu m$) of Anterior Corneal Layers After Laser Ablation

| Layer Type | Free Running Ef:YAG Laser | Q-switched Er:YAG Laser | Optical Parametric Oscillator Laser | Excimer laser (VISX Star) |
|---|---|---|---|---|
| Surface debris | 0 to 0.2 | 0 to 1.0 | 0 to 0.4 | 0 to 0.3 |
| Sub-ablation damage zone | 3 to 6 | 0.5 to 2 | 0.1 to 0.2 | 0.1 to 0.2 |
| Underlying zone | 5 to 12 with large vacuoles | 2 to 6 with medium vacuoles | 0.3 to 2.0 with small vacuoles | 0.3 to 2.0 with no vacuoles |
| Base | Normal stroma and normal endothelium | Normal stroma and normal endothelium | Normal stroma and normal endothelium | Normal stroma and normal endothelium |

Fig. 139A: Er:YAG; Q Switched YAG. Average thickness 5-10$\mu m$

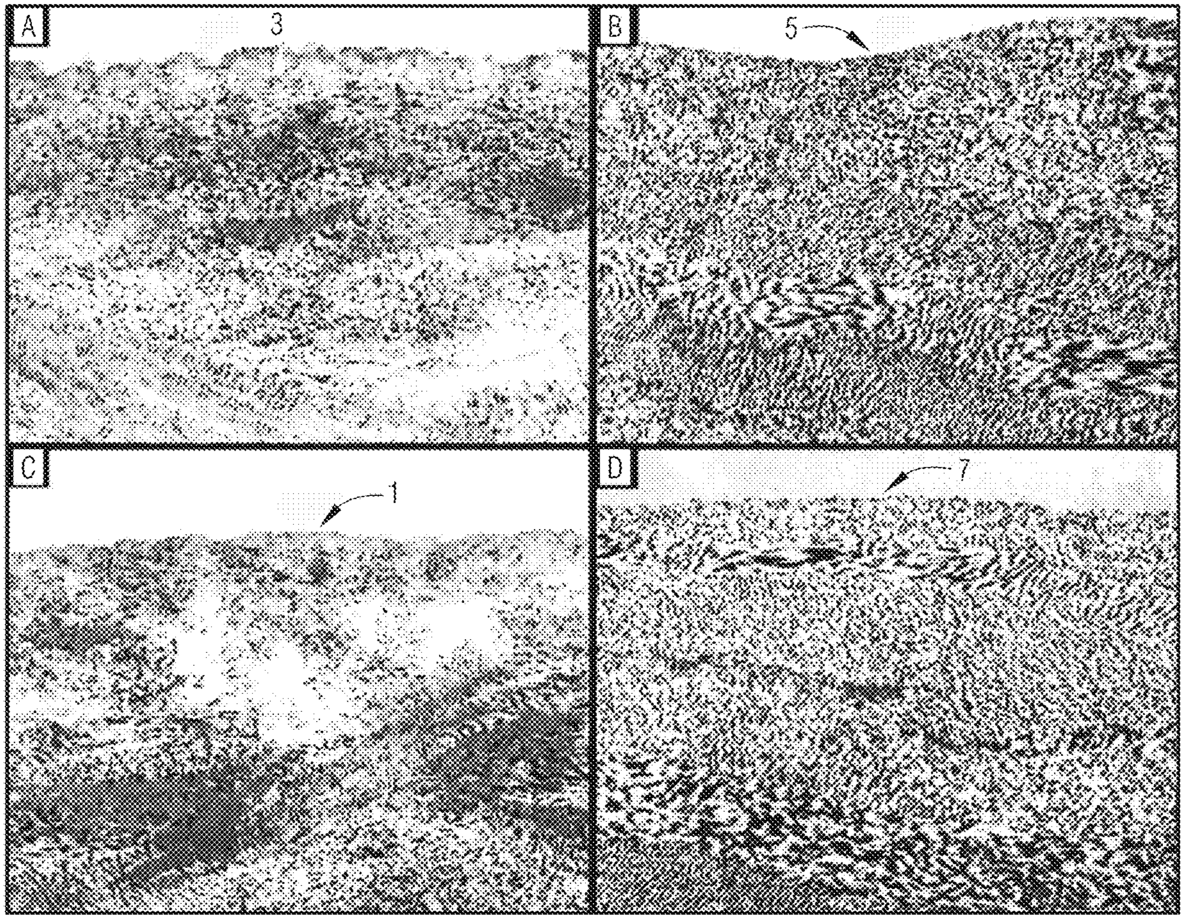

Figure 2. Transmission of electron microscopy of PRK ablations on cat eyes at 10,000X corresponding to: A) Q-switched Er: YAG laser shows slightly rough surface (3) with dark and white damage areas (4) within 1 to 2 $\mu$m of the surface. B) Optical parametric oscillator laser. Note the smooth surface (5) with small damage zone (6) within only one-third micron of the surface. C) Long-pulse Er:YAG laser. Note the thick damage zone (1) and prominent white coagulated areas (2) which are 5 to 10 $\mu$m below the surface. D) Excimer laser. Note the smooth surface (7). Damage zones of less than one-third micron of the surface, similar to C).

Fig. 139B: Er:YAG; Q Switched YAG. Average thickness 5-10$\mu$m

SYSTEMS AND METHODS FOR OCULAR LASER SURGERY AND THERAPEUTIC TREATMENTS

CROSS REFERENCE TO RELATED APPLICATIONS

This application is a continuation of International Patent Appl. No. PCT/US20/31392, filed May 5, 2020, which claims priority to U.S. Provisional Application No. 62/843, 403, filed May 4, 2019 and titled "SYSTEMS AND METHODS FOR OCULAR LASER SURGERY AND THERAPEUTIC TREATMENTS," the entire contents and disclosure of both of which are hereby incorporated by reference.

This application is related to the subject matter disclosed in U.S. application Ser. No. 15/942,513 (filed Mar. 31, 2018), which issued as U.S. Pat. No. 11,026,837, International Appl. No. PCT/US18/25608 (filed Mar. 31, 2018), Taiwan Appl. No. 108111355 (filed Mar. 29, 2019), U.S. application Ser. No. 11/376,969 (filed Mar. 15, 2006), which issued as U.S. Pat. No. 7,871,404, U.S. application Ser. No. 11/850,407 (filed Sep. 5, 2007), U.S. application Ser. No. 11/938,489 (filed Nov. 12, 2007), U.S. application Ser. No. 12/958,037 (filed Dec. 1, 2010), U.S. application Ser. No. 13/342,441 (filed Jan. 3, 2012), which issued as U.S. Pat. No. 8,348,932, U.S. application Ser. No. 13/709,890 (filed Dec. 10, 2012), U.S. application Ser. No. 14/526,426 (filed Oct. 28, 2014), U.S. application Ser. No. 14/861,142 (filed Sep. 22, 2015), U.S. Appl. Ser. No. 15/365,556 (filed Nov. 30, 2016), U.S. application Ser. No. 16/599,096 (filed Oct. 10, 2019), U.S. application Ser. No. 14/213,492 (filed Mar. 14, 2014), U.S. application Ser. No. 16/258,378 (filed Jan. 25, 2019), which issued as U.S. Pat. No. 12,036,150, U.S. application Ser. No. 15/638,308 (filed Jun. 29, 2017), U.S. application Ser. No. 16/702,470 (filed Dec. 3, 2019), and U.S. application Ser. No. 15/638,346 (filed Jun. 29, 2017), which issued as U.S. Pat. No. 11,071,450, each of which is incorporated herein by reference in its entirety.

FIELD

The subject matter described herein relates generally to systems, methods, therapies and devices for laser microporation, and more particularly for to systems, methods and devices for laser ocular microporation rejuvenation of tissue of the eye, specifically regarding aging of connective tissue, rejuvenation of connective tissue by ocular or scleral rejuvenation.

BACKGROUND

The eye is a biomechanical structure, a complex sense organ that contains complex muscular, drainage, and fluid mechanisms responsible for visual function and ocular biotransport. The accommodative system is the primary moving system in the eye organ, facilitating many physiological and visual functions in the eye. The physiological role of the accommodation system is to move aqueous, blood, nutrients, oxygen, carbon dioxide, and other cells, around the eye organ. In general, the loss of accommodative ability in presbyopes has many contributing lenticular, as well as extralenticular and physiological factors that are affected by increasing age. Increasing ocular rigidity with age produces stress and strain on these ocular structures and can affect accommodative ability which can impact the eye in the form of decreased biomechanical efficiency for physiological processes including visual accommodation, aqueous hydrodynamics, vitreous hydrodynamics and ocular pulsatile blood flow to name a few. Current procedures only manipulate optics through some artificial means such as by refractive laser surgery, adaptive optics, or corneal or intraocular implants which exchange power in one optic of the eye and ignore the other optic and the importance of preserving the physiological functions of the accommodative mechanism.

Additionally, current implanting devices in the sclera obtain the mechanical effect upon accommodation. They do not take into account effects of 'pores', 'micropores', or creating a matrix array of pores with a central hexagon, or circle or polygon in 3D tissue. As such, current procedures and devices fail to restore normal ocular physiological functions.

Accordingly, there is a need for systems and methods for restoring normal ocular physiological functions taking into account effects of 'pores' or creating a lattice or matrix array of pores with a central hexagon, or circle or polygon in three-dimensional (3D) tissue.

SUMMARY

Disclosed are systems, devices and methods for laser microporation for rejuvenation of tissue of the eye, for example, regarding aging of connective tissue and rejuvenation of connective tissue by scleral rejuvenation. The systems, devices and methods disclosed herein restore physiological functions of the eye including restoring physiological accommodation or physiological pseudo-accommodation through natural physiological and biomechanical phenomena associated with natural accommodation of the eye. In some embodiments, the laser system may be configured to treat ocular tissue off axis or in a region of the eye which is distinct from the visual axis or directed away from the pupil of the eye where the gaze of the eye is.

In some embodiments, the present disclosure may include a system for delivering microporation medical treatments to biological tissue to improve biomechanics of an eye, the system comprising: a controller; a laser head system comprising: a housing, a laser subsystem for generating a beam of laser irradiation on a treatment-axis not aligned with a patient's visual-axis, operable for use in subsurface ablative medical treatments to create a pattern of pores that improves biomechanics, and a lens operable to focus the beam of laser irradiation onto a target tissue; an eye tracking subsystem for tracking landmarks and movements of the eye; a depth control subsystem for controlling a depth of ablation or microporation on the target tissue; and wherein the controller is operable to control the movements of the laser subsystem including at least one of a pitch movement, a swivel movement and a yaw movement.

In some embodiments, the system may also include a scanning system communicatively coupled to the eye tracking subsystem and the depth control subsystem for scanning a focus spot over an area of the target tissue. The system may also include an avoidance subsystem for identifying biological structures or locations of the eye, and one or more diffractive beam splitter.

In some embodiments, the pattern of pores may include pores of a same size, shape and depth; or the pattern of pores may include pores of different sizes, shapes and depths. The pattern of pores may include pores having equal distance. The pattern of pores may include pores having different distances and wherein the pattern of the pores is at least tightly packed or tessellated or spaced.

The depth of the pores may be proportional to a total laser energy.

In some embodiments, the present disclosure may include a method of delivering microporation medical treatments to biological tissue to improve biomechanics of an eye, comprising: generating, by a laser subsystem, a treatment beam on a treatment-axis not aligned with a patient's visual-axis in a subsurface ablative medical treatment to create a pattern of pores that improves biomechanics; monitoring, by an eye tracking subsystem, an eye position for application of the treatment beam; controlling, by a controller, movements of the laser subsystem including at least one of a pitch movement, a swivel movement and a yaw movement; and focusing, by a lens, the treatment beam onto a target tissue.

The method may further include controlling, by a depth control subsystem, a depth of ablation or microporation on the target tissue; and scanning, by a scanning system communicatively coupled to the eye tracking subsystem and the depth control subsystem, a focus spot over an area of the target tissue.

Other features and advantages of the present invention are or will become apparent to one skilled in the art upon examination of the following figures and detailed description, which illustrate, by way of examples, the principles of the present invention.

The systems, devices, and methods described herein in detail for laser ocular microporation are example embodiments and should not be considered limiting. Other configurations, methods, features and advantages of the subject matter described herein will be or will become apparent to one with skill in the art upon examination of the following figures and detailed description. It is intended that all such additional configurations, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 1 illustrates general anatomy of an eye.

FIG. 3 illustrates an example of posterior treatment zones, according to some embodiments of the present disclosure.

FIGS. 4, 5A and 5B illustrate exemplary tissue treated in microporation, according to some embodiments of the present disclosure.

FIG. 6 illustrates another exemplary OCT depth method to monitor eye motion between pulses of ablation, according to some embodiments of the present disclosure.

FIGS. 7 to 17 illustrate exemplary laser systems, according to some embodiments of the present disclosure.

FIG. 18 illustrates an exemplary process of the laser system, according to some embodiments of the present disclosure.

FIGS. 19 to 25 illustrate exemplary workflows of the laser system, according to some embodiments of the present disclosure.

FIG. 26 illustrates an exemplary process to generate a pore array, according to some embodiments of the present disclosure.

FIG. 27 illustrates another exemplary process to generate a pore array, according to some embodiments of the present disclosure.

FIGS. 28 and 29 illustrate exemplary laser systems with FPGA architecture, according to some embodiments of the present disclosure.

FIG. 30 illustrates another exemplary process of the laser system, according to some embodiments of the present disclosure.

FIG. 31 illustrates exemplary laser system with single scanning mirror, according to some embodiments of the present disclosure.

FIG. 32 illustrates exemplary laser system with capability to optimize pulse parameters, according to some embodiments of the present disclosure.

FIG. 33 illustrates exemplary laser system with OCT imaging/OCT depth control, according to some embodiments of the present disclosure.

FIGS. 34A and 34B illustrate examples of OCT depth control signal with a porcine eye, according to some embodiments of the present disclosure.

FIGS. 35A and 35B illustrate exemplary OCT measurements, according to some embodiments of the present disclosure.

FIG. 36 illustrates laser system may include an OCT control system for dual OCT/DC and Scanning OCT imaging subsystems, according to some embodiments of the present disclosure.

FIG. 37 illustrates laser system may include an OCT control system with integrated OCT/DC and Scanning OCT imaging subsystems, according to some embodiments of the present disclosure.

FIGS. 38 to 42 illustrate examples of combined and or shared components within and OCT system, according to some embodiments of the present disclosure.

FIGS. 43A to 46 illustrate laser system to treat scleral tissue where the OCT scanning system may provide both 2D sectional views and a 3D isometric view of the treatment area, according to some embodiments of the present disclosure.

FIGS. 47 to 49 illustrate exemplary eye tracking processes, according to some embodiments of the present disclosure.

FIGS. 50, 51 and 51A illustrate exemplary functions provided to a doctor, according to some embodiments of the present disclosure.

FIG. 52 illustrates exemplary treatment areas, according to some embodiments of the present disclosure.

FIG. 53 illustrates laser system including a single scanning mirror that combines OCT/DC beam that is scanned over the eye surface in order to map anatomical features, according to some embodiments of the present disclosure.

FIG. 54 illustrates other exemplary treatment areas, according to some embodiments of the present disclosure.

FIG. 55 illustrates exemplary treatment position relative to Schlemm's Canal and Anatomical limbus, according to some embodiments of the present disclosure.

FIG. 56 illustrates camera system providing images to be used for eye tracking, facial feature recognition, treatment alignment, according to some embodiments of the present disclosure.

FIG. 57 illustrates the mirror can be motorized in multiple axis to align the field of view image to target areas, according to some embodiments of the present disclosure.

FIG. 58 illustrates exemplary microscope images at a higher magnification to inspect treatment area, according to some embodiments of the present disclosure.

FIGS. 59 to 61B illustrate laser system including a camera that can image the treatment area and surrounding features, according to some embodiments of the present disclosure.

FIGS. 67 and 68 illustrate treatment areas relative to the limbus, according to some embodiments of the present disclosure.

FIG. 69 illustrates exemplary microscope quality camera images at a higher magnification to inspect treatment area relative to the limbus, according to some embodiments of the present disclosure.

FIG. 70 illustrates an exemplary 3D image from a TOF camera, according to some embodiments of the present disclosure.

FIG. 90 illustrates an exemplary laser system with a laser head system where the patient can be in a sitting position, according to some embodiments of the present disclosure.

FIGS. 91 to 94 illustrate a plurality of off-axis treatment area shapes and positions around the visual axis, according to some embodiments of the present disclosure.

FIG. 95 illustrates exemplary treatment pattern described as 5 critical zones in 5 distinct distances from the outer edge of the anatomical limbus (AL), according to some embodiments of the present disclosure.

FIG. 96 illustrates example of anterior treatment zones, according to some embodiments of the present disclosure.

FIG. 97 illustrates another exemplary treatment pattern described as 5 critical zones in 5 distinct distances from the outer edge of the anatomical limbus (AL), according to some embodiments of the present disclosure.

FIGS. 98 to 100 illustrate other examples of anterior treatment zones, according to some embodiments of the present disclosure.

FIGS. 101 to 104 illustrate other examples of posterior treatment zones, according to some embodiments of the present disclosure.

FIGS. 105 to 108 illustrate round or square pores or other shaped spots, according to some embodiments of the present disclosure.

FIGS. 109 to 111 illustrate multiple patterns, pulses, tessellations, shapes and sizes for both individual micropores or matrices of multiple pores, according to some embodiments of the present disclosure.

FIGS. 112 to 115 illustrate exemplary empirical data, according to some embodiments of the present disclosure.

FIG. 116 illustrates an exemplary histology of micropores, according to some embodiments of the present disclosure.

FIGS. 117 to 119 illustrate exemplary uncrosslinking images, according to some embodiments of the present disclosure.

FIG. 120 illustrates an exemplary Treatment Dome Laser pointing design, according to some embodiments of the present disclosure.

FIGS. 121 to 125 illustrate exemplary optical components, according to some embodiments of the present disclosure.

FIGS. 126A, 126B and 127 illustrate exemplary laser system configured to treat scleral tissue having a single scanning mirror that combines OCT scanning and OCT depth control functions, according to some embodiments of the present disclosure.

FIGS. 128-132 illustrate other exemplary optical components, according to some embodiments of the present disclosure.

FIG. 133 illustrates laser system including a patient table or chair, according to some embodiments of the present disclosure.

FIGS. 134 and 135 illustrate laser system including a patient headrest, according to some embodiments of the present disclosure.

FIGS. 136 to 138 illustrate an exemplary speculum, according to some embodiments of the present disclosure.

FIGS. 139A and 139B illustrate exemplary subsurface images of the tissue ablation, according to some embodiments of the present disclosure.

DETAILED DESCRIPTION

Figure 2B:
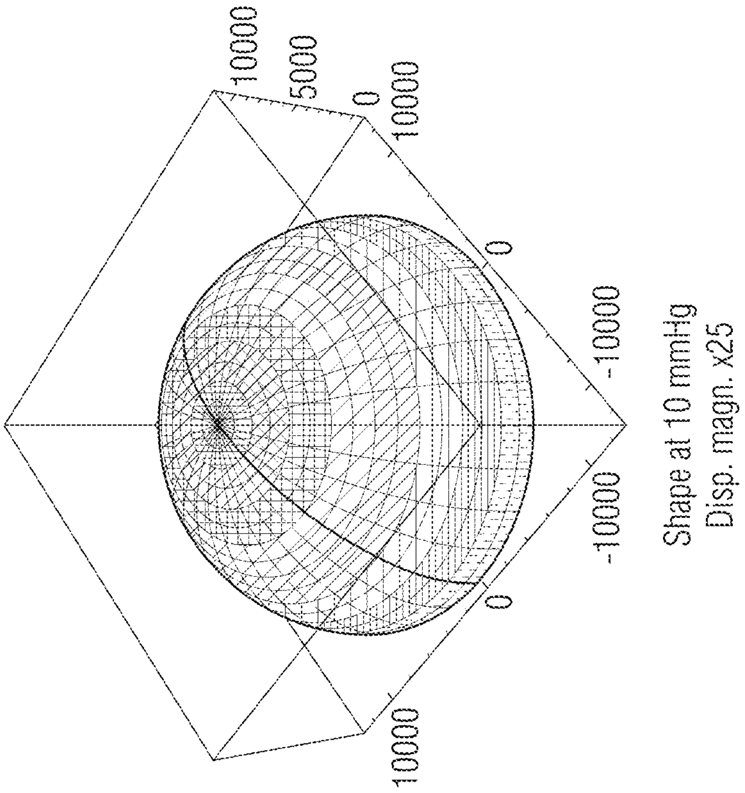
FIGS. 2A to 2E illustrate eye shape and IOP, according to some embodiments of the present disclosure.
Figure 2A:
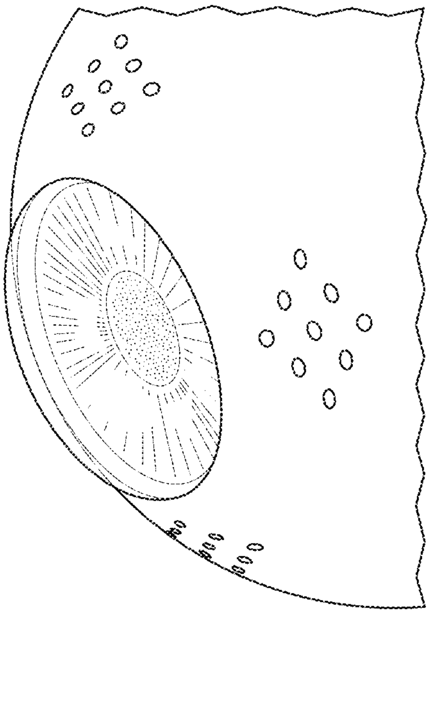
Figure 2D:
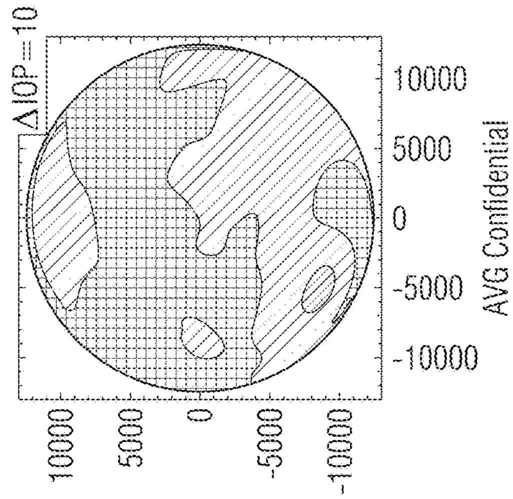
Figure 2E:
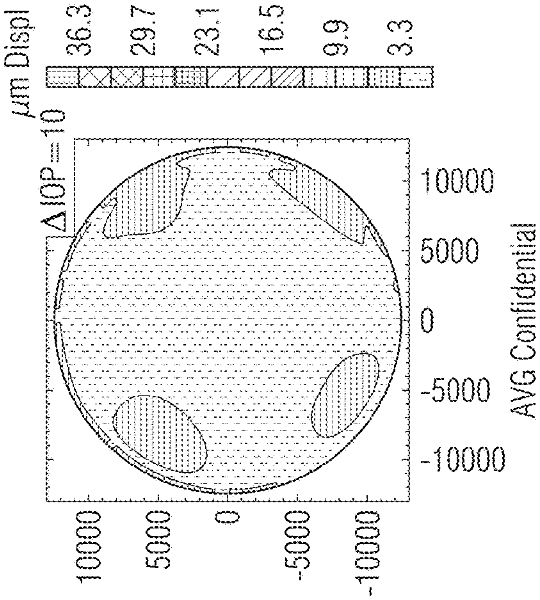
Figure 2C:
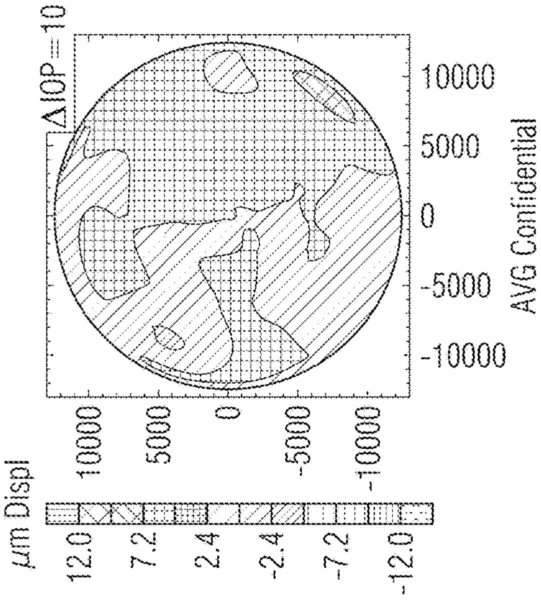
Figure 59:
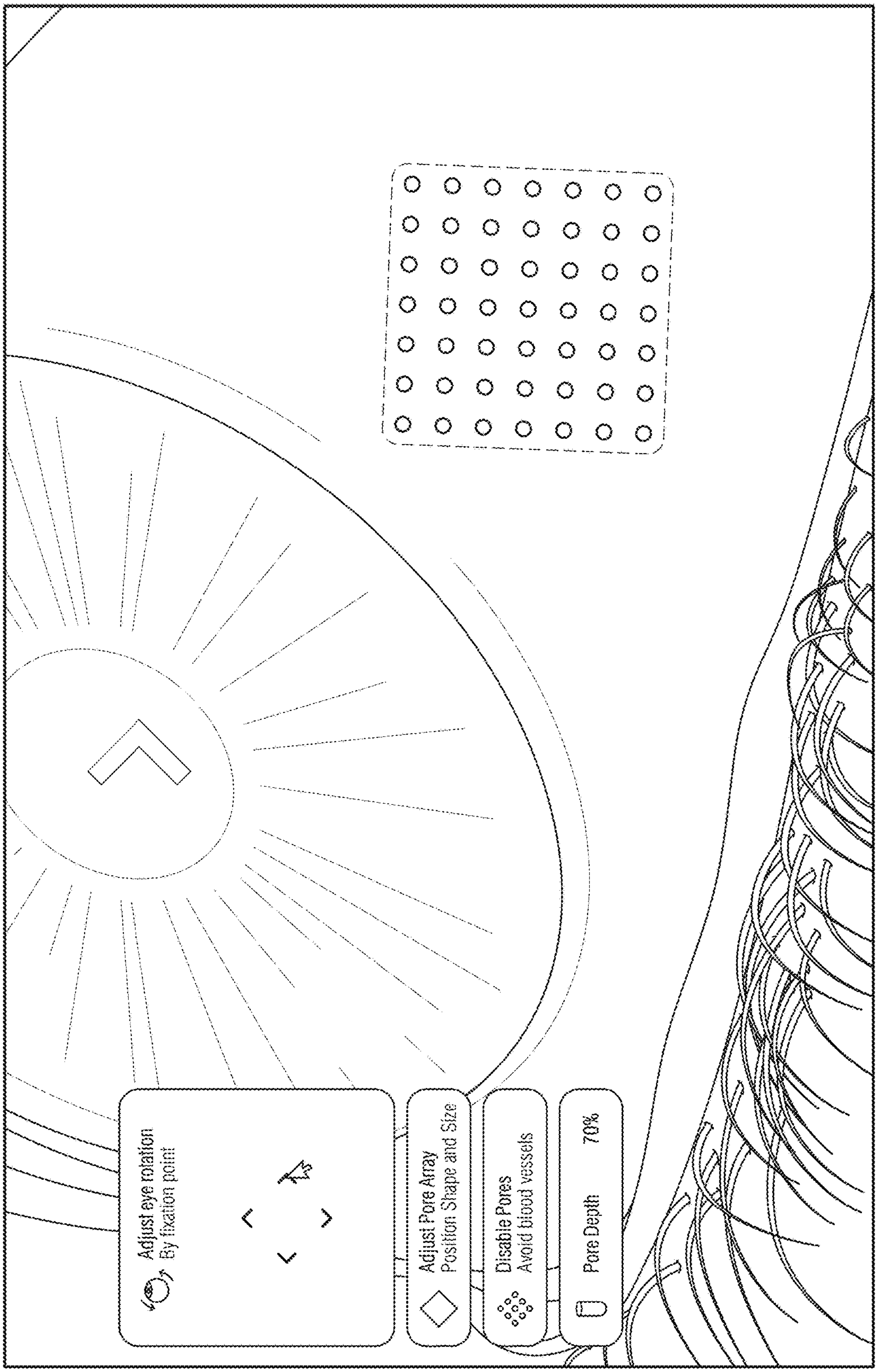
Figure 62:
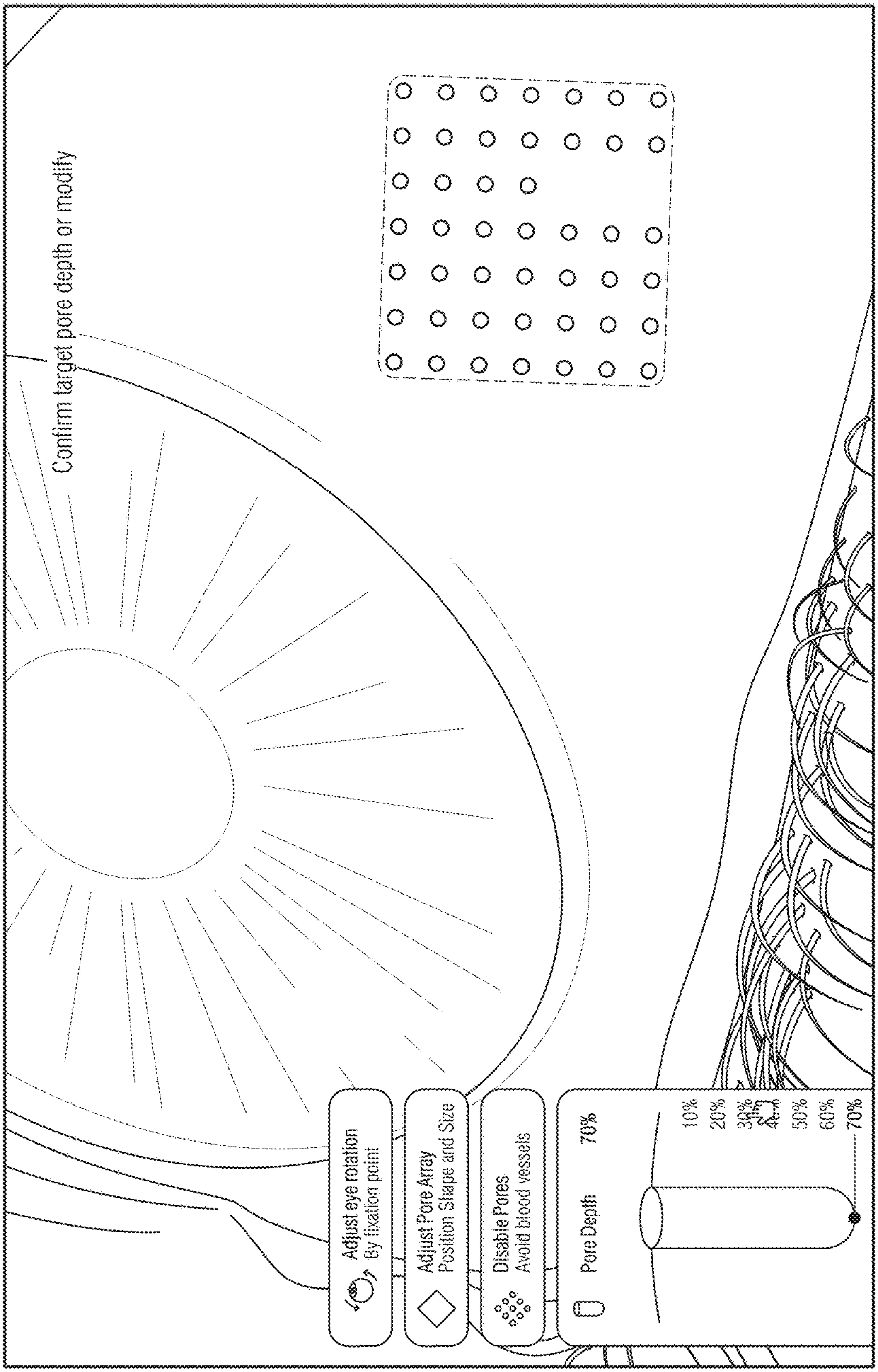
FIGS. 62 to 66 illustrate an exemplary matrix array of micro-excisions, according to some embodiments of the present disclosure.
Figure 63:
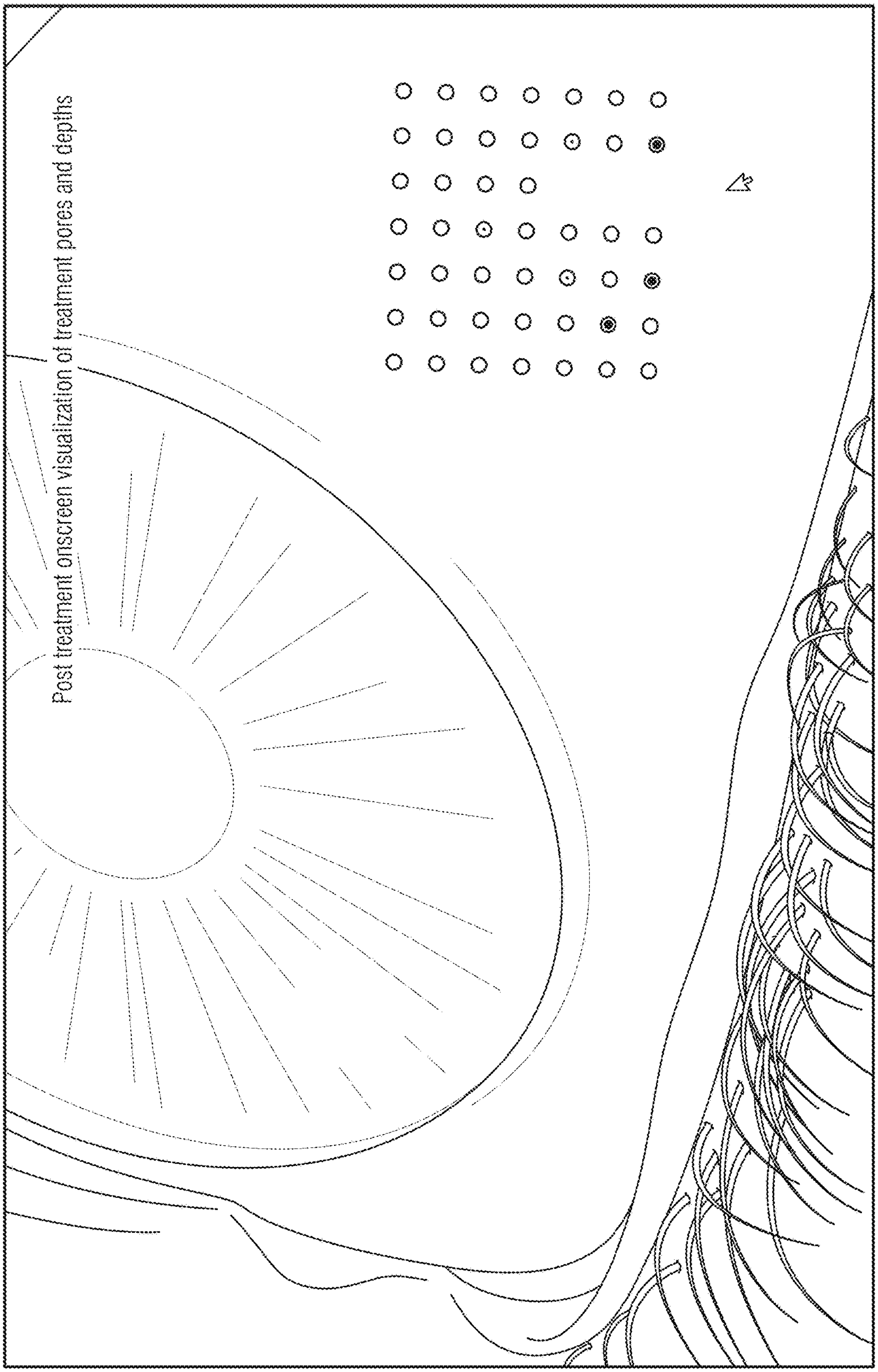
Figure 64:
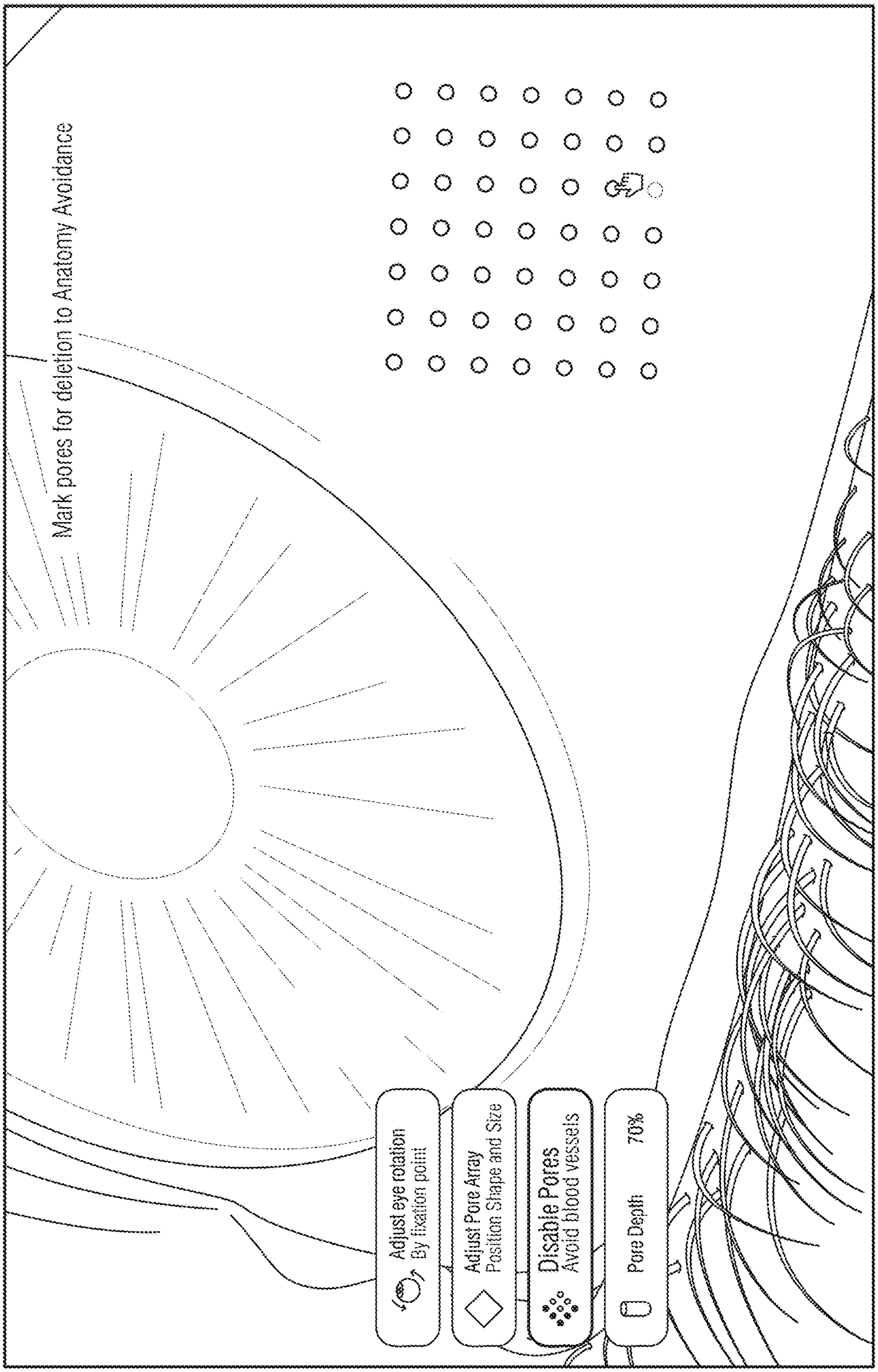

The below described figures illustrate the described invention and method of use in at least one of its preferred, best mode embodiment, which is further defined in detail in the following description. Those having ordinary skill in the art may be able to make alterations and modifications to what is described herein without departing from its spirit and scope. While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. All features, elements, components, functions, and steps described with respect to any embodiment provided herein are intended to be freely combinable and substitutable with those from any other embodiment unless otherwise stated. Therefore, it should be understood that what is illustrated is set forth only for the purposes of example and should not be taken as a limitation on the scope of the present invention.

Generally, the systems and methods of the present disclosure take into consideration combination of pores filling technique and creating matrices of pores in three dimensions (3D). Pores with a particular depth, size and arrangement in a matrix 3D scaffold of tissue produce plastic behavior within the tissue matrix. This affects the biomechanical properties of the ocular tissue, e.g., scleral tissue, allowing it to be more pliable. It is known that connective tissues that contain elastin are 'pliable' and meant to have elasticity. The sclera in fact has natural viscoelasticity.

The systems, devices and methods of the present disclosure may include laser microporation for rejuvenation of tissue of the eye, for example, regarding aging of connective tissue and rejuvenation of connective tissue by scleral rejuvenation. The systems, devices and methods disclosed herein restore physiological functions of the eye including restoring physiological accommodation or physiological pseudo-accommodation through natural physiological and biomechanical phenomena associated with natural accommodation of the eye.

In some embodiments, the system may include a display which included in the laser module to view the tissue area (doctors display), control & safety (see also below) which includes laser supply, electronics and motion control platform as well as safety, direct interface to a base station. The system may also include motion stage; translation stage to position the laser, optics and scanner in the specific area—laser and optics may include 3 mikron module and beam forming optics; depth control system to avoid too deep ablation; eye tracking module; suction and laminar flow for operator safety. The system may include beam deflection synchronized with eye tracking for micropore array generation. Other components and features may include, for example, camera unit for vision. The base station may be an intelligent moveable base station that may include operator display for control and safety, distribution of power to different modules, water cooling of laser system, optional foot pedal, communication interface with external world, debug, updates, and other features, and main supply for wide range power supply for international operation.

As mentioned above, in some embodiments, the described systems, methods and devices of the disclosure may include creating a finite element model of the accommodative mechanism that includes seven major zonule pathways and three ciliary muscle sections, calibrating and validating the model through comparison to previously published experimental measurements of ciliary muscle and lens motion during accommodation, and using the model to investigate the influence of zonular anatomy and ciliary muscle architecture on healthy accommodative function. The model may include geometry of the lens and extra-lenticular structures and simulations utilized novel zonular tensioning and muscle contraction driven accommodation.

In some embodiments, the described systems, methods and devices of the disclosure may include a method to change the biomechanical properties of biological tissue using a complex of matrix formations consisting of perforations on said tissue where the configuration is based on a mathematical algorithm. The change in biomechanical properties of biological tissue is related to elasticity, shock absorption, resilience, mechanical dampening, pliability, stiffness, rigidity, configuration, alignment, deformation, mobility and/or volume of said tissue. The matrix formations of perforations may allow for a non-monotonic force deformation relationship on said tissue with the range of isotropic elastic constant across the medium. Each matrix formation may create a linear algebraic relationship between row length and column length with each perforation of said tissue having continuous linear vector spaces with derivatives up to N. Where N is an infinite number. The complex may create a total surface area wherein each perforation has a proportional relationship to the total surface area of said tissue. The complex can also be arranged to achieve equilibrium of forces, stress and strain and reduce shearing effect the between the matrix formations and the perforation. Each perforation may be excised volume of tissue which defines a point lattice on said tissue where the preferred shape of excised volume is cylindrical. The matrix formation consists of tessellations with or without a repeating pattern wherein the tessellations are Euclidian, Non-Euclidean, regular, semi-regular, hyperbolic, parabolic, spherical, or elliptical and any variation therein. Each perforation may have a linear relationship with the other perforations within each matrix formation and the complex of matrices individually. The tessellations directly or indirectly relate to stress and shear strain atomic relationships between tissues by computing the mathematical array of position vectors between perforations. The atomic relationship is a predictable relationship of the volume removed by each perforation to the change in biomechanical properties seen as an element of the mathematical algorithm. The predictable relationship of the removed volume may be mutually exclusive. The tessellations may be a square which can be subdivided into a tessellation of equiangular circles or polygons to derivative of n. In some embodiments, the mathematical algorithm uses a factor 1 or Phi to find the most efficient placement of matrices to alter the biomechanical properties of said tissue. The factor 1 or Phi may be 1.618 (4 significant digits) representing any fraction of a set of spanning vectors in a lattice having the shortest length relative to all other vectors' length. In some embodiments, the mathematical algorithm of claim 1 includes a nonlinear hyperbolic relationship between planes of biological tissue and at any boundary or partition of neighboring tissues, planes and spaces in and outside of the matrix.

Various embodiments of the laser system are described in U.S. application Ser. No. 15/942,513 (filed Mar. 31, 2018), International Appl. No. PCT/US18/25608 (filed Mar. 31, 2018), Taiwan Appl. No. 108111355 (filed Mar. 29, 2019), U.S. application Ser. No. 11/376,969 (filed Mar. 15, 2006), U.S. application Ser. No. 11/850,407 (filed Sep. 5, 2007), U.S. application Ser. No. 11/938,489 (filed Nov. 12, 2007), U.S. application Ser. No. 12/958,037 (filed Dec. 1, 2010), U.S. application Ser. No. 13/342,441 (filed Jan. 3, 2012), U.S. application Ser. No. 13/709,890 (filed Dec. 10, 2012), U.S. application Ser. No. 14/526,426 (filed Oct. 28, 2014), U.S. application Ser. No. 14/861,142 (filed Sep. 22, 2015), U.S. application Ser. No. 15/365,556 (filed Nov. 30, 2016), U.S. application Ser. No. 16/599,096 (filed Oct. 10, 2019), U.S. application Ser. No. 14/213,492 (filed Mar. 14, 2014), U.S. application Ser. No. 16/258,378 (filed Jan. 25, 2019), U.S. application Ser. No. 15/638,308 (filed Jun. 29, 2017), U.S. application Ser. No. 16/702,470 (filed Dec. 3, 2019), and U.S. application Ser. No. 15/638,346 (filed Jun. 29, 2017), which are incorporated in their entireties herein.

Influence of ocular rigidity and ocular biomechanics on the pathogenesis of age-related presbyopia is an important aspect herein. Descriptions herein are made to modifying the structural stiffness of the ocular connective tissues, namely the sclera of the eye using the systems and methods of the present disclosure.

INTRODUCTION

In order to better appreciate the present disclosure, ocular accommodation, ocular rigidity, ocular biomechanics, and presbyopia will be briefly described. In general, the loss of accommodative ability in presbyopes has many contributing lenticular, as well as extralenticular and physiological factors that are affected by increasing age. Increasing ocular rigidity with age produces stress and strain on these ocular structures and can affect accommodative ability. Overall, understanding the impact of ocular biomechanics, ocular rigidity, and loss of accommodation could produce new ophthalmic treatment paradigms. Scleral therapies may have an important role for treating biomechanical deficiencies in presbyopes by providing at least one means of addressing the true etiology of the clinical manifestation of the loss of accommodation seen with age. The effects of the loss of accommodation have impact on the physiological functions of the eye to include but not limited to visual accommodation, aqueous hydrodynamics, vitreous hydrodynamics, and ocular pulsatile blood flow. Using the systems and methods of the present disclosure to restore more pliable biomechanical properties of ocular connective tissue is a safe procedure and can restore accommodative ability in aging adults.

Accommodation has traditionally been described as the ability of the crystalline lens of the eye to change dioptric power dynamically to adjust to various distances. More recently, accommodation has been better described as a complex biomechanical system having both lenticular and extralenticular components. These components act synchronously with many anatomical and physiological structures in the eye organ to orchestrate not only the visual manifestations that occur with accommodation, but also the physiological functions integral to the eye organ, such as aqueous hydrodynamics and ocular biotransport.

Biomechanics is the study of the origin and effects of forces in biological systems. Biomechanics has remained underutilized in ophthalmology. This biomechanical paradigm deserves to be extended to the anatomical connective tissues of the intricate eye organ. Understanding ocular biomechanics as it relates to accommodation can allow for a more complete picture of the role this primary moving system has on overall eye organ function, while maintaining optical quality for visual tasks.

The eye is a biomechanical structure, a complex sense organ that contains complex muscular, drainage, and fluid mechanisms responsible for visual function and ocular biotransport. The accommodative system is the primary moving system in the eye organ, facilitating many physiological and visual functions in the eye. The physiological role of the accommodation system is to move aqueous, blood, nutrients, oxygen, carbon dioxide, and other cells, around the eye organ. In addition, it acts as a neuroreflexive loop, responding to optical information received through the cornea and lens to fine tune focusing power throughout a range of vision, and is essentially the "heart" of the eye organ.

FIG. 1 illustrates a general anatomy of an eye which will be helpful for the discussions herein. FIGS. 2A to 2E illustrate eye shape and TOP.

Further discussion of biomechanics (including ocular biomechanics), its critical role in the pathophysiology of the eye organ, physiological accommodation in the eye, scleral surgery, critical role of ciliary muscle in many functions of the eye organ including accommodation and aqueous hydrodynamics (outflow/inflow, pH regulation, and IOP) are described in detail in U.S. application Ser. No. 15/942,513, Taiwan Application No. 108111355, and International Appl. No. PCT/US18/25608, which are incorporated in their entireties herein.

U.S. application Ser. No. 15/942,513, Taiwan Application No. 108111355, and International Appl. No. PCT/US18/25608 further describe scleral laser rejuvenation (e.g., in FIGS. 1A-1 to 1A-7 and their corresponding descriptions in U.S. application Ser. No. 15/942,513), the role of ocular rigidity (including "stiffness" of the outer ocular structures of the eye including the sclera and the cornea) in hindering the accommodation apparatus. These descriptions are incorporated in their entirety herein.

The systems and methods of the present disclosure take into consideration combination of pores filling technique and creating matrices of pores in three dimensions. Pores with a specific depth, size and arrangement in a matrix 3D scaffold of tissue produce plastic behavior within the tissue matrix. This affects the biomechanical properties of the scleral tissue allowing it to be more pliable. The plurality of pores may be created in a matrix 3D scaffold, in an array pattern or a lattice(s). Various microporation characteristics may be supported. These may include volume, depth, density, and so on.

It should be noted that although the examples herein describe treating of scleral tissue, the system of the disclosure may also be configured to treat other ocular tissues and tissues.

FIGS. 4, 5A and 5B illustrate micropore and the sclera, and examples of tissue treated in microporation.

FIGS. 62 to 66 illustrate an exemplary matrix array of micro-excisions, using the systems and methods of the present disclosure, in four oblique quadrants.

FIG. 2G in U.S. application Ser. No. 15/942,513 illustrates an exemplary graphical representation of restored ocular compliance, decreased scleral resistive forces, increased ciliary resultant forces, and restored dynamic accommodation following the treatment.

The matrix shape can be arranged in a plurality of dimensions, sizes, shapes, geometries, distributions, and areas. The matrix shape can be either regular or irregular. In some embodiments, it may be advantageous to create a circle, tetrahedral or central hexagon shape. In order to create a central hexagon within a matrix there must be a series of 'pores' with specific composition, depth, and relationship to the other 'pores' in the matrix and spatial tissue between the pores in the matrix. A substantial amount of depth (e.g., at least 85%) of the tissue is also needed to gain the full effect of the entire matrix throughout the dimensions of the circle or polygon. The matrix within the tissue contains a circle or polygon. The central angle of a circle or polygon stays the same regardless of the plurality of spots within the matrix. This is an essential component of the systems and methods of the present disclosure since they take advantage of a matrix with a circle or polygon which includes the unique relationship and properties of the pore pattern in the matrix or lattice.

The central angle of a circle or polygon is the angle subtended at the center of the circle or polygon by one of its sides. Despite the number of sides of the circle or polygon, the central angle of the circle or polygon remains the same.

Current implanting devices in the sclera obtain the mechanical effect upon accommodation. No current devices or methods take into account the effects of 'pores' or creating a matrix array of pores with a central hexagon or circle or polygon in 3D tissue. The systems and methods of the current disclosure may create a pore matrix array in biological tissue to allow the change in the biomechanical properties of the tissue itself to create the mechanical effect upon biological functions of the eye. In some embodiments, a primary requirement of the 'pores' in the matrix may be the circle or polygon.

A circle or polygon by definition can have any number of sides and the area, perimeter, and dimensions of the circle or polygon in 3D can be mathematically measured. In a regular circle or polygon case the central angle is the angle made at the center of the circle or polygon by any two adjacent vertices of the circle or polygon. If one were to draw a line from any two adjacent vertices to the center, they would make the central angle. Because the circle or polygon is regular, all central angles are equal. It does not matter which side one chooses. All central angles would add up to 360° (a full circle), so the measure of the central angle is 360 divided by the number of sides. Or, as a formula:

Central Angle=360/$n$ degrees, where $n$ is the number of sides.

The measure of the central angle thus depends only on the number of sides, not the size of the circle or polygon.

As used herein, circle or polygons are not limited to "regular" or "irregular." Circles or polygons are one of the most all-encompassing shapes in geometry. From the simple triangle, up through squares, rectangles, trapezoids, to dodecagons and beyond.

Further descriptions of circles or polygons (including types and properties) are also discussed in, e.g., U.S. application Ser. No. 15/942,513 and is incorporated herein.

Some embodiments herein illustrate a plurality of circles or polygons within the matrix array. Each can impact the CT (coherence tomography). They may contain enough pores to allow for a 'central hexagon'. A square/diamond shape may be apparent. As a formula:

$$\text{diagonal}=\sqrt{s^2+s^2}$$

where:

s is the length of any side which simplifies to:

$$\text{diagonal}=s\sqrt{2}$$

where:

s is the length of any side

A 'pore' described herein may have a specific form, shape, composition and depth. A pore courses through 3-dimensional tissue through which gases, liquids, or microscopic particles can pass. A pore can be of any size, shape and can be spaced a part or can be tessellated. It should be noted that although certain examples herein refer to a pore as micropore, the term micropore is not meant to be limiting may be used interchangeably with pore. The 'pores' created herein may be circular cylinders or square cylinders to inhibit scar tissue.

The creating of pores within a matrix array changing biomechanical properties of connective tissue is a unique feature of the current disclosure. The creation of various sizes of micropores which are of any size, shape being either spaced a part or tessellated is also a unique feature of the current disclosure.

The 'pore matrix' used herein may be used to control wound healing. In some embodiments, it may include the filling of pores to inhibit scar tissue.

In some embodiments, pores may have at least 5%-95% depth through the connective tissue and help create the intended biomechanical property change. They may have a specific composition, arrangement in the matrix and desirably have the mathematical qualities of a circle or polygon. In three-dimensional (3D) space the intended change in the relationship between the pores in the matrix or lattice is the unique characteristic of the current disclosure (see, e.g., FIGS. 1F(a) to 1F(c) and their corresponding descriptions in U.S. application Ser. No. 15/942,513). The matrix or array can comprise of a 2D Bravais lattice, a 3D Bravais Lattice or a Non-Bravais lattice.

FIGS. 1B-1E of U.S. application Ser. No. 15/942,513 illustrate exemplary pore matrix arrays. The pore matrix arrays herein are the basic building block from which all continuous arrays can be constructed. There may be a plurality of different ways to arrange the pores on the CT in space where each point would have an identical "atmosphere". That is each point would be surrounded by an identical set of points as any other point, so that all points would be indistinguishable from each other. The "pore matrix array" may be differentiated by the relationship between the angles between the sides of the "unit pore" and the distance between pores and the "unit pore". The "unit pore" is the first "pore created" and when repeated at regular intervals in three dimensions will produce the lattice of the matrix array seen on the surface throughout the depth of the tissue. The "lattice parameter" is the length between two points on the corners of a pore. Each of the various lattice parameters is designated by the letters a, b, and c. If two sides are equal, such as in a tetragonal lattice, then the lengths of the two lattice parameters are designated a and c, with b omitted. The angles are designated by the Greek letters α, β, and γ, such that an angle with a specific Greek letter is not subtended by the axis with its Roman equivalent. For example, a is the included angle between the b and c axis.

A hexagonal lattice structure may have two angles equal to 90°, with the other angle (γ) equal to 120°. For this to happen, the two sides surrounding the 120° angle must be equal (a=b), while the third side (c) is at 90° to the other sides and can be of any length.

Matrix array is defined as the particular, repeating arrangement of pores throughout a target connective tissue, e.g., the sclera. Structure refers to the internal arrangement of pores and not the external appearance or surface of the matrix. However, these may not be entirely independent since the external appearance of a matrix of pores is often related to the internal arrangement. There may be a specific distance between each of the pores in the designated matrix to fulfill the mathematical characteristics and properties of the circle or polygon. The pores created may also have a relationship with the remaining tissue within the matrix thus changing the biomechanical properties of the matrix.

Spatial relationships of the pores within the matrix may have geometric and mathematical implications.

Pore Volume Fraction along with bulk density or volumetric density may also have biomechanical, functional, physical, geometric and mathematical implications, as shown in at least FIGS. 98 and 99.

In some embodiments, the laser microporation system of the present disclosure may generally include at least these parameters: 1) a laser radiation having a fluence between about 1-3 μJoules/cm2 and about 2 Joules/cm2; ≥15.0 J/cm$^2$ on the tissue; ≥25.0 J/cm$^2$ on the tissue; laser power 0.1 to 2.5 W, to widen treatment possibilities 2900 nm+/−200 nm; around the mid IR absorption maximum of water; Laser repetition rate and pulse duration may be adjustable by using pre-defined combinations in the range of 100-1000 Hz and 50-225 μs. This range may be seen as a minimum range ≥15.0 J/cm$^2$ on the tissue; ≥25.0 J/cm$^2$ on the tissue; to widen treatment possibilities; 2) irradiated using one or more laser pulses or a series of pulses having a duration of between about 1 ns and about 20 μs. Some embodiments can potentially have a up to 50 W version; 3) The preferred range of Thermal Damage Zone (TDZ) can be less than 20 μm in some embodiments or between 20-50 μm in some embodiments; 4) Parameters of pulse width from 10 μm-600 μm can also be included.

The energy per pulses 1-3 microJoules may link to femtolasers and pico lasers with high rep rates, e.g., 500 Hz (Zeiss) up to several kilohertz (Optimedica). The benefit of the femtolasers and pico-lasers are the small spot sizes (for example, 20 microns and up to 50 microns) and the energy densities are high for minimal thermal problems to surrounding tissues. All this can lead to an effective scleral rejuvenation. In some embodiments, the lasers may produce substantially round and conically shaped pores in sclera with a depth up to perforation of sclera and thermal damage from about 25 μm up to about 90 μm. The pore depth can be controlled by the pulse energy and the number of pulses. The pore diameter may vary by motion artifacts and/or defocusing. The thermal damage may correlate with the number of pulses. The pulse energy may be increased, which may lead to a decrease of number of pulses and with this to a further decrease of thermal damage. The increase of pulse energy may also reduce the irradiation time. An exemplary design of the laser system described may allow for laser profiles optimized for lower thermal damage zone while preserving irradiation time thus maintaining a fast speed for optimal treatment time, and chart showing the correlation between thermal damage zone and pulse (see, e.g., FIG. 1E-2 and FIGS. 1G-1 to 1G-4 and their corresponding descriptions in U.S. application Ser. No. 15/942,513).

In some embodiments, pulse duration and pulse width may be variable based on Adaptive OCT, getting smaller to zero in on the target pre depth.

The nanosecond lasers for micro poring or micro tunneling, in some embodiments, may include the following specifications: wavelengths UV-Visible-Short infrared 350-355 nm; 520-532 nm; 1030-1064 nm typical; -pulse lengths 0.1-500 nanoseconds, passive (or active Q-switching); pulse rep. rate 10 Hz-100 kHz; peak energies 0.01-10 milliJoules; peak powers max. over 10 Megawatts; free beam or fiber delivered.

Scleral rejuvenation can be performed with femto- or pico second lasers and Er:YAG laser. Other preferred embodiments may include laser energy parameters ideal for 2.94 Er:YAG laser or other laser possibilities with Er:YAG preferred laser energy or other lasers of different wavelengths with high water absorption.

MilliJoules and energy densities for different spot sizes/shapes/pores can include:

Spot size 50 microns: a) 0.5 mJoules pp is equal to 25 Joules/cm2; b) 1.0 mJoule pp is equal to 50 Joules/cm2 (possible with Er:YAG); 3) 2.0 mJoules pp is equal to 100 Joules/cm2.

Spot size 100 microns (all these possible with Er:YAG): a) 2.0 mJoules pp is equal to 25 Joules/cm2; b) 5.0 mJoules pp is equal to 62.5 Joules/cn2; c) 9.0 mJoules pp is equal to 112.5 Joules/cm2.

Spot size 200 microns: a) 2.0 mJoules pp is equal to 6.8 Joules/cm2; b) 9.0 mJoules pp is equal to 28.6 Joules/cm2; c) 20.0 mJoules pp is equal to 63.7 Joules/cm2.

Spot size 300 microns: a) 9.0 mJoules pp is equal to 12.8 Joules/cm2—possible with Er:YAG; b) 20.0 mJoules pp is equal to 28 Joules/cm2—possible with DPM-25/30/40/X; c) 30.0 mJoules pp is equal to 42.8 Joules/cm2 d) 40.0 mJoules pp is equal to 57 Joules/cm2 e) 50.0 mJoules pp is equal to 71 Joules/cm2.

Spot size 400 microns: a) 20 mJoules pp is equal to 16 Joules/cm2-D PM-25/30/40/50/X; b) 30 mJoules pp is equal to 24 Joules/cm2; c) 40 mJoules pp is equal to 32 Joules/cm2; d) 50 mJoules pp is equal to 40 Joules/cm2

Figure 86:
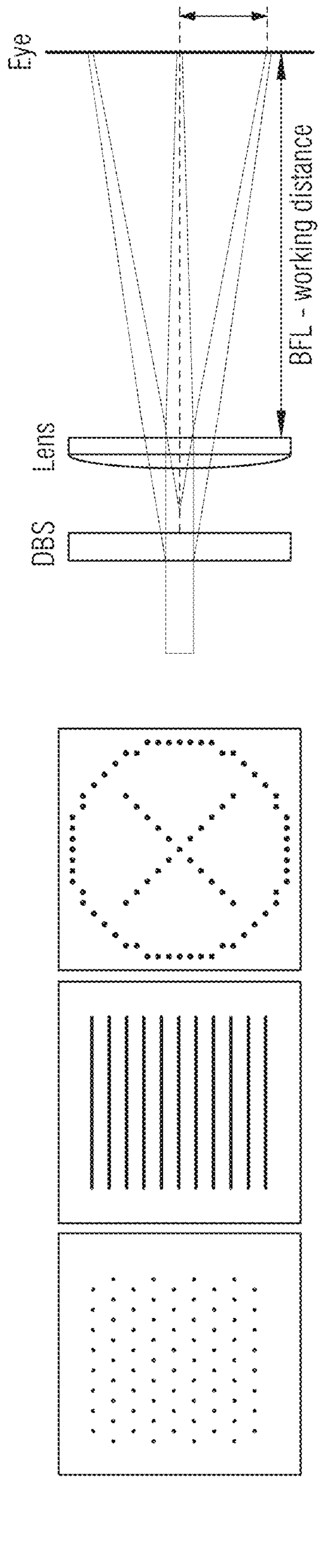
FIGS. 86 and 87 illustrate an exemplary laser system employing diffractive beam splitters (DBS), according to some embodiments of the present disclosure.
Figure 87:
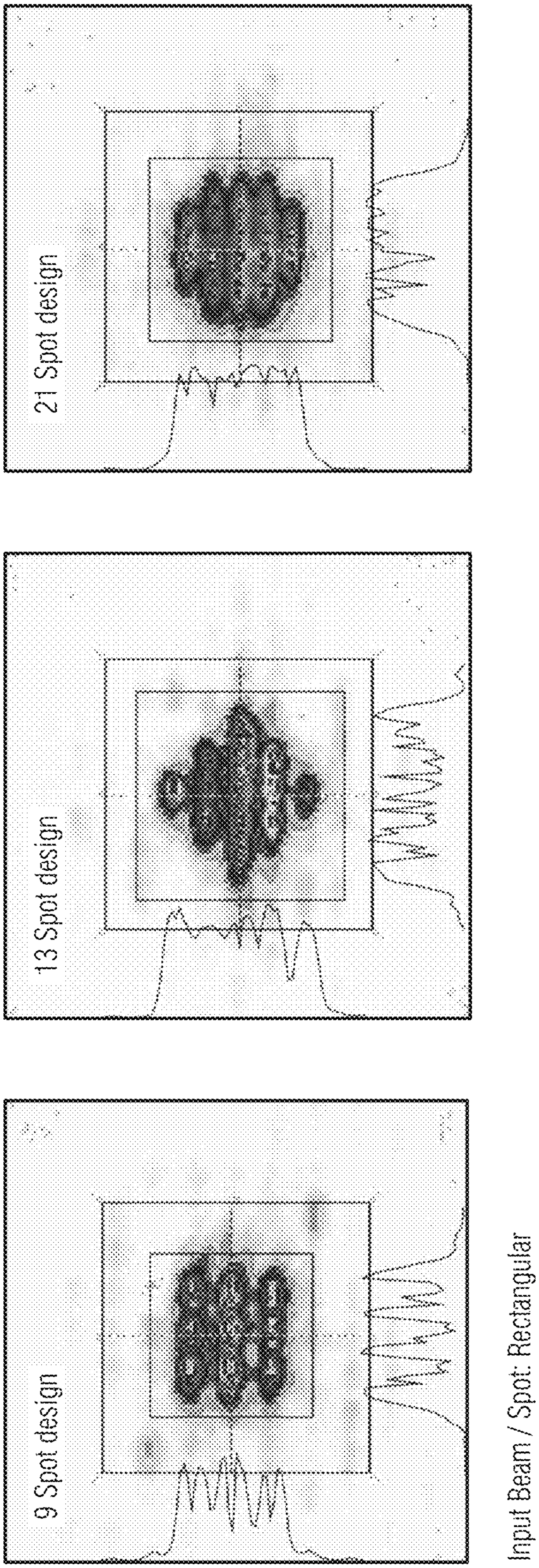

It is noted that round or square pores or other shaped spots are possible as well. See, e.g., FIGS. 105, 106, 107, and 108. These pores traversing 3-dimensional connective tissues at a specific desired depth may result in a plurality of cylinders with a plurality of shapes including but not limited to circular cylinders, square cylinders, polygon cylinders, or conical cylinders. There is some evidence which describes that the penetration, proliferation, differentiation and migration abilities of pores are affected by the size, shape and geometry of the scaffold's pores. Since both viscoelasticity and permeability depend on porosity, orientation, size, distribution and interconnectivity of the pore, there are certain pore sizes which may be more ideal than other depending on the clinical purpose for the poration. The system has flexible capability to change the optical design for a plurality of pore and matrix parameters. Further the pore bottoms can be conical or flat bottomed based on the optical design. Further pore sides may form different shapes (e.g., cylinders or cones) based on the optical design. In some embodiments as shown in at least FIGS. 86 and 87, the system may employ diffractive beam splitters (DBS) to modify the shape and size of the beam, hence the pore.

Regarding femto & picosecond lasers, some available wave lengths include IR 1030 nm; Green 512 nm and UV 343 nm. The peak energies can vary from nanoJoules (at MHz rep rate) via 5-50 microJoules up to several hundred microJoules in picosecond region. Femtosecond lasers having pulse length 100-900 femtosec; peak energies from a nanoJoules to several hundred microJoules, pulse rep. rates from 500 Hz to several Megahertz (Ziemer LOV Z; Ziemer AG, Switzerland: nanoJoules peak energies at over 5 MHz rep. rate, beam quality/density very good-focuses in a small spot—50 micron and under is possible).

The beam quality being so precise in the best femtolasers that, in some embodiments, femtolaser Micro Tunneling of sclera as micro pores using Erbium lasers can be accomplished.

As used herein, nuclear pores can be defined as openings in the nuclear envelope, diameter about 10 nm, through which molecules (such as nuclear proteins synthesize in the cytoplasm) and rna must pass (see, e.g., FIG. 1H and its corresponding descriptions in U.S. application Ser. No. 15/942,513). Pores are generated by a large protein assembly. Perforations in the nuclear membrane may allow select materials to flow in and out.

Formula for porosity in biological tissue may be defined as: X(Xa,t)=qT"(X", t)=x*+u"(X", t), where qT" is a continuously differentiable, invertible mapping from 0 to a, and u" is the cY-constituent displacement. The invertible deformation gradient for the a-constituent (F"), and its Jacobian (J") may be defined as J"=det F", where J" must be strictly positive to prohibit self-interpenetration of each continuum. The right Cauchy-Green tensor % and its inverse, the Piola deformation tensor B for the solid-constituent may be defined as $V=F^{s^t} F^s$, $B=F^{s^{-1}} F^{s^{-t}}$, where the superscript t indicates transposition.

Current theoretical and experimental evidence suggests that creating or maintaining pores in connective tissue accomplishes three important tasks. First, it transports nutrients to the cells in the connective tissue matrix. Second, it carries away the cell waste. Third, the tissue fluid exerts a force on the wall of the sclera or outer ocular coat, a force that is large enough for the cells to sense. This is thought to be the basic mechanotransduction mechanism in the connective tissue, the way in which the ocular coat senses the mechanical load to which it is subjected and the response to the increase in intraocular pressure. Understanding ocular mechanotransduction is fundamental to the understanding of how to treat ocular hypertension, glaucoma and myopia. Furthermore, the porosity or volumetric density of a material or tissue changes its physical and biomechanical properties such as plasticity, compliance, shear, stress, strain, creep, deformation and reformation). Since the ciliary muscles of accommodation are the main agonists of the forces within the both the force dynamics and the hydrodynamics in the eye the ocular outer coat biomechanics are critically important in facilitating or deterring force productions for necessary functions of the eye organ including but not limited to tissue repair, accommodation mechanics, intraocular pressure control, and fluidics inside of the eye. Since progressive age-related crosslinking impacts the biomechanical stiffness or dampening capabilities of the connective tissues of the eye, consideration for manipulating the porosity or bulk density of aged ocular tissues may provide an organic solution to restore or rejuvenate the dynamic functions inside of the eye without the use of implanted devices or drugs. Changing biomechanical tissue properties through microporation means may also improve the tissues' biomechanical response to stress and rejuvenate the tissues.

Deriving the physical properties of a porous medium (e.g., hydraulic conductivity, thermal conductivity, water retention curve) from parameters describing the structure of the medium (e.g., porosity, pore size distribution, specific surface area, bulk density or volumetric density) is an ongoing challenge for scientists, whether in soft tissues or for porosities of bone tissue and their permeabilities. The system may include the ability to utilize multiple patterns, pulses (See, e.g., FIGS. 109, 110 and 111), tessellations, shapes (not to be limited to round, rectangular, square), and sizes for both individual micropores or matrices of multiple pores. Pore depth show to increase with energy and pore width is not changed with multiple pulses but rather using a diffractive beam splitter (e.g., DBS) for custom pore shape, size and design. To verify the assumption of a porous medium having a self-similar scaling behavior, fractal dimensions of various features have been determined experimentally in vitro in animal and human eye globes and in vivo in human eyes. As shown in FIGS. 112, 113, 114 and 115, these empirical data show early evidence that increasing pore density or volumetric density (bulk density) increases biomechanical effects of plasticity, creep and deformation which result in improved visual acuities attributed to improved accommodative forces.

The system may include ability to assure control of ablation depth and warning/control feature that can reliably detect the depth of the tissue ablation and ultimately the interface between the sclera and choroid and effectively prevent ablation beyond the sclera, ability of the system to be ergonomically and clinically practical as well as acceptable for use by the physician, high reliability and controls to assure patient safety and re-producibility of the procedure, ability to scan with a larger working distance in order to produce a fast procedure.

In some embodiments, the systems described in the present disclosure may use a pulsed, Q switched and DPSS (diode pumped solid state) 2.94 μm Er:YAG laser, along with a handheld probe, to ablate pores in the sclera, to modify the plasticity of a region of the sclera, in the treatment of presbyopia and other eye dysfunctions.

System Architectures

In some embodiments, the laser system may be configured to treat ocular tissue, e.g., scleral tissue, where the doctor is presented with an augmented reality view of the treatment protocol, a camera high resolution image of the patient's eye, anticipated micropore treatment locations and treatment patterns located around the limbus, vascular avoidance and eye tracking all through the GUI and Artificial Intelligence (AI) to assist optimal treatment. As shown in FIGS. 61A, 61B, 50, 51, 51A and 63 and will be described further below, the system may offer a doctor the ability to shift the location of the treatment on the patient's eye in the camera image. The system may allow the doctor to rotate the treatment image and view the change. The system may allow the doctor to select individual micropores in the treatment pattern to not be treated based on the doctor's view of the vascular structure of the patient's eye. Once treated, the system may provide the doctor with an image that confirms the target depth of micropores also be able to see 2D and 3D OCT (Optical Coherence Tomography) images to verify the proper pores per the treatment protocol. The system may then provide the doctor with the ability to re-treat individual pores as needed in a second treatment step. The imaging system may collect a spectrum of biometric data and then may reconstruct an accurate 3-D model of the true anatomy of each treatment matrix including each microporation utilizing OCT and Augmented Reality (AR) technology. The system may allow the doctor or user to visualize precisely where the relevant anatomy is in the eye surface and subsurface through the targeted tissue as well as pulse by pulse morphology changes in the tissue and within the micropore. The camera system may be able to produce accurate, high resolution image that accurately measures and provides clear visualization of the targeted tissues pretreatment and post treatment 3D images of the micropore matrix. Using biometric data measured in the x-, y-, and z-axes, the system may be able to overlay treatment layers of augmented reality scenarios for a plurality of treatment possibilities. This multimedia platform allows the doctor to make intelligent treatment decisions and modifications for each person unique anatomy.

FIGS. 7, 8, 9, 10, 11, 12, 13, 14, 15, 16 and 17 show exemplary embodiments of a laser system of the present disclosure. In some embodiments, the laser system may be configured to treat scleral tissue where the system may create micropores by multiple pulses of laser radiation to limit tissue damage, control final micropore depth and reduce treatment time for each micropore based on variations in scleral tissue thickness.

FIG. 7 shows exemplary laser system with no galvo, 5 axis head and separate Z motion. FIG. 8 shows exemplary laser system with control of a laser head with no galvo, 5 axis head and separate Z motion. FIG. 9 shows exemplary laser system with headrest, Z axis motion of laser head. FIG. 10 shows exemplary laser system with galvo mirrors, separate visible laser and OCT/DC fibers combined into treatment laser axis and doctor view of treatment. FIG. 11 shows exemplary laser system that combines OCT/DC and visible laser through a single fiber and shared relay lens with treatment laser with control and display. FIG. 12 shows exemplary laser system that is substantially similar to system in FIG. 11 but including AF lens and dual function OCT system. FIG. 13 shows exemplary laser system that is substantially similar to system in FIG. 12 but with no galvo, 5 axis Head and separate Z motion. FIG. 14 shows exemplary laser system that is substantially similar to system in FIG. 13 but with no galvos, 6 axis with AF lens assembly. FIG. 16 shows exemplary laser system with OCT control system with depth control with visible laser included. FIGS. 15 and 17 show exemplary laser system with bio-feedback system control (OCT and/or camera).

As shown in FIG. 36, in some embodiments, the laser system may include an OCT control system for dual OCT/DC and Scanning OCT imaging subsystems.

Figure 84:
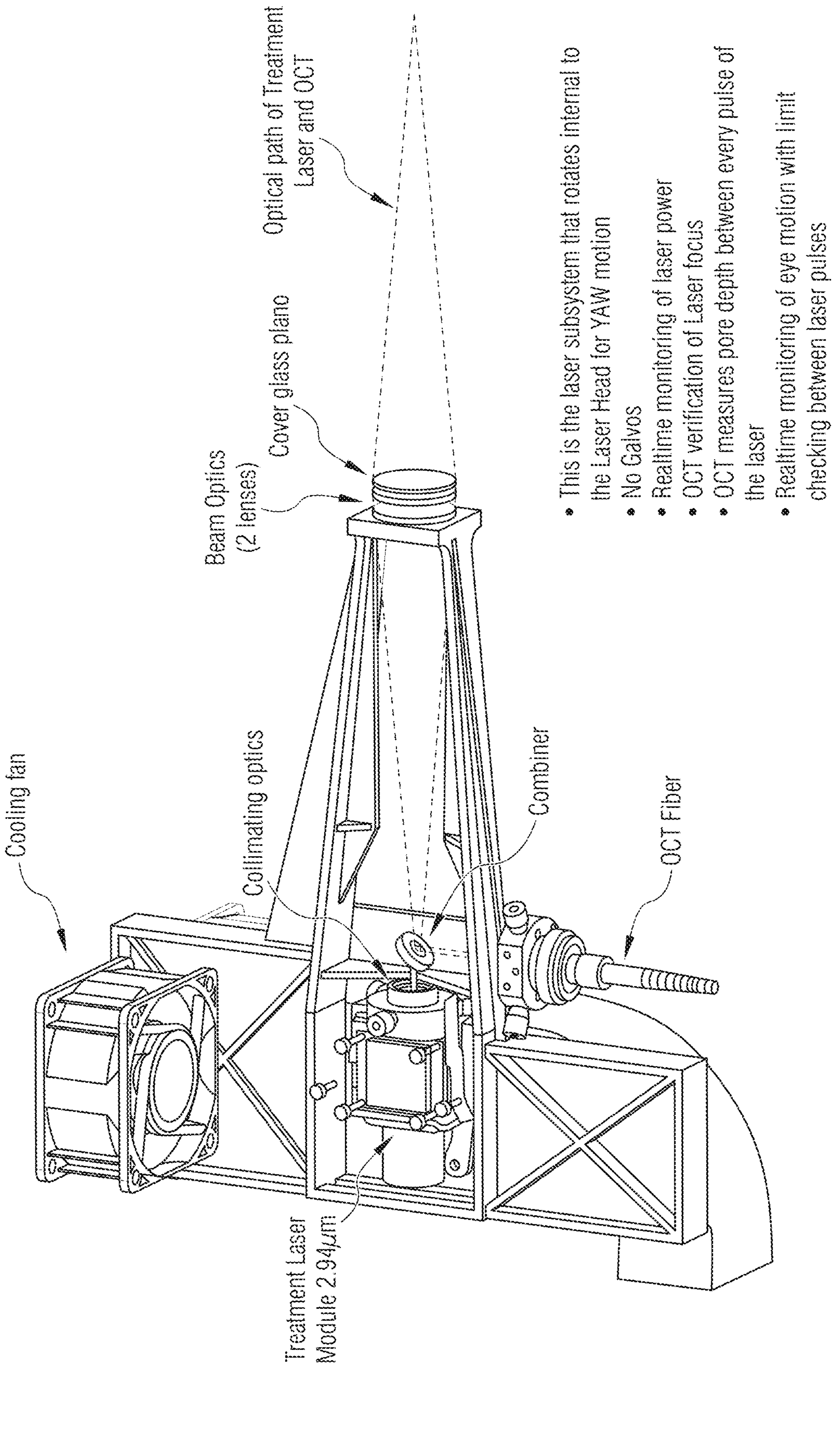

As shown in FIG. 37, in some embodiments, the laser system may include an OCT control system integrated OCT/DC and Scanning OCT imaging subsystems As shown in FIG. 84, in some embodiments, the laser system may include a laser treatment laser subsystem combined with optical fiber-based OCT/DC. This may be a central component in the 5-axis motion control design that is moved around to aim the laser beam.

FIGS. 77, and 80A to 83 illustrate exemplary laser treatment system based on off-axis treatment.

Embodiments and features of the laser system are also described in further detail in U.S. application Ser. No.

15/942,513, Taiwan Application No. 108111355, and International Appl. No. PCT/US18/25608, which are incorporated in their entirety herein. For example, as shown in FIG. 6 of U.S. application Ser. No. 15/942,513, the laser system may include a laser, a laser delivery fiber, a laser control system, a monitoring system, and a beam control system. In another example, in FIG. 7 of U.S. application Ser. No. 15/942,513, the laser system may also include a depth control subsystem, galvo mirrors, a camera (e.g., CCD camera, or suitable camera), a visual microscope, focus subsystem, and beam delivery optics. FIG. 7-1 of U.S. application Ser. No. 15/942,513 illustrates an exemplary laser system including on-axis and off-axis imaging, and depth measurement subsystem. Other exemplary embodiments include laser system with dichroic (in FIG. 3A of U.S. application Ser. No. 15/942,513), laser system with eye tracking subsystem located after galvo mirrors (in FIG. 3A of U.S. application Ser. No. 15/942,513).

In some embodiments, the present disclosure may include a process for delivering microporation medical treatments to improve biomechanics. The method may include generating, by a laser, a treatment beam on a treatment-axis not aligned with a patient's visual-axis in a subsurface laser medical treatment to create an array of micropores that improves biomechanics; controlling, by a controller in electrical communication with the laser, dosimetry of the treatment beam in application to a target tissue; focusing, by a lens, the treatment beam onto the target tissue; monitoring, by an automated off-axis (laser treatment is not coincident with the pupil or line of sight) subsurface anatomy tracking, measuring, and avoidance system, an eye position for application of the treatment beam; and wherein the array pattern of micropores is at least one of a radial pattern, a spiral pattern, a phyllotactic pattern, or an asymmetric pattern.

In some embodiments, the present disclosure may include an ocular laser surgery and therapeutic treatments system that may provide an eye laser therapy process to alleviate the stresses and strain that occur with an increasingly rigid sclera with age by creating compliance in the scleral tissue using a laser generated matrix of micropores in the scleral tissue either spaced apart or tessellated. The system may facilitate biomechanical property changes in the sclera, alleviate compression of the subliminal connective tissue, fascial tissue, and biophysiological structures of the eye, as well as restore accommodative ability and ocular hydrodynamic function compromised. The system may alleviate stress and increase biomechanical compliance over the ciliary muscle, the accommodation complex, aqueous outflow, and key physiological anatomical functions that lie directly beneath the scleral tissue. Age-related crosslinking which causes increased biomechanical stiffness may be directly and indirectly affected by pore creation by uncrosslinking collagen fibrils within the hierarchy of tissues creating a more flexible and compliant connective tissue after treated. For example, in the use of microporation to improve biomechanical compliance in scleral tissue, it allows more force production to be exerted on the lens for accommodative function. FIG. 116 show an exemplary histology of micropores. Histological sections with hematoxylin and eosin (H & E) staining (principal tissue stains used in histology) for the Laser-only-treatment (L) and Laser-treatment-plus-collagen treatment (L+C) groups at different time points show that inflammatory cell infiltration and coagulative necrosis (arrows) at 1 month in all eyes, and these responses subsided with time. At 9 months, there were no inflammatory cells or necrosis observed, and the scleral micropores were still patent and filled with fibroblasts. * indicated scleral micropores. TN denotes Tenon's tissue. Original magnification was 100×. Scale bar was 200 μm.

Embodiments of the laser system are now described in further detail below.

Workflow, Productivity and Safety

In some embodiments, as illustrated in FIGS. 19 and 20, 21, 22, 23, 24, and 25, the laser system may be configured to treat scleral tissue with workflow which may incorporate prior patient data and cover operations through to post treatment verification OCT images.

In some embodiments, the laser system may be configured to treat scleral tissue with customized workflow to generate multiple micropores in multiple quadrants on both eyes. FIGS. 26, 19 and 20, and 27 illustrate exemplary processes to generate a pore array.

In some embodiments, as illustrated in FIGS. 28 and 29, the laser system may include an FPGA architecture to control timing of critical processes, safety processes and image/data processing.

In some embodiments, the laser system may include means of input of a pre-treatment plan to reduce time duration of the treatment, for example, by the creation of an ini.file to load and set-up the system prior to patient and doctor with the system ready to start treatment.

In some embodiments, the laser system may include a means to accept treatment planning input based on a plurality of sources e.g., previous patient records, previous scleral treatment records, doctor choices, updated treatment optimizations and pre-treatment scans by the system). As illustrated in FIGS. 28 and 29, pre-treatment scans by the system may include the use of the camera, eye tracking, feature recognition, OCT scans to establish the treatment plan or qualification of the patient for the scleral treatment.

In some embodiments, the laser system may include means of remote treatment . . . . In an example, the system can be operated remotely by a doctor with an on-site trained technician by means of a remote GUI session over an internet connection with or without Bluetooth devices. The doctor is remote and logged in over secure internet connection with VPN and encrypted pass code. A video connection with monitor camera(s) on laser head looking at the patient and tech with the doc on the other end. The on-site tech positions the patient and installs speculum (See FIGS. 136 to 138). Technician can enter unique passcode from doctor. The doctor can perform all normal functions, but the doctor may need to pre-enable the laser function. The on-site technician does the normal enable and presses the footswitch at doctor's instructions. The doctor is provided with an emergency kill switch. In some embodiments, the on-site technician may complete the treatment and the doctor reviews images remotely.

In some embodiments, the laser system may include a means to remotely monitor the operation of the system, transfer data files, transfer log files, download new software, upload key treatment records, conduct remote service and calibrations. In some embodiments, these functions may be done with or without on-site assistance, and using electronic interface to off-site services.

OCT/Depth Control (DC)

FIGS. 30, 6, and 18 show an exemplary process of the laser system embodiments with bio-feedback control.

In some embodiments, the system may use a single stationary beam from the OCT system for depth control that is colinear with the treatment laser.

In some embodiments, the depth of the micropore can be judged by using OCT measurements between pulses to determine the current depth based on establishing the surface at the bottom of each micropore, and the bottom surface of the sclera. The top surface of the sclera can also be established and can be useful in determining the pore depth. The change in depth of the last pulse, and the remaining scleral thickness and then to determine the optimal pulse length (duration) for the next pulse if required. The above may be performed automatically and in real-time.

In some embodiments, as shown FIG. 27 process, adaptive depth control may create initial long pulses that may be used to reduce the total number of pulses and total time required to complete a micropore to target depth measurement and reducing the probability of patient eye movement during one micropore. Smaller pulses may be used to allow the system to "zero" in on target micropore target depth.

The process shown in FIG. 27 may include the condition where OCT data reading is less than expected indicating the eye moved during pore creation. This process is repeated for each pulse to calculate optimal next pulse width. In some embodiments, the depth of the pore can be compared to an expected value range, if the depth is significantly less than expected this could be an indication that the eye has move or there is a system movement or vibration that has varied the laser pointing. The system may quickly provide an eye movement indication before the next pulse is initiated providing a safety indicator and creating an error reported to the system controller. If movement is small the ablation process for the next pore may continue, but if determined large enough to be significant, the pore creation process may be terminated or paused while eye tracking repositions the laser pointing to continue the pore creation process for safety purposes. In some embodiments, the system may be capable of registering each pulse of each pore in order to restart the microporation in the correct pore unit once the treatment restarts.

As shown in FIG. 16, in some embodiments, the laser system may be configured to treat scleral tissue having an OCT Control System with Depth Control with visible laser (also referred to as an aiming beam) included.

As shown in FIG. 31, in some embodiments, the laser system may be configured to treat scleral tissue having a single scanning mirror that combines OCT beam that is scanned over the eye surface in order to provide an image of micropores at any point during treatment In some embodiments, the system may use a single stationary beam from the OCT system for depth control that is colinear with the treatment laser.

In some embodiments, as shown in FIG. 109, it can be shown that the pore depth is proportional to total laser energy regardless of the number of pulses use to reach the pore depth.

In some embodiments, as shown in FIGS. 110 and 111, it can be shown that the pore diameter is not impacted significantly based on the number of pulses required use to reach the pore depth.

In some embodiments, as shown in FIG. 32, the system (e.g., as shown in at least FIGS. 7, 8, 17 and 30) may include a capability to optimize pulse parameters to achieve optical pulse depth between pulses capable to design volume of tissue removal per pulse to pre-plan and achieve target final depth and volume removal. The system may combine the OCT and laser within one beam, allowing individual micropore viewing combined with depth control. The system may include an ability to use OCT DC signals to determine focal position of the treatment laser for optimal micropore characteristics. The system may include an OCT system that is collinear with the ablation laser and used to identify the interface air to sclera of the patient. The treatment laser may be set-up to the same focal point in Z as the OCT laser. Based on this, the complete system "focus" can be adjusted and monitored that the focus of the laser is on the patient's sclera based on the feedback from the OCT system.

In some embodiments, as shown in at least FIG. 27, the depth of the micropore may be measured inside the micropore by the inline OCT DC subsystem; the measurement may be done from a single beam colinear to the treatment beam, having a slightly smaller beam size. The reflective signal can be sent through a signal processing algorithm to determine the depth before and after laser pulses to provide the micropore depth and the system can abort the next laser pulse if appropriate. In some embodiments, once through the eyes outer layers, pulse energy for resulting depth can be calculated and used to establish the next pulse energy (width) in order to end at the desired depth in minimum number of pulses.

In some embodiments, depth measurement may be provided for each micropore to ensure ablation does not exceed treatment plan, does not exceed a minimum remaining sclera thickness for safety and to determine the remaining depth of the micropore to be ablated. In some embodiments, as shown in FIG. 33, the system (and also FIGS. 7, 8, 17 and 30) may include OCT imaging/OCT depth control with data collected for micropore ablation depth per pulse and total depth provided for final review of OCT and treatment protocol verification. The system may include collinear OCT with treatment laser that may measure and record values after each pulse before the next pulse in microporation. This may be possible based on the sizing of the OCT beam to be equal or smaller than the treatment laser micropore (pore) so the signal is clean and trusted and can be taken quickly without numerous samples. The OCT relay optics (fixed or zoom design) may size the OCT/DC beam smaller than the micropore diameter so the OCT may verify the treatment laser is in focus and the micropore size will be as expected. OCT DC sensor may provide beam size small enough to look down the micropore and provided data and analysis between treatment pulses. In some embodiments, the system may use the signal to monitor eye movement between pulses faster than eye tracking used between micropores.

In some embodiments, as shown in FIGS. 17, 18, and 33, the laser system may be configured to treat scleral tissue where OCT measurement may be done without scanning the OCT beam, sizing the OCT beam diameter to be less than the diameter of the micropore so as to look down the micropore without introducing false readings or signal noise providing a reliable depth measurement of the depth of the pore and the remaining wall of the sclera.

In some embodiments, as shown in FIG. 7, the laser system may be configured to treat scleral tissue where a visible spotting laser beam can be introduced on axis with the treatment laser along the OCT depth control beam, to allow the optimal spot size of the visible spotting laser to approximate the treatment laser and micropore diameters even through these lasers have significantly different wavelengths and focal distances when projected through the optical systems.

As illustrated in FIGS. 17 and 30, in some embodiments, the laser system may include bio-feedback based on camera images and color analysis or OCT data, in conjunction with or not, the illumination system to stop laser treatment (for safety) or to modify the next pulse width to be emitted.

Linearized data makes measurement with OCT for depth in tissue requires significant data analysis to determine the depth of a pore. The system may include a method to integrate overall reflectance allowing depth after individual pulsed to be determined. In some embodiments, the method may include an ability to measure the depth of the micropore in real time and in between pulses for accurate depth control. The algorithm to determine depth may be different for a variety of tissue types. FIGS. 34A and 34B illustrate examples of OCT depth control signal with a porcine eye. As illustrated in FIG. 32, the system may provide the capability to optimize the next pulse parameters to achieve optimal pulse depth. The system may determine pulses to achieve the pre-planned target depth and volume of tissue removal per pore. As illustrated in FIGS. 35A and 35B, OCT measurement of scleral thickness pre-treatment may provide capability to guide the algorithm for optimal treatment dosage.

OCT Scanner (2D and 3D)

In some embodiments, as shown in FIG. 8, the laser system may be configured to treat scleral tissue where a second OCT scanning sensor can be positioned on the treatment laser axis to provide a high-quality scan of the treatment area providing before and after verification of treatment effectiveness. This could be done with the use of a movable mirror to alternate with normal treatment laser operation.

In some embodiments, the OCT depth control and the Scanning OCT imaging system may use separate sensors optimized for each task but share components of the OCT system reducing complexity, size and cost. FIGS. 38 thru 41 and 42 show examples of combined and or shared components within and OCT system.

In some embodiments, the OCT scanning function can be introduced colinear with the treatment beam with the use of a dichroic mirror along the optical centerline that allows the treatment laser to pass through a stationary OCT scanner mirror to allow more frequent scans of the treatment area.

As illustrated in FIGS. 43A, 43B, 44, 45 and 46, in some embodiments, the laser system may be configured to treat scleral tissue where the OCT scanning system may provide both 2D sectional views and a 3D isometric view of the treatment area before, during and after treatment. The system may also provide depth and diameter (or pore cross section shape, i.e., square or rectangular) measurement data for each micropore.

In some embodiments the system may also incorporate and provide tissue layer differentiations from the top surface to the bottom surfaces of all sub-surfaces using augmented, enhanced structural differentiation algorithms and digital tissue staining.

Tracking and Monitoring

Eye Tracking

In some operations, the generation of the micropore may be disturbed, for example, if the patient moves the eye and therefore eye tracking as described herein is needed. Additionally, the system may include a camera to measure the speed of the eye movement. In some embodiments, the present disclosure may include a process, as illustrated in FIG. 47, to handle the case where the speed is so low that only an insignificant movement may be predicted within the pulse train duration for ablation. FIGS. 48 and 49 also illustrates an exemplary eye tracking process.

Feature Recognition

In some embodiments, the laser system may be configured to treat scleral tissue where an eye tracking system may be used to ensure the laser pointing continues to be referenced to the correct treatment position on the eye during a microoperation to correct for eye movement or other mechanical systems. The system may be able to recognize and track a plurality of eye anatomical features including the pupil, the iris, the limbus and/or vascular features (blood vessels) for off axis treatments. Feature recognition may provide information to eye tracking, vascular avoidance (deselection of individual pore locations) and treatment alignment, e.g., to initially get the treatment area positioned to the correct anatomical features as well as anatomy avoidance of untargeted treatment areas.

In some embodiments, the laser system may include feature tracking elements for the purpose of eye tracking. Features tacked may include, e.g., pupil, iris, limbus, vascular structures. The laser system may receive inputs from TOF camera, visual camera, OCT/DC, OCT 3D scanner.

In some embodiments, the system may include feature recognition (may include facial features (e.g., eyebrows, nose, eyelids) from the TOF camera and method of using for position treatment and avoidance The system may include capability to establish position of the eye features to avoid laser exposure, to position laser, for retreat and repositioning, to treat the target tissue while avoiding unintended (untargeted) tissue and output to fixation point, treatment laser angles, vascular avoidance, treatment positioning, and AI systems. The system may align multiple coordinate systems from different sub processes feature analysis (e.g., deep learning, AI) to isolate and gather positional relationships (e.g., pupil, iris, vascular, and others). See also example process in FIGS. 49 and 50. The system may include augmented reality overlay to enhance biometry anatomy and increase learning (as in AI). FIGS. 51 and 51A show exemplary images of feature recognition of the anatomical limbus highlighted through AI analysis and shown as an overlay to the camera image.

In some embodiments, the system may include feature recognition of the subsurface anatomy of the eye (e.g., ciliary muscles, Schlemm's canal) from OCT images that can be used in positioning the treatment area on the eye. FIG. 54 illustrates exemplary images from OCT (DC or Scan) to locate anatomical limbus and Schlemm's Canal in order to automate treatment positioning. The images show OCT biometry and surface anatomy relational to real time pore placement of treatment zone and individual micropores. FIG. 55 illustrates exemplary treatment position relative to Schlemm's Canal and Anatomical limbus.

In some embodiments, the present disclosure may include a process to sum-up individual pore volumes for a treatment area as a pore volume fraction and modify/optimize the balance of the treatment or re-treatment. The process may assume a pore shape based on beam characteristics, use but not limited to OCT depth for the OCT/DC or OCT scan and then calculate pore volume for each pore as completed. This may be an actual value after any aborted pores or vascular avoidance algorithms deletes specific pores from treatment plan. When this is performed in real-time modifications to later pore ablation may improve performance to target. This could also be calculated prior to any retreat to plan optimal treatment.

In some embodiments, eye tracking based on feature recognition can allow the eye tracking to acquire original treatment positioning for retreatment or continue treatment of an individual pores.

Eye Tracking Camera

In some embodiments, the eye-tracking system may include a high resolution/high frame-rate camera and proper illumination. Such illumination may ensure that the patient's face/eye region is properly illuminated for the doctor and the overall procedure, the illumination does not interfere with the feature tracking (eye tracking) by means of introducing artificial reflections on the patient's eye, and proper feature tracking (iris, vascular structure, aiming beam) is given.

In some embodiments, as illustrated in FIG. 56, the camera system can provide images to be used for eye tracking, facial feature recognition, treatment alignment, visual images for the users to work in conjunction with the AI and augmented reality GUI functions.

In some embodiments, the camera system can include a moveable mirror to modify the field of view manually or automatically. As illustrated in FIG. 57, the mirror can be motorized in multiple axis to align the field of view image to target areas.

In some embodiments, the camera system can include a camera with objective optics to provide high quality, high magnification images similar to a surgical microscope. FIG. 58 illustrates exemplary microscope images at a higher magnification to inspect treatment area.

In some embodiments, as illustrated in FIGS. 59, 60, 61A and 61B, the laser system may include a camera that can image the treatment area and surrounding features to determine the proper location of the treatment area relative to the limbus and at the correct angular relationship to the visual axis. In some embodiments, this can also be modified by the doctor manually through a GUI.

Illumination

Due to the fact that different features in the eye as well as the aiming beam can be detected more precisely with a defined illumination wavelength light source (e.g., RGB (red/blue/green) and IR (infrared)), the system includes a dedicated illumination system, including mechanics, light sources, electronics as well as software connection, evaluation and algorithms. Because the eye-tracking camera provides the ability to read out its individual pixels, better feature tracking may be achievable, absolutely necessary from a safety point of view.

Figure 74:
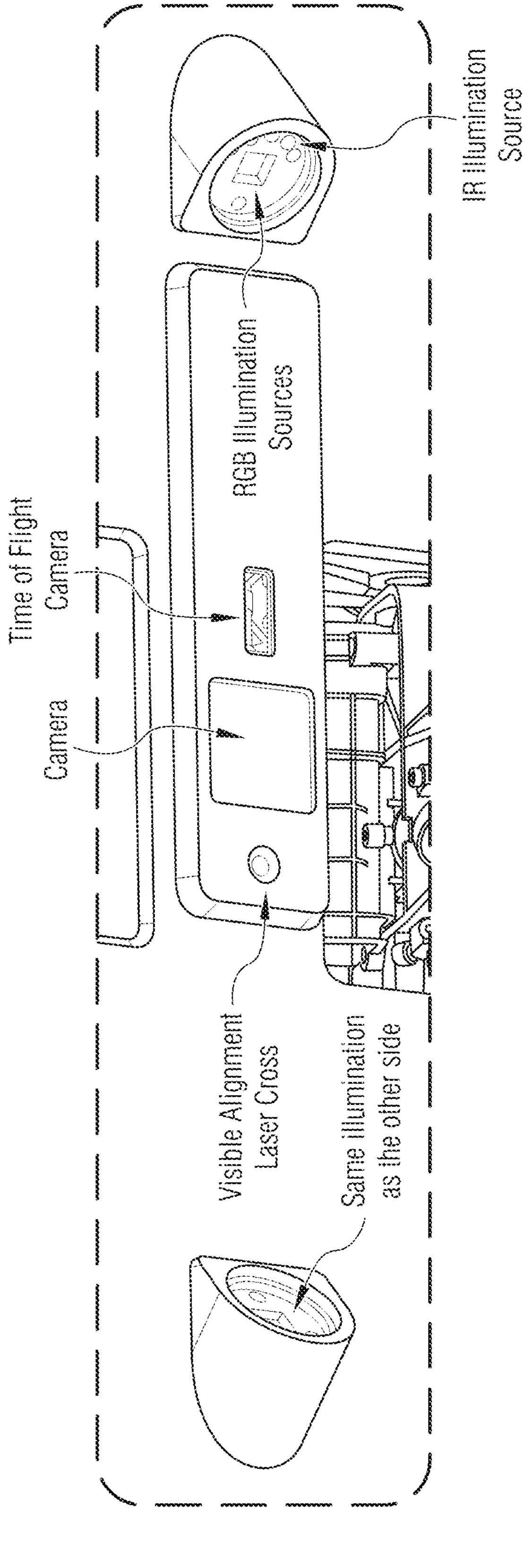
Figure 75:
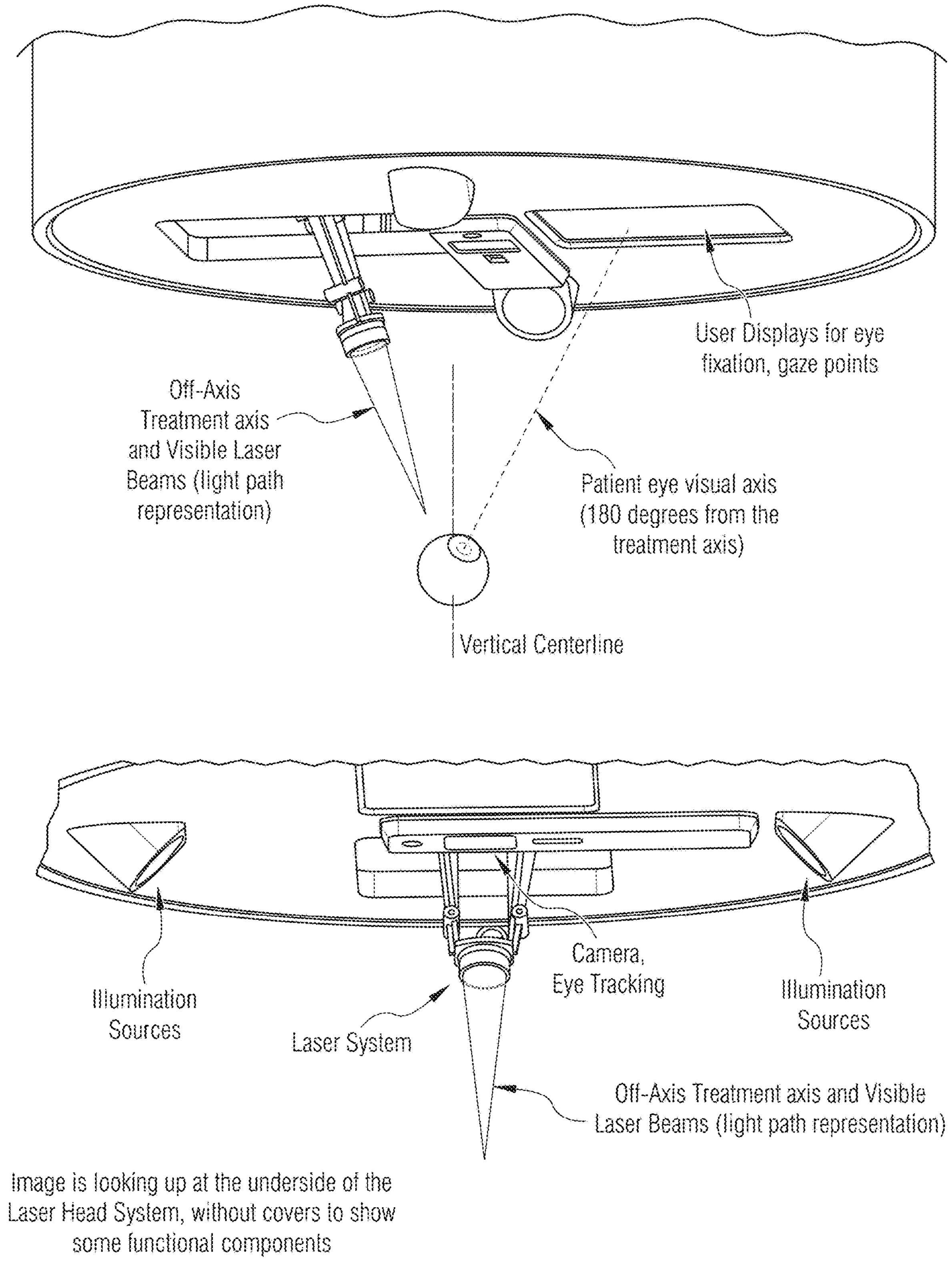

In some embodiments, the laser system may include an illumination system that can optimize measurements and images for various system cameras, and to improve recognition of facial and eye features for tracking and positioning. The illumination system may have multiple wavelength illuminator components, the illumination could be modulated based on the active sensor or cameras sensor. The system may use RGB and IR illumination sources. FIGS. 75 and 74 below show exemplary underside view of a laser head system including camera(s), illumination sources, imaging lenses, display, and visible alignment laser cross. The lenses assembly may vary with actual optical layout used. The display may provide eye fixation, gaze points.

Illumination modulation of RGB and IR sources may be synchronized with camera and sensors to detect features.

In some embodiments, the laser system may include an illumination and camera system to optimize eye tracking performance. In some embodiments, every 33 ms the system may produce white light (e.g., by the RGB diode) and capture a frame for the visualization on the surgeon/assistant screen (to provide the live video feed of the patient). In-between those 33 ms periods the system may use different illuminations of individual colors to detect different features. The individual light pulse durations may be in the range of 10 ms. The iris may be detected best with blue/IR light. The vascular features as well as the aiming beam may be detected best with red/green light. The aiming beam can also be modulated for brightness, that is, the system can find and distinguish the aiming beam from the vascular features (since both is red). This will provide the system with important information of the as-is status of the complete motion system relative to the patient's eye. In addition, the system may read out the individual CCD-cells of the ET-camera, where the system may have access to the RGB channels of each cell. This also enhances GUI images and augmented reality image-based functions.

Vascular Avoidance

Figure 65:
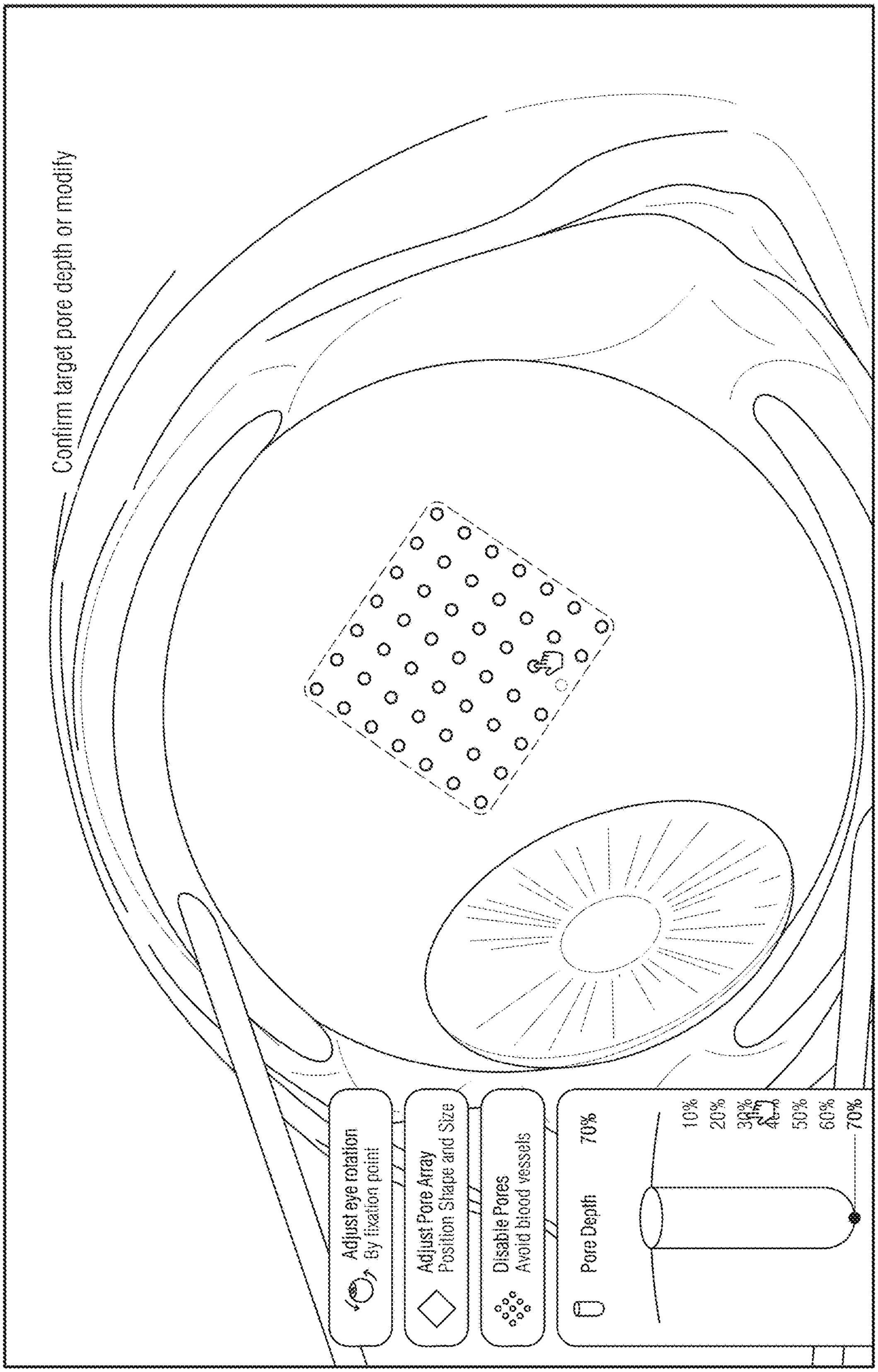
Figure 66:
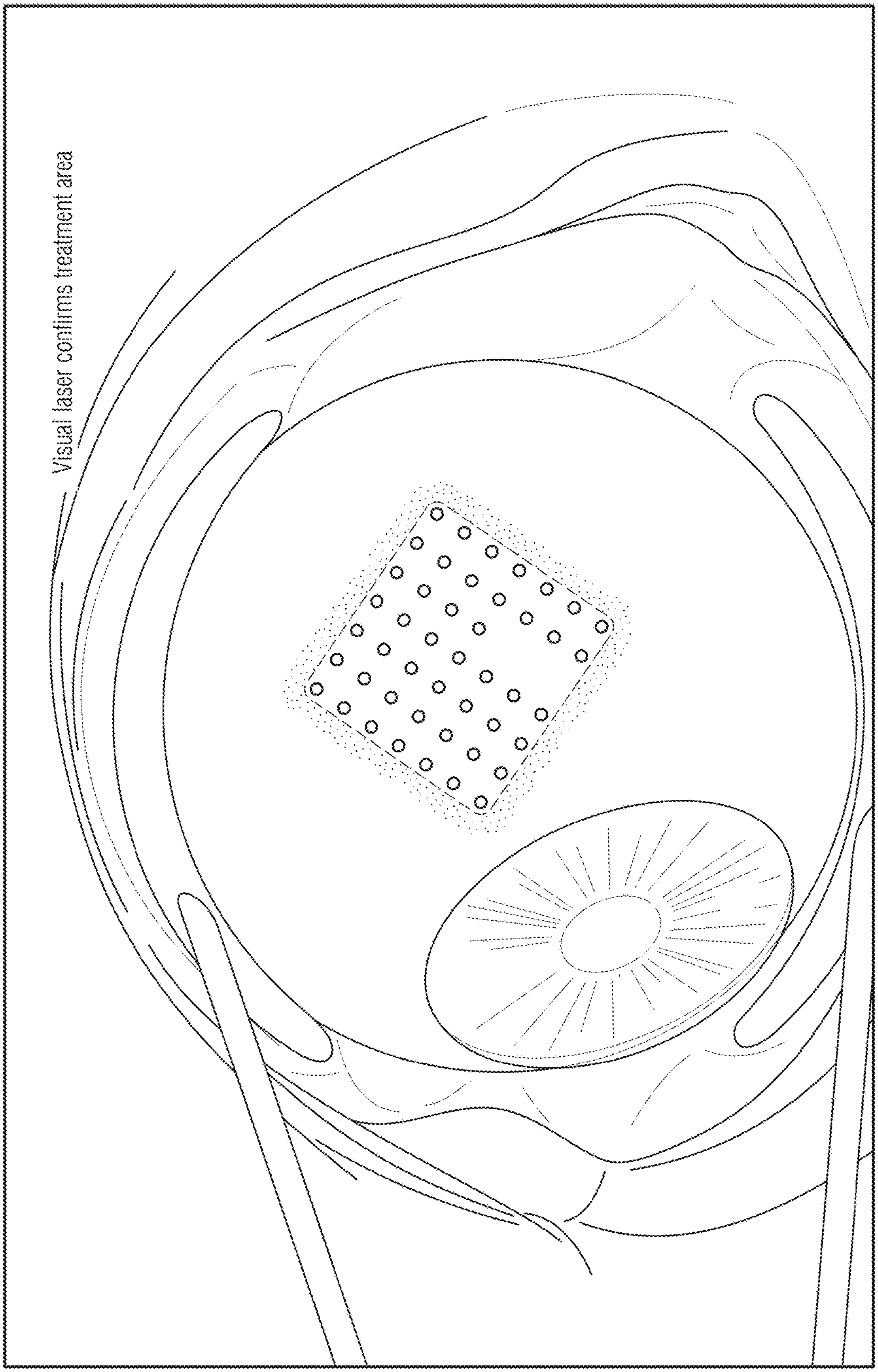

In some embodiments, the eye tracking system may image the treatment area and may either interpret the images or allow a doctor to read the images and determine micropore locations that should be avoided, for example as in vascular avoidance. In some embodiments, the micropores to be avoided can be "marked for no laser treatment" either with doctor assist or through automated image analysis. FIGS. 61A to 64 illustrate exemplary images where pores may be marked for deletion for Anatomy Avoidance, e.g., avoiding blood vessel. FIG. 65 illustrates exemplary image to confirm pore depth, and FIG. 66 illustrates further examples.

In some embodiments, the eye tracking system may analyze camera images, recognize vascular features and determine which pores to delete from the treatment plan automatically.

In some embodiments, the GUI. FIGS. 67 and 68 illustrate treatment areas relative to the limbus and provide an outline on the GUI to aid in treatment alignment. FIGS. 69 and 58 illustrates exemplary microscope quality camera images at a higher magnification to inspect treatment area relative to the limbus.

In some embodiments, the system may include a high-resolution camera to allow inspection similar to an optical microscope. As described above in FIG. 57, the system may include a moveable mirror to select target area with zoom and positioning controls, manual or automatic, based on feature positions from the camera imaging and TOF camera.

FIGS. 61A and 61B illustrate a process, according to some embodiments of the present disclosure, for treatment positioning and anatomy avoidance, the process may be performed manually, semi-automatically or fully automatically through the use of AI, feature detection, camera images and OCT scans by use of static or live camera images of the eye.

Facial Alignment

In some embodiments, as shown in FIGS. 75 and 74, the laser system may include a TOF (time of flight) camera to position the laser head over the patient and to determine key facial features. This system may work in conjunction with a projected visible laser pattern (cross) to image on the patient face as a known feature for analysis of position. The TOF camera may be a time of flight camera, which emits a modulated laser beam and measures the time till reflection. From this information a 3D image may be constructed, as shown in FIG. 70. The TOF camera makes it easy to find the face prior to having the eyes coming into focus of the eye tracking camera and before the OCT/DC beam can find focus on the sclera.

In some embodiments, the TOF camera can provide image data that indicates the eyebrows or the nose, part of the facial structure, are obstructing the clear view of the eye. The fixation and treatment angles may then be modified for the individual patient where features do not obstruct.

In some embodiments, a TOF camera or image analysis can determine the treatment area accessibility and verify eyelid and speculum are clear of laser path.

Treatment Alignment—Positioning

In some embodiments, as shown in FIG. 53, the laser system may include a single scanning mirror that combines OCT/DC beam that is scanned over the eye surface in order to map anatomical features such as edge of limbus, Schlemm's canal, ciliary muscles, edge of retina to assist in treatment positioning and anatomy avoidance.

In some embodiments, the laser system may be configured to treat scleral tissue where the treatment area size, shape and microporation pattern may be modified based on the treatment plan for the microporation patterns. For example, FIGS. J and K of U.S. application Ser. No. 15/942,513 illustrate exemplary golden spiral created from individual treatment patterns, and FIG. 1 of U.S. application Ser. No. 15/942,513 illustrates exemplary treatment protocol for 4 quadrants.

In some embodiments, the laser system may be configured to treat ocular tissue where the center of the treatment area can be modified based on the microporation pattern to be ablated. In some cases, the center of the pattern may be the center of the pupil (or limbus) for ablating a golden spiral in multiple treatment segments.

In some embodiments, the laser system may include a means to modify the pore positioning in the treatment array and normal zones based on patient eye shape to optimally cover the anatomical features and the positional differences of a patient. This could be done based on pre-treatment plan and prior knowledge of the eye shape or based on OCT scan data over an extended treatment area.

Pore Volume and Pore Volume Fraction

Treatment Results—Tissue Removal

In some embodiments, the OCT data and pore shape can be used to calculate tissue volume removal, by zone, after avoidance deletions, after ablated pores based on actual OCT data volume analysis or based on a typical pore for the optical configuration in use. Volume analysis will include both pore volume fraction as well as volumetric density or bulk density. Further analysis of porosity and 3 dimensional scaffold porosity is a unique feature in this system. Re-treat treatment plan can be developed for a second treatment or modified during the current treatment to achieve target volume removal, desired porosity and maximum porosity.

In some embodiments, the deletions from the treatment plan can be used to create a new treatment plan that restores tissue removal to achieve the same treatment efficacy.

The residual eye tissue after pore creation can be used within an FMEA model to assess improved accommodation, ocular fluidics, TOP reduction to inform and to modify the retreatment plan for improve efficacy. AI may be used to inform and direct future treatments.

In some embodiments, as shown in FIG. 98, the Pore Volume Fraction may be altered to produce desirable or improved results. Some evidence has been collected to suggest that increased density and porosity in some cases have doubled efficacy of the treatment, as shown in FIGS. 112-115. Porosity or pore volume fraction is defined as the ratio of the total pore volume to the apparent volume of the tissue. Porosity, volumetric density and 3D scaffold porosity may be used to create a new re-treatment plan. Where Pore Volume is the amount of void created by the treatment and In between the pores are remaining tissue which remains solid. While volumetric density or bulk density is how tightly or densely the pores are packed together. This affects both the porosity as well as the density, which affects a tissues porosity—a property that is the ratio of the volume of a tissues pores to its total volume. The porosity of a tissue depends on several factors, including (1) packing density, (2) the breadth of the pore size distribution (polydisperse vs. monodisperse), (3) the shape of pores, and (4) the interconnectivity of the pores within the matrix array. Porosity refers to the void fraction or the total void space within the volume of the tissue wall and serves as a useful measurement of the potential for customizing treatment patterns to various thicknesses and biomechanical properties of individual tissues where age is a dependent variable for treatment algorithm development. The porosity, P (%), of the tissue is calculated using the following equation, where M is mass per unit area (g/m2) of the tissue, h is the thickness (um) of the and ρ is the relative density of the pore matrix (g/cm3). The term 'packing factor' provides a relative index of the total porosity of a tissue structure. It is calculated by dividing the tissue density by the relative density of the pore matrix and can range theoretically from 0 (all pores and no solids) to 1 (no pores and all solid). Values closer to zero indicate more porosity. The pore density is calculated by dividing M, the mass per unit area of the tissue, by h, its thickness and expressing the answer in units of g/cm3. P=100 [1−M/1000.h.p] Void Ratio is also an important indicator to optimize treatment and retreatment which the system analysis and AI is able to track in 3D tissue scaffolds pulse to pulse and pore to pore. The void ratio is the ratio of the volume of voids (pores) in the tissue to volume of solid tissue remaining in the target tissue matrix area.

$$e=Vv/Vs$$

Where:

e=Void Ratio $V_v$=Volume of voids ($m^3$ or $ft^3$)

$V_s$=Volume of solids ($m^3$ or $ft^3$)

The void ratio is thus a ratio which can be greater than 1. It can also be expressed as a fraction. Both void ratio and porosity differ only in the denominator. Void ratio is the ratio of voids to solids, porosity is the ratio of voids to total volume.

In some embodiments, the laser system may optimize treatment or re-treatment efficacy based on Artificial Intelligence (AI) programs that collect treatment data for a plurality of patients, analyze the results based on but not limited to pore sizes, shapes, depths, patterns, positions, zones treated, eye shapes. The AI program may be assisted by a Finite Element Model (FEM) of the eye either integrated or stand alone, which is described in further detail in U.S. application Ser. Nos. 15/638,346 and 16/702,470 and are incorporated herein. This result may be used to modify the treatment plan automatically or through recommendations to the doctor.

Laser Head System

In some embodiments, the laser system may be configured to treat scleral tissue off axis or in a region of the eye which is distinct from the visual axis or directed away from the pupil of the eye where the gaze of the eye is. The fixation point on the user display (see, e.g., FIG. 75) provides a fixation point to direct and fix the patient's gaze in a distinct axis that is not the visual axis or pupillary axis for the time of single area treatment which can be in an oblique quadrant, 180 degrees away. As shown for example in FIGS. 71 and 72, the laser system may include a laser head system that may provide fixation point. The laser head may move vertically up and down or rotate over the patient.

In some embodiments, the laser system may be configured to treat ocular tissue where the laser beam may be positioned off axis (e.g., not over the visual axis of the eye). The laser treatment is generally perpendicular or substantially perpendicular to the surface of the eye in the center of the treatment area. The eye may be positioned on a fixation target which may not be coincident with the treatment axis, and the eye may also be in an extreme position to expose the ocular tissue treatment area which may be off axis to the visual axis. In some embodiments, the laser beam angle relative to the visual axis may be 51° or substantially about 51°.

Figure 73:
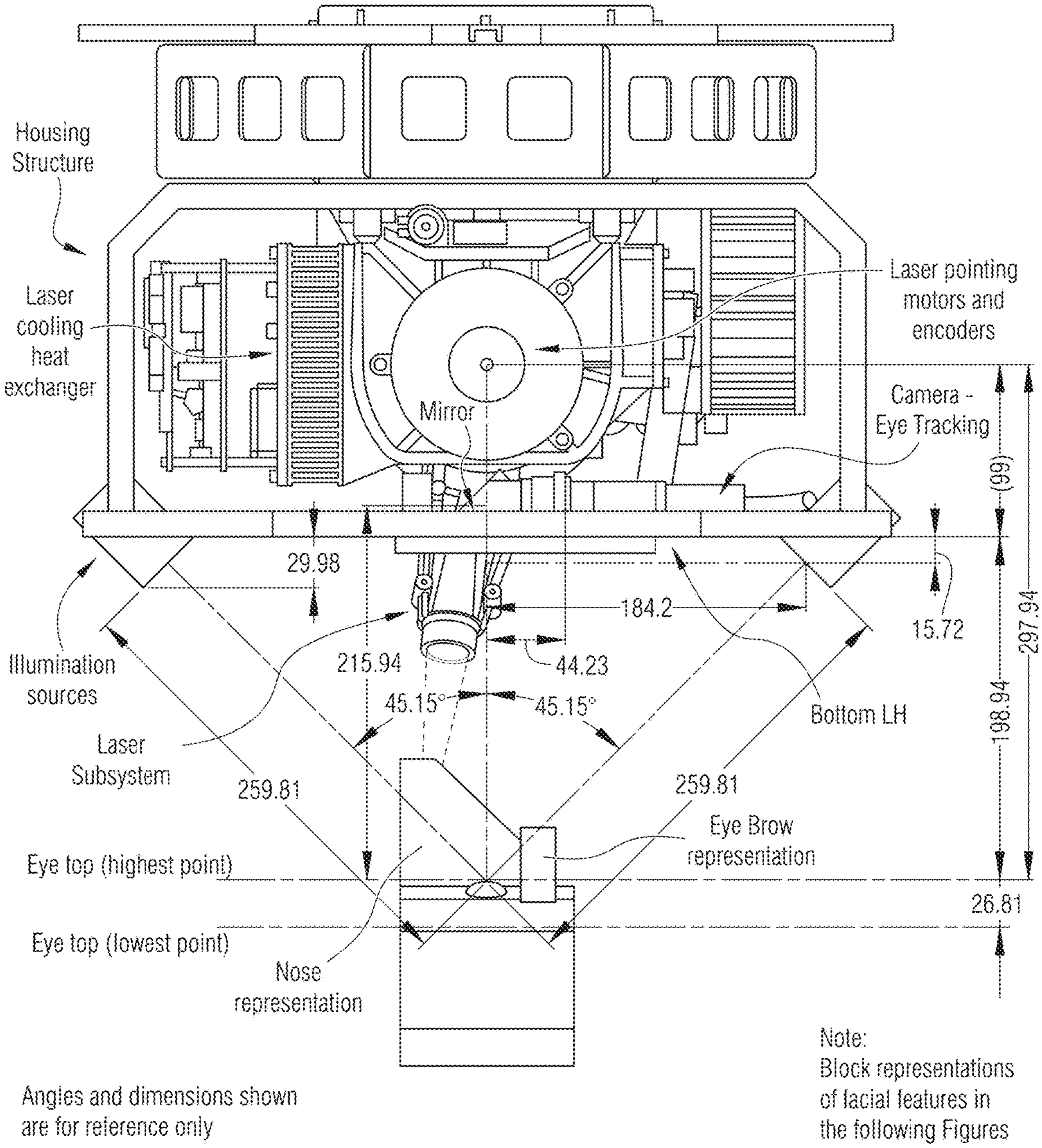
FIGS. 73 to 85 illustrate an exemplary laser head system, according to some embodiments of the present disclosure.

FIGS. 73 to 85 illustrate an exemplary laser head system of the laser system of the present disclosure. As illustrated in FIG. 73, in some embodiments, the laser head may include a housing structure, laser pointing motors and encoders, a laser subsystem. a laser cooling heat exchanger, camera(s) for use in at least eye tracking, and illumination sources. FIGS. 74 and 75 further show bottom view of the laser head, showing a visual alignment laser cross, a display for use in at least eye fixation, and TOF camera.

Figure 76:
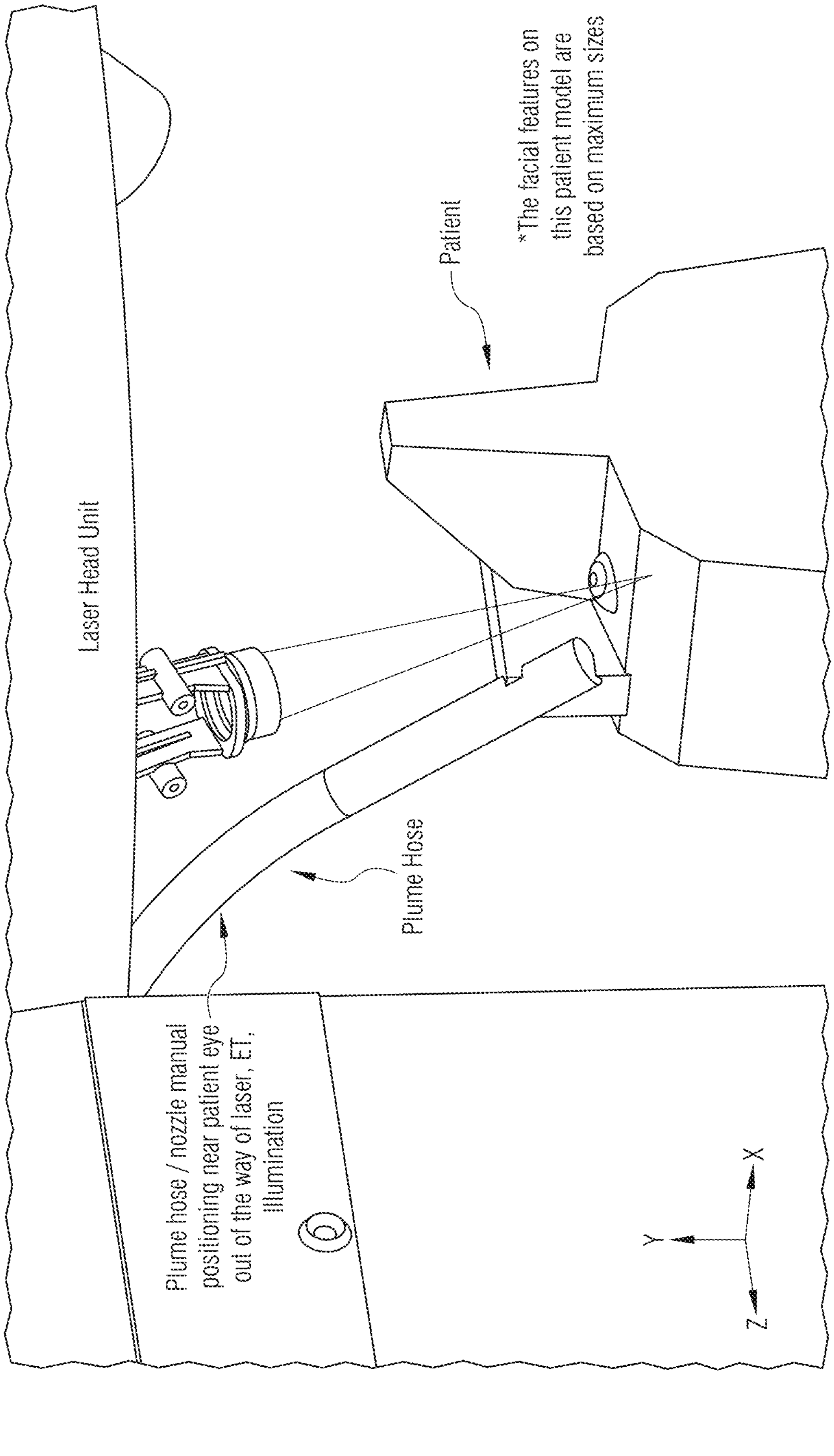

In some embodiments, as shown in FIG. 76, the laser head may include a plume hose which is described in further detail herein.

Figure 77:
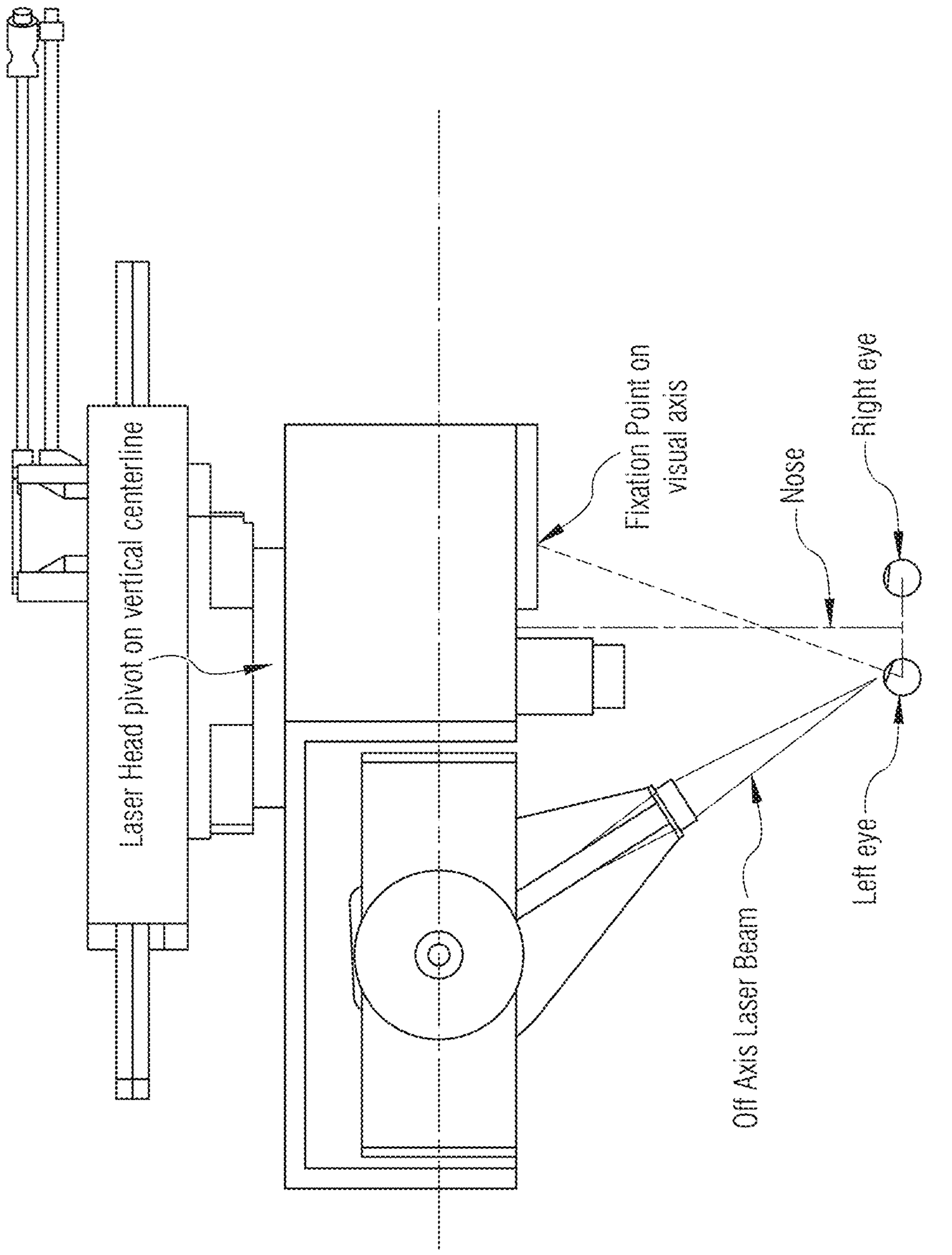
Figure 78:
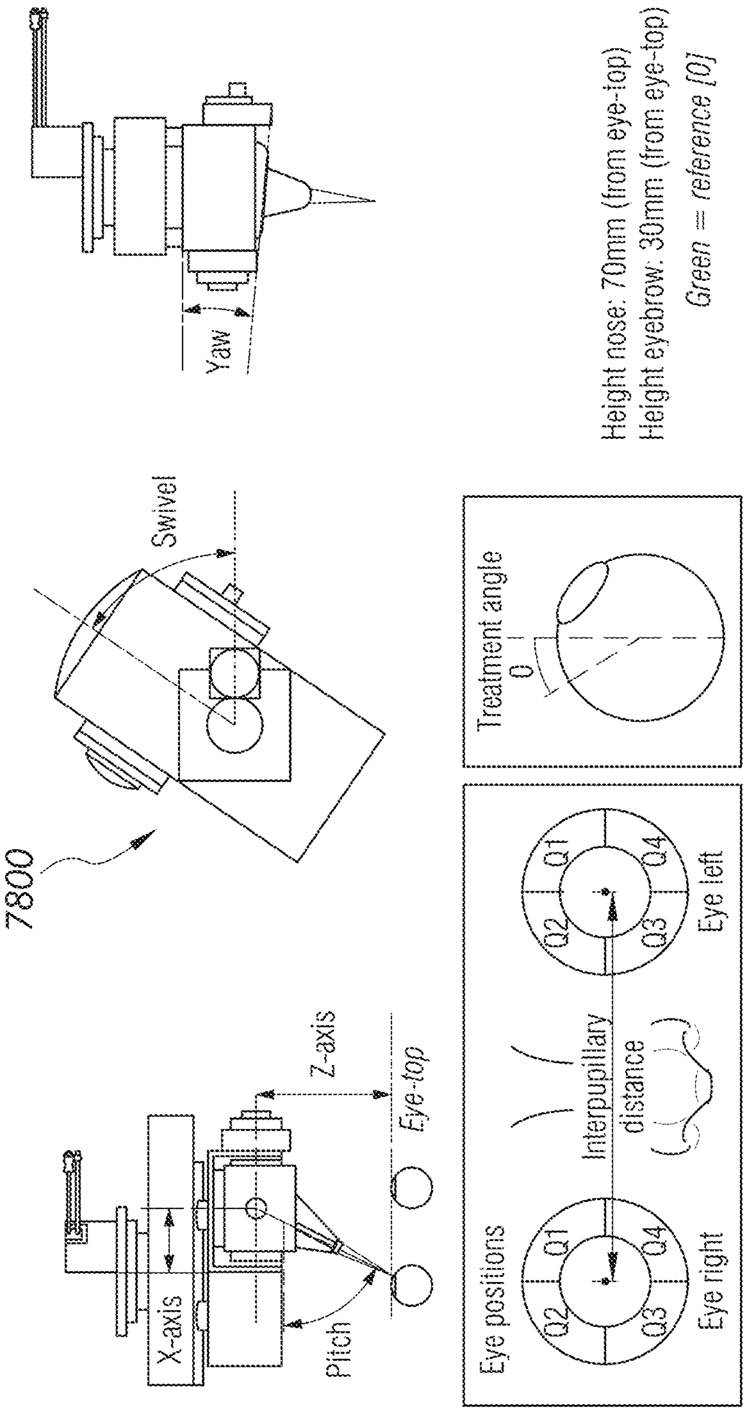
Figure 79:
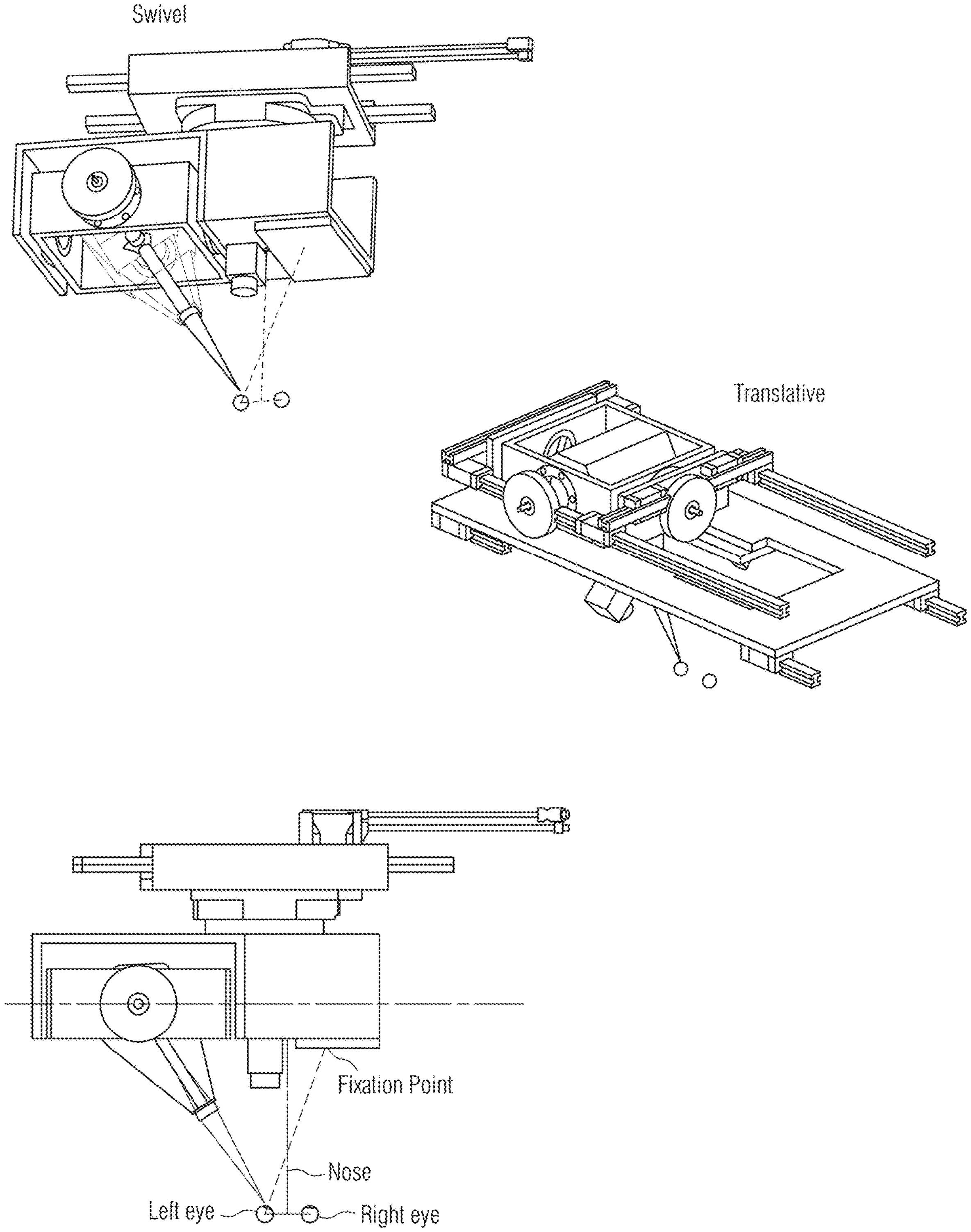
Figure 80:
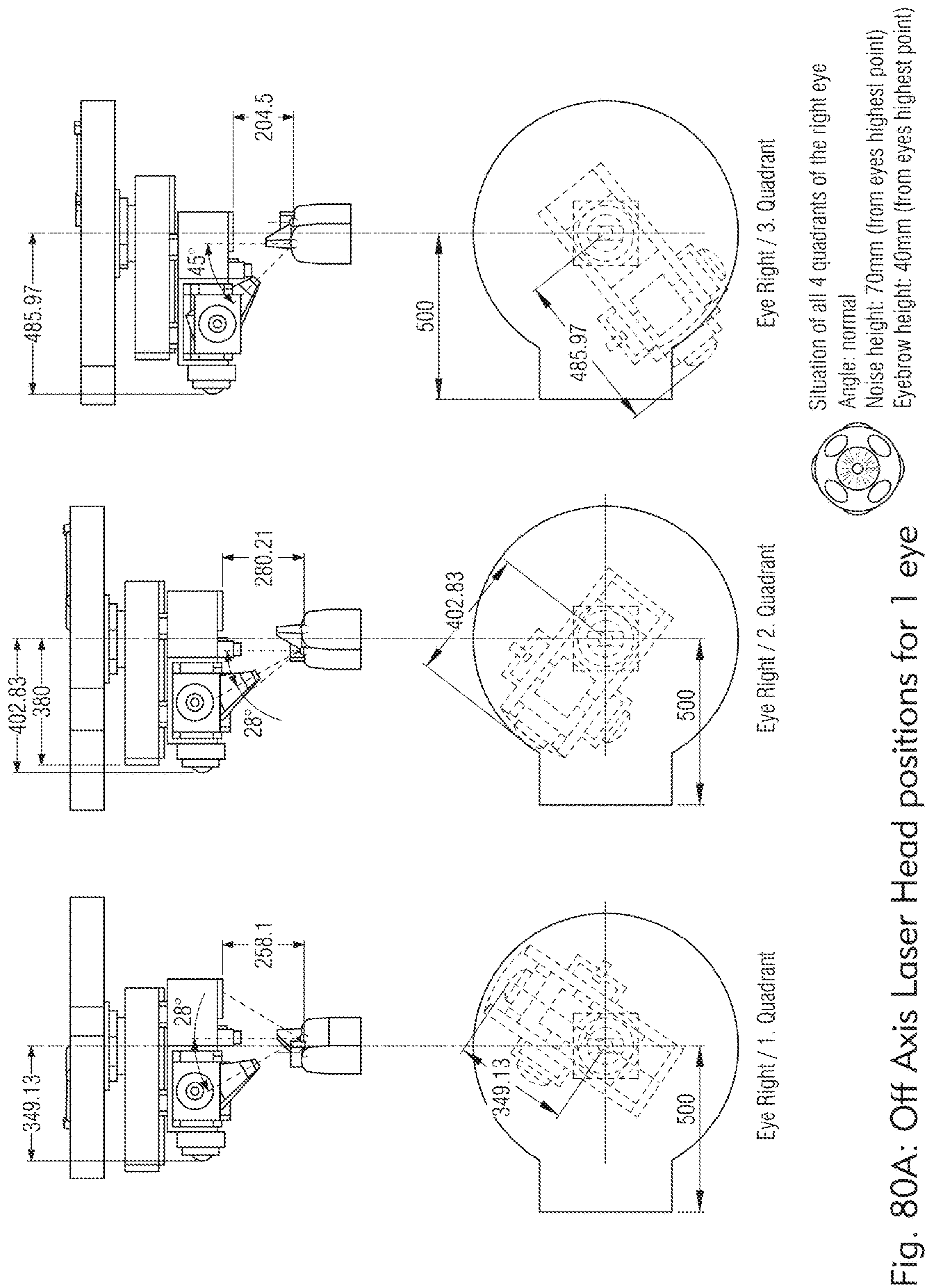
Figure 82:
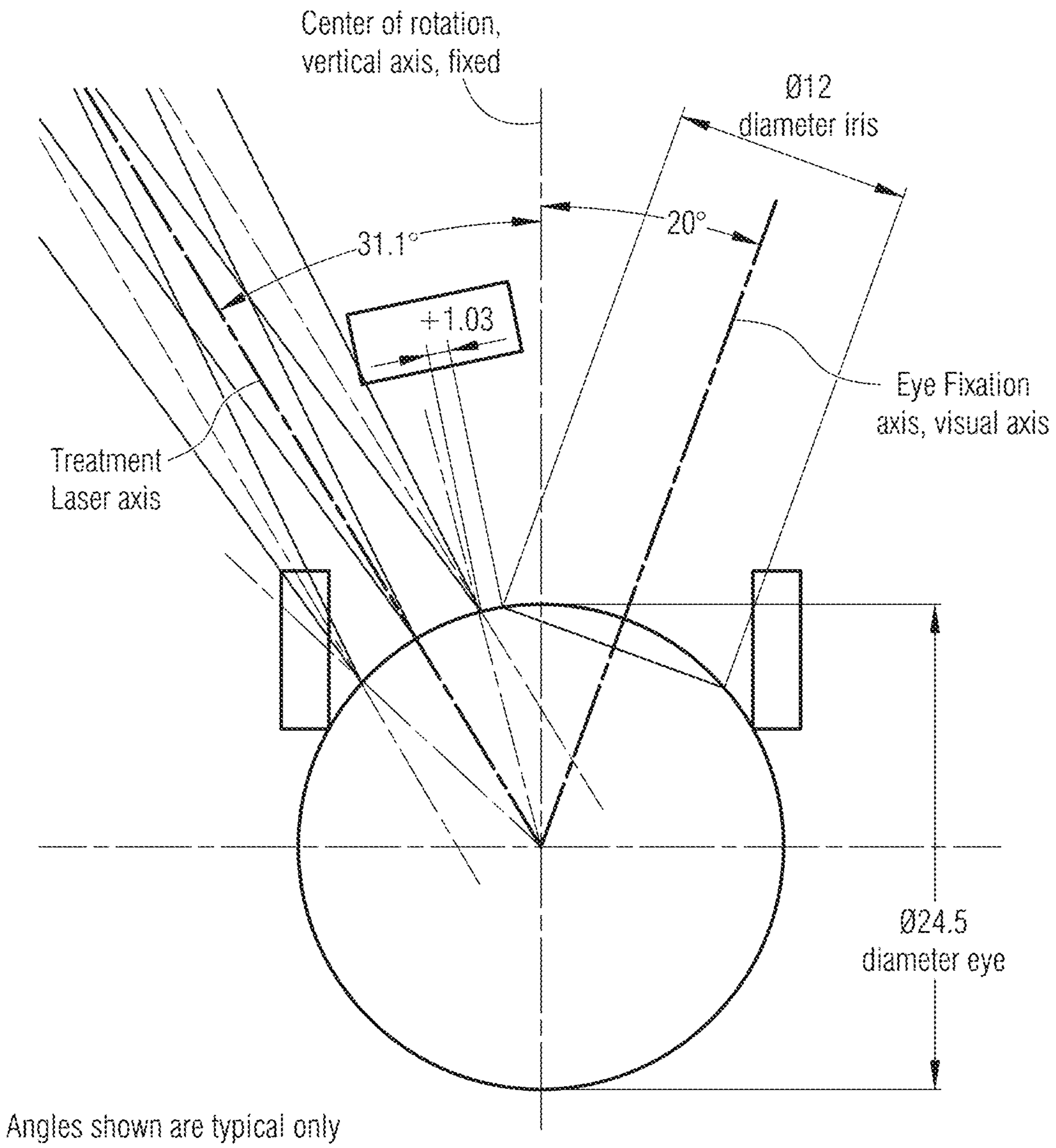
Figure 83:
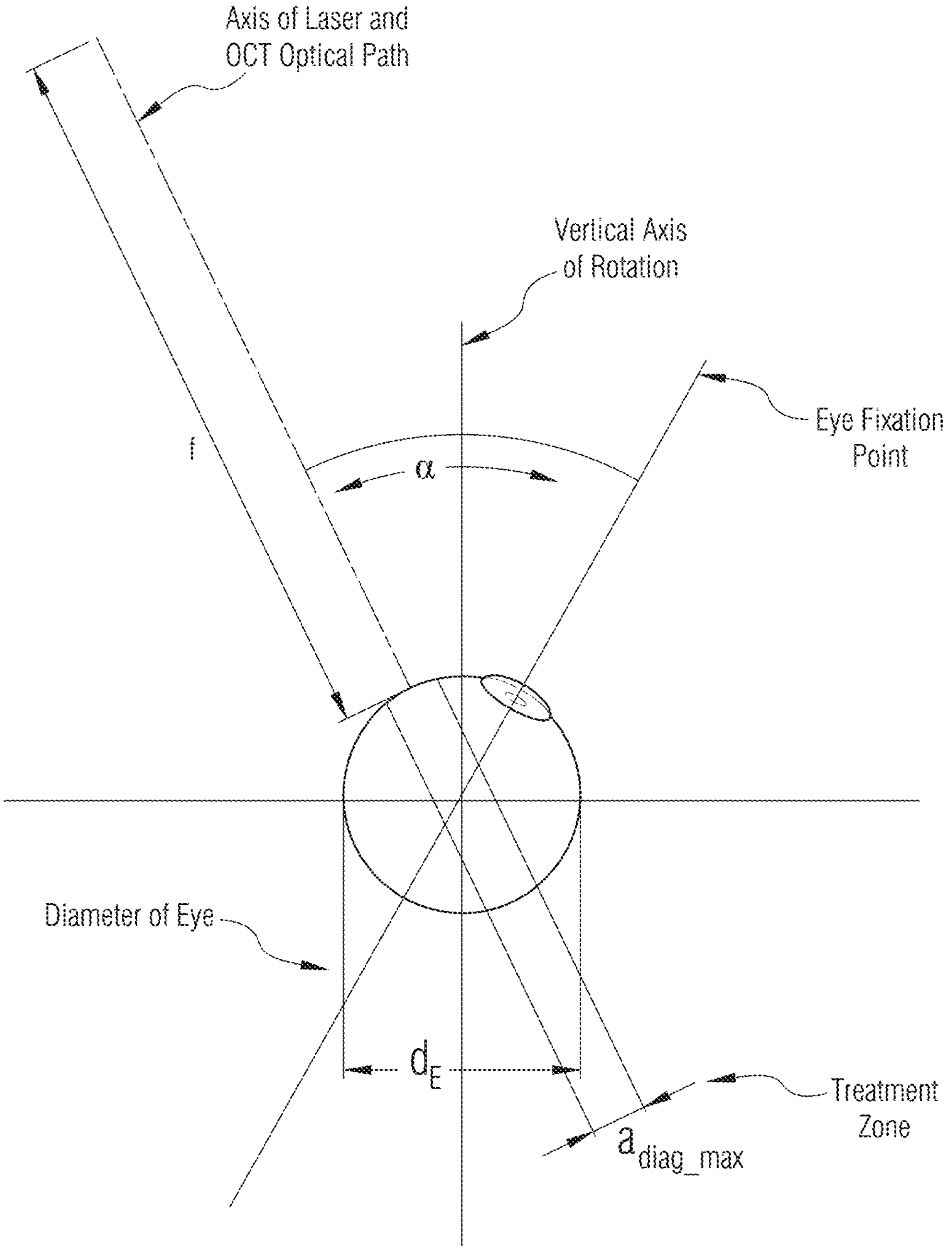

The laser head and the laser subsystem provide the capability of flexible motions. For example, FIGS. 77 to 79 show exemplary laser head system motions in a system without galvo. FIGS. 78 (middle 7800 is top view) and 79 show pitch, swivel and yaw movements of the laser head. Swivel is around the vertical axis. Pitch around the horizontal axis. Yaw is around the horizontal axis 90 degrees off the pitch axis. FIGS. 82 and 83 show exemplary laser focal and angular positions in relation to the top of the eye for off-axis treatments, where the treatment axis is off the visual eye fixation axis. Swivel and translation (x axis) of the whole laser head provide x and y axis motion in conjunction with yaw motion. The use of yaw to control x and y motion introduces a change in focal position and requires then a z axis correction by raising the entire head or in some cases may be done by an auto-focus focusing lens, e.g., as shown in FIGS. 13 and 14.

FIGS. 73, 81, 80A and 80B show exemplary laser head positions for each quadrant of an eye around facial features.

Figure 88:
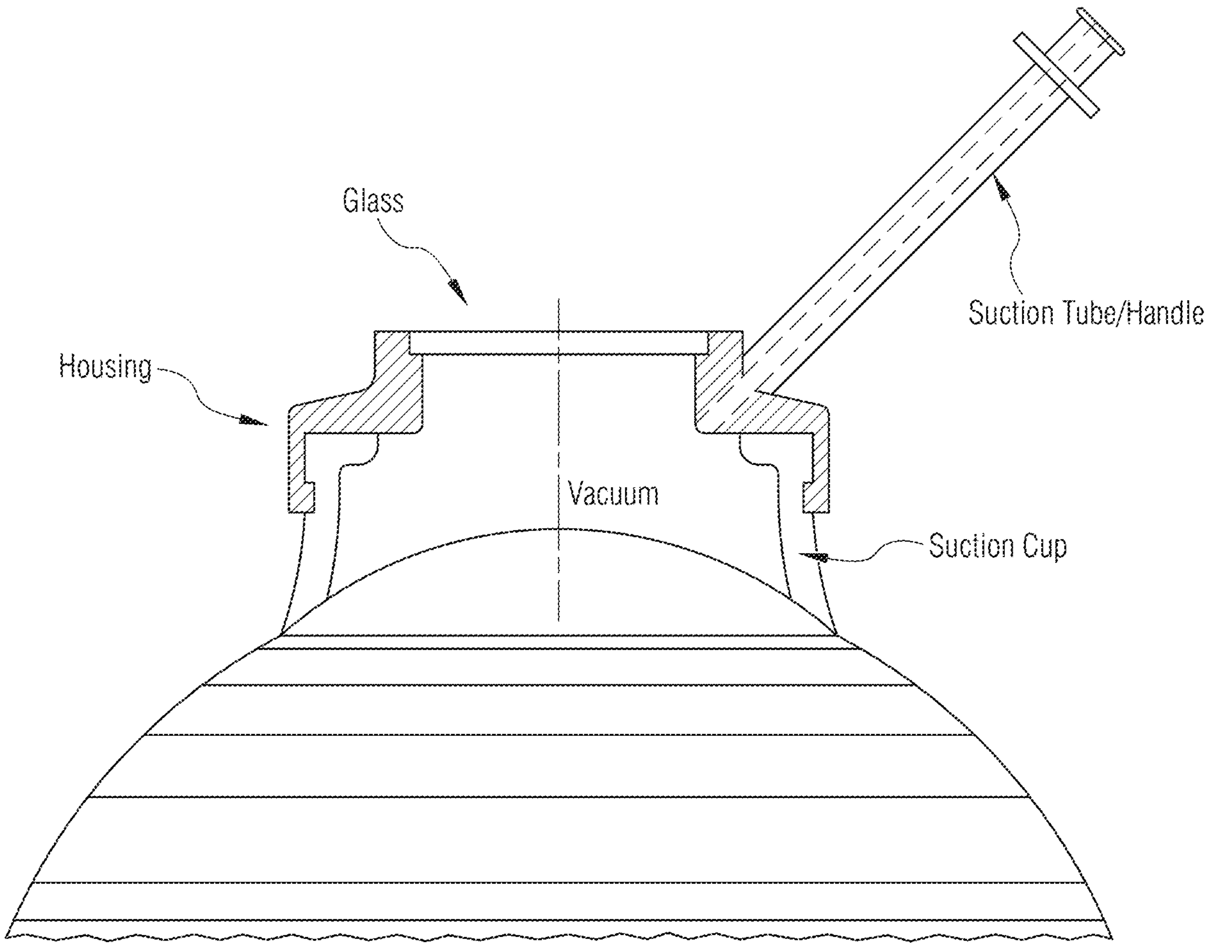
FIGS. 88 and 89 illustrate an exemplary eye docking system, according to some embodiments of the present disclosure.
Figure 89:
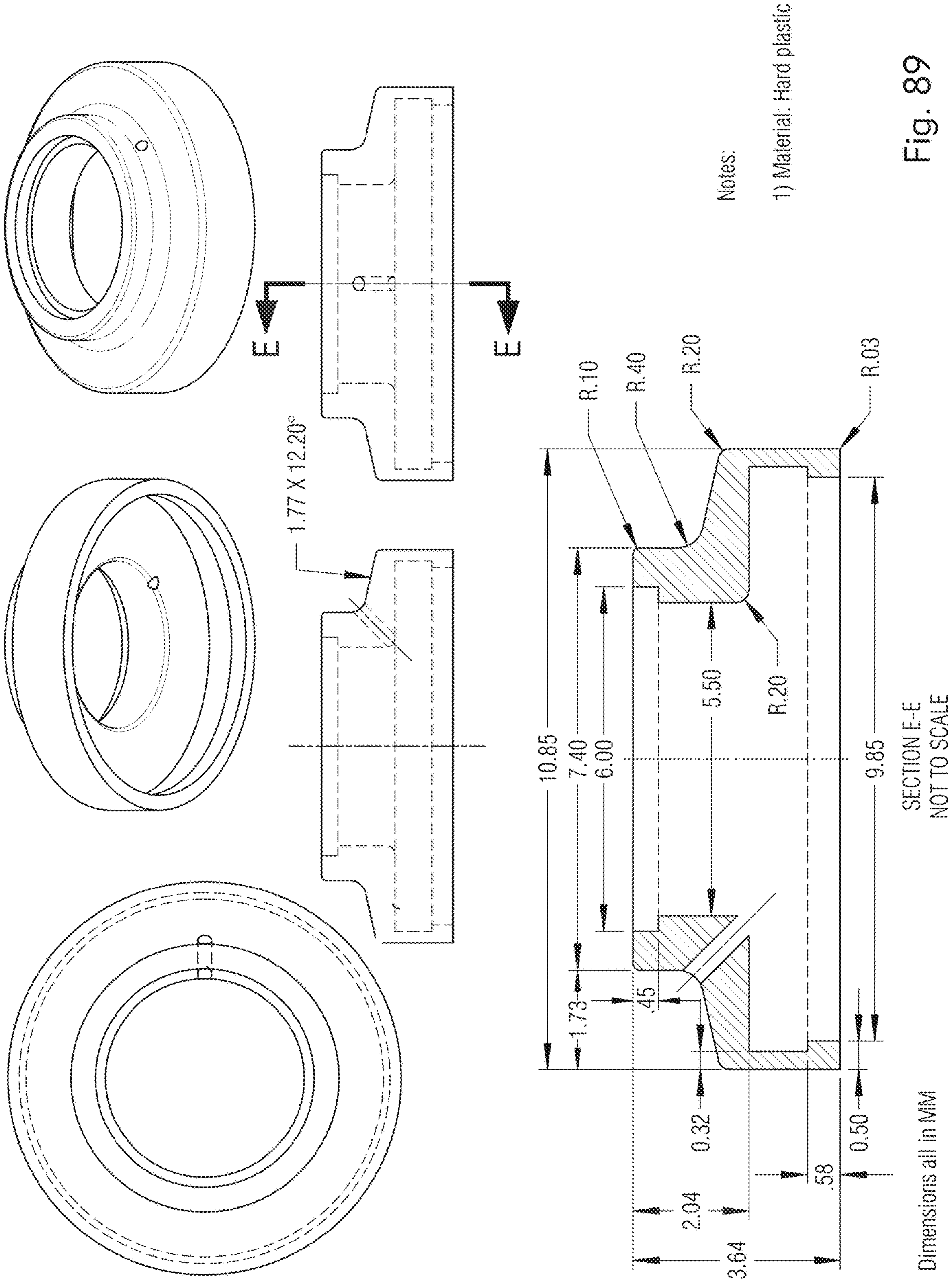

In some embodiments, the laser system may use the eye tracking system to assess patient's ability to hold the eye still enough prior to treatment. The doctor may modify the fixation position (angle) or use an eye docking system to assist the patient in holding the eye still. FIGS. 88 and 89 illustrate an exemplary eye docking system of the present disclosure.

The eye fixation system may store key eye image data to allow the reposition in the treatment area at a later time to complete treatment or augment an earlier treatments (re-treat).

The fixation or gaze point may be customized in relation to the treatment laser beam for each quadrant and for different patients with different facial structures.

As shown in FIG. 75, the laser system may include a patient display that can also be used to communicate other information to the patient including instructions and information.

In some embodiments, the laser system may be configured to treat scleral tissue where the treatment laser beam and the corresponding fixation point and fixation axis are related and controlled for both eyes and quadrants to avoid facial structures (e.g., nose). FIGS. 73 and 77 illustrate exemplary laser head positions for each quadrant around facial features. In some embodiments, the angle between the treatment laser and the visual axis (fixation axis) may be substantially fixed and 180 degrees opposite around the vertical axis. Some patients may have extreme facial features in some quadrants that may require reduction in this angle. The system may allow the treatment axis slightly off perpendicular to the surface of the scalar.

Figure 81:
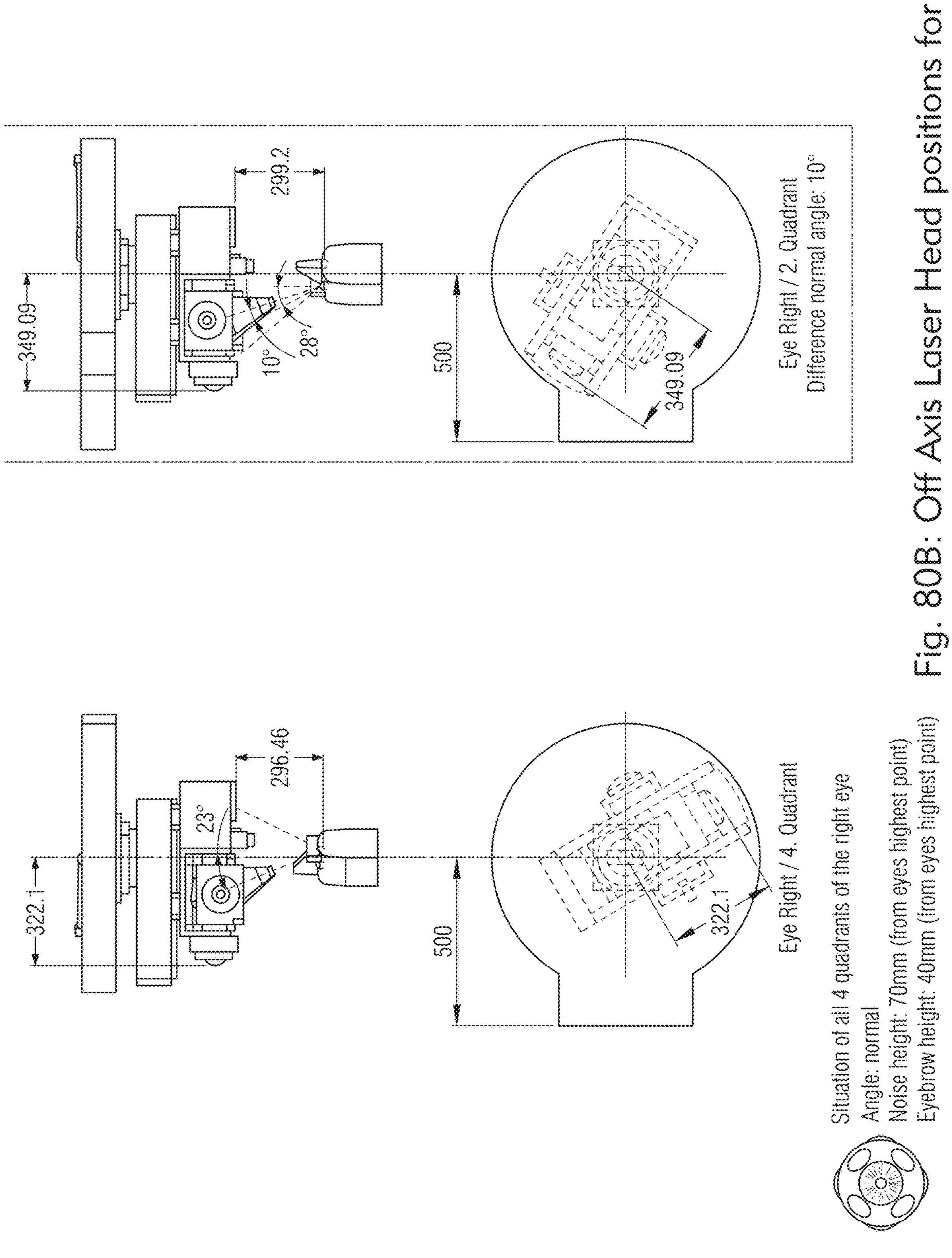

Treatment and Fixation Angle Example: (1) The laser treatment angle can be but is not always a 28°. The system targets to "hit the eye" with the laser at an angle as close to 90° as possible, at the same time considering the boundaries of the facial geometry (e.g., nose, eyebrow). (2) The fixation point is displayed on the screen, and it moves accordingly relative to the position of the quadrant which is currently under treatment to bring the patients "gaze/view" to the proper position so as to hit the eye as close to an angle of 90° as possible. (3) The angle between treatment and the fixation point is not always the same. The specific quadrant (Q) fixation points on the display for each quadrant treatment position. The angle depends on the distance to the patient, which in turn depends on the current quadrant under treatment. FIG. 81 illustrates an exemplary table showing details eye position per quadrant and treatment angle (e.g., as shown in FIG. 73).

In some embodiments, the laser system may include a laser head that can be positioned in other orientations to suit multiple patient positions and room configurations. FIG. 90 shows exemplary laser system with a laser head system where the patient can be in a sitting position.

Optimization of motion speed, direction and focal length between individual micro pores within a treatment area can be achieved through a single or multiple element within the motion control system. The order of pore creation within the treatment area can be controlled to optimize treatment efficacy, an exemplary order is described in FIG. 91.

As shown in FIGS. 38 to 41 and 42, in some embodiments, the laser system may include various combinations of OCT system components being shared and combined to reduce complexity, improve reliability and reduce cost.

Laser System

The eye is made of connective tissue. The damage of aging in living beings is an accelerating downward spiral of aging. Cross-links are a consequence of some classes of metabolic waste, such as advanced glycation end-products (AGEs). In connective tissue like the eye, AGE is caused by crosslinking of the collagen fibrils. Crosslinks increase the biomechanical stiffness of connective tissue. Crosslinking in the sclera causes ocular rigidity and is correlated with the loss of visual accommodation as well as the development of other age-related eye diseases (e.g., ocular hypertension, AMD, and some forms of cataracts). Crosslink breaking or "uncrosslinking" collagen fibrils can reverse AGE and the deleterious effects of age. Some embodiments of the system may include Laser Scleral Microporation (LSM) which is aimed at uncrosslinking scleral microfibrils by creating a matrix of micropores over critical zones of physiological importance to decrease biomechanical stiffness caused by age. The main effect is to allow the ciliary muscle complex to move the lens more freely and efficiently to restore the effective range of focus (EROF) of the eye to see at various distances especially near and intermediate that are lost with age. LSM can also improve small amounts of distance vision focus for latent hyperopes who have lost some of their distance vision due to the loss of the accommodative capability. FIGS. 117, 118 and 119 show exemplary uncrosslinking images.

In some embodiments, the laser therapy process of the present disclosure may target specific treatment areas which are in distinct physiological zones covering critical anatomy inside the eye relative to eye function. Although examples of 3 or 5 physiological zones are described herein, other number of physiological zones may also be considered for treatments.

In some embodiments, a treatment pattern may be described as 5 critical zones in 5 distinct distances from the outer edge of the anatomical limbus (AL), not touching any components or relative tissues of the cornea, as illustrated in FIGS. 2B-1 to 2B-3 of U.S. application Ser. No. 15/942,513, and FIGS. 95 and 97.

In some embodiments, the laser therapy process of the present disclosure may provide different laser treatment angles for different quadrants. For example, the laser may be in focus with respect to the AT limbus. FIGS. 80A, 80B, 73 and 81 show examples of 4 quadrant positions on each eye for treatment. FIGS. 91, 92, 93 and 94 show a plurality of off-axis treatment area shapes and positions around the visual axis. The system may modify the size of the treatment area or the pore pattern within a treatment area over specific zones based on the diameter of the patient's eye globe. The globe diameter may be measured by traditional means pre-treatment or be inferred height of the treatment area through analysis of the OCT scan data that extends from over the AT limbus to the extreme of the planned treatment area to ensure treatment does not extend beyond safe areas, excluding the retina. See exemplary treatment areas in FIGS. 52 and 54.

Treatment Area and Patterns

In some embodiments, the laser system may be configured to treat scleral tissue where the laser beam can be positioned to allow full circumferential or 360-degree treatment around the eye. FIGS. 94 and 93 illustrate exemplary full circumferential or 360-degree golden spiral created from individual treatment patterns. The system may be able to modify gaze points and multiple treatment areas to ablate a pre-determined circumferential pattern or spiral.

In some embodiments, the laser system may be configured to treat the anterior segment zones (AS Zones) of the sclera for micropore creation in desired pattern for desired effects. FIGS. 96, 67, 68, 97, 98, 99 and 100 illustrate examples of anterior treatment zones that may be performed with the system of the present disclosure.

In some embodiments, the laser system may be configured to treat the posterior segment zones (PS Zones) of the sclera for micropore creation in desired pattern for desired effects. FIGS. 3, 101, 102, 103, 104 and 105 shows examples of posterior treatment zones, e.g., 5 zones that may be performed with the system of the present disclosure. FIG. 101 shows exemplary posterior segment critical zones description. FIGS. 102 and 103 show the exemplary posterior segment critical zones on an eye. As shown in FIG. 103, the exemplary posterior eye includes T, temporal, and N, nasal. The optic nerve (a) with its central vessels and surrounding meningeal sheaths is seen. Its center is located about 3 mm nasal and 1 mm inferior to the posterior pole of the eye. Surrounding it are the short posterior ciliary arteries and nerves. The approximate position of the macula is at x. Along the horizontal meridian, which bisects the eye, are the long posterior ciliary arteries and nerves (b). The exits of four vortex veins are shown, one for each quadrant (c). The curved, oblique insertions of the superior oblique (d) and inferior oblique (e) muscles are seen. The cut ends of the four rectus muscles are at f.

Treatment within the defined treatment area may modify micropores in specific zones. A diamond shape is a simple exemplary pattern, others may more constantly favor optimization of pores per zone.

As illustrated in FIGS. 91 and 104, treatment within the defined treatment area can modify micropores in specific zones. The micropore patterns and order of micropore creation may be modified with the treatment area and with specific zones to optimize efficacy of treatment. For example, FIG. 92 shows one order of micropore creation from 1-48. In FIGS. 93 and 94, other examples of multiple treatment area shapes and patterns are shown in multiple locations around the visual axis.

In some embodiments, the laser system may be configured to treat ocular rigidity in the sclera. The system may uncrosslink the age-related increases crosslinks, of fibrils and microfibrils, that occur in connective tissues (FIGS. 5 and 4 show examples of tissue treated in microporeation)—including the connective tissue in the sclera. The system may decrease biomechanical stiffness by breaking bonds (uncrosslinking). FIGS. 118 and 119 illustrate exemplary treatment laser beam ablation of individual pores, and uncrosslinking is breaking bonds in microfibrils and fibrils. It weakens tissue or allows tissue to be more compliant—decreased biomechanical stiffness.

In some embodiments, the array pattern of micropores may be a spiral pattern of an Archimedean spiral, a Euler spiral, a Fermat's spiral, a hyperbolic spiral, a lituus, a logarithmic spiral, a Fibonacci spiral, a golden spiral, a Bravais lattice, a non Bravais lattice, or combinations thereof.

In some embodiments, the array pattern of micropores may have a controlled asymmetry which is an at least partial rotational asymmetry about the center of the array pattern. The at least partial rotational asymmetry may extend to at least 51 percent of the micropores of the array pattern. The at least partial rotational asymmetry may extend to at least 20 micropores of the array pattern. In some embodiments, the array pattern of micropores has a random asymmetry.

In some embodiments, the array pattern of micropores has a controlled symmetry which is an at least partial rotational symmetry about the center of the array pattern. The at least partial rotational symmetry may extend to at least 51 percent of the micropores of the array pattern. The at least partial rotational symmetry may extend to at least 20 micropores of the array pattern. In some embodiments, the array pattern of micropores may have a random symmetry.

In some embodiments, the array pattern has a number of clockwise spirals and a number of counterclockwise spirals. The number of clockwise spirals and the number of counterclockwise spirals may be Fibonacci numbers or multiples of Fibonacci numbers, or they may be in a ratio that converges on the golden ratio.

Laser System and Optical Configurations

In some embodiments, the laser system may be configured to provide the treatment laser within a laser head that can direct the beam in a goniometric manner with up to 5 degrees of motion.

In all cases the exact angular and focal position of the treatment laser can be achieved by combination of motion of multiple elements. In some embodiments, these elements may be included in a laser head system, discussed above and as shown in at least FIGS. 78, 73, 80A, 80B and 77.

As shown in FIG. 10, in some embodiments, the laser system may use galvo mirrors, a separate visible laser and OCT/Depth Control (OCT/DC) fibers that are combined into the treatment laser axis and pass through the same focusing optics showing process control of the OCT/DC and laser operations and providing illumination and camera with direct doctor visibility.

As shown in FIG. 11, in some embodiments, the laser system may use galvo mirrors, the visible laser and OCT/DC that are combined through a single fiber that are combined into the treatment laser axis and pass through the same focusing optics showing process control of the OCT/DC and laser operations and providing illumination and camera with direct doctor visibility.

As shown in FIG. 12, in some embodiments, the laser system in FIG. 11 may also include an OCT scanning system.

As shown in FIG. 13, in some embodiments, the laser system similar to FIG. 12 may operate without the galvos, 5 axis in the laser head and separate Z motion.

As shown in FIG. 14, in some embodiments, the laser similar to FIG. 13 may have a configuration which contains no galvos, 6 axis with an autofocus (AF) lens assembly.

As shown in FIG. 120, in some embodiments, the laser system may include a Treatment Dome Laser pointing design where the Dome concept is the fundamental idea that a laser head moves on a dome surface and always points at the center of the treatment area. The dome is moved in x, y and z to position the center of the dome to the patient's eye—with or without galvos incorporated. In the simplest view, the motion control may move the treatment laser around the patient's eye on the surface of a dome. The dome may be positioned in the x, y and z axis to align with the initial micropore position of the treatment protocol and then step around the dome to the next micropore position. The x, y and z axis may not change over the treatment of one quadrant but may need to be modified for another quadrant.

As shown in FIGS. 121-125, and 128-132, in some embodiments, the laser system may be configured to treat scleral tissue having a plurality optical components to modify the beam (and therefore pore) size, focal point with adjustability done manually or automatically under system control. For example, in FIGS. 121-125, the components may include $CaF_2$ lens, Sapphire combiner, Sapphire half-ball lens, collimate, focus and defocus the optical beam. The Sapphire Combiner provides a means to introduce the OCT and visible laser beams to be collinear with the treatment beam. The $CaF_2$ cylindrical lens is used to circularize the beam. In FIGS. 128-132, a pair of lenses are used to modify the beam diameter at the object plan on the eye, replacing a fixed lens element in previous figures.

Figure 85:
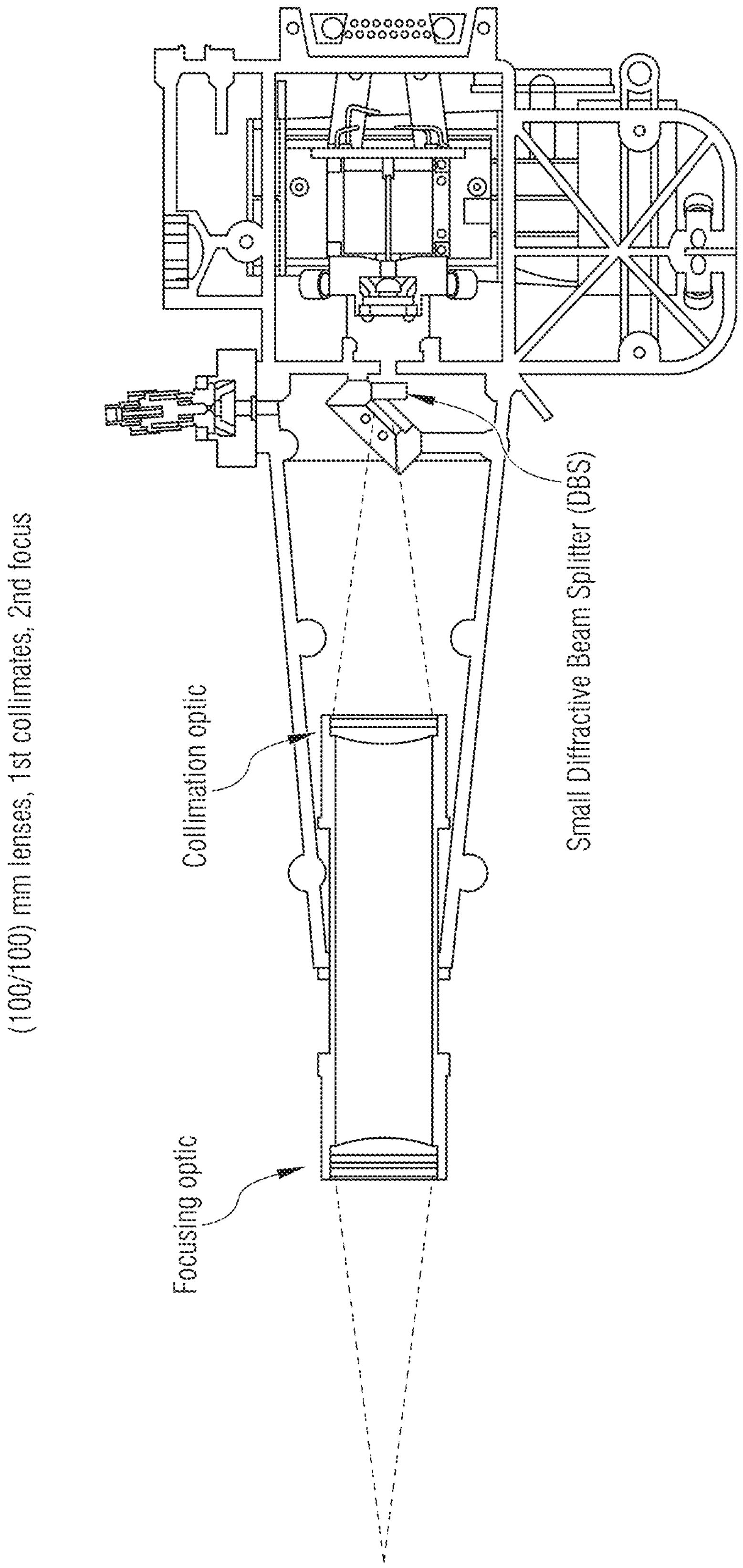

As shown in FIGS. 84 and 85, in some embodiments, the laser system may be configured to treat scleral tissue having a plurality optical components included in a light weight assembly including other optics, Diffractive Beam Splitter (DBS), motors, encoders, laser, laser driver, attachment for OCT fibers and cooling.

In some embodiments, the laser system may include a scanning mirror that can serve as a duplicate axis of motion to make very fast corrections to the beam pointing on the eye. FIGS. 126A and 126B illustrate some specifications and capabilities for a scanning mirror.

As shown in FIGS. 126A, 126B and 127, in some embodiments, the laser system may be configured to treat scleral tissue having a single scanning mirror that combines OCT scanning and OCT depth control functions where the scanning mirror can be modulated to trace a pattern of pulses of the treatment laser over the surface of the eye during ablation of a single pore in a manner to create a different total shape and size of the pore and/or a different bottom shape of the pore. In some cases, a DBS may create a portion of a micropore size and shape. The beam pointing may be moved to trace a larger micropore shape using multiple positions and pulses of the system.

In some embodiments, as illustrated in FIG. 182, the laser system may include a scanning mirror combining OCT scanning and OCT depth control into a single OCT beam, colinear with the treatment laser where the scanning mirror may allow scanning and fixed position functions related to OCT scanning and OCT depth control. In some embodiments, the laser system may use both functions simultaneously, or alternately to combine OCT scanning with the treatment of a quadrant.

As shown in FIGS. 127, 86, 85 and 57, in some embodiments, the laser system may be configured to treat scleral tissue having a single scanning mirror that combines OCT Scanning and OCT depth control functions and beam shaping and sizing diffractive beam splitter (DBS) in the laser head, as shown in FIG. 85. In some embodiments, a plurality of small DBS may alter the beam size and shape. The DBS elements of different optical designs can be exchanged manually or automatically to modify the treatment beam profile colinear with the treatment laser beam. In some embodiments, the DB S may be used to split a single laser beam into several beams each with the characteristic of the original beam, may be used in a divergent beam, may be used to change the spot size, and may be miniaturized if used before the beam combiner. DBS designs may result in arbitrary spot distributions. The single spot size may have no correlation to the spot to spot distance.

Headrest System and Chair

Figure 72:
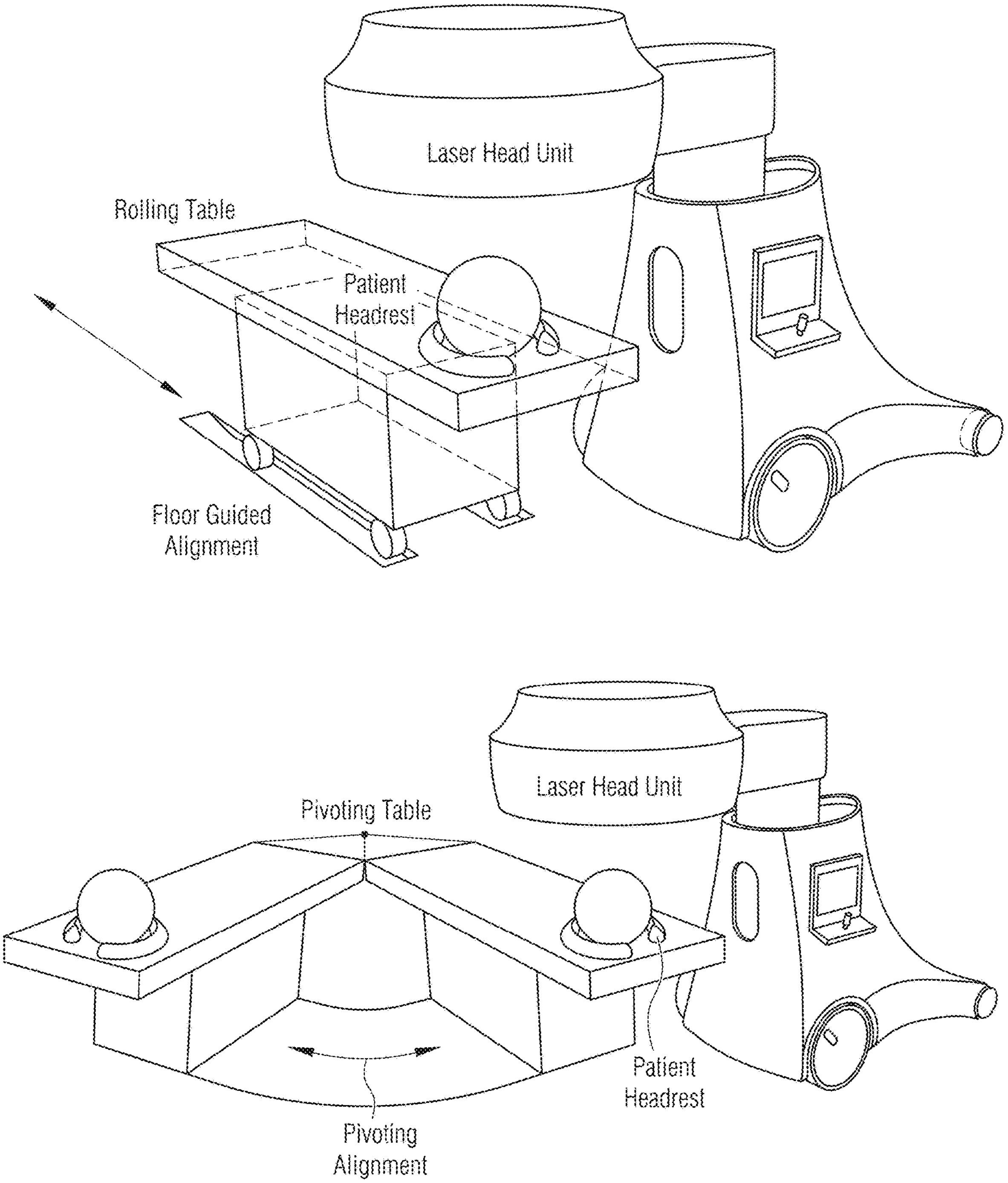

In some embodiments, as illustrated in FIGS. 133 and 72, the laser system may include a patient table or chair that may be attached or positioned to the laser system mechanical structure and will be locked or remain fixed in position to the laser head.

Figure 71:
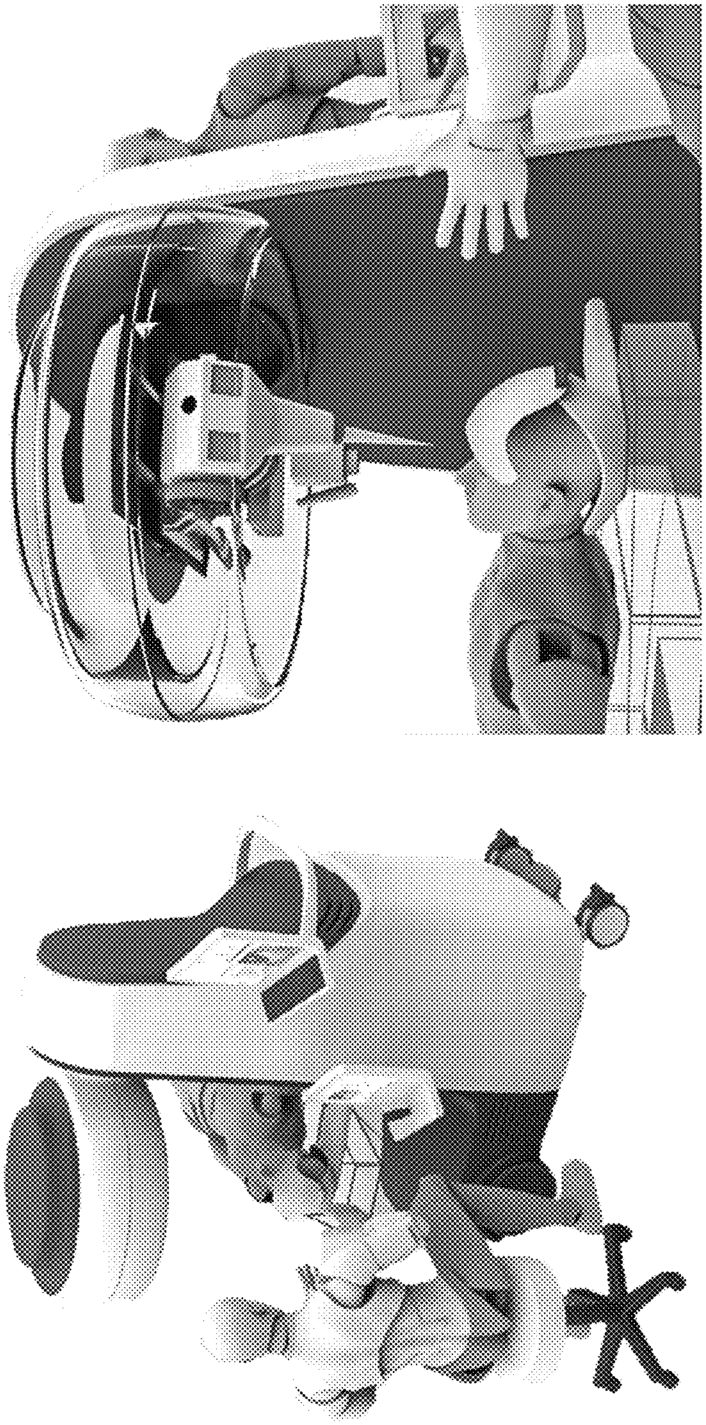
FIGS. 71 and 72 illustrate exemplary laser system including a laser head system that provides fixation point, according to some embodiments of the present disclosure.

In some embodiments, the laser system may include a patient chair that allows the patient to be reclined and moved under the laser system with no touch automation or manually. A preferred embodiment would position the head directly centered within the operational range of the laser head in x and y then provide z motion to move the patients face up centered in the operational range of the laser head. From this position the TOF camera, laser cross and laser head motion control system may align the patient for treatment As shown in FIGS. 9, 71, 134 and 135, in some embodiments, the laser system may include a patient headrest used to hold the patient's head and eye still and to provide a rough position of the eye to the laser head in preparation and during treatment. The headrest may secure the patient's head as needed to assist in holding the eye still. The headrest may be attached to the system as seen in FIG. 71 or to the chair or the treatment table. The headrest may be moved up and down to roughly align the patient's eye in the Z axis. The headrest may also serve as a mounting location for an automated optional eye docking mechanism.

In some embodiments, the headrest may include a helmet mounted on the headrest in a chair or table. Or the headrest may be mounted to the laser system and provide positive locational feedback to the system.

In some embodiments, the headrest may incorporate a tissue plume (as shown in FIG. 76) or buffalo filter management system positioned adjacent to the eye and located properly for each treatment area. In some embodiments, the headrest may include an ablation plume suction in position next to the quadrant being treated as positioned by the doctor.

In some embodiments, the plume management filter system may be incorporated with the system and the evacuation hose/nozzle (or nozzles) may be positioned separate from the headrest manually or automatically on a slide or other apparatus by the system.

In some embodiments, the headrest may include an automated eye docking system to assist in positioning the patient's eye for each quadrant and keeping it still. This may be done with or without doctor assistance.

FIGS. 88 and 89 show an exemplary eye pod accessory component of the laser system that may assist in spreading the eyelids open to expose the treatment areas, stabilizing the eye motion, protect the pupil for stray treatment laser emissions and assisting patients in viewing very far off-axis fixation targets.

System Procedure and Mechanism of Action

FIGS. 19 and 20, and 27 show, in some embodiments, exemplary processes to generate a micropore(s).

In some embodiments, the laser therapy procedure may use an erbium: yttrium-aluminum-garnet (Er:YAG) laser to create microspores in the ocular tissue, e.g., the sclera. These micropores may be created at a plurality of depths with preferred depth range, e.g., from 5%-95% of the sclera, up to the point where the blue hue of the choroid is just visible. The micropores may be created in a plurality of arrays including a matrix array, e.g., 5 mm×5 mm, 7 mm×7 mm, or 14 mm×14 mm matrix array. These microporation matrices break bonds in the scleral fibrils and microfibrils having an 'uncrosslinking' effect in the scleral tissue. A direct consequence of this matrix pattern may be the creation of areas of both positive stiffness (remaining interstitial tissue) and negative stiffness (removed tissue or micropores) in the rigid sclera. These areas of differential stiffness allow the viscoelastic modulus of the treated sclera to be more compliant over the critical zones when subjected to force or stress, such as contraction of the ciliary muscles. Additionally, the treated regions of the sclera may produce a dampening effect in rigid scleral tissue when the ciliary muscles contract, due to increased plasticity. This enhances accommodative effort by directing unresisted forces inward and centripetally toward the lens or facilitating inward upward movement of the accommodative mechanism. This is an advantage over models that postulate a net outward-directed force at the lens equator. For example, techniques which are directed at scleral expansion such as scleral implants or surgical laser radial ablations such as LAPR are all directed at increasing 'space' or circumferential space to allow the sclera to expand for the intention of giving the ciliary muscle room. These techniques are based on the 'lens crowding' theory and aim to induce the outward movement rather than the upward and inward movement of the sclera and ciliary mechanism. Overall, the creation of the micropore matrices in the scleral tissue may induce an 'uncrosslinking effect', severing the fibrils and microfibrils of the layers of the sclera allowing a more compliant response to applied stress. Thus, the mechanism of action of the present disclosure may increase plasticity and compliance of scleral tissue over critical zones of anatomical significance by creating these regions of differential stiffness over the ciliary complex, and thereby improve biomechanical function and efficiency of the accommodation apparatus. FIGS. 2C-1 to 2C-4 of U.S. application Ser. No. 15/942,513 illustrate laser scleral uncrosslinking of scleral fibrils and microfibrils and are incorporated herein.

In some embodiments, the system optics may be capable of focusing the treatment laser, a divergent beam, into individual convergent beam that is directed at a specific pore location at working distance of up to 250 mm. Long working distance >100 mm allows visual line of sight to the eye before, during and after treatment for the user and improves the patient experience of a no touch treatment. The challenge of long working distances for Er:YAG 2.94 um wavelength has disallowed this laser wavelength to break through into more handsfree automated laser systems for commercial applications. Currently, almost all of the Er:YAG 2.94 um commercial systems are either hand held or delivered by articulating arm with an ideal irradiation working distance of less than 500 um and an average irradiation working distance of 3-4 mm. In some embodiments, the irradiation working distance is ideally greater than 100 mm and average irradiation working distance of 100-200 mm allowing for hands free no touch laser treatments.

In some embodiments, the system may be capable of creating a plurality of beam shapes and sizes at the target focal plane by (1) moving optical components along the optical axis, (2) changing the diffractive beam shitter included in the optical path, or a combination of both.

Ocular connective tissues are impacted, like all other connective tissues, by age. The sclera constitutes 5/6 of the oculus and is made up of dense irregular connective tissue. It is comprised primarily of collagen (50-75%), elastin (2-5%), and proteoglycans. The connective tissues of the eye stiffen with increasing age losing their elasticity largely due to the crosslinking that occurs with age. Crosslinking creates an "increase in biomechanical stiffness" in connective tissues such as those in the eye. Crosslinks are bonds between polymer chains, such as those in synthetic biomaterials or the proteins in connective tissues. Crosslinking can be caused by free radicals, ultraviolet light exposure, and aging. In connective tissues, collagen and elastin can crosslink to continuously form fibrils and microfibrils over time. With increasing amounts of fibrils and microfibrils, the sclera stiffens, undergoing a 'sclerosclerosis', as well as a concomitant increase in metabolic physiological stress. As this pathophysiology progresses, the sclera exerts compression and loading stresses on underlying structures, creating biomechanical dysfunction, specifically those related to accommodation. Laser scleral microporation breaks scleral fibrils and microfibrils effectively "uncrosslinking" bonds thereby increasing scleral compliance and "decreasing biomechanical stiffness".

The biomechanical improvements with the treatment may prove to increase the biomechanical efficiency of the accommodative apparatus. In some embodiments, by creating micropores in a matrix over four oblique quadrants, the treatment may restore functional extralenticular forces, and restore a minimum of 1-3 diopters of accommodation. Treatments using the system and methods of the present disclosure may show an average of 1.5 diopters of accommodation post-operatively. This significantly improved the visual acuity in the patients.

Utilizing innovative biometry and imaging technologies that were not previously available has illuminated that the loss of accommodative ability in presbyopes has many contributing lenticular, as well as extralenticular and physiological factors. The lens, lens capsule, choroid, vitreous, sclera, ciliary muscles, and zonules all play a critical role in accommodation, and are affected by increasing age. Increasing ocular rigidity with age produces stress and strain on these ocular structures and can affect accommodative ability.

Scleral therapies may have an important role in treating biomechanical deficiencies in presbyopes, by providing at least one means to address the true etiology of the clinical manifestation of the loss of accommodation seen with age. The treatment, utilizing laser microporation of the sclera to restore more pliable biomechanical properties, is a safe procedure, and can restore accommodative ability in aging adults. As a result, the treatment may improve dynamic accommodative range as well as aqueous outflow. With the advent of improved biometry, imaging, and research focus, information about how the accommodation complex works and how it impacts the entire eye organ can be achieved.

In some embodiments, the laser scleral microporation procedure may involve using the laser described above to perform partial-thickness micro-ablations in the sclera in a matrix in five critical anatomic zones, for example, 0-7.2 mm from the anatomical limbus (AL). In some embodiments, the five zones may include: Zone 0) 0.0-1.3 mm from AL; distance from the AL to the superior boundary of ciliary muscle/scleral spur; Zone 1) 1.3-2.8 mm from AL; distance from the sclera spur to the inferior boundary of the circular muscle; Zone 2) 2.8-4.6 mm from AL; distance from the inferior boundary of the circular muscle to the inferior boundary of the radial muscle; Zone 3) 4.6-6.5 mm from AL; inferior boundary of the radial muscle to the superior boundary of the posterior vitreous zonule zone; and Zone 4) 6.5-7.2 mm from AL; superior boundary of the posterior vitreous zonule zone to the superior boundary of the ora serrata.

As described herein, accommodation of a human eye may occur through a change or deformation of the ocular lens when the eye transitions from distant focus to near focus. This lens change may be caused by contraction of intraocular ciliary muscles (ciliary body), which relieves tension on the lens through suspensory zonule fibers and allows the thickness and surface curvature of the lens to increase. The ciliary muscle can have a ring-shaped and can be composed of three uniquely oriented ciliary fiber groups that contract toward the center and anterior of the eye. These three ciliary fiber groups are known as longitudinal, radial and circular. Deformation of the ciliary muscle due to the contraction of the different muscle fibers translates into or otherwise causes a change in tension to the surface of the ocular lens through zonule fibers, whose complex patterns of attachment to the lens and ciliary muscle dictate the resultant changes in the lens during accommodation. Ciliary muscle contraction also applies biomechanical strain at the connection locations between the ciliary muscle and the ocular sclera, known as the white outer coat of the eye. Additionally, biomechanical compression, strain or stress can be caused during accommodation can occur at connection locations between the ciliary muscle and the choroid, known as the inner connective tissue layer between the sclera and ocular retina. Ciliary muscle contraction can also cause biomechanical forces on the trabecular meshwork, *Lamina cribrosa*, retina, optic nerve and virtually every structure in the eye.

In some embodiments, applying the techniques and models described with respect to the various embodiments herein using simulations can lead to outputs and results that fall within known ranges of accommodation of a young adult human.

3D mathematical models can incorporate mathematics and non-linear Neohookean properties to recreate behavior of the structures of biomechanical, physiological, optical and clinical importance. Additionally, 3D (Finite Element Model) FEM models can incorporate data from imaging, literature and software relating to the human eye.

Visualization of accommodation structures during and after simulations may be included in addition to means for measuring, evaluating and predicting Central Optical Power (COP). These can be used to simulate and view age specific whole eye structures, optics, functions and biomechanics. Further, they can independently simulate properties of the ciliary muscle, extra-lenticular and lenticular movements of the ocular lens and functions on the ocular lens. Individual simulations of anatomical structures and fibers can reveal biomechanical relationships which would otherwise be unknown and undefined. Numerical simulation of the patient's eye can be created using 3D FEM meshing to accomplish these operations.

To elaborate, representative 3D geometry of resting ocular structures can be computationally defined based on extensive review of literature measurements and medical images of the anatomy of young adult eyes and through modeling. Specialized methods implemented in software, such as AMPS software (AMPS Technologies, Pittsburgh, Pa.), can be used to perform geometric meshing, material property and boundary conditions definitions, and finite element analysis during the modeling stage. Ciliary muscle and zonules can be represented as a transverse isotropic material with orientations specified to represent complex fiber directions. Additionally, computational fluid dynamic simulations can be performed in order to produce fiber trajectories, which can then be mapped to the geometric model.

Initially, a lens modeling can include a lens in a relaxed configuration, before being stretched by pre-tensioning zonule fibers to an unaccommodated position and shape. Unaccommodated lens position can be reached when zonules are shortened, e.g., to between 75% and 80% of their starting length, and more particularly to about 77% of their starting length. Then accommodative motion can be simulated by performing active contraction of the various fibers of the ciliary muscle. In some embodiments, this can be accomplished using previous models of skeletal muscle that are modified to represent dynamics particular or otherwise specific or unique to the ciliary muscle. Model results representing lens and ciliary anterior movement and deformed ocular lens thickness at a midline and apex can be validated or otherwise verified by comparing them to existing medical literature measurements for accommodation. In order to investigate contributions of the various ciliary fiber groups to the overall action of the ciliary muscle, simulations can be performed for each fiber group by activating each in isolation while others remain passive or otherwise unchanged.

Various beneficial aspects of the embodiments described below are described with respect to simulations applying pre-tensioning zonules models and contracting ciliary muscle models.

With respect to the pre-tensioning zonules, modeling can include: 1) Creation of 3D material sheets oriented between measured zonular attachment points of insertion on the lens and origination on the ciliary/choroid; 2) specified fiber direction in the plane of the sheet (e.g., fibers directed from origin to insertion); and 3) Transversely isotropic constitutive material with tension development in the preferred direction. Further, with particular respect to 3), advantages have been achieved, including: a) Time-varying tension parameter input regulates the stress developed in the material; b) Time-varying tension input may be tuned to produce required strain in the lens to match measurements of the unaccommodated configuration; c) Age variation in material properties and geometries to produce age-related impact; and d) others. U.S. application Ser. Nos. 15/638,346 and 16/702,470, incorporated herein, describe in further detail modeling of complete ocular FEM of human ocular accommodation.

With respect to the contracting ciliary muscle models, modeling can include: 1) Modified constitutive model to represent smooth and skeletal aspects of ciliary mechanical response; 2) a plurality of, e.g., 3, sets of specified fiber directions to represent physiological orientation of muscle cells and lines of action of force production; and 3) Transversely isotropic constitutive material with active force development in the preferred direction. Further, with particular respect to 3) advantages have been achieved, including: a) Activation parameter input regulates the active stress developed in the material; b) Activation input may be tuned to produce appropriate accommodative response to match literature measurements; c) Activation of individual muscle fiber groups can be varied in isolation to assess contributions to lens strain/stress; d) Activation of individual muscle fiber groups can be varied in isolation to assess contributions to ocular scleral strain/stress; e) Activation of individual muscle fiber groups can be varied in isolation to asses contributions to choroidal strain/stress; and f) others.

In various embodiments, simulation results can be governed by modification of tensioning and activation inputs to the zonule and ciliary materials, as opposed to performing an applied displacement to external node(s) of a mesh.

Thereafter, systems, methods and devices for providing a predictive outcome in the form of a 3D Computer Model with integrated Artificial Intelligence (AI) can be used to find predictive best instructions for a therapeutic ophthalmic correction, manipulation, or rehabilitation of a patient's vision defects, eye disease, or age-related dysfunction are disclosed. The predictive best instruction can be derived from physical structural inputs, neural network simulations, and prospective therapeutic-outcome-influencing. New information can be analyzed in conjunction with optimized, historical therapeutic-outcome information in order to provide various benefits. The concepts herein can be used to perform a multitude of simulations and include a knowledge-based platform so that the system may be able to improve its instruction response as the database is expanded. The concepts herein can also utilize AI to create progressive aging simulations of intended tissues and clinical manifestations of disease states to link treatment planning to outcomes.

In some embodiments, the stored instructions contemplated can preferably be an optimized, custom, microporation algorithm for driving a microoperation electromagnetic laser. The instructions can be provided along with an AI processor via direct integration, stand-alone importation or remotely, e.g., via a Bluetooth or other wireless enabled application or connection. These instructions can be performed a priori or intraoperatively.

In some embodiments, the stored instructions contemplated can preferably be an optimized custom ocular lens simulation algorithm used for simulating manipulation of an implantable intraocular lens in order to improve medical procedures and understanding.

The instructions can also be set up as a 'stand-alone' system, whereby the instructions can be provided with independent research design inputs and outputs to test various conditions and responses of the eye to surgical manipulations, implantation devices, or other therapeutic manipulations of the eye, in order to optimize design and outcome response.

Additionally, these instructions can also include one or more of: an algorithm for image processing interpretation, expansion of ophthalmic imaging data platforms and a companion diagnostic to an imaging device.

As described herein, methods for improving ophthalmic treatments, surgeries, or pharmacological interventions can include obtaining topological, topographical, structural, physiological, morphological, biomechanical, material property, and optical data for a human eye along with applied physics and analyzing through mathematical simulations using artificial intelligence networks.

In some embodiments, applications using simulation can include techniques executed via devices, systems and methods for automated design of an ophthalmic surgical procedure including physical measurements and applied physics of a patient's whole eye are obtained. Techniques known in the art can be used to obtain these measurements. The information measured can be interpolated and extrapolated to fit nodes of a finite element model (FEM) of a human eye for analysis, which can then be analyzed to predict an initial state of stress of the eye and obtain pre-operative conditions of the cornea, lens and other structures. Incision data constituting an "initial" surgical plan can be incorporated into the finite element analysis model. A new analysis can then be performed to simulate resulting deformations, biomechanical effects, stresses, strains, curvatures of the eye as well as dynamic movements of the eye, more specifically the ciliary muscles, lens and accommodative structures. These can be compared to original values thereof and to a vision objective. If necessary, a surgical plan can be modified and resulting new ablation data can be entered into the FEM and the analysis is repeated. This procedure can be repeated as desired or necessary until the vision objectives are met.

Artificial Intelligence and Simulation

In some embodiments, Artificial Intelligence (AI) software can use a learning machine, e.g., an artificial neural network, to conduct machine learning, whereby the system can learn from the data, and therefore has a learning component based on the ongoing database expansion. It can be operative to improve reliability as the database is formulated and updated, heretofore unknown in the prior art of 3D predictive modeling systems, methods and devices.

Simulation can include Age Progression simulation of a patient's eye, having a predictive capacity to simulate ophthalmic surgical outcomes, determine rates of regression of treatments, as well as execute predictive algorithms for future surgical or therapeutic enhancement, heretofore unknown in the prior art of 3D predictive modeling systems, methods and devices.

In some embodiments, the systems of the present disclosure may include a virtual eye simulation analyzer that can include integration of information related to all structures of an eye into a computer program for the purpose of simulating biomechanical and optical functioning of the eye, as well as age related simulations for clinical application purposes. Further detail of the virtual eye simulation analyzer is described in U.S. application Ser. No. 15/942,513 and is incorporated herein.

The simulator can incorporate mathematics and non-linear Neohookean properties in order to recreate behavior of the structures of biomechanical, physiological, optical and others that may be valuable or otherwise of clinical importance. The simulator can use methods known in the art to input data incorporated into a 3D FEM with a patient's unique data based on analysis of their own individual eye or eyes. Further, the simulator can use methods known in the art to input data and create a numerical simulation of the patient's eye using a 3D FEM meshing—essentially creating a custom dynamic real-time "Virtual Eye," heretofore unknown in the prior art of 3D predictive modeling systems, methods and devices.

In some embodiments, the AI may be capable of learning via predictive simulation and can be operative to improve simulative predictions for surgical or therapeutic manipulations of the eye through learning machine, such as artificial neural networks, e.g., in an "ABACUS" program. Such program can also be capable of providing instructions directly to a communicatively coupled processor or processing system to create and apply algorithms, mathematical sequencing, formula generation, data profiling, surgical selection and others. It can also be capable of providing instructions directly to a workstation, an image processing system, a robotic controller or other device for implementation. Further, it can be capable of providing instructions indirectly through a Bluetooth or other remote connection to a robotic controller, an image system or other workstation.

The models herein can have various applications for clinical, research and surgical use, including: 1) use of prior evaluation and simulation of accommodation functions of the eye (examples including Presbyopia indication-IOL design and use, extra-lenticular therapeutics and their uses); 2) use of prior evaluation and simulation of aqueous flow of the eye, such as for glaucoma indications; 3) virtual simulations and real time simulations of efficacy of IOL's, therapeutic treatments and various biomechanical implications; 4) virtual simulations using the AI and CI to reproduce customized aging effects on an individual's biomechanical and physiological functions of their eye which have clinical importance; 5) Surgical Planning; 6) design model (such as FEM) importation and simulation, such as for IOL's and others; 7) Virtual clinical trials and analysis; 8) real-time intraoperative surgical analysis, planning and execution; 9) Performance of a crystalline lens of the eye as it relates to optical and biomechanical dysfunction, cataract formation and the like; and 10) others.

In some embodiments of the invention a dual axis closed loop galvanometer optics assembly may be used.

In some embodiments, the laser system may include a camera correction system with galvos, which is described in further detail in FIG. 3C of U.S. application Ser. No. 15/942,513 which is incorporated herein. FIG. 3D of U.S. application Ser. No. 15/942,513 illustrates an exemplary flow diagram of a camera-based eye tracker process, according to some embodiments of the present disclosure.

In some embodiments, as described in further detail in FIG. 4A in U.S. application Ser. No. 15/942,513, and incorporated herein, the laser system may include a treatment laser emitting a laser beam which travels through relay lens to dichroic or flip-in.

FIG. 4B-1 in U.S. application Ser. No. 15/942,513, incorporated herein, illustrates an exemplary laser treatment system including ablation pore depth according to some embodiments of the present disclosure. FIG. 4B-1 generally shows a treatment laser beam traveling to a dichroic before travelling to a first galvo, then to a second galvo, through focusing optics, and to the patient's eye. FIGS. 4A-1 to 4A-10 in U.S. application Ser. No. 15/942,513 illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

In some embodiments, an Optical Coherence Tomography (OCT) system, may be used to obtain subsurface images of the eye. As such, when coupled to a computer which is coupled to a video monitor, the system provides a user or operator the ability to see subsurface images of the tissue ablation. As noted herein, pore can be between 5% and 95% of the sclera thickness in 3-dimensional space, with average sclera thickness as 700 μm being a typical pore depth. Comparatively the laser microporation can be magnitudes of order larger than refractive surface ablation averaging between 200 μm-300 μm deep compared to other surface refractive ablative procedures which have been performed on corneal tissue that are typically between 10 μm-45 μm in depth on average and generally >120 μm (see FIGS. 139A and 139B).

In at least some embodiments, the system may provide a real-time, intraoperative view of depth levels in the tissue. The system may provide for image segmentation in order to identify sclera interior boundary to help better control depth.

FIGS. 4A-5 and 4B-2 of U.S. application Ser. No. 15/942,513 show exemplary simplified diagrams of an ablation pore in the sclera showing an example of the depth of an ablation in relation to the inner boundary of the sclera, and are incorporated herein.

FIG. 5 of U.S. application Ser. No. 15/942,513 illustrates an exemplary flow diagram of depth control process, according to some embodiments of the present disclosure, and are incorporated herein.

In general, the depth-control system, e.g., an OCT system executes a repetitive B-scan, synchronized with the laser. The B-scan may show the top surface of the conjunctiva and/or sclera, the boundaries of the pore being ablated, and the bottom interface between the sclera and the choroid or ciliary body. Automatic image segmentation algorithms may be employed to identify the top and bottom surfaces of the sclera (for example, 400-1000 microns thick) and the boundaries of the ablated pore. The distance from the top surface of the sclera to the bottom surface of the pore may be automatically computed and compared to the local thickness of the sclera. In some embodiments, this occurs in real time. When the pore depth reaches a predefined number or a fraction of sclera thickness, ablation may be halted, and the scanning system indexed to the next target ablation location. In some embodiments, images may be segmented to identify interior sclera boundaries.

With reference to the steps in FIG. 5 (U.S. application Ser. No. 15/942,513), in the example embodiment a starting or initialization set of steps may occur first. This starting set of steps begins with positioning to a pore coordinate in step 412. AB-scan of the target region occurs in step 414. This scan creates an image which is processed in step 416 in order to segment and identify the sclera boundary. A distance is then computed in step 418 between the conjunctive surface and the sclera boundary.

After completion of this starting set of steps ablation may be initiated in step 420. A laser beam pulse is fired in step 422 followed by a B-scan in step 424. This B-scan creates an image that may then be segmented in step 426 and pore depth and ablation rate are computed from the image. This pore depth and ablation rate are compared to the target depth in step 430. If the target depth has not been reached, then the process loops back to step 422 and repeats. Upon reaching a target depth, step 432 stops the ablation process, and the starting process begins again at step 434 with positioning to next pore coordinates. In some embodiments, the depth-control system can monitor ablation depth during a single pulse and can stop the ablation as a risk mitigation means, there may also be other internal processes running that can end the ablation if the process is out of range; eye tracking operational limits exceeded, max preset # of pulses exceeded, laser power monitoring is not in limits. All of these are risk mitigation measures.

In some embodiments of the present disclosure, spot arrays may be used in order to ablate multiple pores at once. These spot arrays may, in some cases, be created using microlenses and also be affected by the properties of the laser. A larger wavelength may lead to a smaller number of spots with increased spot diameter.

Turning to some other aspects of the present disclosure, preoperative measurement of ocular properties and customization of treatment to an individual patient's needs is beneficial in many embodiments. Preoperative measurement of ocular properties may include measuring intraocular pressure (TOP), scleral thickness, scleral stress/strain, anterior vasculature, accommodative response, and refractive error. Measurement of scleral thickness may include use of optical coherence tomography (OCT). Measurement of scleral stress/strain may include using Brillouin scattering, OCT elastography, photoacoustics (light plus ultrasound). Measurement of anterior vasculature may include using OCT or Doppler OCT. Measurement of refractive error may include using the products such as the iTrace trademarked product from Tracey Technologies Corp. Those of ordinary skill in the art will recognize that other measurements, methods and systems may also be used.

Intraoperative biofeedback loops may be important during a treatment procedure in order to keep the physician informed on the progress of the procedure. Such feedback loops may include use of topographical measurements and monitoring "keep away" zones such as anterior ciliary arteries.

Biofeedback loops may include a closed-loop sensor to correct for nonlinearity in the piezo scanning mechanism. The sensor in some embodiments may offer real-time position feedback, e.g., in a few milliseconds and utilizing capacitive sensors for real-time position feedback. Real-time position feedback may be communicated to a controller, and, upon identification of specific biological features based on tissue characteristics, may cease laser operation intraoperatively.

Sensor/feedback apparatus may also perform biological or chemical "smart sensing" to allow ablation of target tissue and protect or avoid surrounding tissue. In some instances, this smart sensing may be accomplished by using a biochip incorporation in a mask which is activated by light irradiation and senses location, depth, size, shape, or other parameters of an ablation profile. Galvo-optic assemblies are also contemplated in some embodiments and may be used to gage numerous parameters of laser steering and special function.

Those of ordinary skill in the art will recognize that other feedback methods and systems may also be used.

In some embodiments, the systems, methods and devices of the present disclosure may include image display transfer and GUI interface features that can include each image frame taken and send information to a video display after each firing inside the 3-dimension-7-dimension micropore before and after the firing of the laser in dynamic real time and surface view. The GUI may have integrated multi-view system in 7-directionality for image capture including: surface, internal pore, external pore, bottom of the micropore, whole globe eye view, target array area.

In some embodiments, 7-cube may be a preferred projection for the microprocessor but other examples exist in dimensional sphere shape, integrated into the GUI and microprocessor. Orthogonal projections can include examples as shown in FIG. 8 of U.S. application Ser. No. 15/942,513.

In some embodiments, support vector machine (SVM) pattern recognition may be integrated into the AI (artificial intelligence) network directed to the microprocessor path. For the non-linear classification problem, the SVM may turn the input space into a high dimensional space by a nonlinear mapping K(X). Hence, the nonlinear problem may turn into a linear problem and then the optimal separating hyperplane will be calculated in a new high dimensional space, e.g., using Matlab or Mathematica integrated programming. Further detail is described in U.S. application Ser. No. 15/942,513.

Some embodiments can utilize a Serre fibration or Weak fibration. They are able to produce mapping of each cylinder micropore in the array and the total array across the 3D surface and interstitial mapping of pore arrays in cross section. An exemplary 3D mapping 900 is shown in FIG. 9 of U.S. application Ser. No. 15/942,513.

FIG. 10 of U.S. application Ser. No. 15/942,513 illustrates, according to some embodiments of the present disclosure, exemplary design patterns that can be performed as follows. Step 1001: Treatment design/planning may begin with tissue hierarchy which is established using the 7-Sphere mathematical projection over entire sphere to establish congruent treatment platform built on 7D shape and hyperbolic planar tessellation. Step 1002: Off Axis mathematical algorithm derived from tissue hierarchy and Fibonacci patterning is displayed as mathematical imagery. Step 1003: Algorithmic Code is then implemented to develop customized microporation patterns that are reflective of the tissue biorheology including all inputs of rigidity, viscoelastic modulus, topology, topography, biometry etc. Step 1004 (not shown): Anatomy avoidance software may be executed erasing or eliminating untargeted fields, arrays, regions. Step 1005 (not shown): Surgeon/user can also manipulate the targeted or untargeted areas via touch screen interface.

In some embodiments, the described systems, methods and devices of the present disclosure may include the following features of laser user interface system delivery of treatment algorithms. Real time mathematical imagery is incorporated and displayed both in 3D mathematical files which can also be run in a GIF animation format to display apriori information regarding the array effectiveness. The workstation/algorithms work together with the VESA system in order to produce the mathematical imagery to the user/surgeon for ideal configuration of the 3D array on the eye. The topological representation of the image is projected stereographically to the display. The array is prefixed formularies and in addition can be simulated in Fibonacci sequencing with a plurality of densities, spot sizes, micro and nano pore geometries and configurations. The benefit of the Fibonacci sequencing is to produce the most balanced array formulary which corresponds to the body's own natural tissue hierarchy both in macro and micro scales.

The array can also follow a hyperbolic geometry model or a uniform (regular, quasiregular, or semiregular) hyperbolic tiling which is an edge-to-edge filling of the hyperbolic plane which has regular circles or polygons as faces and is vertex-transitive (transitive on its vertices, isogonal, i.e., there is an isometry mapping any vertex onto any other). Examples are shown in FIGS. 10 and 11 of U.S. application Ser. No. 15/942,513 and incorporated herein. It follows that all vertices are congruent, and the tiling has a high degree of rotational and translational symmetry.

The uniform tilings can be identified by their vertex configuration, a sequence of numbers representing the number of sides of the circles or polygons around each vertex. One example below represents the heptagonal tiling which has 3 heptagons around each vertex. It is also regular since all the circles or polygons are the same size, so it can also be given the Schläfli symbol.

The uniform tilings may be regular (if also face- and edge-transitive), quasi-regular (if edge-transitive but not face-transitive) or semi-regular (if neither edge- nor face-transitive). For right triangles (p q 2), there are two regular tilings, represented by Schläfli symbol {p,q} and {q,p}.

In some embodiments, the described systems, methods and devices of the present disclosure may include mechanism of creating an array of micropores wherein the micropore array pattern may have a controlled non-uniform distribution, or a uniform distribution, or a random distribution and may be one of a radial pattern, a spiral pattern, a phyllotactic pattern, an asymmetric pattern, or combinations thereof. The phyllotactic spiral pattern may have clockwise and counterclockwise parastichy according to the present disclosure. FIG. 12 of U.S. application Ser. No. 15/942,513 illustrates an exemplary schematized representation of a creation of an asymmetrical controlled distribution of an array algorithm pattern on an eye with spiral phyllotaxis, where each array of micropore successively appear.

In some embodiments, the micropore array pattern may be one of an Archimedean spiral, a Euler spiral, a Fermat's spiral, a hyperbolic spiral, a lituus, a logarithmic spiral, a Fibonacci spiral, a golden spiral, or combinations thereof.

In some embodiments, the described systems, methods and devices of the present disclosure may include creation of a 3D microporation model on a spherical surface.

In some embodiments, the described systems, methods and devices of the present disclosure may include utilization of Fibonacci and mathematical parameters to optimize surgical execution, outcomes and safety in a laser assisted microporation treatment array having a pattern of pores, e.g., micropores or nanopores, wherein the pattern is a non-uniform distribution pattern that is delivered in cross sectional tissue in alignment with the existing tissue hierarchy on a macro scale and microscale so that there is a congruent rejuvenation effect of the treatment. A treatment array or lattice having a plurality of micropores/nanopores/ablations/incisions/targets may be arranged in a non-uniform distribution pattern, wherein the pattern is spiral or phyllotactic. The patterns may be described by the Vogel equation. Also, included is a plurality of other geometries/densities/depths and shapes having a spiral or phyllotactic patterns of flow paths, such as in the form of open channels or pores. The micropores/nanopores can be specifically adapted to correspond with any given contact lens, mask or other template material or design having a non-uniform distribution pattern. Alternatively, the microporation can be used in conjunction with conventional perforated coated or non-coated polymers such as hydrophilic or hydrophobic types. The array pattern having a non-uniform distribution pattern of micropores, and the lens or mask can be used together as a treatment system FIGS. 4A-1 to 4A-10 and 26-3A of U.S. application Ser. No. 15/942,513 illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue. Additionally, the present disclosure may include various types of automated processing systems to process the delivery of microporations of various compositions and configurations.

Tissue characteristics effected include, among others, porosity, texture, viscoelasticity, void fraction ratio, surface roughness, and uniformity. Surface characteristics, such as roughness and gloss, are measured to determine quality. Such microporation can also affect tissue deformation, pliability and flexibility and have an "orange peel" texture. Hence, the properties of the tissue treated with microporation/nanoporation will generally influence and/or enhance the tissue quality by means of restoring or rejuvenating the biomechanical pliability of the tissue when at rest and under stress/strain as well as tissue permeability In some embodiments, microporation can include a plurality of micropore paths disposed in a pattern. The pattern of micropore paths can comprise regular circles or polygons, irregular circles or polygons, ellipsoids, arcs, spirals, phyllotactic patterns, or combinations thereof. The pattern of micropore paths can comprise radiating arcuate paths, radiating spiral paths, or combinations thereof. The pattern of micropore paths can comprise a combination of inner radiating spiral paths and outer radiating spiral paths. The pattern of air flow paths can comprise a combination of clock-wise radiating spiral paths and counter clock-wise radiating spiral paths. The micropore paths can be discrete, or discontinuous, from each other. Alternatively, one or more of the micropore paths can be fluidly connected. The number of radiating arcuate paths ("arcs"), radiating spiral paths, or combinations thereof can vary.

In some embodiments, microporation can comprise a pattern that is a controlled nonlinear distribution pattern, a controlled linear distribution pattern or a random pattern. In some embodiments, eye contact lens/eye mask can comprise a pattern of micropore paths wherein the pattern of micropore paths is generated from x and y co-ordinates of a controlled non-uniform distribution pattern. The controlled non-uniform distribution pattern used to generate the eye lens/eye mask micropore path can be the same or different than the array pattern of the laser microporation algorithm being used with the eye lens/eye mask. In an embodiment, the controlled non-uniform distribution pattern is the same as the array pattern of the laser microporation algorithm being used with the eye lens/eye mask. In some embodiments, the controlled non-uniform distribution pattern is different than the array pattern of the laser microporation algorithm being used.

In some embodiments, the laser microporation system may have phyllotactic patterns according to the laser microporation algorithm embodiments described herein. An eye lens/eye mask is co-operative with a laser microporation system having phyllotactic patterns when the laser microporation system includes a plurality of micropores, a plurality of openings, a plurality of cavities, a plurality of channels, plurality of passages, or combinations thereof, that are configured in a pattern designed to promote improvement of natural biological functions such as fluid flow, blood flow, muscular movement, as well as static and dynamic biological function through the eye lens/eye mask and tissue having a phyllotactic pattern. The micropores, openings, cavities, channels, passages, or combinations thereof can define biological flow paths that are located along, within, or though the back-up pad, or combinations thereof. In an embodiment, the pattern of micropores, openings, cavities, channels, passages or combinations thereof can be in the form of a regular circles or polygons, irregular circles or polygons, ellipsoids, arcs, spirals, phyllotactic patterns, or combinations thereof. In another embodiment, the air-flow paths can be in the form of a regular circles or polygons, irregular circles or polygons, ellipsoids, arcs, spirals, phyllotactic patterns, or combinations thereof.

In some embodiments, a suitable spiral or phyllotactic pattern can be generated from the x and y co-ordinates of any phyllotactic array pattern of the microporation system embodiments described above. In an embodiment, the x and y co-ordinates of a spiral or phyllotactic pattern are transposed and rotated to determine the x' and y' co-ordinates of the spiral or phyllotactic back-up air flow pattern, wherein 0 is equal to it/n in radians and n is any integer. The (x' and y') can be plotted, such as by the use of computer aided drafting (CAD) software, to generate a suitable pattern such as a spiral or phyllotactic pattern.

The patterns can then be used to define radiating accurate and spiral channels, as well as, annular channels that can intersect the arcuate and spiral channels, or combinations thereof. The annular, arcuate, spiral, or combination channels can produce shape deformation, such as in the form of grooves, cavities, orifices, passages, or other pathways to form. Exemplary embodiments of channel patterns that are based on transposed phyllotactic patterns are also shown in FIGS. 10, 13, and 16 in U.S. application Ser. No. 15/942,513. Additional exemplary embodiments based on transposed phyllotactic patterns are shown in FIGS. 14A-14D, 15A-15F, and 41 in U.S. application Ser. No. 15/942,513.

As shown below, microporation pattern may have a number of clockwise spirals and a number of counterclockwise spirals, wherein the number of clockwise spirals and the number of counterclockwise spirals are Fibonacci numbers or multiples of Fibonacci numbers.

FIG. 14A in U.S. application Ser. No. 15/942,513 illustrates an exemplary embodiment of a microporation pattern which can be implemented directly on the target tissue or alternatively on a contact lens, mask, or other such template having an micropore pattern with a controlled non-uniform distribution of the micropores in the distribution of the Fibonacci sequence, according to some embodiments of the present disclosure.

FIG. 14B in U.S. application Ser. No. 15/942,513 is an exemplary illustration of a phyllotactic spiral pattern having clockwise and counterclockwise parastichy, according to some embodiments of the present disclosure.

FIG. 14C in U.S. application Ser. No. 15/942,513 is another exemplary illustration of a phyllotactic spiral pattern having clockwise and counterclockwise parastichy, according to some embodiments of the present disclosure.

FIGS. 14D to 15F in U.S. application Ser. No. 15/942,513 are exemplary illustrations of the Vogel model, in accordance with some embodiments of the present disclosure.

FIGS. 16A-16N in U.S. application Ser. No. 15/942,513 are exemplary illustrations of exemplary embodiments of microporation derived from icosahedron pattern shapes, according to some embodiments of the present disclosure FIGS. 17A-17B, and 2K-18 and 2K-19 in U.S. application Ser. No. 15/942,513 illustrate exemplary microporation patterns derived from icosahedron pattern shapes representing a fractal sphere and icosahedron/tetrahedron tessellations according to some embodiments of the present disclosure.

Surface Area: The total target tissue surface area affects the amount total tissue material removed. Typically, as the amount of total tissue surface area is increased, the amount of surface material removed is increased. In some embodiments, the total microporation surface area of the target tissue may be equal to the total potential surface of the microporation system (i.e., the microporation target area if there were no micropores) minus the total micropore area (i.e., the sum of the area of all the micropores). Thus, the amount of the total microporation surface area can range from 1% to about 99.5% of the total potential surface area, depending on the amount of desired micropore area. See FIG. 30 in U.S. application Ser. No. 15/942,513 for exemplary surface areas, according to some embodiments of the present disclosure.

Depth: FIGS. 4A-5 to 4A-10 in U.S. application Ser. No. 15/942,513 illustrate that the total target tissue depth may affect the amount of total tissue material removed. Generally, as the amount of total tissue depth is increased, the amount of interstitial or subsurface tissue removed is increased. In some embodiments, the depth of the tissue microporation removed is equal to the total potential subsurface and interstitial tissue of the microporation system (i.e., the total interstitial and subsurface tissue if there were no micropores) minus the total micropore cubic volume (i.e., the sum of the area of all the micropores). Thus, the amount of the total microporation cubic volume can range from 1% to about 95% of the total potential subsurface and interstitial cubic volume of the microporation tissue, depending on the amount of desired micropore cubic volume.

Density of Pores: The density of the pore array, e.g., micropore array, may influence the total amount of micropore area and the total amount of surface, subsurface, and interstitial volume removed. It also may influence the total number of micropores and micropore distribution. A plurality of exemplary density configurations, micropore size and distribution of micropores are illustrated in FIGS. 2K-1-A to 2K-1-C and through 2K-17 in U.S. application Ser. No. 15/942,513. It should be noted that micropores can be delivered randomly, uniformly, or singularly. Volumetric density or bulk density of the micropore array may also influence biomechanical properties.

Number of Pores: The number of pores, e.g., micropores, may influence the total amount of micropore area and the amount of total surface, subsurface, and interstitial volume removed. Additionally, the number of micropores may affect the density and distribution of micropore coverage on the surface of the microporation, which in turn may directly affect the total pore volume fraction of the microporation. In some embodiments, the number of micropores may be at least about 3, at least about 5, at least about 8, at least about 12, or at least about 15. In some other embodiments, the number of micropores may be at least about 45, at least about 96, at least about 151, or at least about 257. For more exemplary parameters, see also FIGS. 31-34B, 37, 38, and 39 in U.S. application Ser. No. 15/942,513.

In some embodiments, the number of pores can range between 9 to 10,000 pursuant to the size of the spot which can range from 1 nm-600 μm. The number of micropores can be within a range comprising any pair of the previous upper and lower limits.

Various parameters and factors may influence the microporation of the present disclosure and are illustrated in FIGS. 31-35 in U.S. application Ser. No. 15/942,513, and also discussed below.

Divergence Angle: In delivering the laser pulse to the target tissue, increasing or decreasing the divergence angle $\alpha$ may affect how the micropores are placed within the pattern and the shape of the clockwise and counterclockwise spirals. The divergence angle is equal to 360° divided by a constant or variable value, thus the divergence angle can be a constant value, or it can vary. In some embodiments, the pattern may have a divergence angle in polar co-ordinates that ranges from about 100° to about 170°. Small changes in divergence angle can significantly alter the array pattern and may show phyllotactic patterns that differ only in the value of the divergence angle. An exemplary divergence angle may be 137.3°. The divergence angle may also be 137.5°, or 137.6°. In some embodiments, the divergence angle is at least about 30°, at least about 45°, at least about 60°; at least about 90°, or at least about 120°. In other embodiments, the divergence angle is less than 180°, such as not greater than about 150°. The divergence angle can be within a range comprising any pair of the previous upper and lower limits. In some other embodiments, the divergence angle ranges from about 90° to about 179°, about 120° to about 150°, about 130° to about 140°, or about 135° to about 139°. In some embodiments, the divergence angle is determined by dividing 360° by an irrational number. In some embodiments, the divergence angle is determined by dividing 360° by the golden ratio. In some embodiments, the divergence angle is in the range of about 137° to about 138°, such as about 137.5° to about 137.6°, such as about 137.50° to about 137.51°. In some embodiments, the divergence angle is 137.508°.

Distance to the Edge of the Microporation Array: In some embodiments, the overall dimensions of the array pattern can be determined based on the geometry of the microporation and intended usage. The distance from the center of the pattern to the outermost micropores can extend to a distance coterminous with the edge of the microporation. Thus, the edges of the outermost micropores can extend to or intersect with the edge of the microporation. Alternatively, the distance from the center of the pattern to the outermost micropores can extend to a distance that allows a certain amount of space between the edges of the outermost micropores and the edge of the microporation to be free of micropores. The minimum distance from the edges of the outermost micropores can specified as desired. In some embodiments, the minimum distance from the edges of the outermost micropores to the outer edge of the microporation is a specific distance, identified as a discreet length or as a percentage of the length of face of the microporation upon which the array pattern appears. The micropores can be widely or closely separated or tessellated.

Size of Pores: In some embodiments, the size of the pores, e.g., micropores, may be determined, at least in part, by the desired total amount of array area for the microporation. The size of the micropores can be constant throughout the pattern or it can vary within the pattern. In some embodiments, the size of the micropores is constant. In some embodiments, the size of the micropores varies with the distance of the micropores from the center of the pattern. There is a plurality of sizes capable in the system. The size of the pores can range from 1 nm-600 μm. In some other embodiments, the size is 50 μm, 100 μm 125 μm, 200 μm, 250 μm, 325 μm, 425 μm, or 600 μm.

Shape of Pores: There is a plurality of shapes capable in the system. Shape of pores, e.g., micropores, themselves created in connective tissue by electromagnetic irradiation may have relative consequence on the tissue reaction and wound healing. Square shapes may heal slower than round shapes. The microporation system is capable of creating a plurality of geometric individual micropore shapes. In some embodiments, the ideal shape is square.

Shape may also be impactful in the micropore array. The amount of coverage can be influenced by the shape of the micropores. The shape of the micropores can be regular or irregular. In some embodiments, the shape of the micropores can be in the form of slits, regular circles or polygons, irregular circles or polygons, ellipsoids, circles, arcs, spirals, channels, other suitable shapes or combinations thereof. In some embodiments, the micropore arrays have the shape of a circle. In some embodiments, the shape of the array may be in the form of one or more geometric patterns, for example, icosahedron or tetrahedron tessellations, wherein multiple circles or polygons (or other shapes) intersect. Shape may also impact desirable or undesirable wound healing and can be modified depending on the purpose of the micropore function.

FIGS. 16A-N in U.S. application Ser. No. 15/942,513 show examples of such shaped micropore arrays. The micropore arrays are configured such that the patterns resemble circles or polygons, which can have slightly accurate edges. Tissue removal in these configurations effect biomechanical properties in a mathematically and geometrically balanced way producing stability to the microporation.

Design Factor: The design factor may influence the overall placement of the microporation array or lattice in 3D tissue and relative to microporation edges with relation to the 'atmosphere' within the tissue. The design of the microporation can be adjusted depending on the inherent shape of the tissue itself or around the intended physiological anatomy or desired impact. This can be a self-dual (infinite) regular Euclidean honeycombs, dual polyhedron, 7 cube, 7 orthoplex or likewise simple lattice, Bravais lattice, or non-Bravais lattice.

Scaling Factor: The scaling factor may influence the overall size and dimensions of the micropore array pattern. The scaling factor can be adjusted so that the edges of the outermost micropores are within a desired distance of the outer edge of the microporation. Additionally, the scaling factor can be adjusted so that the inner edges of the innermost micropores are within a desired distance of the inner edge of the microporation. Duality can be generalized to n-dimensional space and dual polytopes; in two dimension these are called dual circles or polygons, or three dimensions or a plurality of dimensions containing vertices, array's, or likewise containing tessellations both isotropic or anisotropic.

Distance Between Nearest Adjacent Pores: Along with consideration for the number and size of the pores, e.g., micropores, the distance between the centers of the nearest adjacent micropores can be determined. The distance between the centers of any two micropores may be a function of the other array design considerations. In some embodiments, the shortest distance between the center of any two micropores is never repeated (i.e., the pore-to-pore spacing is never the same exact distance). This type of spacing is also an example of controlled asymmetry. In some other embodiments, the shortest distance between the center of any two micropores is always repeated (i.e., the pore-to-pore spacing is always the same exact distance). This type of spacing is also an example of controlled symmetry. In some embodiments, the distance between two micropores are randomly arranged (i.e., the pore-to pore spacing is random). The system thus can provide controlled asymmetry which is at least partial rotational asymmetry about the center of the array design or pattern, random asymmetry which is at least partial rotational random about the center of the array design or pattern, and controlled symmetry which is at least partial rotational about the center of the array design or pattern, and random symmetry which is at least partial rotational random about the center of the array design or pattern.

In some embodiments, the rotational asymmetry may extend to at least 51% of the micropores of the pattern design. In some embodiments, the rotational asymmetry may extend to at least 20 micropores of the array pattern design. In some embodiments, the rotational symmetry may extend to at least 51% of the micropores of the pattern design. In some embodiments, the rotational symmetry may extend to at least 20 micropores of the pattern design. In some embodiments, the rotational random pattern may extend to at least 51% of the micropores of the pattern design. In some embodiments, rotational random pattern may extend to at least 20 micropores of the pattern design.

In some embodiments, the 51% of the aperture pattern may be described in polar co-ordinates by the Vogel model equation: $\varphi=n*\alpha$, $r=c\sqrt{n}$., as described above.

Co-Operative Eye Contact Lens/Eye Mask

The co-operative Eye contact lens/Eye mask (see, e.g., FIGS. 27A, element 2700, and FIG. 40 in U.S. application Ser. No. 15/942,513) can be flexible or rigid, soft or hard. It can be made of any number of various materials including those conventionally used as contact lens or eye masks such as polymers both hydrophilic, hydrophobic or soft gel or collagen or dissolvable materials or special metals. An exemplary flexible lens/mask may include a pliable hydrophilic ("water-loving") plastic.

In some embodiments, the described systems, methods and devices of the present disclosure may include method and apparatus for treatment of sclera and neighboring ocular structures and fractional microporation and resurfacing, laser eye microporation for rejuvenation or restoration of physiological eye function, and/or alleviation of dysfunction or disease. In various embodiments, the arrays may take on a plurality of geometries, densities, configurations, distributions, densities and spot sizes and depths. They may also be preplanned and performed in various time points. It can also penetrate the epi sclera, sclera substantia, or *Lamina fusca* at any percentage of required poration. Electromagnetic energy applications are may also be suitable.

Hydrophobic scleral lens customizable wafer, nano, μm etc.: In various embodiments, a hydrophobic scleral lens customizable wafer can have variable sizes measured generally in millimeters, micrometers or nanometers. Generally, it is a scleral contact lens that can contain a computer-generated customized algorithm for a laser treatment on a patient's sclera. First, spots can be registered that are re-treatable and the spots can be profiled via the mask or lens. The mask can be made of various materials including one or more hydrophobic polymers or blends of polymers that are impenetrable by the laser. This can provide an added level of protection for the surrounding tissue that is not going to be treated in addition to smart mapping technology. A corneal central contact lens can be tinted to protect the cornea from the microscope light and from the laser beam itself. In various embodiments, it can be disposable and not reusable once the pattern is on the eye. Additionally, it can be delivered prepackaged sterilized containers.

This can be created by measuring biometry, morphology, anatomy, topography, keratotomy, scleral thickness, material properties, refractions, light scatter, and other features and qualities that may be imported, uploaded or otherwise inputted into a three dimensional (3D) dynamic FEM module which may be a platform for "Virtual Eye." The system of the disclosure may process the information of both cornea and lens and may run a plurality of algorithmic tests once all of the optics and information have been inputted. The system may apply mathematical and physical scenarios aimed at enhancing accommodative power through manipulation of the scleral, and it may also give desirable Zernike profiling of the cornea which would produce maximum accommodative power in the event that there are Laser Vision Correction (LVC) plus accommodated planning. Once complete the pattern may be generated, e.g., by ISIS (a visualization and eye mapping software for analyzing and reproducing a visual mapping of the eye refractive status the corneal refractive status, e.g., both the lens refractive status and the corneal refractive status, or "dual optic") through Virtual Eye and there is a visualization of said pattern. In some embodiments, ISIS may be a servomechanism.

The wafer may also stamp coordinates at the 12 and 6 o'clock meridians for orientation on the eye by a physician. The wafer may also stamp a unique and different coordinate at the 10/2/4/7 meridians for the treatment quadrant orientation for the physician. The wafer/contact lens may be produced by a corresponding 3D printer which is connected to the mother board of ISIS. Once completed, the lens may be sterilized prior to putting on the patient's eyes.

In some exemplary operations, initially, a laser that can be coupled with or contain an eye tracker in some embodiments may be calibrated or initiated and a lens is put in place by the physician. The wafer may act as both a mask and guide for the laser.

The lens design is called "semiscleral-contact" (SEQ). This lens has as its starting point, a bearing edge of the sclera at the corneal 2.0 mm part consists of three curves. The SEQ lens features 10 fenestrations, which prevents the lens getting stuck. Irregular corneal surfaces can be corrected using RGP contact lenses, corneal lenses ranging in diameter from 8.0 mm to 12.0 mm. Sclera lenses may vary in diameter from 22.0 mm to 25.0 mm.

To build up the lens and final fitting, formulas may be used for the calculation and production of the lens. To narrow the whole range, it may begin with a sagitta fitting set of 2.70 mm extending to 4.10 mm. Differences in the fitting set are similar to a fitting set for RGP lenses with a different radius of 0.05 mm between a normal step.

The SEQ fitting set expires with sagittal 0.1 mm height difference. Despite the DK value of 90, and 10 times fenestration of SEQ lens, an oxygen supply problem may persist. Lenses adjusted in diameters larger than 12.0 mm have a lot of support that it is not moving and thus no tear exchange can occur.

In some exemplary operations, 1) as the laser contains an eye tracker, the lens is put in place by a physician. The wafer acts as both a mask and guide for the laser. 2) This wafer guided system is unique to the laser; the pattern is placed on the eye and through the lens itself which is perforated during the process creating a map receipt of the procedure and registering all spots by the scanner before and after the treatment. 3) ISIS retains this information for this specific patient's eye, 4) In the event that a retreatment is needed. All information (topo, etc.) is imported back into the patient's profile for ISIS to recalculate and reconfigure 'around' the existing spots for further maximization. 5) ISIS calculates COP before and predictable COP after applying the simulation which can inform the patient and surgeon of the amount of COP possible for any particular patient with and without additional LVC. 6) ISIS also demonstrates through use of the FEM virtual eye both the biomechanical functions, optical functions, as well as a vision simulation at all distances. 7) ISIS also demonstrates a post op COP, AA, Refractions, Zernike profile changes etc. and on the back end continues to capture all database information to come up with future more sophisticated and optimizing algorithms. 8) ISIS can also profile various algorithms to enhance the understand of the dual optic system and give changing scenarios based on change of scleral thickness and other biometry, geometry, optics etc. with age. The usefulness of this is infinite but a specific embodiment is that ISIS can generate an age-related treatment map from the patient's initial exam through cataract age. Therefore, ISIS can predict how many spots and what pattern should be used in advance so that the retreatment potential areas will be 'predetermined' by ISIS upon the first wafer. This means that on subsequent visits, ISIS can alert the physician when there is a critical loss of COP and retreatment can start at any time (this would be determined by the physician, patient and ISIS output). 9) ISIS may also have an audible interaction and can also alert the physician during treatment if there is a need for intervention, when it is complete and guide the physician at what exams should be evaluated for accuracy or for more attention. ISIS can make recommendations to the physician, but the physician is in control of the selection of programs ISIS will perform 10) ISIS also has a reference list and can search for papers, knowledge and recent trends as well. 11) ISIS may work like a voice assistant, e.g, Apple Siri.

Laser features for some embodiments may include a Er:YAG Ophthalmic Laser Lasing Medium, an Er:YAG laser with 2.94 μm wavelength; Pulse duration approximately 250 μsec; Rep rate may be 3, 10, 15, 20, 25, 30, 40, 50 pps.

Various net absorption curves of various tissue components can be important. At 2.94 μm, wavelength laser can be the closest wavelength in the near infrared spectrum to the peak absorption of H20 3.00 μm. This allows it to effectively evaporate H20 from the tissue (ablation mechanism) with little thermal effect. Laser Tissue Interaction @ 2.94 μm: 2.94 μm may be a great wavelength for tissue ablation; 10-20× better absorbed by water than $CO_2$ at 10.6 μm; 3× better absorbed by water than Er:YSGG at 2.79 μm; Ablation threshold for water at 2.94 μm about 1 J/cm$^2$. The ablation occurs instantly and may be a surface effect only. This provides very precise ablation with little collateral tissue damage.

Applications for Er:YAG ophthalmic systems can include a broad 510K for excision, incision, evaporization of ocular soft tissue therefore expansion of use is inevitable after it is adopted including in: Ptyerigium surgery; glaucoma surgery; ocular nerve head entrapment (posterior sclera); intra ocular capsulotomy; extra ocular soft tissue surgery; AMD; and others.

Methods and apparatuses for treatment of sclera and neighboring ocular structures and fractional microporation and resurfacing are also contemplated.

As described herein, a system and method for performing fractional resurfacing of a target area of an eye, e.g., the sclera, using electromagnetic radiation are provided. An electromagnetic radiation is generated by an electromagnetic radiation source. The electromagnetic radiation is caused to be applied to a particular portion of a target area of eye preferably the sclera. The electromagnetic radiation can be impeded from affecting another portion of the target area of the eye by a mask or scleral lens. Alternatively, the electromagnetic radiation may be applied to portions of the target area of the sclera other than the particular portion.

Additionally described herein is a method for modifying tissue with a quasi-continuous laser beam to change the optical properties of the eye comprises controllably setting the volumetric power density of the beam and selecting a desired wavelength for the beam. Tissue modification may be accomplished by focusing the beam at a preselected start point in the tissue and moving the beam's focal point in a predetermined manner relative to the start point throughout a specified volume of the tissue or along a specified path in the tissue. Depending on the selected volumetric power density, the tissue on which the focal point is incident can be modified either by photoablation or by a change in the tissue's visco-elastic properties.

Ophthalmic Laser System

In various embodiments, an ophthalmic laser system of the present disclosure may include a laser beam delivery system and an eye tracker responsive to movement of the eye operable with the laser beam delivery system for ablating scleral material of the eye both anterior and/or posterior through placement of laser beam shot on a selected area of the sclera of the eye. The shots are fired in a sequence and pattern such that no laser shots are fired at consecutive locations and no consecutive shots overlap. The pattern is moved in response to the movement of the eye. Since the sclera of the eye is 'off axis' the scanning mechanism is novel in that it does not operate by fixation of the beam over the visual axis of the eye. Referring to FIG. 20 and FIGS. 20A to 20D in U.S. application Ser. No. 15/942,513, rather the 'off axis' scanning mechanism may include an eye docking system utilizing goniometric mirror or guidance system to ablate opposing quadrants of the sclera outside the visual axis. A closed loop feedback system is in place internally to the scanner and also between the eye docking system in and the scanner in the form of a magnetic sensor mechanism which both locks the laser head to the eye docking system and by virtue of biofeedback positioning of the eye to trigger both eye tracking and beam delivery.

In some embodiments, the laser system may include means to select and control the shape and size of the area irradiated by each pulse of laser energy without varying the energy density of the beam. By varying the size of the irradiated area between pulses, some regions of the surface may be eroded more than others and so the surface may be reprofiled. The method and system are suitable, inter alia, for removing corneal ulcers and reprofiling the cornea to remove refractive errors and also for reprofiling optical elements. In some embodiments, the beam from the laser may enter an optical system housed in an articulated arm and terminating in an eyepiece having a suction cup for attachment to an eye. The optical system may include a beam forming arrangement to correct an asymmetric beam cross-section, a first relay telescope, a beam dimensional control system and a second relay telescope. The beam dimension control system may have a stop with a shaped window or a shaped stop portion and movable axially along a converging or diverging beam portion. An alternative beam dimension control system has a stop with a shaped window and positioned between coupled zoom systems. Mirrors, adjustable slits and refractive systems may also be used. The laser can preferably be an Er:YAG laser in some embodiments. The system may include a measurement device to measure the surface profile, and a feedback control system to control the laser operation in accordance with the measured and desired profiles.

In some embodiments, the method, apparatus, and system for template-controlled precision laser interventions described herein improves the accuracy speed range, reliability, versatility, safety, and efficacy of interventions such as laser microsurgery, particularly ophthalmic surgery including ability to perform such laser surgery outside of the visual axis. FIG. 19 in U.S. application Ser. No. 15/942,513 illustrates an exemplary diagram of instrument and system, according to some embodiments of the present disclosure, which are applicable to those specialties wherein the positioning accuracy of the laser treatment is critical, wherever accurate containment of the spatial extent of the laser treatment is desirable, and/or whenever precise operations on a target or series of targets subject to the movement during the procedure are to be affected. The system thus may include the following key components: 1) a user interface, consisting of a video display, microprocessor and controls, GUI interface, 2) an imaging system, which may include a surgical video microscope with zoom capability, 3) an automated 3D target acquisition and tracking system that can follow the movements of the subject issue, for example and eye, during the operation, thus allowing the surgeon user to predetermine his firing pattern based on an image which is automatically stabilized over time, 4) a laser, with which can be focused so that only the precise treatments described by the user interface are affected, 5) a diagnostic system incorporating a mapping and topography, numerical data, mathematical data, geometrical data, imaging data, by means for measuring precise surface and 3D shapes prior to, during and subsequent to a procedure, said measurements to be executed online within time scales not limited to human response times, and can be real time, and 6) fast reliable safety means, whereby the laser firing is interrupted automatically, should any conditions arise to warrant such interruption of the procedure for example a safety concern.

FIGS. 20(E-G) in U.S. application Ser. No. 15/942,513 illustrate further the off-axis features of the laser system, according to some embodiments of the present disclosure. As shown, Beta(β) is the visual axis in all cases and Alpha(α) is the angle between the visual axis and the treatment axis. The rotational symmetry axis is the vertical axis. Treatment areas for the laser preferably are not hidden by eye lids and other features of the patient. Eye fixation axis and the laser beam axis have a fixed angular relationship in order to expose pores in defined treatment zones. The laser beam delivery can be rotated around the vertical axis, β. In some embodiments, key elements may include: laser beam and scan (e.g., OCT) area are on same centerline, and scan area and focal length is matched to laser spot size and focal length. Camera is located just off laser centerline. Eye fixation point may be pre-established angular relationship to the laser delivery beam 180° from the laser delivery beam around β.

FIG. 20I in U.S. application Ser. No. 15/942,513 illustrates another exemplary off-axis scanning, according to some embodiments of the present disclosure. As shown, the treatment may be angular.

In some embodiments, the system may be used in ophthalmic diagnosis and analysis and for support of ophthalmic surgery and may include 3D-7D mapping means for sensing locations, shapes and features on and in a patient's eye in three dimensions, and for generating data and signals representing such locations, shapes and features, display means receiving signals from the 3D-7D mapping means, for presenting to a user images representative of said locations, shapes and features of the eye, at targeted locations including display control means for enabling a user to select the target location and to display a cross section of portions of the eye in real time both during ablation and after each laser pulse, position analysis means associated with and receiving signals from the three dimensional mapping means, for recognizing the occurrence of changes of position of features of the eye, target tracking means associated with the position analysis means, for searching for a feature of target tissue and finding said features new position after such a change of position, and for generating a signal indicative of the new position, and tracking positioning means for receiving said signal from the target tracking means and for executing a change in the aim of the three dimensional mapping means to the new position of said feature of the target tissue, to thereby follow the feature and stabilize the images on the display means.

The display means described in various embodiments of the present disclosure may be a video display, and further including surgical microscope or digital monitor or smart device means directed at the patient's eye, for taking video microscopic images real time of target areas of the ocular tissue and for feeding video image information to the video display means to cause such video microscopic images to be displayed, assisting the user in diagnosis and analysis enabling display of different cross sections of the patient's tissue as selected by the user in real time.

The tracking positioning means may include a turning mirror under automatic control, robotic control, blue tooth control and the system may include an objective lens assembly associated with the mapping means and having a final focusing lens, with the turning mirror positioned within the objective lens assembly and movable with respect to the final focusing lens is an embodiment.

In some embodiments, the system may include a laser pulsed source for producing an infrared to near infrared light laser beam having a power capable of effecting a desired type of surgery in an eye, laser firing control means for enabling a surgeon/user to control the aim, depth, and timing of the firing of the laser to effect the desired surgery, 3D-7D mapping means directed at a patient's eye, for obtaining data representing the location and shapes of features on and inside the eye, microprocessor means for receiving data from the three dimensional mapping means and for converting the data to a format presentable on a screen and useful to the surgeon/user in precisely locating features of the eye and the aim and depth of the laser beam within those features, and display means for displaying microprocessor-generated images representing the topography of the eye and the aim and depth of the laser beam before the next pulse of the laser is fired to the surgeon/user in preparation for and during surgery, with display control means for enabling the surgeon/user to select areas of the eye for display, including images of cross sections of portions of the eye.

The infrared or near infrared pulsed, free running, or continuous or Q-Switched light laser power source may generate a laser beam capable of effecting the desired laser surgery in the patient's tissue, including within transparent tissue of the patient. The system may include an optical path means for receiving the laser beam and redirecting the laser beam and focusing it as appropriate toward a desired target in the tissue to be operated upon, The system may include a laser housing positioned to intercept and direct the optical path means, for taking images of said target along the optical path means and for feeding video image information to the video display means, and tracking for tracking movements of the subject tissue at which the system is targeted without damaging the subject tissue before the next pulse of the laser is fired and shifting the optical path accordingly before the next pulse of the laser is fired, such that information and images generated by the three dimensional mapping means and by the surgical microscope means, as well as the aiming and position of the laser beam, following changes in position of the tissue. Each image frame taken, and information is sent to the video display after each firing inside the 3D-7D micropore before and after the firing of the laser in dynamic real time and surface view. GUI may include integrated multiview system in 7 directionalities for image capture including: surface, internal pore, external pore, bottom of the micropore, whole globe eye view, target array area.

In some embodiments, 7 cube may be the preferred projection for the microprocessor: but other examples exist in dimensional sphere shape, space, and may be integrated into the GUI and microprocessor. Orthogonal projections can include examples shown in FIG. 8 in U.S. application Ser. No. 15/942,513.

The system may include multi-dimensional scaling, linear discriminant analysis and linear dimensionality reduction processing as well as locally linear embedding and isometric maps (ISOMAP). Nonlinear dimensionality reduction methods may also be included.

In some embodiments, the system can allow for a 1D, 2D, 3D, or 4D, and up to 7D conversion of the topological images or fibrations. The fibration is a generalization of the notion of a fiber bundle. A fiber bundle makes precise the idea of one topological space, called a fiber, being "parameterized" by another topological space, called a base. A fibration is like a fiber bundle, except that the fibers need not be the same space, nor homeomorphic; rather, they are just homotopy equivalent. Where the fibrationsis equivalent to the technical properties of the topological space in 3, 4, 5, 6, and 7 dimensional sphere spaces a continuous mapping p:E→B satisfying the homotopy lifting property with respect to any space. Fiber bundles (over paracompact bases) constitute important examples. In homotopy theory, any mapping is 'as good as' a fibration—i.e. any map can be decomposed as a homotopy equivalence into a "mapping path space" followed by a fibration into homotopy fibers.

A laser workstation may be equipped with three programmable axes (X, Y, Z; can be expanded to 5 axes) has an automatic rotary table machine, programmable X, Y, Z-axis and a 2-station rotary table. It can include a Human Machine Interface (HMI) with Security user access level, diagnostic and data logging for validated processes and user friendly operation, as well as a sorter module adaptable for unique pulse modulation, where: pore diameter: 0.1 μm-1000 μm; drill depth max. 0.1 μm-2000 μm; Pore tolerances: >±1-20 μm Operational features can also include networked computer connection, iPad operations, joy stick operations, touch screen operations, iPhone operations, remote or Bluetooth operations, digital camera integrated operations, video integrated operations, and others.

System and Methods for Laser Assisted Ocular Drug Delivery

In some embodiments, the described systems, methods and devices of the present disclosure may be used for laser assisted ocular drug delivery, such as methods and apparatuses for phototherapeutically treating, e.g., by ablating, coagulating, and/or phototherapeutically modulating a target tissue, e.g., scleral tissue and other intraocular tissues such as choroid, subchoroidal space, neuroretina, or others. There is disclosed a method for creating an initial permeation surface (A) in a biological membrane (1) comprising: a) creating a plurality of individual micropores (2 i) in the biological membrane (1), each individual micropore (2 i) having an individual permeation surface (Ai); and b) creating such a number of individual micropores (2 i) and of such shapes, that the initial permeation surface (A), which is the sum of the individual permeation surfaces (Ai) of all individual micropores (2 i), having a desired value. A microporator performing the method is also disclosed. Biological surface may be an eye in this case. In the case of the eye: irradiating the area of the sclera such that the therapeutic agent passes through the open area created by the laser radiation and is thereby delivered to intraocular target tissues in the anterior or posterior globe such as the choroid, neuroretina, retinal epithelium, uvea, vitreous, or aqueous.

U.S. application Ser. No. 15/942,513, incorporated herein, discloses further embodiments of systems, devices and methods of drug delivery that may also be applied to and/or configured for used with the system of the present disclosure.

In some embodiments, the described systems, methods and devices of the present disclosure may be used for, but not limited to, the delivery of drugs, nutraceuticals, grape seed extract, stem cells, plasma rich proteins, light activated smart polymer carriers, and matrix metalloproteinases. FIGS. 20P-1 to 20P-3 in U.S. application Ser. No. 15/942,513 illustrate, in some embodiments, the exemplary targets for choroid plexus drug and nutraceutical delivery.

The drug delivery system may be used within the preoperative/perioperative/postoperative state for any drug delivery needed for a plurality of eye surgeries for use prophylactically or post operatively.

In some embodiments, the laser system may include an eye docking station as described, e.g., in FIGS. 20, 20A-20B in U.S. application Ser. No. 15/942,513. The eye docking station may be positioned above the eye during a medical operation. The eye docking station may provide a view of the four quadrants.

In some embodiments, the laser system may include a nozzle guard as described in FIGS. 21A-21B in U.S. application Ser. No. 15/942,513. In some exemplary operations, the nozzle guard may be attached to a nozzle.

In some embodiments, the laser system may include a workstation as described in FIGS. 21A-21B in U.S. application Ser. No. 15/942,513. The workstation can include the method, apparatus and system for template-controlled precision laser interventions as described above. The workstation may can include GUI interface, an articulating arm, a laser housing unit, a CCD video camera, galvos scanner capable of off axis scanning, aiming beam, three-dimensional mapping means, at least one communicatively coupled microprocessor, power supply, and the display means include means for presenting images to the surgeon/user indicating precise current location of laser aim and depth in computer generated views which comprise generally a plan view and selected cross sectional views of the eye representing features of the eye at different depths, an imaging system connected to the video display means, including three-dimensional to seven-dimensional mapping means for generating, reading, and interpreting data to obtain information regarding the location in seven dimensions of significant features of the tissue to be operated upon, and including microprocessor means for interpreting the data and presenting the data to the video display means in a format useful to the surgeon/user, and be equipped with three programmable axes (X, Y, Z; can be expanded to 5 axes) has an automatic rotary table machine, programmable X, Y, Z-axis and a 2-station rotary table Includes a Human Machine Interface (HMI) with Security user access. Further detail of the workstation is described in U.S. application Ser. No. 15/942,513 and incorporated herein.

In certain embodiments, the physical requirements of the system described herein may be incorporated into a "Cart" type workstation unit with lockable wheels and counter balanced/articulated arm as to prevent tipping of the cart during use or transport (See, e.g, FIGS. 24 and 26-5 of U.S. application Ser. No. 15/942,513). Accessories may include: Applicator insert (disposable part): A disposable part to collect ablated tissue which establishes a hygienic interface between device and tissue. Eye pod (optional): The applicator may be reusable, easy to clean, bio-compatible, and sterilisable. Foot Switch: Foot switch operation for standard laser delivery.

Depth Control

In most tissues, disease progression is accompanied by changes in the mechanical properties. Laser speckle rheology (LSR) is a new technique we have developed to measure the mechanical properties of tissue. By illuminating the sample with coherent laser light and calculating the speckle intensity modulations from reflected laser speckle patterns, LSR calculates τ, the decay time constant of intensity decorrelation which is closely associated with tissue mechanical properties. The use of LSR technology can be validated by measuring mechanical properties of tissue. LSR measurements of τ are performed on a variety of phantom and tissue samples and compared with the complex shear modulus G*, measured using a rheometer. In all cases, strong correlation is observed between τ and G* ($r=0.95$, $p<0.002$). These results demonstrate the efficacy of LSR as a non-invasive and non-contact technology for mechanical evaluation of biological samples.

It is known that disease progression in major killers such as cancer and atherosclerosis, and several other debilitating disorders including neurodegenerative disease and osteoarthritis, is accompanied by changes in tissue mechanical properties. Most available evidence on the significance of biomechanical properties in evaluation of disease can be obtained using conventional mechanical testing, ex vivo, which involves straining, stretching, or manipulating the sample. To address the need for mechanical characterization in situ, a new optical tool can include a LSR.

When a turbid sample, such as tissue, is illuminated by a coherent laser beam, rays interact with tissue particles and travel along paths of different lengths due to multiple scatterings. Self-interference of the returning light creates a pattern of dark and bright spots, known as laser speckle. Due to thermal Brownian motion of scattering particles, light paths can constantly change, and speckle pattern fluctuates with time scales corresponding to the mechanical properties of the medium surrounding the scattering centers.

Open biofeedback loops can be used in various embodiments during intraoperative procedures using chromophore and other biofeedback processes. In chromophore embodiments, saturation of color can be measured with sensitivity to micron levels of accuracy to determine correct and incorrect tissues for surgical procedures. Pulse decisions can be made based on various preset color saturation levels. This is in contrast to current systems that may use color or other metrics only for feedback to imaging equipment and not to actual laser application devices that are applying treatments. Similarly, subsurface anatomy avoidance for predictive depth calibration can use tools to determine depth calculation in real-time to determine how close extraction or other treatment procedures are to completion, while also maintaining active monitoring for undesirable and unforeseen anatomical structures. As such, hydro- or other feature monitoring is different from older systems that may monitor surface levels for reflection but are unable to effectively measure depth in a tissue or other biological substance.

LSR exploits this concept and analyses the intensity decorrelation of backscattered rays to produce an estimate of tissue biomechanics. To this end, LSR calculates the intensity decorrelation function of speckle series, $g_2(t)$, and extracts its decay time constant, τ, as a measure of biomechanical properties.

Laser Speckle Rheology Bench

In some exemplary operations, bulk mechanical properties of tissue and substrates are measured using a bench-top LSR set-up. This set-up includes a laser of a plurality of coherence laser lengths followed by a linear polarizer and a beam expander. A focal length lens and a plane mirror are used to focus the illumination spot at the target tissue site. Laser speckle patterns are imaged using a high-speed CMOS camera. Further detail of LSR measurements is described in U.S. application Ser. No. 15/942,513 and incorporated herein.

Systems and methods herein can be used for measuring the differential path length of photons in a scattering medium utilizing the spectral absorption features of water. Determination of this differential path length is a prerequisite for quantifying chromophore concentration changes measured by near-infrared spectroscopy (NIRS). The quantification of tissue chromophore concentration measurements is used to quantify depth of ablation rates yielded by water absorption and time-resolved measurements through various layers of scleral tissue as it relates to ablation rate of absorption, pulse width and energy of the laser beam. The quantification of tissue chromophore concentration measurements is further described in U.S. application Ser. No. 15/942,513 and incorporated herein.

Further embodiments herein may include the use of a probe design which has been adjusted into multiple source-detector pairs so that it can employ a white light source to obtain continuous spectra of absorption and reduced scattering coefficients. The advantages of this multi-source-detector separation probe are further described in U.S. application Ser. No. 15/942,513 and incorporated herein.

In some embodiments, the laser system of the present disclosure may also include an exemplary multilayer imaging platform. The platform may include: HL—Halogen Lamp; MS—Mirror system DD—digital Driver; L2—projection lens; L3—camera lens; LCTF—liquid crystal tunable filter; and CCD VC—CCD Video Camera, or other suitable video camera. Other suitable cameras may be used. Further detail of a multilayer imaging platform is described in U.S. application Ser. No. 15/942,513 and incorporated herein.

Use of Fluorescence: Fluorescence spectroscopy is a tool used to differentiate targeted and untargeted tissues based on the emission spectral profile from endogenous fluorophores. The laser system may include fluorescence spectroscopy based real time tools for the discrimination of various connective tissue components in this embodiment of the scleral connective tissue of the eye from the adjacent untargeted tissue. This anatomy avoidance system can be reiterated using real time imaging, e.g., OCT imaging sensors as well as chromophore sensors (water, color etc.) or spectroscopy without fluorescence.

The systems of the present disclosure may include a biofeedback sensor, a scanner including a galvanometer and a camera that provide biofeedback that is used to distinguish targeted and untargeted tissues in addition to the transitions within tissues from one chromophore to the next, in the form of a sensitive biofeedback loop. Such transitions are relatively energetic and hence are associated with absorption of ultraviolet, visible and near-infrared wavelengths. On the other hand, currently known systems in the art use simple image facilitated feedback for the laser module it discloses. Since many biological molecules can absorb light via electronic transitions, sensing and monitoring them can be useful generic imaging capabilities.

It should be noted that chromophore sensing and monitoring, which is the use of color differences based on inherent light absorption by different materials as a way to sense and monitor and determine boundaries within a tissue, is an advantageous improvement.

In some exemplary operations, zone treatment simulations may be performed, including: baseline model with sclera stiffness and attachment tightness altered in individual full zones: treated combinations of zones (with and without changing attachment): for example, individually: 0, 1, 2, 3, 4; combined: 1+2+3, 1+2+3+4, 0+1+2+3+4; effective stiffness: modulus of elasticity (E)=1.61 MPa, equivalent to ~30 years old; loose attachment between the sclera and the ciliary/choroid where values in original accommodation model are used.

Effect of zone treatment on ciliary deformation in accommodation may include sclera stiffness, sclera stiffness+attachment.

In some embodiments, different treatment region shapes may be applied to one sclera quadrant with reference to multiple (e.g., 3 or 5) critical zones baseline simulation: original model of healthy accommodation with "old" sclera: stiff starting sclera: modulus of elasticity (E)=2.85 MPa, equivalent to ~50 years old; tight attachment between the sclera and the ciliary/choroid, all other parameters changed (ciliary activation, stiffness of other components, etc.).

In some exemplary operations, shape treatment simulations may include: baseline model with regionally "treated" sclera stiffness: treated different area shapes (without changing attachment)→treated stiffness: modulus of elasticity (E)=1.61 MPa, equivalent to ~30 years old; effective stiffness in each zone may be determined by amount of shape area in each zone and values in original accommodation model.

Effect of shape treatment on ciliary deformation in accommodation may include sclera stiffness only.

Treated stiffness may depend on: pore volume fraction in the treated region→% sclera volume removed by treatment; pore volume fraction is varied by changing parameters of ablation pores; and others. Resultant stiffness estimated as microscale mixture: pores assumed to be parallel evenly spaced/sized within volume=volume fraction (% of total sclera volume); remaining volume is "old" sclera (E=2.85 MPa); need to remove ~43.5% of volume to change sclera stiffness in the treated area from old (e.g., 50 year-old) to young (e.g., 30 year-old); protocols (combinations of density % & depth) allow for a maximum volume fraction of 13.7%, equivalent to a new stiffness of 2.46 MPa; array size=side length of the square area of treatment (mm).

In some embodiments, parameters considered include those illustrated in FIGS. 26-3A, 26-3A1, 26-3A2, and 36 in U.S. application Ser. No. 15/942,513.

The following parameters are considered and illustrated in FIG. 107.

Treated surface area=surface area of sclera where treatment is applied (mm^2), where treated surface area=array squared.

Thickness=thickness of sclera in the treated area (mm), assumed uniform.

Treated volume=volume of sclera where treatment is applied (mm^2) treated volume=treated surface area*thickness=array$^2$*thickness.

Density %=percent of treated surface area occupied by pores (%).

Spot size=surface area of one pore (mm^2).

# pores=number of pores in the treated region.

$$\#\text{ pores} = \frac{\text{density }\% * \text{treated surface area}}{\text{spot size} * 100} = \frac{\text{density }\% * array^2}{\text{spot size} * 100}$$

*round to nearest whole number.

Total pore surface area=total area within the treated surface area occupied by pores $$\text{total pore surface area} = \text{spot size} * \text{pores} \approx \frac{\text{density }\% * \text{treated surface area}}{100} \approx \frac{\text{density }\% * array^2}{100}$$

Depth=depth of one pore (mm); dependent on pulse per pore (ppp) parameter.

depth %=percent of the thickness extended into by the pore.

$$\text{depth }\% = \frac{\text{depth}}{\text{thickness}} * 100$$

Total pore volume=total area within the treated surface area occupied by pores

Volume fraction=percent of treated volume occupied by pores (%), i.e. percent of sclera volume removed by the laser.

$$\text{volume fraction} = \frac{\text{total pore volume}}{\text{treated volume}} * 100 \approx \frac{\text{density }\% * \text{depth}}{\text{thickness}} = \frac{\text{density }\% * \text{depth }\%}{100}$$

Relationships between treatment parameters include: input parameters of laser treatment; properties of the sclera; input to calculate new stiffness.

Calculating new stiffness of sclera in the treated region.

Volume fraction=percent of treated volume occupied by pores (%), i.e., percent of sclera volume removed by the laser.

$$\text{volume fraction} = \frac{\text{total pore volume}}{\text{treated volume}} * 100 \approx \frac{\text{density }\% * \text{depth}}{\text{thickness}} = \frac{\text{density }\% * \text{depth }\%}{100}$$

Stiffness=modulus of elasticity of sclera before treatment (MPa).

Treated stiffness=modulus of elasticity of sclera after treatment (MPa); estimated from microscale mixture model.

$$\text{treated stiffness} = \left(1 - \frac{\text{volume fraction}}{100}\right) * \text{stiffness} \approx \left(1 - \frac{\text{density }\% * \text{depth}}{\text{thickness} * 100}\right) * \text{stiffness} = \left(1 - \frac{\text{density }\% * \text{depth}\%}{10000}\right) * \text{stiffness}$$

Input parameters of laser treatment: properties of the sclera, input to calculate new stiffness input to finite element model of treated zones, effect of volume fraction on ciliary deformation in accommodation:

sclera stiffness only, full zone region treated (region fraction=1).

Protocols=range of possible combinations of density % and depth, sclera in all zones changed to treated stiffness corresponding with pore volume fraction.

Effect of volume fraction on ciliary deformation in accommodation: sclera stiffness+attachment, full zone region treated (region fraction=1), healthy=original accommodation model results.

Protocols=range of possible combinations of density % and depth, sclera in all zones changed to treated stiffness corresponding with pore volume fraction effect of volume fraction on ciliary deformation in accommodation: sclera stiffness+treatment area shape.

Protocols=range of possible combinations of density % and depth, sclera in all zones changed to treated stiffness corresponding with pore volume fraction and region fraction of treated area.

J/cm2 calculation: J/cm2×Hz (1/sec)×Pore size (cm2)=W; J/cm2=W/Hz/pore size. Example: spot is actually a "square", therefore the area would be based on square calculation: 7.2 J/cm2=1.1 w/300 Hz/(225 μm $10^{-4})^2$.

Factors that may affect ablation depth % on living eyes in surgery include: moisture content on surface and inside the tissue, tenon or conjuntiva layer, laser firing angle, thermal damage, may consider water spray, Cryo spray/refrigerated eye drops, Cryo hydrogel cartridge in the laser disposable system (perioperative medications such as antibiotics/steroids).

In some embodiments, the described systems, methods and devices of the disclosure may further include following features.

Adjustable micropore density: dose and inflammation control could be achieved thanks to a variable number of micropores created per application area. Adjustable micropore size; dose and flexible patterning of microporation. Adjustable micropore thermal profile: the system can create micropores with adjustable thermal profiles that minimize creation of a coagulation zone. Adjustable depth with depth recognition: the system creates micropores in a controlled manner and prevent too deep ablation Anatomy recognition to avoid blood vessels. Laser security level: the device is a Laser Class 1c device, the system detects the eye contact and the eye pod covers the cornea. Integrated smoke evacuation and filtration: fractional ablation can be conducted without any extra need in installing a smoke evacuation system, since smoke, vapor and tissue particles will be sucked out directly by integrated systems. Laser system will have an integrated real time video camera (e.g., an endo camera, CCD camera) with biofeedback loop to laser guidance system integrated with GUI display for depth control/limit control.

In some embodiments, the described systems, methods and devices of the disclosure may provide: Laser system biofeedback loop integrates chromophore recognition of color change using melanin content (computer integration of various micropore staging for color change; a prior depth information in the 3 zones of thickness; laser system capable of integrating a priori scleral thickness mapping for communication with laser guidance planning and scleral microporation; use of OCT or UBM or 3D tomography; laser system programming release code with controlled pulses per procedure; electronically linked to reporting to a data report (calibration data, and service data, statistics etc.). Laser system components may be built in modular fashion for easy service maintenance and repair management. Self-calibrating setup as well as real time procedure calibration prior to treatment, after treatment and before subsequent treatment may be included. All calibrations may be recorded in database. Other features may include communication port for online communication (e.g., WIFI service trouble shooting, report generation, and communication to server, WIFI access to diagnostic information (error code/parts requirement) and dispense either trouble shooting repair and maintenance or dispense an order for service by service representative). Some embodiments may include spare parts service kit for service maintenance and repair for onsite repair; laser system key card integration with controlled pulses programming with time limitation included; aiming beam with flexible shape to set boundary conditions and also to trigger if the laser nozzle is on axis, level and positioning; aiming beam coincident with alignment fixation beam to trigger system Go/No-Go for starting treatment ablation; laser system requirements containing an eye tracking system and corresponding eye fixation system for safety of ablation to control for eye movement; laser system requirements having ability to go 'on axis' delivery through a gonio mirror system to deliver microporation on the sclera, or through a slit lamp application or free space application. These may require higher power, good beam quality as well as integration of fixation target and/or eye tracking system. Good beam quality may mean: laser system focusing down to 50 μm and up to 425 μm. The laser system may be capable of doing a quick 360 dg procedure through galvos scanning and use of robotics to change quadrant treatments within 40-45 seconds per whole eye (e.g., 4 quadrants in each eye about 10 seconds per quadrant; 1-2 seconds repositioning laser to subsequent quadrant). The laser system may be a workstation with integration of foot pedal, computer monitor; OCT; CCD video camera and/or microscope system. The laser system may include patient positioning table/chair module that is flexible from supine position; flexible angle; or seated; and motorized chair.

In some exemplary operations, the described systems, methods and devices of the disclosure may include the following medical procedure: 1) The user manual may give information about the correct handling of the system. 2) Put the eye-applicator onto the treatment area and place the applicator unit on the eye-applicator. 3) The user can set the treatment parameters. 4) The user starts the treatment procedure. 5) The user may be informed about the on-going state of the treatment. 6) The user may be informed about the calibration of the energy on the eye before and after the treatment. 7) To prevent undesired odors, ablation smoke may be prevented from spreading. 8) The user may be informed about the visualization of the eye during the treatment, between quadrants and after the treatment.

Microporations—Exemplary Parameters

| Term | Definition | |
|---|---|---|
| Procedure | full eye - 4 quadrants | |
| Treatment site and size | Procedure: average area 300 cm2 (=mean value) partial treatments: average area 50 cm2 | |
| Scenarios | Maximal utilisation case | Expected utilisation case |
| No. of treatments per day | | |
| Array size | 5 mm (Variable between 2 mm-14 mm) | 5 mm (Variable between 2 mm-14 mm) |
| "Standard" microporation (MP) parameters; based on preliminary experiments: | | |
| MP1 | 300 Hz repetition rate, 125 μs laser pulse duration, 5 pulses per pore, 5% | |
| MP2 | 200 Hz repetition rate, 175 μs laser pulse duration, 5 pulses per pore, 7% | |
| MP3 | 100 Hz repetition rate, 225 μs laser pulse duration, 7 pulses per pore, 8% | |
| MP4 | 200 Hz repetition rate, 225 μs laser pulse duration, 5 pulses per pore, 6% | |

System operation may be through pre-approved electronic key card. Visualization required during surgery: Lighting of eye to aid visualization to be provided—either external light source or incorporated into laser adaptor fixation device, a video camera and GUI interface to computer monitor may be a required module. Patient can be in horizontal or inclined or seated position. Shielding for eye safety of patient during procedures may be needed. Operation: The system may allow activating the laser when applicator and insert are attached, on proper tissue contact and with verified user access. Pore depth monitor: maximum depth monitored by end switch (optical or equal monitored). Management of eye movement intra-procedure: Eye tracking technology with corresponding eye fixation targets may be included for fully non-contact eye procedure. Vasculature avoidance: Scan/define ocular vasculature may be provided to avoid microporation in this area. See FIGS. 4A-1 to 4A-10 in U.S. application Ser. No. 15/942,513 which illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

Performance requirements may include: Variable pore size, pore array size and pore location. Exemplary preparation time: 5 min from power-on of the device until start of microporation process (assuming average user reaction time). Robotics incorporation by quadrant to achieve treatment time requirements. Treatment time may be <60 s, 45 s for one procedure. Diameter of micropores: Adjustable between 50 μm-600 μm. Tissue ablation rate: adjustable between 1 to 15%. Microporation array size: Area adjustable up to between 1 mm×1 mm and up to 14×14 mm, square shaped pore custom shape array. Multiple ablation pattern capability. Short press to activate and deactivate laser: the actual microporation process may be started by pressing a foot switch only for a short amount of time, instead of pressing it during the entire microporation. Stopping the laser can be done identically. Ablated pore depth: 5% to 95% of scleral thickness. Biocompatibility: All tissue contact parts are to be constructed with materials that are in compliance with medical device requirements.

In some embodiments, the system may include: laser wavelength: 2900 nm+/−200 nm; around the mid IR absorption maximum of water. Maximum laser fluency: ≥15.0 $J/cm^2$ on the tissue ≥25.0 $J/cm^2$ on the tissue; to widen treatment possibilities 2900 nm+/−200 nm; around the mid IR absorption maximum of water. Laser setting combinations: Laser repetition rate and pulse duration may be adjustable by using pre-defined combinations in the range of 100-500 Hz and 50-225 μs. Said range may be a minimum range, e.g., ≥15.0 $J/cm^2$ on the tissue, or ≥25.0 $J/cm^2$ on the tissue, to widen treatment possibilities. Aggressive treatments number of pulses per pore: "Aggressive" settings may also be selectable to create micropores far into the dermis, e.g., with a depth >1 mm. As the depth is mainly fluence-controlled, a high number of pulses per pores should automatically lead to larger depth values. Therefore, the pulse per pore (PPP) values may be adjustable between 1-15 PPP. Shock and vibration:

In some embodiments, the described systems, methods and devices of the disclosure may include a protection lens as illustrated in FIGS. 27A to 27C in U.S. application Ser. No. 15/942,513.

In some embodiments, the described systems, methods and devices of the disclosure may include speculum as illustrated in various embodiments in FIGS. 136 to 138, and FIGS. 28A to 29B in U.S. application Ser. No. 15/942,513.

One or more of the components, processes, features, and/or functions illustrated in the figures may be rearranged and/or combined into a single component, block, feature or function or embodied in several components, steps, or functions. Additional elements, components, processes, and/or functions may also be added without departing from the disclosure. The apparatus, devices, and/or components illustrated in the Figures may be configured to perform one or more of the methods, features, or processes described in the Figures. The algorithms described herein may also be efficiently implemented in software and/or embedded in hardware.

Note that the aspects of the present disclosure may be described herein as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

In various embodiments, algorithms and other software used to implement the systems and methods disclosed herein are generally stored in non-transitory computer readable memory and generally contain instructions that, when executed by one or more processors or processing systems coupled therewith, perform steps to carry out the subject matter described herein. Implementation of the imaging, machine-learning, prediction, automated correcting and other subject matter described herein can be used with current and future developed medical systems and devices to perform medical procedures that provide benefits that are, to date, unknown in the art.

In some embodiments, the described systems, methods and devices are performed prior to or contemporaneous with various medical procedures. In some embodiments, they may be implemented in their own systems, methods and devices, along with any required components to accomplish their respective goals, as would be understood by those in the art. It should be understood that medical procedures benefitting from the herein described material are not limited to implementation using the material described hereafter, but other previous, currently performed and future developed procedures can benefit as well.

The enablements described above are considered novel over the prior art and are considered critical to the operation of at least one aspect of the disclosure and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus, if an element can be understood in the context of this specification as including more than one meaning, then its use must be understood as being generic to all possible meanings supported by the specification and by the word or words describing the element.

The definitions of the words or drawing elements described above are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

In the foregoing description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used above, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, processes, operations, values, and the like.

It should be noted that where a discrete value or range of values is set forth herein (e.g., 5, 6, 10, 100, etc.), it is noted that the value or range of values may be claimed more broadly than as a discrete number or range of numbers, unless indicated otherwise. Any discrete values mentioned herein are merely provided as examples.

Definitions for various terms as used above and throughout the present disclosure may have definitions as defined in U.S. application Ser. No. 15/942,513, U.S. Provisional Application No. 62/843,403, Taiwan Application No. 108111355, and International Appl. No. PCT/US18/25608, which are incorporated in their entireties herein.

The invention claimed is:

1. A system for delivering microporation medical treatments to biological tissue to improve biomechanics of an eye, the system comprising:

a controller;

a laser head system comprising:

a housing, a laser subsystem for generating a beam of laser radiation on a treatment-axis not aligned with a patient's visual-axis, operable for use in subsurface ablative medical treatments to create a pattern of pores that improves biomechanics, and a lens operable to focus the beam of laser irradiation onto a target tissue;

an eye tracking subsystem for tracking landmarks and movements of the eye;

a depth control subsystem for controlling a depth of microporation on the target tissue; and wherein the controller is operable to control the movements of the laser subsystem including at least one of a pitch movement, a swivel movement and a yaw movement.

2. The system of claim 1, further comprises a scanning system communicatively coupled to the eye tracking subsystem and the depth control subsystem for scanning a focus spot over an area of the target tissue.

3. The system of claim 1, further comprises an avoidance subsystem for identifying biological structures or locations of the eye.

4. The system of claim 1, further comprises one or more diffractive beam splitters.

5. The system of claim 1, wherein the pattern of pores includes pores of a same size, shape and depth.

6. The system of claim 1, wherein the pattern of pores includes pores of different sizes, shapes and depths.

7. The system of claim 1, wherein the pattern of pores includes pores having equal distance.

8. The system of claim 1, wherein the pattern of pores includes pores having different distances and wherein the pattern of the pores is at least tightly packed or tessellated or spaced.

9. The system of claim 1, wherein a depth of the pores is proportional to a total laser energy.

10. The system of claim 1, wherein a depth of the pores is measured and judged by the depth control subsystem.

11. The system of claim 10, wherein the depth of the pores is measured between pulses.

12. The system of claim 10, wherein the depth of the pores is measured and judged between pulses.

13. The system of claim 1, wherein the pattern of pores is a spiral pattern.

14. The system of claim 13, wherein the pattern of pores is a spiral pattern of an Archimedean spiral, a Euler spiral, a Fermat's spiral, a hyperbolic spiral, a lituus, a logarithmic spiral, a Fibonacci spiral, a golden spiral, or combinations thereof.

15. The system of claim 1, wherein the pattern of pores is a matrix array.

16. The system of claim 1, wherein the laser head system further comprises a display to provide eye fixation.

17. The system of claim 1, wherein the laser head system further comprises illumination sources.

18. The system of claim 1, wherein the laser head system further comprises a camera system to optimize eye tracking performance.

* * * * *